United States Patent
Berger et al.

(10) Patent No.: US 10,935,546 B2
(45) Date of Patent: Mar. 2, 2021

(54) FLUORESCENT AMP-KINASE BIOSENSORS

(71) Applicants: Universite Grenoble Alpes, Saint-Martin-d'Hères (FR); European Molecular Biology Laboratory, Heidelberg (DE)

(72) Inventors: Imre Berger, Saint Egrève (FR); Martin Pelosse, Grenoble (FR); Uwe Schlattner, Montbonnot (FR)

(73) Assignees: Universite Grenoble Alpes, Saint Martin d'Heres (FR); European Molecular Biology Laboratory, Heidelberg (DE)

( * ) Notice: Subject to any disclaimer, the term of this patent is extended or adjusted under 35 U.S.C. 154(b) by 577 days.

(21) Appl. No.: 15/319,646

(22) PCT Filed: Jun. 18, 2015

(86) PCT No.: PCT/EP2015/063780
§ 371 (c)(1),
(2) Date: Dec. 16, 2016

(87) PCT Pub. No.: WO2015/193466
PCT Pub. Date: Dec. 23, 2015

(65) Prior Publication Data
US 2017/0205400 A1   Jul. 20, 2017

(51) Int. Cl.
*G01N 33/542*  (2006.01)
*C12Q 1/48*    (2006.01)
*C12N 9/12*    (2006.01)
*G01N 33/50*   (2006.01)

(52) U.S. Cl.
CPC .............. *G01N 33/542* (2013.01); *C12N 9/12* (2013.01); *C12Q 1/485* (2013.01); *C12Y 207/11031* (2013.01); *G01N 33/5008* (2013.01); *G01N 2333/91215* (2013.01); *G01N 2500/00* (2013.01); *G01N 2500/10* (2013.01)

(58) Field of Classification Search
CPC ...... C12N 9/12; C07K 2319/30; C12Q 1/485; G01N 33/573; G01N 33/542; G01N 33/5008; G01N 2333/91215; G01N 2500/10; C12Y 207/11031
USPC ...................................... 435/194, 69.7, 15, 7
See application file for complete search history.

(56) References Cited

U.S. PATENT DOCUMENTS 7,119,205 B2   10/2006   Iyengar

FOREIGN PATENT DOCUMENTS

| WO | 2008070455 | 6/2008 | |
| WO | WO-2008070455 A2 * | 6/2008 | ............... C12N 9/12 |

OTHER PUBLICATIONS

Brenda, EC 2.7.11.31—[hydroxymethylglutaryl-CoA reductase (NADPH)] kinase (AMPK): Reaction, Crystallization, Protein Variants. Downloaded Oct. 19, 2020.*

(Continued)

*Primary Examiner* — Sheridan Swope
(74) *Attorney, Agent, or Firm* — Cuenot, Forsythe & Kim, LLC; Stanley A. Kim

(57) ABSTRACT

The present invention deals with heterotrimeric AMP-activated protein kinase (AMPK) comprising a fluorophore pair wherein the conformational change can be measured by FRET. It represents an advanced tool to screen and identify AMPK interactors in vitro and in cells in vivo. Such invention can also be considered as a reporter of the cellular energy status as it allows the spatiotemporal monitoring, in situ, of fluctuations in the ratio of AMP and ADP versus ATP.

15 Claims, 10 Drawing Sheets
Specification includes a Sequence Listing.

(56) References Cited

OTHER PUBLICATIONS

Carling, David et al: "A common bicyclic protein kinase cascade inactivates the regulatory enzymes of fatty acid and cholesterol biosynthesis," Federation of European Biochemical Societies, Nov. 1987, vol. 223, No. 2:217-222.
Evans, Josie M.M. et al: "Metformin and reduced risk of cancer in diabetic patients," BMJ, Jun. 2005, vol. 330:1304-1305.
Hardie, D. Grahame et al: "The AMP-activated/SNF1 protein kinase subfamily: metabolic sensors of the eukaryotic cell?", Annu. Rev. Biochem., 1998, vol. 67:821-855.
Riek, Uwe et al: "Structural properties of AMP-activated protein kinase—dimerization, molecular shape, and changes upon ligand binding," The Journal of Biological Chemistry, 2008, vol. 283, No. 26:18331-18343.
Srivastava, Rai Ajit K. et al: "AMP-activated protein kinase: an emerging drug target to regulate imbalances in lipid and carbohydrate metabolism to treat cardio-metabolic diseases," Journal of Lipid Research, 2012, vol. 53:2490-2514.
Anonymous: "Team: Gothenburg—Sweden/Project/More," Jan. 1, 2010, pp. 1-4; <http://2010.igem.org/Team:Gothenburg-Sweden/Project/more>; retrieved from the Internet on Dec. 5, 2016.
Komatsu, N. et al: "Development of an optimized backbone of FRET biosensors for kinases and GTPases," Molecular Biology of the Cell, Dec. 1, 2011, vol. 22:4647-4656.
Schisler, Jonathan C. et al: "CHIP protects against cardiac pressure overload through regulation of AMPK," The Journal of Clinical Investigation, Aug. 2013, vol. 123, No. 8:3588-3599.
Merkx, Maarten et al: "Rational design of FRET sensor proteins based on mutually exclusive domain interactions," Biochem Soc Trans, Oct. 2013, vol. 41, No. 5:1-9.
Hardie, Grahame D.: "AMP-activated/SNF1 protein kinases: conserved guardians of cellular energy," Nature Reviews Molecular Cell Biology, Oct. 2007, vol. 8, No. 10:774-785.
Komatsu, N. et al.: Supplemental Information,"Development of an optimized backbone of FRET biosensors for kinases and GTPases," Molecular Biology of the Cell, Dec. 1, 2011, vol. 22:1-16.
Schisler, Jonathan C. et al.: Supplementary Data Table of Contents,"CHIP protects against cardiac pressure overload through regulation of AMPK," The Journal of Clinical Investigation, Aug. 2013, vol. 123, No. 8:1-46.

\* cited by examiner

SEQUENCE LISTING

<160> NUMBER OF SEQ ID NOS: 99

<210> SEQ ID NO 1
<211> LENGTH: 8
<212> TYPE: PRT
<213> ORGANISM: Artificial Sequence
<220> FEATURE:
<223> OTHER INFORMATION: putative alpha helix

<400> SEQUENCE: 1

Glu Glu Glu Glu Lys Lys Lys Lys
1               5

<210> SEQ ID NO 2
<211> LENGTH: 4260
<212> TYPE: DNA
<213> ORGANISM: Artificial sequence
<220> FEATURE:
<223> OTHER INFORMATION: Rat alpha2 subunit pACE plasmid

<400> SEQUENCE: 2

```
ggaattccag ataacttcgt ataatgtatg ctatacgaag ttatggtacc gcggccgcgt      60
agaggatctg ttgatcagca gttcaacctg ttgatagtac ttcgttaata cagatgtagg     120
tgttggcacc atgcataact ataacggtcc taaggtagcg acctaggtat cgataatacg     180
actcactata ggggaattgt gagcggataa caattcccct ctagaaataa ttttgtttaa     240
ctttaagaag gagatataat gggcagtagt caccatcacc accatcatca tcaccatcat     300
agtagtgaaa acctgtattt tcaggggcat atggctgaga agcagaagca cgacgggcgt     360
gtgaagatcg acactacgt gctgggggac accctgggcg tcggcacctt cggcaaagtg     420
aagattggag aacatcaatt gacaggccat aaagtggcag ttaagatctt aaatagacag     480
aagattcgca gtttagatgt tgttggaaaa ataaaacgag aaattcaaaa tcttaaactc     540
tttcgtcatc ctcatattat caaactctac caagtgatca gcactccaac agacttttt      600 atggtaatgg aatatgtgtc tggaggtgaa ttgttcgact acatctgtaa acacgggagg     660
gttgaagagg tggaagctcg ccggctcttc cagcagattc tgtctgccgt ggactactgt     720
cacaggcaca tggttgtcca cagggacctg aagccagaga acgtgttgct ggacgcccag     780
atgaatgcta agatagctga cttcggactc tctaatatga tgtcagatgg tgaatttcta     840
cgaactagct gtggatcgcc aaattatgca gcaccggagg tcatctcagg aaggctgtat     900
gcgggtcctg aggttgatat ctggagctgt ggtgttatcc tgtatgccct tctctgtggc     960
accctcccgt tcgacgatga gcacgtgcct acgctctta agaagatccg agggggtgtg    1020
ttctacatcc cggagtatct caaccgttct attgccactc tgctgatgca catgctgcag    1080
gtggacccct tgaagcgagc aactatcaaa gacatacgag agcatgaatg gtttaaacag    1140
gatttgccca gttacctctt tcctgaagac ccctcctatg atgctaacgt cattgatgat    1200
gaggctgtga agaagtatg tgaaaaattt gagtgtacag aatcagaagt gatgaacagt    1260
ttatacagtg gtgaccctca agaccagctc gcagtggctt atcatctcat cattgacaat    1320
cggagaataa tgaaccaagc cagtgagttc taccctcgcct ccagtcctcc aacgggttcc    1380
ttcatggacg atatggccat gcacattccc cccggcctga accacatccc tgaaaggatg    1440
ccacctctca tagcagacag ccccaaagca cgctgtccac tggatgcact caacacaact    1500
aagcccaaat cttagctgt gaaaaaagcc aagtggcacc ttgggatccg aagccagagc    1560
aaaccatacg acattatggc ggaggtgtac cgagctatga agcagctgga ctttgaatgg    1620
```

```
aaggtagtga atgcatacca tcttcgagta agaagaaaaa acccagtgac tggcaattac    1680
gtgaaaatga gcttacagct ttacctggtt gacaatcgga gctatctgct ggactttaaa    1740
agcatcgatg atgaggtggt ggagcagagg tctggttctt caacacctca gcgctcctgt    1800
tctgctgccg gcctccacag acctcggtca agtgtcgatt ccagcacagc cgagaaccat    1860
tcactgtctg gctctctcac tggttctttg actggcagca ctttgtcctc cgcttccccg    1920
cgcctgggca gtcataccat ggattttttt gaaatgtgcg ccagtcttat cactgcttta    1980
gcccgtaagc tttaactcga gagatccggc tgctaacaaa gcccgaaagg aagctgagtt    2040
ggctgctgcc accgctgagc aataactagc ataacccctt ggggcctcta acgggtctt     2100 gaggggtttt ttggtttaaa cccatctaat tggactagta gcccgcctaa tgagcgggct    2160 ttttttttaat tcccctattt gtttattttt ctaaatacat tcaaatatgt atccgctcat    2220
gagacaataa ccctgataaa tgcttcaata atattgaaaa aggaagagta tgagtattca    2280
acatttccgt gtcgcccttt ttcccttttt tgcggcattt tgccttcctg ttttgctca     2340 cccagaaacg ctcgtgaaag taaaagacgc agaggaccat tgggggcac gagtgggata     2400 catagaactg gacttgaata gcggtaaaat ccttgagagt tttcgccctg aagagcgttt    2460
tccaatgatg agcactttca aagttctgct atgtggagca gtattatccc gtgtagatgc    2520
ggggcaagag caactcggac gacgaataca ctattcgcag aatgacttgg ttgaatactc    2580
cccagtgaca gaaaagcacc ttacggacgg aatgacggta agagaattat gtagtgccgc    2640
cataacgatg agtgataaca ctgcggcgaa cttacttctg acaaccatcg gtggaccgaa    2700
ggaattaacc gcttttttgc acaatatggg agaccatgta actcgccttg accgttggga    2760
accagaactg aatgaagcca taccaaacga cgagcgagac accacaatgc ctgcggcaat    2820
ggcaacaaca ttacgcaaac tattaactgg cgaactactt actctggctt cacggcaaca    2880
attaatagac tggcttgaag cggataaagt tgcaggacca ctactgcgtt cggcacttcc    2940
tgctggctgg tttattgctg ataaatctgg gcaggagag cgtggttcac ggggtatcat     3000
tgccgcactt ggaccagatg gtaagccttc ccgtatcgta gttatctaca cgacgggtag    3060
tcaggcaact atggacgaac gaaatagaca gattgctgaa atagggggctt cactgattaa    3120 gcattggtaa accgatacaa ttaaaggctc cttttggagc cttttttttt ggacggaccg    3180
gtagaaaaga tcaaaggatc ttcttgagat cctttttttc tgcgcgtaat ctgctgcttg    3240
caaacaaaaa aaccaccgct accagcggtg gtttgtttgc cggatcaaga gctaccaact    3300 cttttttccga aggtaactgg cttcagcaga gcgcagatac caaatactgt ccttctagtg    3360
tagccgtagt taggccacca cttcaagaac tctgtagcac cgcctacata cctcgctctg    3420
ctaatcctgt taccagtggc tgctgccagt ggcgataagt cgtgtcttac cgggttggac    3480
tcaagacgat agttaccgga taaggcgcag cggtcgggct gaacggggg ttcgtgcaca     3540 cagcccagct tggagcgaac gacctacacc gaactgagat acctacagcg tgagctatga    3600
gaaagcgcca cgcttcccga agggagaaag gcggacaggt atccggtaag cggcagggtc    3660
ggaacaggag agcgcacgag ggagcttcca gggggaaacg cctggtatct ttatagtcct    3720
gtcgggtttc gccacctctg acttgagcgt cgatttttgt gatgctcgtc agggggggcgg    3780 agcctatgga aaaacgccag caacgcggcc ttttttacggt tcctggcctt tgctggcct    3840 tttgctcaca tgttctttcc tgcgttatcc cctgattctg tggataaccg tattaccgcc    3900
tttgagtgag ctgataccgc tcgccgcagc cgaacgaccg agcgcagcga gtcagtgagc    3960
gaggaagcgg aagagcgcct gatgcggtat tttctcctta cgcatctgtg cggtatttca    4020
```

```
caccgcaatg gtgcactctc agtacaatct gctctgatgc cgcatagtta agccagtata    4080
cactccgcta tcgctacgtg actgggtcat ggctgcgccc cgacaccgc caacacccgc    4140 tgacgcgccc tgacgggctt gtctgctccc ggcatccgct acagacaag ctgtgaccgt    4200 ctccgggagc tgcatgtgtc agaggttttc accgtcatca ccgaaacgcg cgaggcaggg    4260
```

<210> SEQ ID NO 3
<211> LENGTH: 578
<212> TYPE: PRT
<213> ORGANISM: Rattus norvegicus

<400> SEQUENCE: 3

```
Met Gly Ser Ser His His His His His His His His Ser Ser
1               5                   10                  15

Glu Asn Leu Tyr Phe Gln Gly His Met Ala Glu Lys Gln Lys His Asp
            20                  25                  30

Gly Arg Val Lys Ile Gly His Tyr Val Leu Gly Asp Thr Leu Gly Val
        35                  40                  45

Gly Thr Phe Gly Lys Val Lys Ile Gly Glu His Gln Leu Thr Gly His
    50                  55                  60

Lys Val Ala Val Lys Ile Leu Asn Arg Gln Lys Ile Arg Ser Leu Asp
65                  70                  75                  80

Val Val Gly Lys Ile Lys Arg Glu Ile Gln Asn Leu Lys Leu Phe Arg
                85                  90                  95

His Pro His Ile Ile Lys Leu Tyr Gln Val Ile Ser Thr Pro Thr Asp
            100                 105                 110

Phe Phe Met Val Met Glu Tyr Val Ser Gly Gly Glu Leu Phe Asp Tyr
        115                 120                 125

Ile Cys Lys His Gly Arg Val Glu Glu Val Glu Ala Arg Arg Leu Phe
    130                 135                 140

Gln Gln Ile Leu Ser Ala Val Asp Tyr Cys His Arg His Met Val Val
145                 150                 155                 160

His Arg Asp Leu Lys Pro Glu Asn Val Leu Leu Asp Ala Gln Met Asn
                165                 170                 175

Ala Lys Ile Ala Asp Phe Gly Leu Ser Asn Met Met Ser Asp Gly Glu
            180                 185                 190

Phe Leu Arg Thr Ser Cys Gly Ser Pro Asn Tyr Ala Ala Pro Glu Val
        195                 200                 205

Ile Ser Gly Arg Leu Tyr Ala Gly Pro Glu Val Asp Ile Trp Ser Cys
    210                 215                 220

Gly Val Ile Leu Tyr Ala Leu Leu Cys Gly Thr Leu Pro Phe Asp Asp
225                 230                 235                 240

Glu His Val Pro Thr Leu Phe Lys Lys Ile Arg Gly Gly Val Phe Tyr
                245                 250                 255

Ile Pro Glu Tyr Leu Asn Arg Ser Ile Ala Thr Leu Leu Met His Met
            260                 265                 270

Leu Gln Val Asp Pro Leu Lys Arg Ala Thr Ile Lys Asp Ile Arg Glu
        275                 280                 285

His Glu Trp Phe Lys Gln Asp Leu Pro Ser Tyr Leu Phe Pro Glu Asp
    290                 295                 300

Pro Ser Tyr Asp Ala Asn Val Ile Asp Asp Glu Ala Val Lys Glu Val
305                 310                 315                 320

Cys Glu Lys Phe Glu Cys Thr Glu Ser Glu Val Met Asn Ser Leu Tyr
                325                 330                 335
```

Ser Gly Asp Pro Gln Asp Gln Leu Ala Val Ala Tyr His Leu Ile Ile
                340                 345                 350

Asp Asn Arg Arg Ile Met Asn Gln Ala Ser Glu Phe Tyr Leu Ala Ser
            355                 360                 365

Ser Pro Pro Thr Gly Ser Phe Met Asp Met Ala Met His Ile Pro
    370                 375                 380

Pro Gly Leu Lys Pro His Pro Glu Arg Met Pro Pro Leu Ile Ala Asp
385                 390                 395                 400

Ser Pro Lys Ala Arg Cys Pro Leu Asp Ala Leu Asn Thr Thr Lys Pro
                405                 410                 415

Lys Ser Leu Ala Val Lys Lys Ala Lys Trp His Leu Gly Ile Arg Ser
            420                 425                 430

Gln Ser Lys Pro Tyr Asp Ile Met Ala Glu Val Tyr Arg Ala Met Lys
        435                 440                 445

Gln Leu Asp Phe Glu Trp Lys Val Val Asn Ala Tyr His Leu Arg Val
450                 455                 460

Arg Arg Lys Asn Pro Val Thr Gly Asn Tyr Val Lys Met Ser Leu Gln
465                 470                 475                 480

Leu Tyr Leu Val Asp Asn Arg Ser Tyr Leu Leu Asp Phe Lys Ser Ile
                485                 490                 495

Asp Asp Glu Val Val Glu Gln Arg Ser Gly Ser Thr Pro Gln Arg
            500                 505                 510

Ser Cys Ser Ala Ala Gly Leu His Arg Pro Arg Ser Ser Val Asp Ser
        515                 520                 525

Ser Thr Ala Glu Asn His Ser Leu Ser Gly Ser Leu Thr Gly Ser Leu
530                 535                 540

Thr Gly Ser Thr Leu Ser Ser Ala Ser Pro Arg Leu Gly Ser His Thr
545                 550                 555                 560

Met Asp Phe Phe Glu Met Cys Ala Ser Leu Ile Thr Ala Leu Ala Arg
                565                 570                 575

Lys Leu

<210> SEQ ID NO 4
<211> LENGTH: 5007
<212> TYPE: DNA
<213> ORGANISM: Artificial sequence
<220> FEATURE:
<223> OTHER INFORMATION: Rat alpha2-eCFP pACE plasmid

<400> SEQUENCE: 4
ttgagatcct ttttttctgc gcgtaatctg ctgcttgcaa acaaaaaaac caccgctacc      60
agcggtggtt tgtttgccgg atcaagagct accaactctt tttccgaagg taactggctt     120
cagcagagcg cagataccaa atactgtcct tctagtgtag ccgtagttag gccaccactt     180
caagaactct gtagcaccgc ctacatacct cgctctgcta atcctgttac cagtggctgc     240
tgccagtggc gataagtcgt gtcttaccgg gttggactca agacgatagt taccggataa     300
ggcgcagcgg tcgggctgaa cggggggttc gtgcacacag cccagcttgg agcgaacgac     360
ctacaccgaa ctgagatacc tacagcgtga gctatgagaa agcgccacgc ttcccgaagg     420
gagaaaggcg gacaggtatc cggtaagcgg cagggtcgga acaggagagc gcacgaggga     480
gcttccaggg ggaaacgcct ggtatcttta tagtcctgtc gggtttcgcc acctctgact     540
tgagcgtcga ttttttgtgat gctcgtcagg ggggcggagc ctatggaaaa acgccagcaa     600
cgcggccttt ttacggttcc tggccttttg ctggcctttt gctcacatgt tctttcctgc     660

```
gttatcccct gattctgtgg ataaccgtat taccgccttt gagtgagctg ataccgctcg    720
ccgcagccga acgaccgagc gcagcgagtc agtgagcgag gaagcggaag agcgcctgat    780
gcggtatttt ctccttacgc atctgtgcgg tatttcacac cgcaatggtg cactctcagt    840
acaatctgct ctgatgccgc atagttaagc cagtatacac tccgctatcg ctacgtgact    900
gggtcatggc tgcgcccga cacccgccaa cacccgctga cgcgccctga cgggcttgtc    960
tgctcccggc atccgcttac agacaagctg tgaccgtctc cgggagctgc atgtgtcaga   1020
ggttttcacc gtcatcaccg aaacgcgcga ggcaggggga attccagata acttcgtata   1080
atgtatgcta tacgaagtta tggtaccgcg gccgcgtaga ggatctgttg atcagcagtt   1140
caacctgttg atagtacttc gttaatacag atgtaggtgt tggcaccatg cataactata   1200
acggtcctaa ggtagcgacc taggtatcga taatacgact cactataggg gaattgtgag   1260
cggataacaa ttcccctcta gaaataattt tgtttaactt taagaaggag atataatggg   1320
cagtagtcac catcaccacc accatcatca ccatcatagt agtgaaaacc tgtattttca   1380
ggggcatatg gctgagaagc agaagcacga cgggcgtgtg aagatcggac actacgtgct   1440
gggggacacc ctgggcgtcg gcaccttcgg caaagtgaag attggagaac atcaattgac   1500
aggccataaa gtggcagtta agatcttaaa tagacagaag attcgcagtt tagatgttgt   1560
tggaaaaata aaacgagaaa ttcaaaatct taaactcttt cgtcatcctc atattatcaa   1620
actctaccaa gtgatcagca ctccaacaga cttttttatg gtaatggaat atgtgtctgg   1680
aggtgaattg ttcgactaca tctgtaaaca cgggagggtt gaagaggtgg aagctcgccg   1740
gctcttccag cagattctgt ctgccgtgga ctactgtcac aggcacatgg ttgtccacag   1800
ggacctgaag ccagagaacg tgttgctgga cgcccagatg aatgctaaga tagctgactt   1860
cggactctct aatatgatgt cagatggtga atttctacga actagctgtg gatcgccaaa   1920
ttatgcagca ccggaggtca tctcaggaag gctgtatgcg ggtcctgagg ttgatatctg   1980
gagctgtggt gttatcctgt atgcccttct ctgtggcacc ctcccgttcg acgatgagca   2040
cgtgcctacg ctctttaaga agatccgagg gggtgtgttc tacatcccgg agtatctcaa   2100
ccgttctatt gccactctgc tgatgcacat gctgcaggtg gacccttga agcgagcaac   2160 tatcaaagac atacgagagc atgaatggtt taaacaggat ttgcccagtt acctctttcc   2220
tgaagacccc tcctatgatg ctaacgtcat tgatgatgag gctgtgaaag aagtatgtga   2280
aaaatttgag tgtacagaat cagaagtgat gaacagttta tacagtggtg accctcaaga   2340
ccagctcgca gtggcttatc atctcatcat tgacaatcgg agaataatga accaagccag   2400
tgagttctac ctcgcctcca gtcctccaac gggttccttc atggacgata tggccatgca   2460
cattcccccc ggcctgaaac cacatcctga aggatgccca cctctcatag cagacagccc   2520
caaagcacgc tgtccactgg atgcactcaa cacaactaag cccaaatctt tagctgtgaa   2580
aaaagccaag tggcaccttg ggatccgaag ccagagcaaa ccatacgaca ttatggcgga   2640
ggtgtaccga gctatgaagc agctggactt tgaatggaag gtagtgaatg cataccatct   2700
tcgagtaaga agaaaaaacc cagtgactgg caattacgtg aaaatgagct tacagcttta   2760
cctggttgac aatcggagct atctgctgga cttttaaaagc atcgatgatg aggtggtgga   2820
gcagaggtct ggttcttcaa cacctcagcg ctcctgttct gctgccggcc tccacagacc   2880
tcggtcaagt gtcgattcca gcacagccga gaaccattca ctgtctggct ctctcactgg   2940
ttctttgact ggcagcactt tgtcctccgc ttccccgcgc ctgggcagtc ataccatgga   3000
```

```
ttttttttgaa atgtgcgcca gtcttatcac tgctttagcc cgtaagctta tggtgagcaa    3060
gggcgaggag ctgttcaccg gggtggtgcc catcctggtc gagctggacg gcgacgtaaa    3120
cggccacaag ttcagcgtgt ccggcgaggg cgagggcgat gccacctacg gcaagctgac    3180
cctgaagttc atctgcacca ccggcaagct gcccgtgccc tggcccaccc tcgtgaccac    3240
cctgacctgg ggcgtgcagt gcttcagccg ctaccccgac cacatgaagc agcacgactt    3300
cttcaagtcc gccatgcccg aaggctacgt ccaggagcgc accatcttct tcaaggacga    3360
cggcaactac aagacccgcg ccgaggtgaa gttcgagggc gacaccctgg tgaaccgcat    3420
cgagctgaag ggcatcgact tcaaggagga cggcaacatc ctggggcaca agctggagta    3480
caactacatc agccacaacg tctatatcac cgccgacaag cagaagaacg gcatcaaggc    3540
caacttcaag atccgccaca acatcgagga cggcagcgtg cagctcgccg accactacca    3600
gcagaacacc cccatcggcg acggccccgt gctgctgccc gacaaccact acctgagcac    3660
ccagtccgcc ctgagcaaag accccaacga gaagcgcgat cacatggtcc tgctggagtt    3720
cgtgaccgcc gccgggatca ctctcggcat ggacgagctg tacaagtccg gactcagatc    3780
tcgacgagct cactgataac tcgagagatc cggctgctaa caaagcccga aggaagctg     3840 agttggctgc tgccaccgct gagcaataac tagcataacc ccttggggcc tctaaacggg    3900
tcttgagggg ttttttggtt taaacccatc taattggact agtagcccgc ctaatgagcg    3960
ggcttttttt taattcccct atttgtttat ttttctaaat acattcaaat atgtatccgc    4020
tcatgagaca ataaccctga taaatgcttc aataatattg aaaaaggaag agtatgagta    4080
ttcaacattt ccgtgtcgcc cttattccct ttttttgcggc attttgcctt cctgtttttg    4140
ctcacccaga aacgctcgtg aaagtaaaag acgcagagga ccaattgggg gcacgagtgg    4200
gatacataga actggacttg aatagcggta aaatccttga gagttttcgc cctgaagagc    4260
gttttccaat gatgagcact ttcaaagttc tgctatgtgg agcagtatta tcccgtgtag    4320
atgcggggca agagcaactc ggacgacgaa tacactattc gcagaatgac ttggttgaat    4380
actccccagt gacagaaaag caccttacgg acggaatgac ggtaagagaa ttatgtagtg    4440
ccgccataac gatgagtgat aacactgcgg cgaacttact tctgacaacc atcggtggac    4500
cgaaggaatt aaccgctttt ttgcacaata tgggagacca tgtaactcgc cttgaccgtt    4560
gggaaccaga actgaatgaa gccataccaa cgacgagcg agacaccaca atgcctgcgg    4620
caatggcaac aacattacgc aaactattaa ctggcgaact acttactctg gcttcacggc    4680
aacaattaat agactggctt gaagcggata aagttgcagg accactactg cgttcggcac    4740
ttcctgctgg ctggtttatt gctgataaat ctggggcagg agagcgtggt tcacggggta    4800
tcattgccgc acttggacca gatggtaagc cttcccgtat cgtagttatc tacacgacgg    4860
gtagtcaggc aactatggac gaacgaaata gacagattgc tgaaataggg gcttcactga    4920
ttaagcattg gtaaaccgat acaattaaag gctccttttg gagcctttt ttttggacgg     4980 accggtagaa aagatcaaag gatcttc                                       5007
```

<210> SEQ ID NO 5
<211> LENGTH: 826
<212> TYPE: PRT
<213> ORGANISM: Artificial sequence
<220> FEATURE:
<223> OTHER INFORMATION: Rat alpha2-eCFP

<400> SEQUENCE: 5

Met Gly Ser Ser His His His His His His His His His Ser Ser

-continued

```
1               5                   10                  15
Glu Asn Leu Tyr Phe Gln Gly His Met Ala Glu Lys Gln Lys His Asp
                20                  25                  30
Gly Arg Val Lys Ile Gly His Tyr Val Leu Gly Asp Thr Leu Gly Val
                35                  40                  45
Gly Thr Phe Gly Lys Val Lys Ile Gly Glu His Gln Leu Thr Gly His
            50                  55                  60
Lys Val Ala Val Lys Ile Leu Asn Arg Gln Lys Ile Arg Ser Leu Asp
65                  70                  75                  80
Val Val Gly Lys Ile Lys Arg Glu Ile Gln Asn Leu Lys Leu Phe Arg
                85                  90                  95
His Pro His Ile Ile Lys Leu Tyr Gln Val Ile Ser Thr Pro Thr Asp
                100                 105                 110
Phe Phe Met Val Met Glu Tyr Val Ser Gly Gly Glu Leu Phe Asp Tyr
                115                 120                 125
Ile Cys Lys His Gly Arg Val Glu Glu Val Glu Ala Arg Arg Leu Phe
                130                 135                 140
Gln Gln Ile Leu Ser Ala Val Asp Tyr Cys His Arg His Met Val Val
145                 150                 155                 160
His Arg Asp Leu Lys Pro Glu Asn Val Leu Leu Asp Ala Gln Met Asn
                165                 170                 175
Ala Lys Ile Ala Asp Phe Gly Leu Ser Asn Met Met Ser Asp Gly Glu
                180                 185                 190
Phe Leu Arg Thr Ser Cys Gly Ser Pro Asn Tyr Ala Ala Pro Glu Val
                195                 200                 205
Ile Ser Gly Arg Leu Tyr Ala Gly Pro Glu Val Asp Ile Trp Ser Cys
                210                 215                 220
Gly Val Ile Leu Tyr Ala Leu Leu Cys Gly Thr Leu Pro Phe Asp Asp
225                 230                 235                 240
Glu His Val Pro Thr Leu Phe Lys Lys Ile Arg Gly Gly Val Phe Tyr
                245                 250                 255
Ile Pro Glu Tyr Leu Asn Arg Ser Ile Ala Thr Leu Leu Met His Met
                260                 265                 270
Leu Gln Val Asp Pro Leu Lys Arg Ala Thr Ile Lys Asp Ile Arg Glu
                275                 280                 285
His Glu Trp Phe Lys Gln Asp Leu Pro Ser Tyr Leu Phe Pro Glu Asp
                290                 295                 300
Pro Ser Tyr Asp Ala Asn Val Ile Asp Asp Glu Ala Val Lys Glu Val
305                 310                 315                 320
Cys Glu Lys Phe Glu Cys Thr Glu Ser Glu Val Met Asn Ser Leu Tyr
                325                 330                 335
Ser Gly Asp Pro Gln Asp Gln Leu Ala Val Ala Tyr His Leu Ile Ile
                340                 345                 350
Asp Asn Arg Arg Ile Met Asn Gln Ala Ser Glu Phe Tyr Leu Ala Ser
                355                 360                 365
Ser Pro Pro Thr Gly Ser Phe Met Asp Asp Met Ala Met His Ile Pro
                370                 375                 380
Pro Gly Leu Lys Pro His Pro Glu Arg Met Pro Pro Leu Ile Ala Asp
385                 390                 395                 400
Ser Pro Lys Ala Arg Cys Pro Leu Asp Ala Leu Asn Thr Thr Lys Pro
                405                 410                 415
Lys Ser Leu Ala Val Lys Lys Ala Lys Trp His Leu Gly Ile Arg Ser
                420                 425                 430
```

```
Gln Ser Lys Pro Tyr Asp Ile Met Ala Glu Val Tyr Arg Ala Met Lys
        435                 440                 445
Gln Leu Asp Phe Glu Trp Lys Val Val Asn Ala Tyr His Leu Arg Val
    450                 455                 460
Arg Arg Lys Asn Pro Val Thr Gly Asn Tyr Val Lys Met Ser Leu Gln
465                 470                 475                 480
Leu Tyr Leu Val Asp Asn Arg Ser Tyr Leu Leu Asp Phe Lys Ser Ile
                485                 490                 495
Asp Asp Glu Val Val Glu Gln Arg Ser Gly Ser Ser Thr Pro Gln Arg
            500                 505                 510
Ser Cys Ser Ala Ala Gly Leu His Arg Pro Arg Ser Ser Val Asp Ser
        515                 520                 525
Ser Thr Ala Glu Asn His Ser Leu Ser Gly Ser Leu Thr Gly Ser Leu
    530                 535                 540
Thr Gly Ser Thr Leu Ser Ser Ala Ser Pro Arg Leu Gly Ser His Thr
545                 550                 555                 560
Met Asp Phe Phe Glu Met Cys Ala Ser Leu Ile Thr Ala Leu Ala Arg
                565                 570                 575
Lys Leu Met Val Ser Lys Gly Glu Glu Leu Phe Thr Gly Val Val Pro
            580                 585                 590
Ile Leu Val Glu Leu Asp Gly Asp Val Asn Gly His Lys Phe Ser Val
        595                 600                 605
Ser Gly Glu Gly Glu Gly Asp Ala Thr Tyr Gly Lys Leu Thr Leu Lys
    610                 615                 620
Phe Ile Cys Thr Thr Gly Lys Leu Pro Val Pro Trp Pro Thr Leu Val
625                 630                 635                 640
Thr Thr Leu Thr Trp Gly Val Gln Cys Phe Ser Arg Tyr Pro Asp His
                645                 650                 655
Met Lys Gln His Asp Phe Phe Lys Ser Ala Met Pro Glu Gly Tyr Val
            660                 665                 670
Gln Glu Arg Thr Ile Phe Phe Lys Asp Asp Gly Asn Tyr Lys Thr Arg
        675                 680                 685
Ala Glu Val Lys Phe Glu Gly Asp Thr Leu Val Asn Arg Ile Glu Leu
    690                 695                 700
Lys Gly Ile Asp Phe Lys Glu Asp Gly Asn Ile Leu Gly His Lys Leu
705                 710                 715                 720
Glu Tyr Asn Tyr Ile Ser His Asn Val Tyr Ile Thr Ala Asp Lys Gln
                725                 730                 735
Lys Asn Gly Ile Lys Ala Asn Phe Lys Ile Arg His Asn Ile Glu Asp
            740                 745                 750
Gly Ser Val Gln Leu Ala Asp His Tyr Gln Gln Asn Thr Pro Ile Gly
        755                 760                 765
Asp Gly Pro Val Leu Leu Pro Asp Asn His Tyr Leu Ser Thr Gln Ser
    770                 775                 780
Ala Leu Ser Lys Asp Pro Asn Glu Lys Arg Asp His Met Val Leu Leu
785                 790                 795                 800
Glu Phe Val Thr Ala Ala Gly Ile Thr Leu Gly Met Asp Glu Leu Tyr
                805                 810                 815
Lys Ser Gly Leu Arg Ser Arg Arg Ala His
            820                 825
```

<210> SEQ ID NO 6
<211> LENGTH: 5010

<212> TYPE: DNA
<213> ORGANISM: Artificial sequence
<220> FEATURE:
<223> OTHER INFORMATION: Rat eCFP-alpha2, pACE plasmid

<400> SEQUENCE: 6

| | | | | | |
|---|---|---|---|---|---|
| ggaattccag | ataacttcgt | ataatgtatg | ctatacgaag | ttatggtacc | gcggccgcgt | 60 |
| agaggatctg | ttgatcagca | gttcaacctg | ttgatagtac | ttcgttaata | cagatgtagg | 120 |
| tgttggcacc | atgcataact | ataacggtcc | taaggtagcg | acctaggtat | cgataatacg | 180 |
| actcactata | ggggaattgt | gagcggataa | caattcccct | ctagaaataa | ttttgtttaa | 240 |
| ctttaagaag | gagatataat | gggcagtagt | caccatcacc | accaccatca | tcaccatcat | 300 |
| agtagtgaaa | acctgtattt | tcaggggcat | atggtgagca | agggcgagga | gctgttcacc | 360 |
| ggggtggtgc | ccatcctggt | cgagctggac | ggcgacgtaa | acggccacaa | gttcagcgtg | 420 |
| tccggcgagg | gcgagggcga | tgccacctac | ggcaagctga | ccctgaagtt | catctgcacc | 480 |
| accggcaagc | tgcccgtgcc | ctggcccacc | ctcgtgacca | ccctgacctg | gggcgtgcag | 540 |
| tgcttcagcc | gctaccccga | ccacatgaag | cagcacgact | tcttcaagtc | cgccatgccc | 600 |
| gaaggctacg | tccaggagcg | caccatcttc | ttcaaggacg | acggcaacta | caagacccgc | 660 |
| gccgaggtga | agttcgaggg | cgacaccctg | gtgaaccgca | tcgagctgaa | gggcatcgac | 720 |
| ttcaaggagg | acggcaacat | cctggggcac | aagctggagt | acaactacat | cagccacaac | 780 |
| gtctatatca | ccgccgacaa | gcagaagaac | ggcatcaagg | ccaacttcaa | gatccgccac | 840 |
| aacatcgagg | acggcagcgt | gcagctcgcc | gaccactacc | agcagaacac | ccccatcggc | 900 |
| gacggccccg | tgctgctgcc | cgacaaccac | tacctgagca | cccagtccgc | cctgagcaaa | 960 |
| gaccccaacg | agaagcgcga | tcacatggtc | ctgctggagt | tcgtgaccgc | cgccgggatc | 1020 |
| actctcggca | tggacgagct | gtacaagtcc | ggactcagat | ctcgacgagc | tcacggcggt | 1080 |
| atggctgaga | agcagaagca | cgacgggcgt | gtgaagatcg | acactacgt | gctgggggac | 1140 |
| accctgggcg | tcggcacctt | cggcaaagtg | aagattggag | aacatcaatt | gacaggccat | 1200 |
| aaagtggcag | ttaagatctt | aaatagacag | aagattcgca | gtttagatgt | tgttggaaaa | 1260 |
| ataaaacgag | aaattcaaaa | tcttaaactc | tttcgtcatc | ctcatattat | caaactctac | 1320 |
| caagtgatca | gcactccaac | agactttttt | atggtaatgg | aatatgtgtc | tggaggtgaa | 1380 |
| ttgttcgact | acatctgtaa | acacgggagg | gttgaagagg | tggaagctcg | ccggctcttc | 1440 |
| cagcagattc | tgtctgccgt | ggactactgt | cacaggcaca | tggttgtcca | cagggacctg | 1500 |
| aagccagaga | acgtgttgct | ggacgcccag | atgaatgcta | agatagctga | cttcggactc | 1560 |
| tctaatatga | tgtcagatgg | tgaatttcta | cgaactagct | gtggatcgcc | aaattatgca | 1620 |
| gcaccggagg | tcatctcagg | aaggctgtat | gcgggtcctg | aggttgatat | ctggagctgt | 1680 |
| ggtgttatcc | tgtatgccct | tctctgtggc | accctcccgt | tcgacgatga | gcacgtgcct | 1740 |
| acgctcttta | agaagatccg | aggggtgtgt | tctacatcc | cggagtatct | caaccgttct | 1800 |
| attgccactc | tgctgatgca | catgctgcag | gtggacccct | gaagcgagc | aactatcaaa | 1860 |
| gacatacgag | agcatgaatg | gtttaaacag | gatttgccca | gttacctctt | tcctgaagac | 1920 |
| ccctcctatg | atgctaacgt | cattgatgat | gaggctgtga | agaagtatg | tgaaaaattt | 1980 |
| gagtgtacag | aatcagaagt | gatgaacagt | ttatacagtg | gtgaccctca | agaccagctc | 2040 |
| gcagtggctt | atcatctcat | cattgacaat | cggagaataa | tgaaccaagc | cagtgagttc | 2100 |
| tacctcgcct | ccagtcctcc | aacgggttcc | ttcatggacg | atatggccat | gcacattccc | 2160 |

```
cccggcctga aaccacatcc tgaaaggatg ccacctctca tagcagacag ccccaaagca    2220
cgctgtccac tggatgcact caacacaact aagcccaaat ctttagctgt gaaaaaagcc    2280
aagtggcacc ttgggatccg aagccagagc aaaccatacg acattatggc ggaggtgtac    2340
cgagctatga agcagctgga cttt gaatgg aaggtagtga atgcatacca tcttcgagta    2400
agaagaaaaa acccagtgac tggcaattac gtgaaaatga gcttacagct ttacctggtt    2460
gacaatcgga gctatctgct ggactttaaa agcatcgatg atgaggtggt ggagcagagg    2520
tctggttctt caacacctca gcgctcctgt tctgctgccg gcctccacag acctcggtca    2580
agtgtcgatt ccagcacagc cgagaaccat tcactgtctg gctctctcac tggttctttg    2640
actggcagca ctttgtcctc cgcttccccg cgcctgggca gtcataccat ggattttttt    2700
gaaatgtgcg ccagtcttat cactgcttta gcccgtaagc tttaactcga gagatccggc    2760
tgctaacaaa gcccgaaagg aagctgagtt ggctgctgcc accgctgagc aataactagc    2820
ataccccctt ggggcctcta acgggtctt gaggggtttt ttggtttaaa cccatctaat    2880
tggactagta gcccgcctaa tgagcgggct tttttttaat tcccctattt gtttattttt    2940
ctaaatacat tcaaatatgt atccgctcat gagacaataa ccctgataaa tgcttcaata    3000
atattgaaaa aggaagagta tgagtattca acatttccgt gtcgccctta ttccctttt    3060 tgcggcattt tgccttcctg tttttgctca cccagaaacg ctcgtgaaag taaaagacgc    3120
agaggaccaa ttgggggcac gagtgggata catagaactg gacttgaata gcggtaaaat    3180
ccttgagagt tttcgccctg aagagcgttt tccaatgatg agcactttca aagttctgct    3240
atgtggagca gtattatccc gtgtagatgc ggggcaagag caactcggac gacgaataca    3300
ctattcgcag aatgacttgg ttgaatactc cccagtgaca gaaaagcacc ttacggacgg    3360
aatgacggta agagaattat gtagtgccgc cataacgatg agtgataaca ctgcggcgaa    3420
cttacttctg acaaccatcg gtggaccgaa ggaattaacc gcttttttgc acaatatggg    3480
agaccatgta actcgccttg accgttggga accagaactg aatgaagcca taccaaacga    3540
cgagcgagac accacaatgc ctgcggcaat ggcaacaaca ttacgcaaac tattaactgg    3600
cgaactactt actctggctt cacggcaaca attaatagac tggcttgaag cggataaagt    3660
tgcaggacca ctactgcgtt cggcacttcc tgctggctgg tttattgctg ataaatctgg    3720
ggcaggagag cgtggttcac ggggtatcat tgccgcactt ggaccagatg gtaagccttc    3780
ccgtatcgta gttatctaca cgacgggtag tcaggcaact atggacgaac gaaatagaca    3840
gattgctgaa atagggggctt cactgattaa gcattggtaa accgatacaa ttaaaggctc    3900
cttttggagc ctttttttttt ggacggaccg gtagaaaaga tcaaaggatc ttcttgagat    3960
cctttttttc tgcgcgtaat ctgctgcttg caaacaaaaa aaccaccgct accagcggtg    4020
gtttgtttgc cggatcaaga gctaccaact ctttttccga aggtaactgg cttcagcaga    4080
gcgcagatac caaatactgt ccttctagtg tagccgtagt taggccacca cttcaagaac    4140
tctgtagcac cgcctacata cctcgctctg ctaatcctgt taccagtggc tgctgccagt    4200
ggcgataagt cgtgtcttac cgggttggac tcaagacgat agttaccgga taaggcgcag    4260
cggtcgggct gaacgggggg ttcgtgcaca cagcccagct tggagcgaac gacctacacc    4320
gaactgagat acctacagcg tgagctatga aaagcgccha cgcttcccga agggagaaag    4380
gcggacaggt atccggtaag cggcagggtc ggaacaggag agcgcacgag ggagcttcca    4440
gggggaaacg cctggtatct ttatagtcct gtcgggtttc gccacctctg acttgagcgt    4500
cgatttttgt gatgctcgtc aggggggcgg agcctatgga aaaacgccag caacgcggcc    4560
```

-continued

```
ttttttacggt tcctggcctt ttgctggcct tttgctcaca tgttctttcc tgcgttatcc    4620
cctgattctg tggataaccg tattaccgcc tttgagtgag ctgataccgc tcgccgcagc    4680
cgaacgaccg agcgcagcga gtcagtgagc gaggaagcgg aagagcgcct gatgcggtat    4740
tttctcctta cgcatctgtg cggtatttca caccgcaatg gtgcactctc agtacaatct    4800
gctctgatgc cgcatagtta agccagtata cactccgcta tcgctacgtg actgggtcat    4860
ggctgcgccc cgacacccgc caacacccgc tgacgcgccc tgacgggctt gtctgctccc    4920
ggcatccgct tacagacaag ctgtgaccgt ctccgggagc tgcatgtgtc agaggttttc    4980
accgtcatca ccgaaacgcg cgaggcaggg                                      5010
```

<210> SEQ ID NO 7
<211> LENGTH: 828
<212> TYPE: PRT
<213> ORGANISM: Rattus norvegicus

<400> SEQUENCE: 7

```
Met Gly Ser Ser His His His His His His Ser Ser
1               5                   10                  15

Glu Asn Leu Tyr Phe Gln Gly His Met Val Ser Lys Gly Glu Glu Leu
            20                  25                  30

Phe Thr Gly Val Val Pro Ile Leu Val Glu Leu Asp Gly Asp Val Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Trp Gly Val Gln Cys Phe
                85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Ile Ser His Asn Val Tyr
                165                 170                 175

Ile Thr Ala Asp Lys Gln Lys Asn Gly Ile Lys Ala Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Leu Leu Pro Asp Asn His
    210                 215                 220

Tyr Leu Ser Thr Gln Ser Ala Leu Ser Lys Asp Pro Asn Glu Lys Arg
225                 230                 235                 240

Asp His Met Val Leu Leu Glu Phe Val Thr Ala Ala Gly Ile Thr Leu
                245                 250                 255

Gly Met Asp Glu Leu Tyr Lys Ser Gly Leu Arg Ser Arg Arg Ala His
            260                 265                 270

Gly Gly Met Ala Glu Lys Gln Lys His Asp Gly Arg Val Lys Ile Gly
        275                 280                 285
```

-continued

His Tyr Val Leu Gly Asp Thr Leu Gly Val Gly Thr Phe Gly Lys Val
290                 295                 300

Lys Ile Gly Glu His Gln Leu Thr Gly His Lys Val Ala Val Lys Ile
305                 310                 315                 320

Leu Asn Arg Gln Lys Ile Arg Ser Leu Asp Val Val Gly Lys Ile Lys
            325                 330                 335

Arg Glu Ile Gln Asn Leu Lys Leu Phe Arg His Pro His Ile Ile Lys
                340                 345                 350

Leu Tyr Gln Val Ile Ser Thr Pro Thr Asp Phe Phe Met Val Met Glu
        355                 360                 365

Tyr Val Ser Gly Gly Glu Leu Phe Asp Tyr Ile Cys Lys His Gly Arg
370                 375                 380

Val Glu Glu Val Glu Ala Arg Arg Leu Phe Gln Gln Ile Leu Ser Ala
385                 390                 395                 400

Val Asp Tyr Cys His Arg His Met Val Val His Arg Asp Leu Lys Pro
            405                 410                 415

Glu Asn Val Leu Leu Asp Ala Gln Met Asn Ala Lys Ile Ala Asp Phe
                420                 425                 430

Gly Leu Ser Asn Met Met Ser Asp Gly Glu Phe Leu Arg Thr Ser Cys
        435                 440                 445

Gly Ser Pro Asn Tyr Ala Ala Pro Glu Val Ile Ser Gly Arg Leu Tyr
450                 455                 460

Ala Gly Pro Glu Val Asp Ile Trp Ser Cys Gly Val Ile Leu Tyr Ala
465                 470                 475                 480

Leu Leu Cys Gly Thr Leu Pro Phe Asp Asp Glu His Val Pro Thr Leu
            485                 490                 495

Phe Lys Lys Ile Arg Gly Gly Val Phe Tyr Ile Pro Glu Tyr Leu Asn
                500                 505                 510

Arg Ser Ile Ala Thr Leu Leu Met His Met Leu Gln Val Asp Pro Leu
        515                 520                 525

Lys Arg Ala Thr Ile Lys Asp Ile Arg Glu His Glu Trp Phe Lys Gln
530                 535                 540

Asp Leu Pro Ser Tyr Leu Phe Pro Glu Asp Pro Ser Tyr Asp Ala Asn
545                 550                 555                 560

Val Ile Asp Asp Glu Ala Val Lys Glu Val Cys Glu Lys Phe Glu Cys
            565                 570                 575

Thr Glu Ser Glu Val Met Asn Ser Leu Tyr Ser Gly Asp Pro Gln Asp
                580                 585                 590

Gln Leu Ala Val Ala Tyr His Leu Ile Ile Asp Asn Arg Arg Ile Met
        595                 600                 605

Asn Gln Ala Ser Glu Phe Tyr Leu Ala Ser Ser Pro Pro Thr Gly Ser
610                 615                 620

Phe Met Asp Asp Met Ala Met His Ile Pro Pro Gly Leu Lys Pro His
625                 630                 635                 640

Pro Glu Arg Met Pro Pro Leu Ile Ala Asp Ser Pro Lys Ala Arg Cys
            645                 650                 655

Pro Leu Asp Ala Leu Asn Thr Thr Lys Pro Lys Ser Leu Ala Val Lys
                660                 665                 670

Lys Ala Lys Trp His Leu Gly Ile Arg Ser Gln Ser Lys Pro Tyr Asp
        675                 680                 685

Ile Met Ala Glu Val Tyr Arg Ala Met Lys Gln Leu Asp Phe Glu Trp
690                 695                 700

Lys Val Val Asn Ala Tyr His Leu Arg Val Arg Arg Lys Asn Pro Val

| | | | |
|---|---|---|---|
| 705 | 710 | 715 | 720 |

Thr Gly Asn Tyr Val Lys Met Ser Leu Gln Leu Tyr Leu Val Asp Asn
                725                 730                 735

Arg Ser Tyr Leu Leu Asp Phe Lys Ser Ile Asp Asp Glu Val Val Glu
            740                 745                 750

Gln Arg Ser Gly Ser Ser Thr Pro Gln Arg Ser Cys Ser Ala Ala Gly
            755                 760                 765

Leu His Arg Pro Arg Ser Ser Val Asp Ser Ser Thr Ala Glu Asn His
            770                 775                 780

Ser Leu Ser Gly Ser Leu Thr Gly Ser Leu Thr Gly Ser Thr Leu Ser
785                 790                 795                 800

Ser Ala Ser Pro Arg Leu Gly Ser His Thr Met Asp Phe Phe Glu Met
                805                 810                 815

Cys Ala Ser Leu Ile Thr Ala Leu Ala Arg Lys Leu
            820                 825

<210> SEQ ID NO 8
<211> LENGTH: 2710
<212> TYPE: DNA
<213> ORGANISM: Artificial sequence
<220> FEATURE:
<223> OTHER INFORMATION: Human beta2 subunit in pDC plasmid

<400> SEQUENCE: 8

```
tatcgataat acgactcact atagggaat tgtgagcgga taacaattcc cctctagaaa      60
taattttgtt taactttaag aaggagatat acatatgagg cctatgggaa acaccaccag    120
cgaccgggtg tccggggagc gccacggcgc caaggctgca cgctccgagg gcgcaggcgg    180
ccatgccccg gggaaggagc acaagatcat ggtgggagt acggacgacc ccagcgtgtt    240
cagcctccct gactccaagc tccctgggga caaagagttt gtatcatggc agcaggattt    300
ggaggactcc gtaaagccca cagcaggc cggcccact gttatccgct ggtctgaagg      360
aggcaaggag gtcttcatct ctgggtcttt caacaattgg agcaccaaga ttccactgat    420
taagagccat aatgactttg ttgccatcct ggacctccct gagggagagc accaatacaa    480
gttctttgtg gatggacagt gggttcatga tccatcagag cctgtggtta ccagtcagct    540
tggcacaatt aacaatttga tccatgtcaa gaaatctgat tttgaggtgt tcgatgcttt    600
aaagttagat tctatggaaa gttctgagac atcttgtaga gacctttcca gctcaccccc    660
agggccttat ggtcaagaaa tgtatgcgtt tcgatctgag gaaagattca atccccacc    720 catccttcct cctcatctac ttcaagttat tcttaacaaa gacactaata tttcttgtga    780
cccagcctta ctccctgagc ccaaccatgt tatgctgaac catctctatg cattgtccat    840
taaggacagt gtgatggtcc ttagcgcaac ccatcgctac aagaagaagt atgttactac    900
tctgctatac aagcccattg tgcactaagc atgctagcat aaccccttgg ggcctctaaa    960
cgggtcttga ggggtttttt ggtttaaacc catgtgcctg gcagataact tcgtataatg   1020
tatgctatac gaagttatgg taccgcggcc gcgtagagga tctgttgatc agcagttcaa   1080
cctgttgata gtacgtacta agctctcatg tttcacgtac taagctctca tgtttaacgt   1140
actaagctct catgtttaac gaactaaacc ctcatggcta acgtactaag ctctcatggc   1200
taacgtacta agctctcatg tttcacgtac taagctctca tgtttgaaca ataaaattaa   1260
tataaatcag caacttaaat agcctctaag gttttaagtt ttataagaaa aaaagaata   1320 tataaggctt ttaaagcttt taaggttaa cggttgtgga caacaagcca gggatgtaac   1380
```

```
gcactgagaa gccccttagag cctctcaaag caatttttgag tgacacagga acacttaacg      1440
gctgacagaa ttagcttcac gctgccgcaa gcactcaggg cgcaagggct gctaaaggaa      1500
gcggaacacg tagaaagcca gtccgcagaa acggtgctga ccccggatga atgtcagctg      1560
ggaggcagaa taaatgatca tatcgtcaat tattacctcc acggggagag cctgagcaaa      1620
ctggcctcag gcatttgaga agcacacggt cacactgctt ccggtagtca ataaaccggt      1680
aaaccagcaa tagacataag cggctatttta cgaccctgc cctgaaccga cgaccgggtc      1740
gaatttgctt tcgaatttct gccattcatc cgcttattat cacttattca ggcgtagcaa      1800
ccaggcgttt aagggcacca ataactgcct taaaaaaatt acgccccgcc ctgccactca      1860
tcgcagtact gttgtaattc attaagcatt ctgccgacat ggaagccatc acaaacggca      1920
tgatgaacct gaatcgccag cggcatcagc accttgtcgc cttgcgtata atatttgccc      1980
atggtgaaaa cggggcgaa gaagttgtcc atattggcca cgtttaaatc aaaactggtg      2040
aaactcaccc agggattggc tgagacgaaa aacatattct caataaaccc tttagggaaa      2100
taggccaggt tttcaccgta acacgccaca tcttgcgaat atatgtgtag aaactgccgg      2160
aaatcgtcgt ggtattcact ccagagcgat gaaaacgttt cagtttgctc atggaaaacg      2220
gtgtaacaag ggtgaacact atcccatatc accagctcac cgtctttcat tgccatacgg      2280
aattccggat gagcattcat caggcgggca agaatgtgaa taaaggccgg ataaaacttg      2340
tgcttatttt tctttacggt cttttaaaaag gccgtaatat ccagctgaac ggtctggtta      2400
taggtacatt gagcaactga ctgaaatgcc tcaaaatgtt ctttacgatg ccattgggat      2460
atatcaacgg tggtatatcc agtgattttt ttctccattt tagcttcctt agctcctgaa      2520
aatctcgata actcaaaaaa tacgcccggt agtgatctta tttcattatg gtgaaagttg      2580 gacccctctta cgtgccgatc aacgtctcat tttcgccaaa agttggccca gatcaacgtc      2640 tcatttttcgc caaaagttgg cccagatcta tgtcgggtgc ggagaaagag gtaatgaaat      2700
ggcacctagg                                                              2710

<210> SEQ ID NO 9
<211> LENGTH: 272
<212> TYPE: PRT
<213> ORGANISM: Homo sapiens

<400> SEQUENCE: 9

Met Gly Asn Thr Thr Ser Asp Arg Val Ser Gly Glu Arg His Gly Ala
1               5                   10                  15

Lys Ala Ala Arg Ser Glu Gly Ala Gly Gly His Ala Pro Gly Lys Glu
            20                  25                  30

His Lys Ile Met Val Gly Ser Thr Asp Asp Pro Ser Val Phe Ser Leu
        35                  40                  45

Pro Asp Ser Lys Leu Pro Gly Asp Lys Glu Phe Val Ser Trp Gln Gln
    50                  55                  60

Asp Leu Glu Asp Ser Val Lys Pro Thr Gln Gln Ala Arg Pro Thr Val
65                  70                  75                  80

Ile Arg Trp Ser Glu Gly Gly Lys Glu Val Phe Ile Ser Gly Ser Phe
                85                  90                  95

Asn Asn Trp Ser Thr Lys Ile Pro Leu Ile Lys Ser His Asn Asp Phe
            100                 105                 110

Val Ala Ile Leu Asp Leu Pro Glu Gly Glu His Gln Tyr Lys Phe Phe
        115                 120                 125

Val Asp Gly Gln Trp Val His Asp Pro Ser Glu Pro Val Val Thr Ser
```

```
                130               135               140
Gln Leu Gly Thr Ile Asn Asn Leu Ile His Val Lys Lys Ser Asp Phe
145                 150               155                 160

Glu Val Phe Asp Ala Leu Lys Leu Asp Ser Met Glu Ser Ser Glu Thr
                165               170               175

Ser Cys Arg Asp Leu Ser Ser Pro Pro Gly Pro Tyr Gly Gln Glu
            180               185               190

Met Tyr Ala Phe Arg Ser Glu Glu Arg Phe Lys Ser Pro Pro Ile Leu
            195               200               205

Pro Pro His Leu Leu Gln Val Ile Leu Asn Lys Asp Thr Asn Ile Ser
        210               215               220

Cys Asp Pro Ala Leu Leu Pro Glu Pro Asn His Val Met Leu Asn His
225               230               235               240

Leu Tyr Ala Leu Ser Ile Lys Asp Ser Val Met Val Leu Ser Ala Thr
                245               250               255

His Arg Tyr Lys Lys Lys Tyr Val Thr Thr Leu Leu Tyr Lys Pro Ile
            260               265               270
```

<210> SEQ ID NO 10
<211> LENGTH: 3508
<212> TYPE: DNA
<213> ORGANISM: Artificial sequence
<220> FEATURE:
<223> OTHER INFORMATION: Human beta2-YFP pDC plasmid

<400> SEQUENCE: 10

```
cgccccgccc tgccactcat cgcagtactg ttgtaattca ttaagcattc tgccgacatg     60
gaagccatca caaacggcat gatgaacctg aatcgccagc ggcatcagca ccttgtcgcc    120
ttgcgtataa tatttgccca tggtgaaaac gggggcgaag aagttgtcca tattggccac    180
gtttaaatca aaactggtga actcacccca gggattggct gagacgaaaa acatattctc    240
aataaaccct ttagggaaat aggccaggtt ttcaccgtaa cacgccacat cttgcgaata    300
tatgtgtaga aactgccgga atcgtcgtg gtattcactc cagagcgatg aaaacgtttc     360
agtttgctca tggaaaacgg tgtaacaagg gtgaacacta tcccatatca ccagctcacc    420
gtctttcatt gccatacgga attccggatg agcattcatc aggcgggcaa gaatgtgaat    480
aaaggccgga taaaacttgt gcttattttt ctttacggtc tttaaaaagg ccgtaatatc    540
cagctgaacg gtctggttat aggtacattg agcaactgac tgaaatgcct caaaatgttc    600
tttacgatgc cattgggata tatcaacggt ggtatatcca gtgatttttt tctccatttt    660
agcttcctta gctcctgaaa atctcgataa ctcaaaaaat acgcccggta gtgatcttat    720
ttcattatgg tgaaagttgg accctcttac gtgccgatca acgtctcatt tcgccaaaa     780
gttggcccag atcaacgtct cattttcgcc aaaagttggc ccagatctat gtcgggtgcg    840
gagaaagagg taatgaaatg gcacctaggt atcgataata cgactcacta tagggggaatt    900
gtgagcggat aacaattccc ctctagaaat aattttgttt aactttaaga aggagatata    960
catatgaggc tatgggaaaa caccaccagc gaccgggtgt ccggggagcg ccacggcgcc   1020
aaggctgcac gctccgaggg cgcaggcggc catgccccgg ggaaggagca caagatcatg   1080
gtggggagta cggacgaccc cagcgtgttc agcctccctg actccaagct ccctggggac   1140
aaagagtttg tatcatggca gcaggatttg gaggactccg taaagccac acagcaggcc   1200
cggcccactt tatccgctg gtctgaagga ggcaaggagg tcttcatctc tgggtctttc    1260
aacaattgga gcaccaagat tccactgatt aagagccata atgactttgt tgccatcctg   1320
```

-continued

```
gacctccctg agggagagca ccaatacaag ttctttgtgg atggacagtg ggttcatgat    1380
ccatcagagc ctgtggttac cagtcagctt ggcacaatta caatttgat ccatgtcaag    1440
aaatctgatt ttgaggtgtt cgatgcttta aagttagatt ctatggaaag ttctgagaca    1500
tcttgtagag acctttccag ctcacccccca gggcctatg gtcaagaaat gtatgcgttt    1560
cgatctgagg aaagattcaa atccccaccc atccttcctc ctcatctact tcaagttatt    1620
cttaacaaag acactaatat ttcttgtgac ccagccttac tccctgagcc caaccatgtt    1680
atgctgaacc atctctatgc attgtccatt aaggacagtg tgatggtcct tagcgcaacc    1740
catcgctaca agaagaagta tgttactact ctgctataca agcccattgt gcacatggtg    1800
agcaagggcg aggagctgtt caccggggtg gtgcccatcc tggtcgagct ggacggcgac    1860
gtaaacggcc acaagttcag cgtgtccggc gagggcgagg gcgatgccac ctacggcaag    1920
ctgaccctga agttcatctg caccaccggc aagctgcccg tgccctggcc caccctcgtg    1980
accaccttcg gctacggcct gcagtgcttc gcccgctacc ccgaccacat gaagcagcac    2040
gacttcttca agtccgccat gcccgaaggc tacgtccagg agcgcaccat cttcttcaag    2100
gacgacggca actacaagac ccgcgccgag gtgaagttcg agggcgacac cctggtgaac    2160
cgcatcgagc tgaagggcat cgacttcaag gaggacggca acatcctggg gcacaagctg    2220
gagtacaact acaacagcca caacgtctat atcatggccg acaagcagaa gaacggcatc    2280
aaggtgaact tcaagatccg ccacaacatc gaggacggca gcgtgcagct cgccgaccac    2340
taccagcaga acacccccat cggcgacggc cccgtgctgc tgcccgacaa ccactacctg    2400
agctaccagt ccgccctgag caaagacccc aacgagaagc gcgatcacat ggtcctgctg    2460
gagttcgtga ccgccgccgg gatcactctc ggcatggacg agctgtacaa gtccggactc    2520
agatctcgag ctcaagcttc gaattctgca gtcgacggta ccgcgggccc gggatccacc    2580
ggatctagat gataagcatg ctagcataac cccttgggc tctaaacgg tcttgaggg    2640
gttttttggt ttaaacccat gtgcctggca gataacttcg tataatgtat gctatacgaa    2700
gttatggtac cgcggccgcg tagaggatct gttgatcagc agttcaacct gttgatagta    2760
cgtactaagc tctcatgttt cacgtactaa gctctcatgt ttaacgtact aagctctcat    2820
gtttaacgaa ctaaaccctc atggctaacg tactaagctc tcatggctaa cgtactaagc    2880
tctcatgttt cacgtactaa gctctcatgt ttgaacaata aaattaatat aaatcagcaa    2940
cttaaatagc ctctaaggtt ttaagtttta taagaaaaaa aagaatatat aaggctttta    3000
aagcttttaa ggtttaacgg ttgtggacaa caagccaggg atgtaacgca ctgagaagcc    3060
cttagagcct ctcaaagcaa ttttgagtga cacaggaaca cttaacggct gacagaatta    3120
gcttcacgct gccgcaagca ctcagggcgc aagggctgct aaaggaagcg gaacacgtag    3180
aaagccagtc cgcagaaacg gtgctgaccc cggatgaatg tcagctggga ggcagaataa    3240
atgatcatat cgtcaattat tacctccacg gggagagcct gagcaaactg gcctcaggca    3300
tttgagaagc acacggtcac actgcttccg gtagtcaata aaccggtaaa ccagcaatag    3360
acataagcgg ctatttaacg accctgccct gaaccgacga ccgggtcgaa tttgctttcg    3420
aatttctgcc attcatccgc ttattatcac ttattcaggc gtagcaacca ggcgtttaag    3480
ggcaccaata actgccttaa aaaaatta                                      3508
```

<210> SEQ ID NO 11
<211> LENGTH: 539
<212> TYPE: PRT

<213> ORGANISM: Artificial sequence
<220> FEATURE:
<223> OTHER INFORMATION: Human beta2-YFP

<400> SEQUENCE: 11

```
Met Gly Asn Thr Thr Ser Asp Arg Val Ser Gly Glu Arg His Gly Ala
1               5                   10                  15

Lys Ala Ala Arg Ser Glu Gly Ala Gly Gly His Ala Pro Gly Lys Glu
            20                  25                  30

His Lys Ile Met Val Gly Ser Thr Asp Pro Ser Val Phe Ser Leu
        35                  40                  45

Pro Asp Ser Lys Leu Pro Gly Asp Lys Glu Phe Val Ser Trp Gln Gln
50                  55                  60

Asp Leu Glu Asp Ser Val Lys Pro Thr Gln Gln Ala Arg Pro Thr Val
65                  70                  75                  80

Ile Arg Trp Ser Glu Gly Gly Lys Glu Val Phe Ile Ser Gly Ser Phe
                85                  90                  95

Asn Asn Trp Ser Thr Lys Ile Pro Leu Ile Lys Ser His Asn Asp Phe
                100                 105                 110

Val Ala Ile Leu Asp Leu Pro Glu Gly Glu His Gln Tyr Lys Phe Phe
            115                 120                 125

Val Asp Gly Gln Trp Val His Asp Pro Ser Glu Pro Val Val Thr Ser
130                 135                 140

Gln Leu Gly Thr Ile Asn Asn Leu Ile His Val Lys Lys Ser Asp Phe
145                 150                 155                 160

Glu Val Phe Asp Ala Leu Lys Leu Asp Ser Met Glu Ser Ser Glu Thr
                165                 170                 175

Ser Cys Arg Asp Leu Ser Ser Ser Pro Pro Gly Pro Tyr Gly Gln Glu
            180                 185                 190

Met Tyr Ala Phe Arg Ser Glu Glu Arg Phe Lys Ser Pro Pro Ile Leu
        195                 200                 205

Pro Pro His Leu Leu Gln Val Ile Leu Asn Lys Asp Thr Asn Ile Ser
    210                 215                 220

Cys Asp Pro Ala Leu Leu Pro Glu Pro Asn His Val Met Leu Asn His
225                 230                 235                 240

Leu Tyr Ala Leu Ser Ile Lys Asp Ser Val Met Val Leu Ser Ala Thr
                245                 250                 255

His Arg Tyr Lys Lys Lys Tyr Val Thr Thr Leu Leu Tyr Lys Pro Ile
            260                 265                 270

Val His Met Val Ser Lys Gly Glu Glu Leu Phe Thr Gly Val Val Pro
        275                 280                 285

Ile Leu Val Glu Leu Asp Gly Asp Val Asn Gly His Lys Phe Ser Val
    290                 295                 300

Ser Gly Glu Gly Glu Gly Asp Ala Thr Tyr Gly Lys Leu Thr Leu Lys
305                 310                 315                 320

Phe Ile Cys Thr Thr Gly Lys Leu Pro Val Pro Trp Pro Thr Leu Val
                325                 330                 335

Thr Thr Phe Gly Tyr Gly Leu Gln Cys Phe Ala Arg Tyr Pro Asp His
            340                 345                 350

Met Lys Gln His Asp Phe Phe Lys Ser Ala Met Pro Glu Gly Tyr Val
        355                 360                 365

Gln Glu Arg Thr Ile Phe Phe Lys Asp Asp Gly Asn Tyr Lys Thr Arg
    370                 375                 380

Ala Glu Val Lys Phe Glu Gly Asp Thr Leu Val Asn Arg Ile Glu Leu
```

```
               385                 390                 395                 400
Lys Gly Ile Asp Phe Lys Glu Asp Gly Asn Ile Leu Gly His Lys Leu
                405                 410                 415

Glu Tyr Asn Tyr Asn Ser His Asn Val Tyr Ile Met Ala Asp Lys Gln
            420                 425                 430

Lys Asn Gly Ile Lys Val Asn Phe Lys Ile Arg His Asn Ile Glu Asp
        435                 440                 445

Gly Ser Val Gln Leu Ala Asp His Tyr Gln Gln Asn Thr Pro Ile Gly
    450                 455                 460

Asp Gly Pro Val Leu Leu Pro Asp Asn His Tyr Leu Ser Tyr Gln Ser
465                 470                 475                 480

Ala Leu Ser Lys Asp Pro Asn Glu Lys Arg Asp His Met Val Leu Leu
                485                 490                 495

Glu Phe Val Thr Ala Ala Gly Ile Thr Leu Gly Met Asp Glu Leu Tyr
            500                 505                 510

Lys Ser Gly Leu Arg Ser Arg Ala Gln Ala Ser Asn Ser Ala Val Asp
        515                 520                 525

Gly Thr Ala Gly Pro Gly Ser Thr Gly Ser Arg
    530                 535

<210> SEQ ID NO 12
<211> LENGTH: 3502
<212> TYPE: DNA
<213> ORGANISM: Artificial Sequence
<220> FEATURE:
<223> OTHER INFORMATION: Human YFP-beta2

<400> SEQUENCE: 12
cgccccgccc tgccactcat cgcagtactg ttgtaattca ttaagcattc tgccgacatg      60
gaagccatca caaacggcat gatgaacctg aatcgccagc ggcatcagca ccttgtcgcc     120
ttgcgtataa tatttgccca tggtgaaaac gggggcgaag aagttgtcca tattggccac     180
gtttaaatca aaactggtga aactcaccca gggattggct gagacgaaaa acatattctc     240
aataaaccct ttagggaaat aggccaggtt ttcaccgtaa cacgccacat cttgcgaata     300
tatgtgtaga aactgccgga atcgtcgtg gtattcactc cagagcgatg aaaacgtttc      360
agtttgctca tggaaaacgg tgtaacaagg gtgaacacta tcccatatca ccagctcacc     420
gtctttcatt gccatacgga attccggatg agcattcatc aggcgggcaa gaatgtgaat     480
aaaggccgga taaaacttgt gcttattttt ctttacggtc tttaaaaagg ccgtaatatc     540
cagctgaacg gtctggttat aggtacattg agcaactgac tgaaatgcct caaaatgttc     600
tttacgatgc cattgggata tatcaacggt ggtatatcca gtgatttttt tctccatttt     660
agcttcctta gctcctgaaa atctcgataa ctcaaaaaat acgcccggta gtgatcttat     720
ttcattatgg tgaaagttgg accctcttac gtgccgatca acgtctcatt tcgccaaaa      780 gttggcccag atcaacgtct catttttcgcc aaaagttggc ccagatctat gtcgggtgcg     840
gagaaagagg taatgaaatg gcacctaggt atcgataata cgactcacta gggggaatt      900 gtgagcggat aacaatttcc ctctagaaat aattttgttt aactttaaga aggagatata     960
catatggtga gcaagggcga ggagctgttc accggggtgg tgcccatcct ggtcgagctg    1020
gacggcgacg taaacggcca agttcagc gtgtccggcg agggcgaggg cgatgccacc     1080
tacggcaagc tgaccctgaa gttcatctgc accaccggca agctgcccgt gccctggccc    1140
accctcgtga ccaccttcgg ctacggcctg cagtgcttcg cccgctaccc cgaccacatg    1200
```

```
aagcagcacg acttcttcaa gtccgccatg cccgaaggct acgtccagga gcgcaccatc    1260
ttcttcaagg acgacggcaa ctacaagacc cgcgccgagg tgaagttcga gggcgacacc    1320
ctggtgaacc gcatcgagct gaagggcatc gacttcaagg aggacggcaa catcctgggg    1380
cacaagctgg agtacaacta caacagccac aacgtctata tcatggccga caagcagaag    1440
aacggcatca aggtgaactt caagatccgc cacaacatcg aggacggcag cgtgcagctc    1500
gccgaccact accagcagaa cacccccatc ggcgacggcc ccgtgctgct gcccgacaac    1560
cactacctga gctaccagtc cgccctgagc aaagacccca cgagaagcg cgatcacatg     1620 gtcctgctgg agttcgtgac cgccgccggg atcactctcg gcatggacga gctgtacaag    1680
tccggactca gatctcgagc tcaagcttcg aattctgcag tcgacggtac cgcgggcccg    1740
ggatccaccg gatctagaag gcctatggga acaccacca gcgaccgggt gtccggggag     1800
cgccacggcg ccaaggctgc acgctccgag ggcgcaggcg ccatgccc ggggaaggag      1860 cacaagatca tggtggggag tacgacgac cccagcgtgt tcagcctccc tgactccaag     1920
ctccctgggg acaaagagtt tgtatcatgg cagcaggatt tggaggactc cgtaaagccc    1980
acacagcagg cccggcccac tgttatccgc tggtctgaag gaggcaagga ggtcttcatc    2040
tctgggtctt tcaacaattg gagcaccaag attccactga ttaagagcca taatgacttt    2100
gttgccatcc tggacctccc tgagggagag caccaataca gttctttgt ggatggacag     2160 tgggttcatg atccatcaga gcctgtggtt accagtcagc ttggcacaat taacaatttg    2220
atccatgtca agaaatctga ttttgaggtg ttcgatgctt taaagttaga ttctatggaa    2280
agttctgaga catcttgtag agacctttcc agctcacccc cagggcctta tggtcaagaa    2340
atgtatgcgt ttcgatctga ggaaagattc aaatccccac ccatccttcc tcctcatcta    2400
cttcaagtta ttcttaacaa agacactaat atttcttgtg acccagcctt actccctgag    2460
cccaaccatg ttatgctgaa ccatctctat gcattgtcca ttaaggacag tgtgatggtc    2520
cttagcgcaa cccatcgcta caagaagaag tatgttacta ctctgctata caagcccatt    2580
gtgcactaag catgctagca taacccttg gggcctctaa acgggtcttg aggggttttt     2640
tggtttaaac ccatgtgcct ggcagataac ttcgtataat gtatgctata cgaagttatg    2700
gtaccgcggc cgcgtagagg atctgttgat cagcagttca acctgttgat agtacgtact    2760
aagctctcat gtttcacgta ctaagctctc atgtttaacg tactaagctc tcatgtttaa    2820
cgaactaaac cctcatggct aacgtactaa gctctcatgg ctaacgtact aagctctcat    2880
gtttcacgta ctaagctctc atgtttgaac aataaaatta atataaatca gcaacttaaa    2940
tagcctctaa ggttttaagt tttataagaa aaaaagaat atataaggct tttaaagctt     3000
ttaaggttta acggttgtgg acaacaagcc agggatgtaa cgcactgaga agcccttaga    3060
gcctctcaaa gcaattttga gtgacacagg aacacttaac ggctgacaga attagcttca    3120
cgctgccgca agcactcagg gcgcaagggc tgctaaagga gcggaacac gtagaaagcc     3180 agtccgcaga aacggtgctg accccggatg aatgtcagct gggaggcaga ataaatgatc    3240
atatcgtcaa ttattacctc cacggggaga gcctgagcaa actggcctca ggcatttgag    3300
aagcacacgg tcacactgct tccggtagtc aataaaccgg taaaccagca atagacataa    3360
gcggctattt aacgaccctg ccctgaaccg acgaccgggt cgaatttgct ttcgaatttc    3420
tgccattcat ccgcttatta tcacttattc aggcgtagca accaggcgtt taagggcacc    3480 ataactgcc ttaaaaaaat ta                                              3502
```

<210> SEQ ID NO 13
<211> LENGTH: 539
<212> TYPE: PRT
<213> ORGANISM: Artificial Sequence
<220> FEATURE:
<223> OTHER INFORMATION: Human YFP-b2

<400> SEQUENCE: 13

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Ala Val Asp Gly Thr
                245                 250                 255

Ala Gly Pro Gly Ser Thr Gly Ser Arg Arg Pro Met Gly Asn Thr Thr
            260                 265                 270

Ser Asp Arg Val Ser Gly Glu Arg His Gly Ala Lys Ala Ala Arg Ser
        275                 280                 285

Glu Gly Ala Gly Gly His Ala Pro Gly Lys Glu His Lys Ile Met Val
    290                 295                 300

Gly Ser Thr Asp Asp Pro Ser Val Phe Ser Leu Pro Asp Ser Lys Leu
305                 310                 315                 320

Pro Gly Asp Lys Glu Phe Val Ser Trp Gln Gln Asp Leu Glu Asp Ser
                325                 330                 335

Val Lys Pro Thr Gln Gln Ala Arg Pro Thr Val Ile Arg Trp Ser Glu
            340                 345                 350

Gly Gly Lys Glu Val Phe Ile Ser Gly Ser Phe Asn Asn Trp Ser Thr
        355                 360                 365

Lys Ile Pro Leu Ile Lys Ser His Asn Asp Phe Val Ala Ile Leu Asp
```

```
                370                 375                 380
Leu Pro Glu Gly Glu His Gln Tyr Lys Phe Phe Val Asp Gly Gln Trp
385                 390                 395                 400

Val His Asp Pro Ser Glu Pro Val Val Thr Ser Gln Leu Gly Thr Ile
                405                 410                 415

Asn Asn Leu Ile His Val Lys Lys Ser Asp Phe Glu Val Phe Asp Ala
            420                 425                 430

Leu Lys Leu Asp Ser Met Glu Ser Ser Glu Thr Ser Cys Arg Asp Leu
        435                 440                 445

Ser Ser Ser Pro Pro Gly Pro Tyr Gly Gln Glu Met Tyr Ala Phe Arg
450                 455                 460

Ser Glu Glu Arg Phe Lys Ser Pro Pro Ile Leu Pro Pro His Leu Leu
465                 470                 475                 480

Gln Val Ile Leu Asn Lys Asp Thr Asn Ile Ser Cys Asp Pro Ala Leu
                485                 490                 495

Leu Pro Glu Pro Asn His Val Met Leu Asn His Leu Tyr Ala Leu Ser
            500                 505                 510

Ile Lys Asp Ser Val Met Val Leu Ser Ala Thr His Arg Tyr Lys Lys
        515                 520                 525

Lys Tyr Val Thr Thr Leu Leu Tyr Lys Pro Ile
    530                 535

<210> SEQ ID NO 14
<211> LENGTH: 2890
<212> TYPE: DNA
<213> ORGANISM: Artificial Sequence
<220> FEATURE:
<223> OTHER INFORMATION: Rat gamma1, pDS plasmid

<400> SEQUENCE: 14
atgagggaag cggtgatcgc cgaagtatcg actcaactat cagaggtagt tggcgtcatc    60
gagcgccatc tcgaaccgac gttgctggcc gtacatttgt acggctccgc agtggatggc   120
ggcctgaagc cacacagtga tattgatttg ctggttacgg tgaccgtaag gcttgatgaa   180
acaacgcggc gagcttttga tcaacgacct tttggaaactt cggcttcccc tggagagagc   240
gagattctcc gcgctgtaga agtcaccatt gttgtgcacg acgacatcat tccgtggcgt   300
tatccagcta agcgcgaact gcaatttgga gaatggcagc gcaatgacat tcttgcaggt   360
atcttcgagc cagccacgat cgacattgat ctggctatct tgctgacaaa agcaagagaa   420
catagcgttg ccttggtagg tccagcggcg gaggaactct ttgatccggt tcctgaacag   480
gatctatttg aggcgctaaa tgaaacctta acgctatgga actcgccgcc cgactgggct   540
ggcgatgagc gaaatgtagt gcttacgttg tcccgcattt ggtacagcgc agtaaccggc   600
aaaatcgcgc cgaaggatgt cgctgccgac tgggcaatgg agcgcctgcc ggcccagtat   660
cagcccgtca tacttgaagc tagacaggct tatcttggac aagaagaaga tcgcttggcc   720
tcgcgcgcag atcagttgga agaatttgtc cactacgtga aggcgagat caccaaggta   780 gtcggcaaat aatgtctaac aattcgttca agccgacgga tctatgtcgg gtgcggagaa   840
agaggtaatg aaatggcacc taggtatcga tggctttaca ctttatgctt ccggctcgta   900
tgttgtgtgg aattgtgagc ggataacaat ttcacacagg aaacagctat gaccatgatt   960
acgaatttct agaaataatt ttgtttaact ttaagaagga gatatacata tggagtcggt  1020
tgctgcagag agcgctccag ctccggagaa tgaacactct caagacccc ggaatcgaa   1080 cagtagtgtg tacaccacct tcatgaagtc tcatcgctgc tatgacctga tccccacaag  1140
```

```
ctccaagctg gtggtatttg atacttcgct gcaggtaaag aaagccttct ttgccctggt   1200
gactaacggt gttcgtgctg cccctttgtg ggatagtaag aagcagagct tgtgggcat    1260 gctgaccatc actgacttca tcaatattct gcaccgatac tacaagtcag ccctggtgca   1320
gatctatgaa ctggaggagc acaagataga gacttggaga gaggtctacc tgcaagactc   1380
ctttaagcca cttgtctgca tttctccaaa tgccagcttg ttcgatgctg tctcttcatt   1440
aattcgaaat aagatccaca ggcttccagt tattgacccg gagtcaggca cacccttgta   1500
cattcttact cacaagcgga tcctcaagtt cctcaagttg tttatcactg agttccccaa   1560
gccggaattc atgtctaagt ctctggaaga gctacagatt ggcacctacg ccaatattgc   1620
catggtccgt accactacac ctgtctatgt ggctctgggc atctttgtac agcaccgagt   1680
ctccgccttg cctgtggtgg atgagaaagg gcgtgtggtg gacatctact ccaagtttga   1740
tgtgattaat ttggcagcag aaaagacata caacaaccta gatgtgtctg tgacaaaagc   1800
cctacagcac cggtcacact acttcgaggg tgttctcaag tgctacctac atgagactct   1860
agaagcaatc atcaatagac tggtggaagc agaggttcac cgtctggtgg tggtggatga   1920
acatgacgtg gtcaagggca ttgtatcgct gtctgacatc ttacaggctc tggtgctcac   1980
aggtggagag aagaagccct gataactagt tccgtttaaa cccatgtgcc tggcagataa   2040
cttcgtataa tgtatgctat acgaagttat ggtacgtact aagctctcat gtttcacgta   2100
ctaagctctc atgtttaacg tactaagctc tcatgtttaa cgaactaaac cctcatggct   2160
aacgtactaa gctctcatgg ctaacgtact aagctctcat gtttcacgta ctaagctctc   2220
atgtttgaac aataaaatta atataaatca gcaacttaaa tagcctctaa ggttttaagt   2280
tttataagaa aaaaagaat atataaggct tttaaagctt ttaaggttta acggttgtgg    2340
acaacaagcc agggatgtaa cgcactgaga agcccttaga gcctctcaaa gcaattttga   2400
gtgacacagg aacacttaac ggctgacata attcagcttc acgctgccgc aagcactcag   2460
ggcgcaaggg ctgctaaagg aagcggaaca cgtagaaagc cagtccgcag aaacggtgct   2520
gaccccggat gaatgtcagc tgggaggcag aataaatgat catatcgtca attattacct   2580
ccacggggag agcctgagca aactggcctc aggcatttga gaagcacacg gtcacactgc   2640
ttccggtagt caataaaccg gtaagtagcg tatgcgctca cgcaactggt ccagaaccct   2700
taccgaacgc agcggtggta acggcgcagt ggcggttttc atggcttgtt atgactgttt    2760
ttttggggta cagtctatgc ctcgggcatc caagcagcaa gcgcgttacg ccgtgggtcg   2820
atgtttgatg ttatggagca gcaacgatgt tacgcagcag ggcagtcgcc ctaaaacaaa   2880
gttaaacatc                                                         2890
```

<210> SEQ ID NO 15
<211> LENGTH: 330
<212> TYPE: PRT
<213> ORGANISM: Rattus norvegicus

<400> SEQUENCE: 15

Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val

```
                    50                  55                  60
Thr Asn Gly Val Arg Ala Ala Pro Leu Trp Asp Ser Lys Lys Gln Ser
 65                  70                  75                  80

Phe Val Gly Met Leu Thr Ile Thr Asp Phe Ile Asn Ile Leu His Arg
                     85                  90                  95

Tyr Tyr Lys Ser Ala Leu Val Gln Ile Tyr Glu Leu Glu Glu His Lys
                100                 105                 110

Ile Glu Thr Trp Arg Glu Val Tyr Leu Gln Asp Ser Phe Lys Pro Leu
            115                 120                 125

Val Cys Ile Ser Pro Asn Ala Ser Leu Phe Asp Ala Val Ser Ser Leu
130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro
                325                 330

<210> SEQ ID NO 16
<211> LENGTH: 3640
<212> TYPE: DNA
<213> ORGANISM: Artificial Sequence
<220> FEATURE:
<223> OTHER INFORMATION: Rat gamma1-eCFP, pDS plasmid

<400> SEQUENCE: 16
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc cacacagtga tattgatttg ctggttacgg tgaccgtaag gcttgatgaa     180
acaacgcggc gagctttgat caacgaccct ttggaaactt cggcttcccc tggagagagc     240
gagattctcc gcgctgtaga agtcaccatt gttgtgcacg acgacatcat tccgtggcgt     300
tatccagcta agcgcgaact gcaatttgga gaatggcagc gcaatgacat tcttgcaggt     360
atcttcgagc cagccacgat cgacattgat ctggctatct tgctgacaaa agcaagagaa     420
catagcgttg ccttggtagg tccagcggcg gaggaactct ttgatccggt tcctgaacag     480
```

-continued

```
gatctatttg aggcgctaaa tgaaacctta acgctatgga actcgccgcc cgactgggct        540
ggcgatgagc gaaatgtagt gcttacgttg tcccgcattt ggtacagcgc agtaaccggc        600
aaaatcgcgc cgaaggatgt cgctgccgac tgggcaatgg agcgcctgcc ggcccagtat        660
cagcccgtca tacttgaagc tagacaggct tatcttggac aagaagaaga tcgcttggcc        720

tcgcgcgcag atcagttgga agaatttgtc cactacgtga aaggcgagat caccaaggta        780
gtcggcaaat aatgtctaac aattcgttca agccgacgga tctatgtcgg gtgcggagaa        840
agaggtaatg aaatggcacc taggtatcga tggctttaca ctttatgctt ccggctcgta        900

tgttgtgtgg aattgtgagc ggataacaat ttcacacagg aaacagctat gaccatgatt        960
acgaatttct agaaataatt tgtttaact taagaagga gatatacata tggagtcggt       1020
tgctgcagag agcgctccag ctccggagaa tgaacactct caagagaccc cggaatcgaa       1080
cagtagtgtg tacaccacct tcatgaagtc tcatcgctgc tatgacctga tccccacaag       1140
ctccaagctg gtggtatttg atacttcgct gcaggtaaag aaagccttct ttgccctggt       1200
gactaacggt gttcgtgctg cccctttgtg ggatagtaag aagcagagct ttgtgggcat       1260
gctgaccatc actgacttca tcaatattct gcaccgatac tacaagtcag ccctggtgca       1320
gatctatgaa ctggaggagc acaagataga gacttggaga gaggtctacc tgcaagactc       1380
ctttaagcca cttgtctgca tttctccaaa tgccagcttg ttcgatgctg tctcttcatt       1440
aattcgaaat aagatccaca ggcttccagt tattgacccg gagtcaggca acaccttgta       1500
cattcttact cacaagcgga tcctcaagtt cctcaagttg tttatcactg agttccccaa       1560
gccggaattc atgtctaagt ctctggaaga gctacagatt ggcacctacg ccaatattgc       1620
catggtccgt accactacac ctgtctatgt ggctctgggc atctttgtac agcaccgagt       1680
ctccgccttg cctgtggtgg atgagaaagg gcgtgtggtg gacatctact ccaagtttga       1740

tgtgattaat ttggcagcag aaaagacata caacaaccta gatgtgtctg tgacaaaagc       1800
cctacagcac cggtcacact acttcgaggg tgttctcaag tgctacctac atgagactct       1860
agaagcaatc atcaatagac tggtggaagc agaggttcac cgtctggtgg tggtggatga       1920
acatgacgtg gtcaagggca ttgtatcgct gtctgacatc ttacaggctc tggtgctcac       1980
aggtggagag aagaagcccg ctagcatggt gagcaagggc gaggagctgt tcaccggggt       2040
ggtgcccatc ctggtcgagc tggacggcga cgtaaacggc cacaagttca gcgtgtccgg       2100
cgagggcgag ggcgatgcca cctacggcaa gctgaccctg aagttcatct gcaccaccgg       2160
caagctgccc gtgccctggc ccaccctcgt gaccaccctg acctggggcg tgcagtgctt       2220
cagccgctac cccgaccaca tgaagcagca cgacttcttc aagtccgcca tgcccgaagg       2280
ctacgtccag gagcgcacca tcttcttcaa ggacgacggc aactacaaga cccgcgccga       2340
ggtgaagttc gagggcgaca ccctggtgaa ccgcatcgag ctgaagggca tcgacttcaa       2400
ggaggacggc aacaтcctгg gcacaagct ggagtacaac tacatcagcc acaacgtcta       2460

tatcaccgcc gacaagcaga agaacggcat caaggccaac ttcaagatcc gccacaacat       2520
cgaggacggc agcgtgcagc tcgccgacca ctaccagcag aacaccccca tcggcgacgg       2580
ccccgtgctg ctgcccgaca ccactacctg agcacccag tccgccctga caaagaccc       2640 caacgagaag cgcgatcaca tggtcctgct ggagttcgtg accgccgccg ggatcactct       2700
cggcatggac gagctgtaca gtccggact cagatctcga cgagctcact gataactagt       2760

tccgtttaaa cccatgtgcc tggcagataa cttcgtataa tgtatgctat acgaagttat       2820
ggtacgtact aagctctcat gtttcacgta ctaagctctc atgtttaacg tactaagctc       2880
```

```
tcatgtttaa cgaactaaac cctcatggct aacgtactaa gctctcatgg ctaacgtact    2940
aagctctcat gtttcacgta ctaagctctc atgtttgaac aataaaatta atataaatca    3000
gcaacttaaa tagcctctaa ggttttaagt tttataagaa aaaaagaat atataaggct     3060 tttaaagctt ttaaggttta acggttgtgg acaacaagcc agggatgtaa cgcactgaga    3120
agcccttaga gcctctcaaa gcaattttga gtgacacagg aacacttaac ggctgacata    3180
attcagcttc acgctgccgc aagcactcag ggcgcaaggg ctgctaaagg aagcggaaca    3240
cgtagaaagc cagtccgcag aaacggtgct gaccccggat gaatgtcagc tgggaggcag    3300
aataaatgat catatcgtca attattacct ccacggggag agcctgagca aactggcctc    3360
aggcatttga gaagcacacg gtcacactgc ttccggtagt caataaaccg gtaagtagcg    3420
tatgcgctca cgcaactggt ccagaaacctt gaccgaacgc agcggtggta acggcgcagt    3480
ggcggttttc atggcttgtt atgactgttt ttttggggta cagtctatgc ctcgggcatc    3540
caagcagcaa gcgcgttacg ccgtgggtcg atgtttgatg ttatggagca gcaacgatgt    3600
tacgcagcag ggcagtcgcc ctaaaacaaa gttaaacatc                          3640
```

<210> SEQ ID NO 17
<211> LENGTH: 580
<212> TYPE: PRT
<213> ORGANISM: Rattus norvegicus

<400> SEQUENCE: 17

```
Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
                20                  25                  30

Lys Ser His Arg Cys Tyr Asp Leu Ile Pro Thr Ser Ser Lys Leu Val
            35                  40                  45

Val Phe Asp Thr Ser Leu Gln Val Lys Lys Ala Phe Phe Ala Leu Val
        50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240
```

```
Ser Lys Phe Asp Val Ile Asn Leu Ala Ala Glu Lys Thr Tyr Asn Asn
            245                 250                 255

Leu Asp Val Ser Val Thr Lys Ala Leu Gln His Arg Ser His Tyr Phe
                260                 265                 270

Glu Gly Val Leu Lys Cys Tyr Leu His Glu Thr Leu Glu Ala Ile Ile
            275                 280                 285

Asn Arg Leu Val Glu Ala Glu Val His Arg Leu Val Val Val Asp Glu
        290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro Ala Ser Met Val Ser Lys
                325                 330                 335

Gly Glu Glu Leu Phe Thr Gly Val Val Pro Ile Leu Val Glu Leu Asp
            340                 345                 350

Gly Asp Val Asn Gly His Lys Phe Ser Val Ser Gly Glu Gly Glu Gly
        355                 360                 365

Asp Ala Thr Tyr Gly Lys Leu Thr Leu Lys Phe Ile Cys Thr Thr Gly
    370                 375                 380

Lys Leu Pro Val Pro Trp Pro Thr Leu Val Thr Thr Leu Thr Trp Gly
385                 390                 395                 400

Val Gln Cys Phe Ser Arg Tyr Pro Asp His Met Lys Gln His Asp Phe
                405                 410                 415

Phe Lys Ser Ala Met Pro Glu Gly Tyr Val Gln Glu Arg Thr Ile Phe
            420                 425                 430

Phe Lys Asp Asp Gly Asn Tyr Lys Thr Arg Ala Glu Val Lys Phe Glu
        435                 440                 445

Gly Asp Thr Leu Val Asn Arg Ile Glu Leu Lys Gly Ile Asp Phe Lys
    450                 455                 460

Glu Asp Gly Asn Ile Leu Gly His Lys Leu Glu Tyr Asn Tyr Ile Ser
465                 470                 475                 480

His Asn Val Tyr Ile Thr Ala Asp Lys Gln Lys Asn Gly Ile Lys Ala
                485                 490                 495

Asn Phe Lys Ile Arg His Asn Ile Glu Asp Gly Ser Val Gln Leu Ala
            500                 505                 510

Asp His Tyr Gln Gln Asn Thr Pro Ile Gly Asp Gly Pro Val Leu Leu
        515                 520                 525

Pro Asp Asn His Tyr Leu Ser Thr Gln Ser Ala Leu Ser Lys Asp Pro
    530                 535                 540

Asn Glu Lys Arg Asp His Met Val Leu Leu Glu Phe Val Thr Ala Ala
545                 550                 555                 560

Gly Ile Thr Leu Gly Met Asp Glu Leu Tyr Lys Ser Gly Leu Arg Ser
                565                 570                 575

Arg Arg Ala His
            580

<210> SEQ ID NO 18
<211> LENGTH: 3640
<212> TYPE: DNA
<213> ORGANISM: Artificial Sequence
<220> FEATURE:
<223> OTHER INFORMATION: Rat eCFP-gamma1

<400> SEQUENCE: 18
atgagggaag cggtgatcgc cgaagtatcg actcaactat cagaggtagt tggcgtcatc      60
```

```
gagcgccatc tcgaaccgac gttgctggcc gtacatttgt acggctccgc agtggatggc    120
ggcctgaagc cacacagtga tattgatttg ctggttacgg tgaccgtaag gcttgatgaa    180
acaacgcggc gagctttgat caacgacctt ttggaaactt cggcttcccc tggagagagc    240
gagattctcc gcgctgtaga agtcaccatt gttgtgcacg acgacatcat tccgtggcgt    300
tatccagcta agcgcgaact gcaatttgga gaatggcagc gcaatgacat tcttgcaggt    360
atcttcgagc cagccacgat cgacattgat ctggctatct tgctgacaaa agcaagagaa    420
catagcgttg ccttggtagg tccagcggcg gaggaactct ttgatccggt tcctgaacag    480
gatctatttg aggcgctaaa tgaaaccttt acgctatgga actcgccgcc cgactgggct    540
ggcgatgagc gaaatgtagt gcttacgttg tcccgcattt ggtacagcgc agtaaccggc    600
aaaatcgcgc cgaaggatgt cgctgccgac tgggcaatgg agcgcctgcc ggcccagtat    660
cagcccgtca tacttgaagc tagacaggct tatcttggac aagaagaaga tcgcttggcc    720
tcgcgcgcag atcagttgga agaatttgtc cactacgtga aaggcgagat caccaaggta    780
gtcggcaaat aatgtctaac aattcgttca agccgacgga tctatgtcgg gtgcggagaa    840
agaggtaatg aaatggcacc taggtatcga tggctttaca ctttatgctt ccggctcgta    900
tgttgtgtgg aattgtgagc ggataacaat ttcacacagg aaacagctat gaccatgatt    960
acgaatttct agaaataatt ttgtttaact ttaagaagga gatatacata tggtgagcaa   1020
gggcgaggag ctgttcaccg gggtggtgcc catcctggtc gagctggacg gcgacgtaaa   1080
cggccacaag ttcagcgtgt ccggcgaggg cgagggcgat gccacctacg gcaagctgac   1140
cctgaagttc atctgcacca ccggcaagct gcccgtgccc tggcccaccc tcgtgaccac   1200
cctgacctgg ggcgtgcagt gcttcagccg ctaccccgac cacatgaagc agcacgactt   1260
cttcaagtcc gccatgcccg aaggctacgt ccaggagcgc accatcttct tcaaggacga   1320
cggcaactac aagacccgcg ccgaggtgaa gttcgagggc gacaccctgg tgaaccgcat   1380
cgagctgaag ggcatcgact tcaaggagga cggcaacatc ctggggcaca gctggagta   1440
caactacatc agccacaacg tctatatcac cgccgacaag cagaagaacg gcatcaaggc   1500
caacttcaag atccgccaca acatcgagga cggcagcgtg cagctcgccg accactacca   1560
gcagaacacc cccatcggcg acggccccgt gctgctgccc gacaaccact acctgagcac   1620
ccagtccgcc ctgagcaaag accccaacga gaagcgcgat cacatggtcc tgctggagtt   1680
cgtgaccgcc gccgggatca ctctcggcat ggacgagctg tacaagtccg gactcagatc   1740
tcgacgagct cacgctagca tggagtcggt tgctgcagag agcgctccag ctccggagaa   1800
tgaacactct caagagaccc cggaatcgaa cagtagtgtg tacaccacct tcatgaagtc   1860
tcatcgctgc tatgacctga tccccacaag ctccaagctg gtggtatttg atacttcgct   1920
gcaggtaaag aaagccttct ttgccctggt gactaacggt gttcgtgctg cccctttgtg   1980
ggatagtaag aagcagagct ttgtgggcat gctgaccatc actgacttca tcaatattct   2040
gcaccgatac tacaagtcag ccctggtgca gatctatgaa ctggaggagc acaagataga   2100
gacttggaga gaggtctacc tgcaagactc ctttaagcca cttgtctgca tttctccaaa   2160
tgccagcttg ttcgatgctg tctcttcatt aattcgaaat aagatccaca ggcttccagt   2220
tattgacccg gagtcaggca acaccttgta cattcttact cacaagcgga tcctcaagtt   2280
cctcaagttg tttatcactg agttcccaa gccggaattc atgtctaagt ctctggaaga   2340
gctacagatt ggcacctacg ccaatattgc catggtccgt accactacac ctgtctatgt   2400
ggctctgggc atctttgtac agcaccgagt ctccgccttg cctgtggtgg atgagaaagg   2460
```

-continued

```
gcgtgtggtg gacatctact ccaagtttga tgtgattaat ttggcagcag aaaagacata    2520
caacaaccta gatgtgtctg tgacaaaagc cctacagcac cggtcacact acttcgaggg    2580
tgttctcaag tgctacctac atgagactct agaagcaatc atcaatagac tggtggaagc    2640
agaggttcac cgtctggtgg tggtggatga acatgacgtg gtcaagggca ttgtatcgct    2700
gtctgacatc ttacaggctc tggtgctcac aggtggagag aagaagccct gataactagt    2760
tccgtttaaa cccatgtgcc tggcagataa cttcgtataa tgtatgctat acgaagttat    2820
ggtacgtact aagctctcat gtttcacgta ctaagctctc atgtttaacg tactaagctc    2880
tcatgtttaa cgaactaaac cctcatggct aacgtactaa gctctcatgg ctaacgtact    2940
aagctctcat gtttcacgta ctaagctctc atgtttgaac aataaaatta atataaatca    3000
gcaacttaaa tagcctctaa ggttttaagt tttataagaa aaaaaagaat atataaggct    3060
tttaaagctt ttaaggttta acggttgtgg acaacaagcc agggatgtaa cgcactgaga    3120
agcccttaga gcctctcaaa gcaattttga gtgacacagg aacacttaac ggctgacata    3180
attcagcttc acgctgccgc aagcactcag gcgcaaggg ctgctaaagg aagcggaaca    3240
cgtagaaagc cagtccgcag aaacggtgct gaccccggat gaatgtcagc tgggaggcag    3300
aataaatgat catatcgtca attattacct ccacggggag agcctgagca aactggcctc    3360
aggcatttga gaagcacacg gtcacactgc ttccggtagt caataaaccg gtaagtagcg    3420
tatgcgctca cgcaactggt ccagaacctt gaccgaacgc agcggtggta acggcgcagt    3480
ggcggttttc atggcttgtt atgactgttt ttttggggta cagtctatgc ctcgggcatc    3540
caagcagcaa gcgcgttacg ccgtgggtcg atgtttgatg ttatgagca gcaacgatgt    3600 tacgcagcag ggcagtcgcc ctaaaacaaa gttaaacatc                          3640
```

<210> SEQ ID NO 19
<211> LENGTH: 580
<212> TYPE: PRT
<213> ORGANISM: Artificial Sequence
<220> FEATURE:
<223> OTHER INFORMATION: Rat eCFP-gamma1

<400> SEQUENCE: 19

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
```

-continued

```
            145                 150                 155                 160
        Gly Ile Lys Ala Asn Phe Lys Ile Arg His Asn Ile Glu Asp Gly Ser
                        165                 170                 175
        Val Gln Leu Ala Asp His Tyr Gln Gln Asn Thr Pro Ile Gly Asp Gly
                        180                 185                 190
        Pro Val Leu Leu Pro Asp Asn His Tyr Leu Ser Thr Gln Ser Ala Leu
                        195                 200                 205
        Ser Lys Asp Pro Asn Glu Lys Arg Asp His Met Val Leu Leu Glu Phe
                210                 215                 220
        Val Thr Ala Ala Gly Ile Thr Leu Gly Met Asp Glu Leu Tyr Lys Ser
        225                 230                 235                 240
        Gly Leu Arg Ser Arg Arg Ala His Ala Ser Met Glu Ser Val Ala Ala
                        245                 250                 255
        Glu Ser Ala Pro Ala Pro Glu Asn Glu His Ser Gln Glu Thr Pro Glu
                        260                 265                 270
        Ser Asn Ser Ser Val Tyr Thr Thr Phe Met Lys Ser His Arg Cys Tyr
                        275                 280                 285
        Asp Leu Ile Pro Thr Ser Ser Lys Leu Val Val Phe Asp Thr Ser Leu
                290                 295                 300
        Gln Val Lys Lys Ala Phe Phe Ala Leu Val Thr Asn Gly Val Arg Ala
        305                 310                 315                 320
        Ala Pro Leu Trp Asp Ser Lys Lys Gln Ser Phe Val Gly Met Leu Thr
                        325                 330                 335
        Ile Thr Asp Phe Ile Asn Ile Leu His Arg Tyr Tyr Lys Ser Ala Leu
                        340                 345                 350
        Val Gln Ile Tyr Glu Leu Glu Glu His Lys Ile Glu Thr Trp Arg Glu
                        355                 360                 365
        Val Tyr Leu Gln Asp Ser Phe Lys Pro Leu Val Cys Ile Ser Pro Asn
                        370                 375                 380
        Ala Ser Leu Phe Asp Ala Val Ser Ser Leu Ile Arg Asn Lys Ile His
        385                 390                 395                 400
        Arg Leu Pro Val Ile Asp Pro Glu Ser Gly Asn Thr Leu Tyr Ile Leu
                        405                 410                 415
        Thr His Lys Arg Ile Leu Lys Phe Leu Lys Leu Phe Ile Thr Glu Phe
                        420                 425                 430
        Pro Lys Pro Glu Phe Met Ser Lys Ser Leu Glu Glu Leu Gln Ile Gly
                        435                 440                 445
        Thr Tyr Ala Asn Ile Ala Met Val Arg Thr Thr Thr Pro Val Tyr Val
                450                 455                 460
        Ala Leu Gly Ile Phe Val Gln His Arg Val Ser Ala Leu Pro Val Val
        465                 470                 475                 480
        Asp Glu Lys Gly Arg Val Val Asp Ile Tyr Ser Lys Phe Asp Val Ile
                        485                 490                 495
        Asn Leu Ala Ala Glu Lys Thr Tyr Asn Asn Leu Asp Val Ser Val Thr
                        500                 505                 510
        Lys Ala Leu Gln His Arg Ser His Tyr Phe Glu Gly Val Leu Lys Cys
                        515                 520                 525
        Tyr Leu His Glu Thr Leu Glu Ala Ile Ile Asn Arg Leu Val Glu Ala
                530                 535                 540
        Glu Val His Arg Leu Val Val Asp Glu His Asp Val Val Lys Gly
        545                 550                 555                 560
        Ile Val Ser Leu Ser Asp Ile Leu Gln Ala Leu Val Leu Thr Gly Gly
                        565                 570                 575
```

Glu Lys Lys Pro
        580

<210> SEQ ID NO 20
<211> LENGTH: 3691
<212> TYPE: DNA
<213> ORGANISM: Artificial Sequence
<220> FEATURE:
<223> OTHER INFORMATION: Rat gamma1-YFP, pDS plasmid

<400> SEQUENCE: 20

| | | | | | |
|---|---|---|---|---|---|
| ctatgtcggg | tgcggagaaa | gaggtaatga | aatggcacct | aggtatcgat | ggctttacac | 60 |
| tttatgcttc | cggctcgtat | gttgtgtgga | attgtgagcg | gataacaatt | tcacacagga | 120 |
| aacagctatg | accatgatta | cgaatttcta | gaaataattt | tgtttaactt | taagaaggag | 180 |
| atatacatat | ggagtcggtt | gctgcagaga | gcgctccagc | tccggagaat | gaacactctc | 240 |
| aagagacccc | ggaatcgaac | agtagtgtgt | acaccacctt | catgaagtct | catcgctgct | 300 |
| atgacctgat | ccccacaagc | tccaagctgg | tggtatttga | tacttcgctg | caggtaaaga | 360 |
| aagccttctt | tgccctggtg | actaacggtg | ttcgtgctgc | ccctttgtgg | atagtaaga | 420 |
| agcagagctt | tgtgggcatg | ctgaccatca | ctgacttcat | caatattctg | caccgatact | 480 |
| acaagtcagc | cctggtgcag | atctatgaac | tggaggagca | caagatagag | acttggagag | 540 |
| aggtctacct | gcaagactcc | tttaagccac | ttgtctgcat | ttctccaaat | gccagcttgt | 600 |
| tcgatgctgt | ctcttcatta | attcgaaata | agatccacag | gcttccagtt | attgacccgg | 660 |
| agtcaggcaa | caccttgtac | attcttactc | acaagcggat | cctcaagttc | ctcaagttgt | 720 |
| ttatcactga | gttccccaag | ccggaattca | tgtctaagtc | tctggaagag | ctacagattg | 780 |
| gcacctacgc | caatattgcc | atggtccgta | ccactacacc | tgtctatgtg | gctctgggca | 840 |
| tctttgtaca | gcaccgagtc | tccgccttgc | ctgtggtgga | tgagaaaggg | cgtgtggtgg | 900 |
| acatctactc | caagtttgat | gtgattaatt | tggcagcaga | aaagacatac | aacaacctag | 960 |
| atgtgtctgt | gacaaaagcc | ctacagcacc | ggtcacacta | cttcgagggt | gttctcaagt | 1020 |
| gctacctaca | tgagactcta | gaagcaatca | tcaatagact | ggtggaagca | gaggttcacc | 1080 |
| gtctggtggt | ggtggatgaa | catgacgtgg | tcaagggcat | tgtatcgctg | tctgacatct | 1140 |
| tacaggctct | ggtgctcaca | ggtggagaga | agaagcccgc | tagcatggtg | agcaagggcg | 1200 |
| aggagctgtt | caccggggtg | gtgcccatcc | tggtcgagct | ggacggcgac | gtaaacggcc | 1260 |
| acaagttcag | cgtgtccggc | gagggcgagg | gcgatgccac | ctacggcaag | ctgaccctga | 1320 |
| agttcatctg | caccaccggc | aagctgcccg | tgccctggcc | caccctcgtg | accaccttcg | 1380 |
| gctacggcct | gcagtgcttc | gcccgctacc | ccgaccacat | gaagcagcac | gacttcttca | 1440 |
| agtccgccat | gcccgaaggc | tacgtccagg | agcgcaccat | cttcttcaag | gacgacggca | 1500 |
| actacaagac | ccgcgccgag | gtgaagttcg | agggcgacac | cctggtgaac | cgcatcgagc | 1560 |
| tgaagggcat | cgacttcaag | gaggacggca | acatcctggg | gcacaagctg | gagtacaact | 1620 |
| acaacagcca | caacgtctat | atcatggccg | acaagcagaa | gaacggcatc | aaggtgaact | 1680 |
| tcaagatccg | ccacaacatc | gaggacggca | gcgtgcagct | cgccgaccac | taccagcaga | 1740 |
| acacccccat | cggcgacggc | cccgtgctgc | tgcccgacaa | ccactacctg | agctaccagt | 1800 |
| ccgccctgag | caaagacccc | aacgagaagc | gcgatcacat | ggtcctgctg | gagttcgtga | 1860 |
| ccgccgccgg | gatcactctc | ggcatggacg | agctgtacaa | gtccggactc | agatctcgag | 1920 |
| ctcaagcttc | gaattctgca | gtcgacggta | ccgcgggccc | gggatccacc | ggatctagat | 1980 |

```
gataactagt tccgtttaaa cccatgtgcc tggcagataa cttcgtataa tgtatgctat      2040
acgaagttat ggtacgtact aagctctcat gtttcacgta ctaagctctc atgtttaacg      2100
tactaagctc tcatgtttaa cgaactaaac cctcatggct aacgtactaa gctctcatgg      2160
ctaacgtact aagctctcat gtttcacgta ctaagctctc atgtttgaac aataaaatta      2220
atataaatca gcaacttaaa tagcctctaa ggttttaagt tttataagaa aaaaagaat       2280 atataaggct tttaaagctt ttaaggttta acggttgtgg acaacaagcc agggatgtaa      2340
cgcactgaga agcccttaga gcctctcaaa gcaattttga gtgacacagg aacacttaac      2400
ggctgacata attcagcttc acgctgccgc aagcactcag ggcgcaaggg ctgctaaagg      2460
aagcggaaca cgtagaaagc cagtccgcag aaacggtgct gaccccggat gaatgtcagc      2520
tgggaggcag aataaatgat catatcgtca attattacct ccacggggag agcctgagca      2580
aactggcctc aggcatttga gaagcacacg gtcacactgc ttccggtagt caataaaccg      2640
gtaagtagcg tatgcgctca cgcaactggt ccagaacctt gaccgaacgc agcggtggta      2700
acggcgcagt ggcggttttc atggcttgtt atgactgttt ttttgggta cagtctatgc       2760 ctcgggcatc caagcagcaa gcgcgttacg ccgtgggtcg atgtttgatg ttatggagca      2820
gcaacgatgt tacgcagcag ggcagtcgcc ctaaaacaaa gttaaacatc atgagggaag      2880
cggtgatcgc cgaagtatcg actcaactat cagaggtagt tggcgtcatc gagcgccatc      2940
tcgaaccgac gttgctggcc gtacatttgt acggctccgc agtggatggc ggcctgaagc      3000
cacacagtga tattgatttg ctggttacgg tgaccgtaag gcttgatgaa acaacgcggc      3060
gagctttgat caacgaccct ttggaaactt cggcttcccc tggagagagc gagattctcc      3120
gcgctgtaga agtcaccatt gttgtgcacg acgacatcat tccgtggcgt tatccagcta      3180
agcgcgaact gcaatttgga gaatggcagc gcaatgacat tcttgcaggt atcttcgagc      3240
cagccacgat cgacattgat ctggctatct tgctgacaaa agcaagagaa catagcgttg      3300
ccttggtagg tccagcggcg gaggaactct ttgatccggt tcctgaacag gatctatttg      3360
aggcgctaaa tgaaacctta acgctatgga actcgccgcc cgactgggct ggcgatgagc      3420
gaaatgtagt gcttacgttg tcccgcattt ggtacagcgc agtaaccggc aaaatcgcgc      3480
cgaaggatgt cgctgccgac tgggcaatgg agcgcctgcc ggcccagtat cagcccgtca      3540
tacttgaagc tagacaggct tatcttggac aagaagaaga tcgcttggcc tcgcgcgcag      3600
atcagttgga agaatttgtc cactacgtga aaggcgagat caccaaggta gtcggcaaat      3660
aatgtctaac aattcgttca agccgacgga t                                    3691
```

<210> SEQ ID NO 21
<211> LENGTH: 597
<212> TYPE: PRT
<213> ORGANISM: Artificial Sequence
<220> FEATURE:
<223> OTHER INFORMATION: Rat gamma1-YFP

<400> SEQUENCE: 21

Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val

```
                50                  55                  60
Thr Asn Gly Val Arg Ala Ala Pro Leu Trp Asp Ser Lys Lys Gln Ser
 65                  70                  75                  80

Phe Val Gly Met Leu Thr Ile Thr Asp Phe Ile Asn Ile Leu His Arg
                 85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro Ala Ser Met Val Ser Lys
                325                 330                 335

Gly Glu Glu Leu Phe Thr Gly Val Val Pro Ile Leu Val Glu Leu Asp
            340                 345                 350

Gly Asp Val Asn Gly His Lys Phe Ser Val Ser Gly Glu Gly Glu Gly
        355                 360                 365

Asp Ala Thr Tyr Gly Lys Leu Thr Leu Lys Phe Ile Cys Thr Thr Gly
370                 375                 380

Lys Leu Pro Val Pro Trp Pro Thr Leu Val Thr Thr Phe Gly Tyr Gly
385                 390                 395                 400

Leu Gln Cys Phe Ala Arg Tyr Pro Asp His Met Lys Gln His Asp Phe
                405                 410                 415

Phe Lys Ser Ala Met Pro Glu Gly Tyr Val Gln Glu Arg Thr Ile Phe
            420                 425                 430

Phe Lys Asp Asp Gly Asn Tyr Lys Thr Arg Ala Glu Val Lys Phe Glu
        435                 440                 445

Gly Asp Thr Leu Val Asn Arg Ile Glu Leu Lys Gly Ile Asp Phe Lys
450                 455                 460

Glu Asp Gly Asn Ile Leu Gly His Lys Leu Glu Tyr Asn Tyr Asn Ser
465                 470                 475                 480
```

His Asn Val Tyr Ile Met Ala Asp Lys Gln Lys Asn Gly Ile Lys Val
                485                 490                 495

Asn Phe Lys Ile Arg His Asn Ile Glu Asp Gly Ser Val Gln Leu Ala
            500                 505                 510

Asp His Tyr Gln Gln Asn Thr Pro Ile Gly Asp Gly Pro Val Leu Leu
            515                 520                 525

Pro Asp Asn His Tyr Leu Ser Tyr Gln Ser Ala Leu Ser Lys Asp Pro
        530                 535                 540

Asn Glu Lys Arg Asp His Met Val Leu Leu Glu Phe Val Thr Ala Ala
545                 550                 555                 560

Gly Ile Thr Leu Gly Met Asp Glu Leu Tyr Lys Ser Gly Leu Arg Ser
                565                 570                 575

Arg Ala Gln Ala Ser Asn Ser Ala Val Asp Gly Thr Ala Gly Pro Gly
            580                 585                 590

Ser Thr Gly Ser Arg
        595

<210> SEQ ID NO 22
<211> LENGTH: 3691
<212> TYPE: DNA
<213> ORGANISM: Artificial Sequence
<220> FEATURE:
<223> OTHER INFORMATION: Rat YFP-gamma1, pDS plasmid

<400> SEQUENCE: 22

```
atgagggaag cggtgatcgc cgaagtatcg actcaactat cagaggtagt tggcgtcatc    60
gagcgccatc tcgaaccgac gttgctggcc gtacatttgt acggctccgc agtggatggc   120
ggcctgaagc cacacagtga tattgatttg ctggttacgg tgaccgtaag gcttgatgaa   180
acaacgcggc gagctttgat caacgacctt ttggaaactt cggcttcccc tggagagagc   240
gagattctcc gcgctgtaga agtcaccatt gttgtgcacg acgacatcat tccgtggcgt   300
tatccagcta agcgcgaact gcaatttgga gaatggcagc gcaatgacat tcttgcaggt   360
atcttcgagc cagccacgat cgacattgat ctggctatct tgctgacaaa agcaagagaa   420
catagcgttg ccttggtagg tccagcggcg gaggaactct ttgatccggt tcctgaacag   480
gatctatttg aggcgctaaa tgaaacctta acgctatgga actcgccgcc cgactgggct   540
ggcgatgagc gaaatgtagt gcttacgttg tcccgcattt ggtacagcgc agtaaccggc   600
aaaatcgcgc cgaaggatgt cgctgccgac tgggcaatgg agcgcctgcc ggcccagtat   660
cagcccgtca tacttgaagc tagacaggct tatcttggac aagaagaaga tcgcttggcc   720
tcgcgcgcag atcagttgga agaatttgtc cactacgtga aggcgagat caccaaggta   780
gtcggcaaat aatgtctaac aattcgttca agccgacgga tctatgtcgg gtgcggagaa   840
agaggtaatg aaatggcacc taggtatcga tggctttaca ctttatgctt ccggctcgta   900
tgttgtgtgg aattgtgagc ggataacaat ttcacacagg aaacagctat gaccatgatt   960
acgaatttct agaaataatt tgtttaact ttaagaagga gatatacata tggtgagcaa  1020
gggcgaggag ctgttcaccg gggtggtgcc catcctggtc gagctggacg gcgacgtaaa  1080
cggccacaag ttcagcgtgt ccggcgaggg cgagggcgat gccacctacg gcaagctgac  1140
cctgaagttc atctgcacca ccggcaagct gcccgtgccc tggcccaccc tcgtgaccac  1200
cttcggctac ggcctgcagt gcttcgcccg ctacccgac cacatgaagc agcacgactt  1260
cttcaagtcc gccatgcccg aaggctacgt ccaggagcgc accatcttct tcaaggacga  1320
```

```
cggcaactac aagacccgcg ccgaggtgaa gttcgagggc gacaccctgg tgaaccgcat    1380
cgagctgaag ggcatcgact tcaaggagga cggcaacatc ctggggcaca agctggagta    1440
caactacaac agccacaacg tctatatcat ggccgacaag cagaagaacg gcatcaaggt    1500
gaacttcaag atccgccaca acatcgagga cggcagcgtg cagctcgccg accactacca    1560
gcagaacacc cccatcggcg acggccccgt gctgctgccc gacaaccact acctgagcta    1620
ccagtccgcc ctgagcaaag accccaacga gaagcgcgat cacatggtcc tgctggagtt    1680
cgtgaccgcc gccgggatca ctctcggcat ggacgagctg tacaagtccg gactcagatc    1740
tcgagctcaa gcttcgaatt ctgcagtcga cggtaccgcg ggcccgggat ccaccggatc    1800
tagagctagc atggagtcgg ttgctgcaga gagcgctcca gctccggaga atgaacactc    1860
tcaagagacc ccggaatcga acagtagtgt gtacaccacc ttcatgaagt ctcatcgctg    1920
ctatgacctg atccccacaa gctccaagct ggtggtattt gatacttcgc tgcaggtaaa    1980
gaaagccttc tttgccctgg tgactaacgg tgttcgtgct gccccttttgt gggatagtaa    2040 gaagcagagc tttgtgggca tgctgaccat cactgacttc atcaatattc tgcaccgata    2100
ctacaagtca gccctggtgc agatctatga actggaggag cacaagatag agacttggag    2160
agaggtctac ctgcaagact cctttaagcc acttgtctgc atttctccaa atgccagctt    2220
gttcgatgct gtctcttcat taattcgaaa taagatccac aggcttccag ttattgaccc    2280
gggagtcagg aacaccttgt acattcttac tcacaagcgg atcctcaagt tcctcaagtt    2340
gtttatcact gagttcccca gccggaatt catgtctaag tctctggaag agctacagat    2400
tggcacctac gccaatattg ccatggtccg taccactaca cctgtctatg tggctctggg    2460
catctttgta cagcaccgag tctccgcctt gcctgtggtg gatgagaaag ggcgtgtggt    2520
ggacatctac tccaagtttg atgtgattaa tttggcagca gaaaagacat acaacaacct    2580
agatgtgtct gtgacaaaag ccctacagca ccggtcacac tacttcgagg gtgttctcaa    2640
gtgctaccta catgagactc tagaagcaat catcaataga ctggtggaag cagaggttca    2700
ccgtctggtg gtggtggatg aacatgacgt ggtcaagggc attgtatcgc tgtctgacat    2760
cttacaggct ctggtgctca caggtggaga agaagcccc tgataactag ttccgtttaa    2820
acccatgtgc ctgcagata cttcgtata atgtatgcta tacgaagtta tggtacgtac    2880
taagctctca tgtttcacgt actaagctct catgtttaac gtactaagct ctcatgttta    2940
acgaactaaa ccctcatggc taacgtacta agctctcatg ctaacgtac taagctctca    3000 tgtttcacgt actaagctct catgtttgaa caataaaatt aatataaatc agcaacttaa    3060
atagcctcta aggttttaag ttttataaga aaaaaagaa tatataaggc ttttaaagct    3120
tttaaggttt aacggttgtg gacaacaagc caggatgta acgcactgag aagcccttag    3180
agcctctcaa agcaattttg agtgacacag gaacacttaa cggctgacat aattcagctt    3240
cacgctgccg caagcactca gggcgcaagg gctgctaaag gaagcggaac acgtagaaag    3300
ccagtccgca gaaacggtgc tgaccccgga tgaatgtcag ctgggaggca gaataaatga    3360
tcatatcgtc aattattacc tccacgggga gagcctgagc aaactggcct caggcatttg    3420
agaagcacac ggtcacactg cttccggtag tcaataaacc ggtaagtagc gtatgcgctc    3480
acgcaactgg tccagaacct tgaccgaacg cagcggtggt aacggcgcag tggcggtttt    3540
catggcttgt tatgactgtt tttttggggt acagtctatg cctcgggcat ccaagcagca    3600
agcgcgttac gccgtgggtc gatgtttgat gttatggagc agcaacgatg ttacgcagca    3660
gggcagtcgc cctaaaacaa agttaaacat c                                   3691
```

<210> SEQ ID NO 23
<211> LENGTH: 597
<212> TYPE: PRT
<213> ORGANISM: Artificial Sequence
<220> FEATURE:
<223> OTHER INFORMATION: YFP-gamma1

<400> SEQUENCE: 23

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Ala Val Asp Gly Thr
                245                 250                 255

Ala Gly Pro Gly Ser Thr Gly Ser Arg Ala Ser Met Glu Ser Val Ala
            260                 265                 270

Ala Glu Ser Ala Pro Ala Pro Glu Asn Glu His Ser Gln Glu Thr Pro
        275                 280                 285

Glu Ser Asn Ser Ser Val Tyr Thr Thr Phe Met Lys Ser His Arg Cys
    290                 295                 300

Tyr Asp Leu Ile Pro Thr Ser Ser Lys Leu Val Val Phe Asp Thr Ser
305                 310                 315                 320

Leu Gln Val Lys Lys Ala Phe Phe Ala Leu Val Thr Asn Gly Val Arg
                325                 330                 335

Ala Ala Pro Leu Trp Asp Ser Lys Lys Gln Ser Phe Val Gly Met Leu
            340                 345                 350

Thr Ile Thr Asp Phe Ile Asn Ile Leu His Arg Tyr Tyr Lys Ser Ala
        355                 360                 365
```

-continued

Leu Val Gln Ile Tyr Glu Leu Glu Glu His Lys Ile Glu Thr Trp Arg
        370                 375                 380

Glu Val Tyr Leu Gln Asp Ser Phe Lys Pro Leu Val Cys Ile Ser Pro
385                 390                 395                 400

Asn Ala Ser Leu Phe Asp Ala Val Ser Ser Leu Ile Arg Asn Lys Ile
                405                 410                 415

His Arg Leu Pro Val Ile Asp Pro Glu Ser Gly Asn Thr Leu Tyr Ile
                420                 425                 430

Leu Thr His Lys Arg Ile Leu Lys Phe Leu Lys Leu Phe Ile Thr Glu
                435                 440                 445

Phe Pro Lys Pro Glu Phe Met Ser Lys Ser Leu Glu Glu Leu Gln Ile
        450                 455                 460

Gly Thr Tyr Ala Asn Ile Ala Met Val Arg Thr Thr Pro Val Tyr
465                 470                 475                 480

Val Ala Leu Gly Ile Phe Val Gln His Arg Val Ser Ala Leu Pro Val
                485                 490                 495

Val Asp Glu Lys Gly Arg Val Val Asp Ile Tyr Ser Lys Phe Asp Val
                500                 505                 510

Ile Asn Leu Ala Ala Glu Lys Thr Tyr Asn Asn Leu Asp Val Ser Val
        515                 520                 525

Thr Lys Ala Leu Gln His Arg Ser His Tyr Phe Glu Gly Val Leu Lys
        530                 535                 540

Cys Tyr Leu His Glu Thr Leu Glu Ala Ile Ile Asn Arg Leu Val Glu
545                 550                 555                 560

Ala Glu Val His Arg Leu Val Val Val Asp Glu His Asp Val Val Lys
                565                 570                 575

Gly Ile Val Ser Leu Ser Asp Ile Leu Gln Ala Leu Val Leu Thr Gly
                580                 585                 590

Gly Glu Lys Lys Pro
        595

<210> SEQ ID NO 24
<211> LENGTH: 5007
<212> TYPE: DNA
<213> ORGANISM: Artificial Sequence
<220> FEATURE:
<223> OTHER INFORMATION: Rat a2-CFP_T172A, pACE plasmid

<400> SEQUENCE: 24
ggaattccag ataacttcgt ataatgtatg ctatacgaag ttatggtacc gcggccgcgt      60
agaggatctg ttgatcagca gttcaacctg ttgatagtac ttcgttaata cagatgtagg    120
tgttggcacc atgcataact ataacggtcc taaggtagcg acctaggtat cgataatacg    180
actcactata ggggaattgt gagcggataa caattcccct ctagaaataa ttttgtttaa    240
ctttaagaag gagatataat gggcagtagt caccatcacc accatcatca tcaccatcat    300
agtagtgaaa acctgtattt tcagggcat atggctgaga agcagaagca cgacgggcgt    360
gtgaagatcg acactacgt gctggggac accctgggcg tcggcacctt cggcaaagtg    420
aagattggag aacatcaatt gacaggccat aaagtggcag ttaagatctt aaatagacag    480
aagattcgca gtttagatgt tgttggaaaa ataaaacgag aaattcaaaa tcttaaactc    540
tttcgtcatc ctcatattat caaactctac caagtgatca gcactccaac agactttttt    600
atggtaatgg aatatgtgtc tggaggtgaa ttgttcgact acatctgtaa acacgggagg    660
gttgaagagg tggaagctcg ccggctcttc cagcagattc tgtctgccgt ggactactgt    720

```
cacaggcaca tggttgtcca cagggacctg aagccagaga acgtgttgct ggacgcccag    780
atgaatgcta agatagctga cttcggactc tctaatatga tgtcagatgg tgaatttcta    840
cgagctagct gtggatcgcc aaattatgca gcaccggagg tcatctcagg aaggctgtat    900
gcgggtcctg aggttgatat ctggagctgt ggtgttatcc tgtatgccct tctctgtggc    960
accctcccgt tcgacgatga gcacgtgcct acgctcttta agaagatccg agggggtgtg   1020
ttctacatcc cggagtatct caaccgttct attgccactc tgctgatgca catgctgcag   1080
gtggacccct tgaagcgagc aactatcaaa gacatacgag agcatgaatg gtttaaacag   1140
gatttgccca gttacctctt tcctgaagac ccctcctatg atgctaacgt cattgatgat   1200
gaggctgtga agaagtatg tgaaaaattt gagtgtacag aatcagaagt gatgaacagt   1260
ttatacagtg gtgaccctca agaccagctc gcagtggctt atcatctcat cattgacaat   1320
cggagaataa tgaaccaagc cagtgagttc tacctcgcct ccagtcctcc aacgggttcc   1380
ttcatggacg atagtgccat gcatattccc cccggcctga accacatcc tgaaaggatg   1440 ccacctctca tagcagacag ccccaaagca cgctgtccac tggatgcact caacacaact   1500
aagcccaaat ctttagctgt gaaaaaagcc aagtggcacc ttgggatccg aagccagagc   1560
aaaccatacg acattatggc ggaggtgtac cgagctatga agcagctgga ctttgaatgg   1620
aaggtagtga atgcatacca tcttcgagta agaagaaaaa acccagtgac tgcaaattac   1680
gtgaaaatga gcttacagct ttacctggtt gacaatcgga gctatctgct ggactttaaa   1740
agcatcgatg atgaggtggt ggagcagagg tctggttctt caacacctca gcgctcctgt   1800
tctgctgccg gcctccacag acctcggtca agtgtcgatt ccagcacagc cgagaaccat   1860
tcactgtctg gctctctcac tggttctttg actggcagca ctttgtcctc cgcttccccg   1920
cgcctgggca gtcataccat ggatttttt gaaatgtgcg ccagtcttat cactgcttta   1980
gcccgtaagc ttatggtgag caagggcgag gagctgttca ccggggtggt gcccatcctg   2040
gtcgagctgg acggcgacgt aaacggccac aagttcagcg tgtccggcga gggcgagggc   2100
gatgccacct acggcaagct gaccctgaag ttcatctgca ccaccggcaa gctgcccgtg   2160
ccctggccca ccctcgtgac cacccctgacc tggggcgtgc agtgcttcag ccgctacccc   2220
gaccacatga agcagcacga cttcttcaag tccgccatgc ccgaaggcta cgtccaggag   2280
cgcaccatct tcttcaagga cgacggcaac tacaagaccc gcgccgaggt gaagttcgag   2340
ggcgacaccc tggtgaaccg catcgagctg aagggcatcg acttcaagga ggacggcaac   2400
atcctggggc acaagctgga gtacaactac atcagccaca acgtctatat caccgccgac   2460
aagcagaaga acggcatcaa ggccaacttc aagatccgcc acaacatcga ggacggcagc   2520
gtgcagctcg ccgaccacta ccagcagaac acccccatcg gcgacggccc cgtgctgctg   2580
cccgacaacc actacctgag cacccagtcc gccctgagca agacccccaa cgagaagcgc   2640
gatcacatgg tcctgctgga gttcgtgacc gccgccggga tcactctcgg catggacgag   2700
ctgtacaagt ccggactcag atctcgacga gctcactgat aactcgagag atccggctgc   2760
taacaaagcc cgaaaggaag ctgagttggc tgctgccacc gctgagcaat aactagcata   2820
accccttggg gcctctaaac gggtcttgag ggtttttttg gtttaaaccc atctaattgg   2880
actagtagcc cgcctaatga gcgggctttt ttttaattcc cctatttgtt tatttttcta   2940
aatacattca aatatgtatc cgctcatgag acaataaccc tgataaatgc ttcaataata   3000
ttgaaaaagg aagagtatga gtattcaaca tttccgtgtc gcccttattc ccttttttgc   3060
```

| | | | |
|---|---|---|---|
| ggcattttgc | cttcctgttt | ttgctcaccc | agaaacgctc | gtgaaagtaa | aagacgcaga | 3120 |
| ggaccaattg | ggggcacgag | tgggatacat | agaactggac | ttgaatagcg | gtaaaatcct | 3180 |
| tgagagtttt | cgccctgaag | agcgttttcc | aatgatgagc | actttcaaag | ttctgctatg | 3240 |
| tggagcagta | ttatcccgtg | tagatgcggg | gcaagagcaa | ctcggacgac | gaatacacta | 3300 |
| ttcgcagaat | gacttggttg | aatactcccc | agtgacagaa | aagcacctta | cggacggaat | 3360 |
| gacggtaaga | gaattatgta | gtgccgccat | aacgatgagt | gataacactg | cggcgaactt | 3420 |
| acttctgaca | accatcggtg | gaccgaagga | attaaccgct | tttttgcaca | atatgggaga | 3480 |
| ccatgtaact | cgccttgacc | gttgggaacc | agaactgaat | gaagccatac | caaacgacga | 3540 |
| gcgagacacc | acaatgcctg | cggcaatggc | aacaacatta | cgcaaactat | taactggcga | 3600 |
| actacttact | ctggcttcac | ggcaacaatt | aatagactgg | cttgaagcgg | ataaagttgc | 3660 |
| aggaccacta | ctgcgttcgg | cacttcctgc | tggctggttt | attgctgata | aatctggggc | 3720 |
| aggagagcgt | ggttcacggg | gtatcattgc | cgcacttgga | ccagatggta | agccttcccg | 3780 |
| tatcgtagtt | atctacacga | cgggtagtca | ggcaactatg | gacgaacgaa | atagacagat | 3840 |
| tgctgaaata | ggggcttcac | tgattaagca | ttggtaaacc | gatacaatta | aaggctcctt | 3900 |
| ttggagcctt | ttttttgga | cggaccggta | gaaaagatca | aaggatcttc | ttgagatcct | 3960 |
| tttttttctgc | gcgtaatctg | ctgcttgcaa | acaaaaaaac | caccgctacc | agcggtggtt | 4020 |
| tgtttgccgg | atcaagagct | accaactctt | tttccgaagg | taactggctt | cagcagagcg | 4080 |
| cagataccaa | atactgtcct | tctagtgtag | ccgtagttag | gccaccactt | caagaactct | 4140 |
| gtagcaccgc | ctacataccct | cgctctgcta | atcctgttac | cagtggctgc | tgccagtggc | 4200 |
| gataagtcgt | gtcttaccgg | gttggactca | agacgatagt | taccggataa | ggcgcagcgg | 4260 |
| tcgggctgaa | cggggggttc | gtgcacacag | cccagcttgg | agcgaacgac | ctacaccgaa | 4320 |
| ctgagatacc | tacagcgtga | gctatgagaa | agcgccacgc | ttcccgaagg | gagaaaggcg | 4380 |
| gacaggtatc | cggtaagcgg | cagggtcgga | acaggagagc | gcacgaggga | gcttccaggg | 4440 |
| ggaaacgcct | ggtatcttta | tagtcctgtc | gggtttcgcc | acctctgact | tgagcgtcga | 4500 |
| tttttgtgat | gctcgtcagg | ggggcggagc | ctatggaaaa | acgccagcaa | cgcggccttt | 4560 |
| ttacggttcc | tggccttttg | ctggccttttt | gctcacatgt | tctttcctgc | gttatcccct | 4620 |
| gattctgtgg | ataaccgtat | taccgccttt | gagtgagctg | ataccgctcg | ccgcagccga | 4680 |
| acgaccgagc | gcagcgagtc | agtgagcgag | gaagcggaag | agcgcctgat | gcggtatttt | 4740 |
| ctccttacgc | atctgtgcgg | tatttcacac | cgcaatggtg | cactctcagt | acaatctgct | 4800 |
| ctgatgccgc | atagttaagc | cagtatacac | tccgctatcg | ctacgtgact | gggtcatggc | 4860 |
| tgcgccccga | cacccgccaa | cacccgctga | cgcgccctga | cgggcttgtc | tgctcccggc | 4920 |
| atccgcttac | agacaagctg | tgaccgtctc | cgggagctgc | atgtgtcaga | ggttttcacc | 4980 |
| gtcatcaccg | aaacgcgcga | ggcaggg | | | | 5007 |

<210> SEQ ID NO 25
<211> LENGTH: 826
<212> TYPE: PRT
<213> ORGANISM: Artificial Sequence
<220> FEATURE:
<223> OTHER INFORMATION: Rat alpha2-CFP_T172A

<400> SEQUENCE: 25

Met Gly Ser Ser His His His His His His His His Ser Ser
1               5                   10                  15

```
Glu Asn Leu Tyr Phe Gln Gly His Met Ala Glu Lys Gln Lys His Asp
                20                  25                  30
Gly Arg Val Lys Ile Gly His Tyr Val Leu Gly Asp Thr Leu Gly Val
            35                  40                  45
Gly Thr Phe Gly Lys Val Lys Ile Gly Glu His Gln Leu Thr Gly His
 50                  55                  60
Lys Val Ala Val Lys Ile Leu Asn Arg Gln Lys Ile Arg Ser Leu Asp
 65                  70                  75                  80
Val Val Gly Lys Ile Lys Arg Glu Ile Gln Asn Leu Lys Leu Phe Arg
                85                  90                  95
His Pro His Ile Ile Lys Leu Tyr Gln Val Ile Ser Thr Pro Thr Asp
                100                 105                 110
Phe Phe Met Val Met Glu Tyr Val Ser Gly Gly Glu Leu Phe Asp Tyr
            115                 120                 125
Ile Cys Lys His Gly Arg Val Glu Glu Val Glu Ala Arg Arg Leu Phe
130                 135                 140
Gln Gln Ile Leu Ser Ala Val Asp Tyr Cys His Arg His Met Val Val
145                 150                 155                 160
His Arg Asp Leu Lys Pro Glu Asn Val Leu Leu Asp Ala Gln Met Asn
                165                 170                 175
Ala Lys Ile Ala Asp Phe Gly Leu Ser Asn Met Met Ser Asp Gly Glu
            180                 185                 190
Phe Leu Arg Ala Ser Cys Gly Ser Pro Asn Tyr Ala Ala Pro Glu Val
            195                 200                 205
Ile Ser Gly Arg Leu Tyr Ala Gly Pro Glu Val Asp Ile Trp Ser Cys
210                 215                 220
Gly Val Ile Leu Tyr Ala Leu Leu Cys Gly Thr Leu Pro Phe Asp Asp
225                 230                 235                 240
Glu His Val Pro Thr Leu Phe Lys Lys Ile Arg Gly Gly Val Phe Tyr
                245                 250                 255
Ile Pro Glu Tyr Leu Asn Arg Ser Ile Ala Thr Leu Leu Met His Met
            260                 265                 270
Leu Gln Val Asp Pro Leu Lys Arg Ala Thr Ile Lys Asp Ile Arg Glu
            275                 280                 285
His Glu Trp Phe Lys Gln Asp Leu Pro Ser Tyr Leu Phe Pro Glu Asp
            290                 295                 300
Pro Ser Tyr Asp Ala Asn Val Ile Asp Asp Glu Ala Val Lys Glu Val
305                 310                 315                 320
Cys Glu Lys Phe Glu Cys Thr Glu Ser Glu Val Met Asn Ser Leu Tyr
                325                 330                 335
Ser Gly Asp Pro Gln Asp Gln Leu Ala Val Ala Tyr His Leu Ile Ile
            340                 345                 350
Asp Asn Arg Arg Ile Met Asn Gln Ala Ser Glu Phe Tyr Leu Ala Ser
            355                 360                 365
Ser Pro Pro Thr Gly Ser Phe Met Asp Asp Ser Ala Met His Ile Pro
        370                 375                 380
Pro Gly Leu Lys Pro His Pro Glu Arg Met Pro Pro Leu Ile Ala Asp
385                 390                 395                 400
Ser Pro Lys Ala Arg Cys Pro Leu Asp Ala Leu Asn Thr Thr Lys Pro
                405                 410                 415
Lys Ser Leu Ala Val Lys Lys Ala Lys Trp His Leu Gly Ile Arg Ser
            420                 425                 430
Gln Ser Lys Pro Tyr Asp Ile Met Ala Glu Val Tyr Arg Ala Met Lys
```

-continued

```
                435                 440                 445
Gln Leu Asp Phe Glu Trp Lys Val Val Asn Ala Tyr His Leu Arg Val
450                 455                 460
Arg Arg Lys Asn Pro Val Thr Gly Asn Tyr Val Lys Met Ser Leu Gln
465                 470                 475                 480
Leu Tyr Leu Val Asp Asn Arg Ser Tyr Leu Leu Asp Phe Lys Ser Ile
                485                 490                 495
Asp Asp Glu Val Val Glu Gln Arg Ser Gly Ser Ser Thr Pro Gln Arg
                500                 505                 510
Ser Cys Ser Ala Ala Gly Leu His Arg Pro Arg Ser Ser Val Asp Ser
                515                 520                 525
Ser Thr Ala Glu Asn His Ser Leu Ser Gly Ser Leu Thr Gly Ser Leu
                530                 535                 540
Thr Gly Ser Thr Leu Ser Ser Ala Ser Pro Arg Leu Gly Ser His Thr
545                 550                 555                 560
Met Asp Phe Phe Glu Met Cys Ala Ser Leu Ile Thr Ala Leu Ala Arg
                565                 570                 575
Lys Leu Met Val Ser Lys Gly Glu Glu Leu Phe Thr Gly Val Val Pro
                580                 585                 590
Ile Leu Val Glu Leu Asp Gly Asp Val Asn Gly His Lys Phe Ser Val
                595                 600                 605
Ser Gly Glu Gly Glu Gly Asp Ala Thr Tyr Gly Lys Leu Thr Leu Lys
610                 615                 620
Phe Ile Cys Thr Thr Gly Lys Leu Pro Val Pro Trp Pro Thr Leu Val
625                 630                 635                 640
Thr Thr Leu Thr Trp Gly Val Gln Cys Phe Ser Arg Tyr Pro Asp His
                645                 650                 655
Met Lys Gln His Asp Phe Phe Lys Ser Ala Met Pro Glu Gly Tyr Val
                660                 665                 670
Gln Glu Arg Thr Ile Phe Phe Lys Asp Asp Gly Asn Tyr Lys Thr Arg
                675                 680                 685
Ala Glu Val Lys Phe Glu Gly Asp Thr Leu Val Asn Arg Ile Glu Leu
                690                 695                 700
Lys Gly Ile Asp Phe Lys Glu Asp Gly Asn Ile Leu Gly His Lys Leu
705                 710                 715                 720
Glu Tyr Asn Tyr Ile Ser His Asn Val Tyr Ile Thr Ala Asp Lys Gln
                725                 730                 735
Lys Asn Gly Ile Lys Ala Asn Phe Lys Ile Arg His Asn Ile Glu Asp
                740                 745                 750
Gly Ser Val Gln Leu Ala Asp His Tyr Gln Gln Asn Thr Pro Ile Gly
                755                 760                 765
Asp Gly Pro Val Leu Leu Pro Asp Asn His Tyr Leu Ser Thr Gln Ser
                770                 775                 780
Ala Leu Ser Lys Asp Pro Asn Glu Lys Arg Asp His Met Val Leu Leu
785                 790                 795                 800
Glu Phe Val Thr Ala Ala Gly Ile Thr Leu Gly Met Asp Glu Leu Tyr
                805                 810                 815
Lys Ser Gly Leu Arg Ser Arg Arg Ala His
                820                 825

<210> SEQ ID NO 26
<211> LENGTH: 5007
<212> TYPE: DNA
<213> ORGANISM: Artificial Sequence
```

<220> FEATURE:
<223> OTHER INFORMATION: Rat alpha2-CFP_T172D, pACE plasmid

<400> SEQUENCE: 26

| | | | | | |
|---|---|---|---|---|---|
| ggaattccag | ataacttcgt | ataatgtatg | ctatacgaag | ttatggtacc | gcggccgcgt | 60 |
| agaggatctg | ttgatcagca | gttcaacctg | ttgatagtac | ttcgttaata | cagatgtagg | 120 |
| tgttggcacc | atgcataact | ataacggtcc | taaggtagcg | acctaggtat | cgataatacg | 180 |
| actcactata | ggggaattgt | gagcggataa | caattcccct | ctagaaataa | ttttgtttaa | 240 |
| ctttaagaag | gagatataat | gggcagtagt | caccatcacc | accaccatca | tcaccatcat | 300 |
| agtagtgaaa | acctgtattt | tcagggcat | atggctgaga | agcagaagca | cgacgggcgt | 360 |
| gtgaagatcg | acactacgt | gctggggac | accctgggcg | tcggcacctt | cggcaaagtg | 420 |
| aagattggag | aacatcaatt | gacaggccat | aaagtggcag | ttaagatctt | aaatagacag | 480 |
| aagattcgca | gtttagatgt | tgttggaaaa | ataaaacgag | aaattcaaaa | tcttaaactc | 540 |
| tttcgtcatc | ctcatattat | caaactctac | caagtgatca | gcactccaac | agactttttt | 600 |
| atggtaatgg | aatatgtgtc | tggaggtgaa | ttgttcgact | acatctgtaa | acacgggagg | 660 |
| gttgaagagg | tggaagctcg | ccggctcttc | cagcagattc | tgtctgccgt | ggactactgt | 720 |
| cacaggcaca | tggttgtcca | cagggacctg | aagccagaga | acgtgttgct | ggacgcccag | 780 |
| atgaatgcta | gatagctga | cttcggactc | tctaatatga | tgtcagatgg | tgaatttcta | 840 |
| cgagacagct | gtggatcgcc | aaattatgca | gcaccggagg | tcatctcagg | aaggctgtat | 900 |
| gcgggtcctg | aggttgatat | ctggagctgt | ggtgttatcc | tgtatgccct | tctctgtggc | 960 |
| accctcccgt | tcgacgatga | gcacgtgcct | acgctcttta | agaagatccg | aggggtgtg | 1020 |
| ttctacatcc | cggagtatct | caaccgttct | attgccactc | tgctgatgca | catgctgcag | 1080 |
| gtggacccct | tgaagcgagc | aactatcaaa | gacatacgag | agcatgaatg | gtttaaacag | 1140 |
| gatttgccca | gttacctctt | tcctgaagac | ccctcctatg | atgctaacgt | cattgatgat | 1200 |
| gaggctgtga | agaagtatg | tgaaaaattt | gagtgtacag | aatcagaagt | gatgaacagt | 1260 |
| ttatacagtg | gtgaccctca | agaccagctc | gcagtggctt | atcatctcat | cattgacaat | 1320 |
| cggagaataa | tgaaccaagc | cagtgagttc | tacctcgcct | ccagtcctcc | aacgggttcc | 1380 |
| ttcatggacg | atagtgccat | gcatattccc | cccggcctga | accacatcc | tgaaaggatg | 1440 |
| ccacctctca | tagcagacag | ccccaaagca | cgctgtccac | tggatgcact | caacacaact | 1500 |
| aagcccaaat | ctttagctgt | gaaaaaagcc | aagtggcacc | ttgggatccg | aagccagagc | 1560 |
| aaaccatacg | acattatggc | ggaggtgtac | cgagctatga | agcagctgga | ctttgaatgg | 1620 |
| aaggtagtga | atgcatacca | tcttcgagta | agaagaaaaa | acccagtgac | tggcaattac | 1680 |
| gtgaaaatga | gcttacagct | ttacctggtt | gacaatcgga | gctatctgct | ggactttaaa | 1740 |
| agcatcgatg | atgaggtggt | ggagcagagg | tctggttctt | caacacctca | gcgctcctgt | 1800 |
| tctgctgccg | gcctccacag | acctcggtca | agtgtcgatt | ccagcacagc | cgagaaccat | 1860 |
| tcactgtctg | gctctctcac | tggttctttg | actggcagca | ctttgtcctc | cgcttccccg | 1920 |
| cgcctgggca | gtcataccat | ggattttttt | gaaatgtgcg | ccagtctat | cactgctttta | 1980 |
| gcccgtaagc | ttatggtgag | caaggcgag | gagctgttca | ccggggtggt | gcccatcctg | 2040 |
| gtcgagctgg | acggcgacgt | aaacggccac | aagttcagcg | tgtccggcga | gggcgagggc | 2100 |
| gatgccacct | acggcaagct | gaccctgaag | ttcatctgca | ccaccggcaa | gctgcccgtg | 2160 |
| ccctggccca | ccctcgtgac | caccctgacc | tggggcgtgc | agtgcttcag | ccgctacccc | 2220 |

```
gaccacatga agcagcacga cttcttcaag tccgccatgc ccgaaggcta cgtccaggag    2280
cgcaccatct tcttcaagga cgacggcaac tacaagaccc gcgccgaggt gaagttcgag    2340
ggcgacaccc tggtgaaccg catcgagctg aagggcatcg acttcaagga ggacggcaac    2400 atcctgggc acaagctgga gtacaactac atcagccaca cgtctatat caccgccgac      2460 aagcagaaga acggcatcaa ggccaacttc aagatccgcc acaacatcga ggacggcagc    2520
gtgcagctcg ccgaccacta ccagcagaac cccccatcg cgacggccc cgtgctgctg      2580 cccgacaacc actacctgag cacccagtcc gccctgagca agacccccaa cgagaagcgc    2640
gatcacatgg tcctgctgga gttcgtgacc gccgccggga tcactctcgg catggacgag    2700
ctgtacaagt ccggactcag atctcgacga gctcactgat aactcgagag atccggctgc    2760
taacaaagcc cgaaaggaag ctgagttggc tgctgccacc gctgagcaat aactagcata    2820
accccttggg gcctctaaac gggtcttgag gggttttttg gtttaaaccc atctaattgg    2880
actagtagcc cgcctaatga gcgggctttt ttttaattcc cctatttgtt tattttcta    2940 aatacattca aatatgtatc cgctcatgag acaataaccc tgataaatgc ttcaataata    3000 ttgaaaagg aagagtatga gtattcaaca tttccgtgtc gcccttattc ccttttttgc     3060 ggcatttttgc cttcctgttt ttgctcaccc agaaacgctc gtgaaagtaa agacgcaga    3120 ggaccaattg ggggcacgag tgggatacat agaactggac ttgaatagcg gtaaaatcct    3180
tgagagtttt cgccctgaag agcgttttcc aatgatgagc actttcaaag ttctgctatg    3240
tggagcagta ttatcccgtg tagatgcggg gcaagagcaa ctcggacgac gaatacacta    3300
ttcgcagaat gacttggttg aatactcccc agtgacagaa aagcaccta cggacggaat    3360 gacggtaaga gaattatgta gtgccgccat aacgatgagt gataacactg cggcgaactt    3420
acttctgaca accatcggtg gaccgaagga attaaccgct tttttgcaca atatgggaga    3480
ccatgtaact cgccttgacc gttgggaacc agaactgaat gaagccatac caaacgacga    3540
gcgagacacc acaatgcctg cggcaatggc aacaacatta cgcaaactat taactggcga    3600
actacttact ctggcttcac ggcaacaatt aatagactgg cttgaagcgg ataaagttgc    3660
aggaccacta ctgcgttcgg cacttcctgc tggctggttt attgctgata atctggggc     3720 aggagagcgt ggttcacggg gtatcattgc cgcacttgga ccagatggta agccttcccg    3780
tatcgtagtt atctacacga cgggtagtca ggcaactatg gacgaacgaa atagacagat    3840
tgctgaaata ggggcttcac tgattaagca ttggtaaacc gatacaatta aaggctcctt    3900
ttggagcctt ttttttgga cggaccggta gaaaagatca aaggatcttc ttgagatcct    3960 tttttctgc gcgtaatctg ctgcttgcaa acaaaaaaac caccgctacc agcggtggtt    4020
tgtttgccgg atcaagagct accaactctt tttccgaagg taactggctt cagcagagcg    4080
cagataccaa atactgtcct tctagtgtag ccgtagttag gccaccactt caagaactct    4140
gtagcaccgc ctacatacct cgctctgcta atcctgttac cagtggctgc tgccagtggc    4200
gataagtcgt gtcttaccgg gttggactca agacgatagt taccggataa ggcgcagcgg    4260
tcgggctgaa cggggggttc gtgcacacag cccagcttgg agcgaacgac ctacaccgaa    4320
ctgagatacc tacagcgtga gctatgagaa agcgccacgc ttcccgaagg gagaaaggcg    4380
gacaggtatc cggtaagcgg cagggtcgga acaggagagc gcacgaggga gcttccaggg    4440
ggaaacgcct ggtatcttta tagtcctgtc gggtttcgcc acctctgact tgagcgtcga    4500
tttttgtgat gctcgtcagg ggggcggagc ctatggaaaa acgccagcaa cgcggccttt    4560
ttacggttcc tggccttttg ctggcctttt gctcacatgt tctttcctgc gttatcccct    4620
```

```
gattctgtgg ataaccgtat taccgccttt gagtgagctg ataccgctcg ccgcagccga    4680
acgaccgagc gcagcgagtc agtgagcgag gaagcggaag agcgcctgat gcggtatttt    4740
ctccttacgc atctgtgcgg tatttcacac cgcaatggtg cactctcagt acaatctgct    4800
ctgatgccgc atagttaagc cagtatacac tccgctatcg ctacgtgact gggtcatggc    4860
tgcgccccga cacccgccaa cacccgctga cgcgccctga cgggcttgtc tgctcccggc    4920
atccgcttac agacaagctg tgaccgtctc cgggagctgc atgtgtcaga ggttttcacc    4980
gtcatcaccg aaacgcgcga ggcaggg                                        5007
```

<210> SEQ ID NO 27
<211> LENGTH: 826
<212> TYPE: PRT
<213> ORGANISM: Artificial Sequence
<220> FEATURE:
<223> OTHER INFORMATION: Rat alpha2-CFP_T172D

<400> SEQUENCE: 27

```
Met Gly Ser Ser His His His His His His Ser Ser
1               5                  10                  15

Glu Asn Leu Tyr Phe Gln Gly His Met Ala Glu Lys Gln Lys His Asp
            20                  25                  30

Gly Arg Val Lys Ile Gly His Tyr Val Leu Gly Asp Thr Leu Gly Val
        35                  40                  45

Gly Thr Phe Gly Lys Val Lys Ile Gly Glu His Gln Leu Thr Gly His
    50                  55                  60

Lys Val Ala Val Lys Ile Leu Asn Arg Gln Lys Ile Arg Ser Leu Asp
65                  70                  75                  80

Val Val Gly Lys Ile Lys Arg Glu Ile Gln Asn Leu Lys Leu Phe Arg
                85                  90                  95

His Pro His Ile Ile Lys Leu Tyr Gln Val Ile Ser Thr Pro Thr Asp
            100                 105                 110

Phe Phe Met Val Met Glu Tyr Val Ser Gly Gly Glu Leu Phe Asp Tyr
        115                 120                 125

Ile Cys Lys His Gly Arg Val Glu Glu Val Glu Ala Arg Arg Leu Phe
    130                 135                 140

Gln Gln Ile Leu Ser Ala Val Asp Tyr Cys His Arg His Met Val Val
145                 150                 155                 160

His Arg Asp Leu Lys Pro Glu Asn Val Leu Leu Asp Ala Gln Met Asn
                165                 170                 175

Ala Lys Ile Ala Asp Phe Gly Leu Ser Asn Met Met Ser Asp Gly Glu
            180                 185                 190

Phe Leu Arg Asp Ser Cys Gly Ser Pro Asn Tyr Ala Ala Pro Glu Val
        195                 200                 205

Ile Ser Gly Arg Leu Tyr Ala Gly Pro Glu Val Asp Ile Trp Ser Cys
    210                 215                 220

Gly Val Ile Leu Tyr Ala Leu Leu Cys Gly Thr Leu Pro Phe Asp Asp
225                 230                 235                 240

Glu His Val Pro Thr Leu Phe Lys Lys Ile Arg Gly Gly Val Phe Tyr
                245                 250                 255

Ile Pro Glu Tyr Leu Asn Arg Ser Ile Ala Thr Leu Leu Met His Met
            260                 265                 270

Leu Gln Val Asp Pro Leu Lys Arg Ala Thr Ile Lys Asp Ile Arg Glu
        275                 280                 285
```

-continued

His Glu Trp Phe Lys Gln Asp Leu Pro Ser Tyr Leu Phe Pro Glu Asp
290                 295                 300

Pro Ser Tyr Asp Ala Asn Val Ile Asp Glu Ala Val Lys Glu Val
305                 310                 315                 320

Cys Glu Lys Phe Glu Cys Thr Glu Ser Glu Val Met Asn Ser Leu Tyr
                325                 330                 335

Ser Gly Asp Pro Gln Asp Gln Leu Ala Val Ala Tyr His Leu Ile Ile
                340                 345                 350

Asp Asn Arg Arg Ile Met Asn Gln Ala Ser Glu Phe Tyr Leu Ala Ser
                355                 360                 365

Ser Pro Pro Thr Gly Ser Phe Met Asp Asp Ser Ala Met His Ile Pro
370                 375                 380

Pro Gly Leu Lys Pro His Pro Glu Arg Met Pro Pro Leu Ile Ala Asp
385                 390                 395                 400

Ser Pro Lys Ala Arg Cys Pro Leu Asp Ala Leu Asn Thr Thr Lys Pro
                405                 410                 415

Lys Ser Leu Ala Val Lys Ala Lys Trp His Leu Gly Ile Arg Ser
                420                 425                 430

Gln Ser Lys Pro Tyr Asp Ile Met Ala Glu Val Tyr Arg Ala Met Lys
                435                 440                 445

Gln Leu Asp Phe Glu Trp Lys Val Val Asn Ala Tyr His Leu Arg Val
450                 455                 460

Arg Arg Lys Asn Pro Val Thr Gly Asn Tyr Val Lys Met Ser Leu Gln
465                 470                 475                 480

Leu Tyr Leu Val Asp Asn Arg Ser Tyr Leu Leu Asp Phe Lys Ser Ile
                485                 490                 495

Asp Asp Glu Val Val Glu Gln Arg Ser Gly Ser Ser Thr Pro Gln Arg
                500                 505                 510

Ser Cys Ser Ala Ala Gly Leu His Arg Pro Arg Ser Ser Val Asp Ser
                515                 520                 525

Ser Thr Ala Glu Asn His Ser Leu Ser Gly Ser Leu Thr Gly Ser Leu
530                 535                 540

Thr Gly Ser Thr Leu Ser Ser Ala Ser Pro Arg Leu Gly Ser His Thr
545                 550                 555                 560

Met Asp Phe Phe Glu Met Cys Ala Ser Leu Ile Thr Ala Leu Ala Arg
                565                 570                 575

Lys Leu Met Val Ser Lys Gly Glu Glu Leu Phe Thr Gly Val Val Pro
                580                 585                 590

Ile Leu Val Glu Leu Asp Gly Asp Val Asn Gly His Lys Phe Ser Val
                595                 600                 605

Ser Gly Glu Gly Glu Gly Asp Ala Thr Tyr Gly Lys Leu Thr Leu Lys
610                 615                 620

Phe Ile Cys Thr Thr Gly Lys Leu Pro Val Pro Trp Pro Thr Leu Val
625                 630                 635                 640

Thr Thr Leu Thr Trp Gly Val Gln Cys Phe Ser Arg Tyr Pro Asp His
                645                 650                 655

Met Lys Gln His Asp Phe Phe Lys Ser Ala Met Pro Glu Gly Tyr Val
                660                 665                 670

Gln Glu Arg Thr Ile Phe Phe Lys Asp Asp Gly Asn Tyr Lys Thr Arg
                675                 680                 685

Ala Glu Val Lys Phe Glu Gly Asp Thr Leu Val Asn Arg Ile Glu Leu
690                 695                 700

Lys Gly Ile Asp Phe Lys Glu Asp Gly Asn Ile Leu Gly His Lys Leu

```
                        705                 710                 715                 720
                Glu Tyr Asn Tyr Ile Ser His Asn Val Tyr Ile Thr Ala Asp Lys Gln
                                725                 730                 735

Lys Asn Gly Ile Lys Ala Asn Phe Lys Ile Arg His Asn Ile Glu Asp
                                740                 745                 750

Gly Ser Val Gln Leu Ala Asp His Tyr Gln Gln Asn Thr Pro Ile Gly
                                755                 760                 765

Asp Gly Pro Val Leu Leu Pro Asp Asn His Tyr Leu Ser Thr Gln Ser
                                770                 775                 780

Ala Leu Ser Lys Asp Pro Asn Glu Lys Arg Asp His Met Val Leu Leu
                785                 790                 795                 800

Glu Phe Val Thr Ala Ala Gly Ile Thr Leu Gly Met Asp Glu Leu Tyr
                                805                 810                 815

Lys Ser Gly Leu Arg Ser Arg Arg Ala His
                                820                 825

<210> SEQ ID NO 28
<211> LENGTH: 2839
<212> TYPE: DNA
<213> ORGANISM: Artificial Sequence
<220> FEATURE:
<223> OTHER INFORMATION: Rat gamma1_L128D+V129D, pDS plasmid

<400> SEQUENCE: 28
atgagggaag cggtgatcgc cgaagtatcg actcaactat cagaggtagt tggcgtcatc       60
gagcgccatc tcgaaccgac gttgctggcc gtacatttgt acggctccgc agtggatggc      120
ggcctgaagc cacacagtga tattgatttg ctggttacgg tgaccgtaag gcttgatgaa      180
acaacgcggc gagctttgat caacgacctt ttggaaactt cggcttcccc tggagagagc      240
gagattctcc gcgctgtaga agtcaccatt gttgtgcacg acgacatcat tccgtggcgt      300
tatccagcta agcgcgaact gcaatttgga gaatggcagc gcaatgacat tcttgcaggt      360
atcttcgagc cagccacgat cgacattgat ctggctatct tgctgacaaa agcaagagaa      420
catagcgttg ccttggtagg tccagcggcg gaggaactct ttgatccggt tcctgaacag      480
gatctatttg aggcgctaaa tgaaacctta acgctatgga actcgccgcc cgactgggct      540
ggcgatgagc gaaatgtagt gcttacgttg tcccgcattt ggtacagcgc agtaaccggc      600
aaaatcgcgc cgaaggatgt cgctgccgac tgggcaatgg agcgcctgcc ggcccagtat      660
cagcccgtca tacttgaagc tagacaggct tatcttggac aagaagaa tcgcttggcc      720 tcgcgcgcag atcagttgga agaatttgtc cactacgtga aaggcgagat caccaaggta      780
gtcggcaaat aatgtctaac aattcgttca agccgacgga tctatgtcgg gtgcggagaa      840
agaggtaatg aaatggcacc taggtatcga taatacgact cactataggg aattgtgag       900 cggataacaa ttcccctcta gaaataattt tgtttaactt taagaaggag atatacatat      960
ggagtcggtt gctgcagaga gcgctccagc tccggagaat gaacactctc aagagacccc     1020
ggaatcgaac agtagtgtgt acaccacctt catgaagtct catcgctgct atgacctgat     1080
ccccacaagc tccaagctgg tggtatttga tacttcgctg caggtaaaga aagccttctt     1140
tgccctggtg actaacggtg ttcgtgctgc cccttttgtg gatagtaaga agcagagctt     1200
tgtgggcatg ctgaccatca ctgacttcat caatattctg caccgatact acaagtcagc     1260
cctggtgcag atctatgaac tggaggagca agatagag acttggagag aggtctacct     1320
gcaggactcc tttaagccag atgattgcat ttctccaaat gccagcttgt tcgatgctgt     1380
```

-continued

```
ctcttcatta attcgaaata agatccacag gcttccagtt attgacccgg agtcaggcaa    1440
caccttgtac attcttactc acaagcggat cctcaagttc ctcaagttgt ttatcactga    1500
gttccccaag ccggaattca tgtctaagtc tctggaagag ctacagattg gcacctacgc    1560
caatattgcc atggtccgta ccactacacc tgtctatgtg gctctgggca tctttgtaca    1620
gcaccgagtc tccgccttgc ctgtggtgga tgagaaaggg cgtgtggtgg acatctactc    1680
caagtttgat gtgattaatt tggcagcaga aaagacatac aacaacctag atgtgtctgt    1740
gacaaaagcc ctacagcacc ggtcacacta cttcgagggt gttctcaagt gctacctaca    1800
tgagactcta gaagcaatca tcaatagact ggtggaagca gaggttcacc gtctggtggt    1860
ggtggatgaa catgacgtgg tcaagggcat tgtatcgctg tctgacatct acaggctct    1920 ggtgctcaca ggtggagaga agaagccctg ataactagtt ccgtttaaac ccatgtgcct    1980
ggcagataac ttcgtataat gtatgctata cgaagttatg gtacgtacta agctctcatg    2040
tttcacgtac taagctctca tgtttaacgt actaagctct catgtttaac gaactaaacc    2100
ctcatggcta acgtactaag ctctcatggc taacgtacta agctctcatg tttcacgtac    2160
taagctctca tgtttgaaca ataaaattaa tataaatcag caacttaaat agcctctaag    2220
gttttaagtt ttataagaaa aaaagaata tataaggctt ttaaagcttt taaggtttaa    2280
cggttgtgga caacaagcca gggatgtaac gcactgagaa gcccttagag cctctcaaag    2340
caattttgag tgcacagga acacttaacg gctgacataa ttcagcttca cgctgccgca    2400
agcactcagg gcgcaagggc tgctaaagga agcggaacac gtagaaagcc agtccgcaga    2460
aacggtgctg accccggatg aatgtcagct gggaggcaga ataaatgatc atatcgtcaa    2520
ttattacctc cacggggaga gcctgagcaa actggcctca ggcatttgag aagcacacgg    2580
tcacactgct tccggtagtc aataaaccgg taagtagcgt atgcgctcac gcaactggtc    2640
cagaaccttg accgaacgca gcggtggtaa cggcgcagtg gcggttttca tggcttgtta    2700
tgactgtttt tttggggtac agtctatgcc tcgggcatcc aagcagcaag cgcgttacgc    2760
cgtgggtcga tgtttgatgt tatggagcag caacgatgtt acgcagcagg gcagtcgccc    2820
taaaacaaag ttaaacatc                                                 2839
```

<210> SEQ ID NO 29
<211> LENGTH: 330
<212> TYPE: PRT
<213> ORGANISM: Artificial Sequence
<220> FEATURE:
<223> OTHER INFORMATION: Rat gamma1_L128D+V129D, pDS plasmid

<400> SEQUENCE: 29

```
Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
                20                  25                  30

Lys Ser His Arg Cys Tyr Asp Leu Ile Pro Thr Ser Ser Lys Leu Val
            35                  40                  45

Val Phe Asp Thr Ser Leu Gln Val Lys Lys Ala Phe Ala Leu Val
        50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
```

```
                100                 105                 110
Ile Glu Thr Trp Arg Glu Val Tyr Leu Gln Asp Ser Phe Lys Pro Asp
        115                 120                 125

Asp Cys Ile Ser Pro Asn Ala Ser Leu Phe Asp Ala Val Ser Ser Leu
130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
    290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro
                325                 330

<210> SEQ ID NO 30
<211> LENGTH: 2839
<212> TYPE: DNA
<213> ORGANISM: Artificial Sequence
<220> FEATURE:
<223> OTHER INFORMATION: Rat gamma1_S315P, pDS plasmid

<400> SEQUENCE: 30
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc acacagtga tattgatttg ctggttacgg tgaccgtaag gcttgatgaa      180
acaacgcggc gagctttgat caacgacctt ttggaaactt cggcttcccc tggagagagc     240
gagattctcc gcgctgtaga agtcaccatt gttgtgcacg acgacatcat tccgtggcgt     300
tatccagcta agcgcgaact gcaatttgga gaatggcagc gcaatgacat tcttgcaggt     360
atcttcgagc cagccacgat cgacattgat ctggctatct tgctgacaaa agcaagagaa     420
catagcgttg ccttggtagg tccagcggcg gaggaactct ttgatccggt tcctgaacag     480
gatctatttg aggcgctaaa tgaaaccttaacgctatgga actcgccgcc cgactgggct     540
ggcgatgagc gaaatgtagt gcttacgttg tcccgcattt ggtacagcgc agtaaccggc     600
aaaatcgcgc cgaaggatgt cgctgccgac tgggcaatgg agcgcctgcc ggcccagtat     660
cagcccgtca tacttgaagc tagacaggct tatcttggac aagaagaaga tcgcttggcc     720
tcgcgcgcag atcagttgga agaatttgtc cactacgtga aggcgagat caccaaggta     780
```

```
gtcggcaaat aatgtctaac aattcgttca agccgacgga tctatgtcgg gtgcggagaa    840
agaggtaatg aaatggcacc taggtatcga taatacgact cactataggg gaattgtgag    900
cggataacaa ttcccctcta gaaataattt tgtttaactt taagaaggag atatacatat    960
ggagtcggtt gctgcagaga gcgctccagc tccggagaat gaacactctc aagagacccc   1020
ggaatcgaac agtagtgtgt acaccacctt catgaagtct catcgctgct atgacctgat   1080
ccccacaagc tccaagctgg tggtatttga tacttcgctg caggtaaaga aagccttctt   1140
tgccctggtg actaacggtg ttcgtgctgc ccctttgtgg gatagtaaga agcagagctt   1200
tgtgggcatg ctgaccatca ctgacttcat caatattctg caccgatact acaagtcagc   1260
cctggtgcag atctatgaac tggaggagca agatagag acttggagag aggtctacct   1320
gcaagactcc tttaagccac ttgtctgcat ttctccaaat gccagcttgt tcgatgctgt   1380
ctcttcatta attcgaaata agatccacag gcttccagtt attgacccgg agtcaggcaa   1440
caccttgtac attcttactc acaagcggat cctcaagttc ctcaagttgt ttatcactga   1500
gttccccaag ccggaattca tgtctaagtc tctggaagag ctacagattg caccctacgc   1560
caatattgcc atggtccgta ccactacacc tgtctatgtg gctctgggca tctttgtaca   1620
gcaccgagtc tccgccttgc ctgtggtgga tgagaaaggg cgtgtggtgg acatctactc   1680
caagtttgat gtgattaatt tggcagcaga aaagacatac aacaacctag atgtgtctgt   1740
gacaaaagcc ctacagcacc ggtcacacta cttcgagggt gttctcaagt gctacctaca   1800
tgagactcta gaagcaatca tcaatagact ggtggaagca gaggttcacc gtctggtggt   1860
ggtggatgaa catgacgtgg tcaagggcat tgtatcgctg cccgatatct tacaggctct   1920
ggtgctcaca ggtggagaga agaagccctg ataactagtt ccgtttaaac ccatgtgcct   1980
ggcagataac ttcgtataat gtatgctata cgaagttatg gtacgtacta agctctcatg   2040
tttcacgtac taagctctca tgtttaacgt actaagctct catgtttaac gaactaaacc   2100
ctcatggcta acgtactaag ctctcatggc taacgtacta agctctcatg tttcacgtac   2160
taagctctca tgtttgaaca ataaaattaa tataaatcag caacttaaat agcctctaag   2220
gttttaagtt ttataagaaa aaaaagaata tataaggctt ttaaagcttt taaggtttaa   2280
cggttgtgga caacaagcca gggatgtaac gcactgagaa gcccttagag cctctcaaag   2340
caattttgag tgacacagga acacttaacg gctgacataa ttcagcttca cgctgccgca   2400
agcactcagg gcgcaagggc tgctaaagga agcggaacac gtagaaagcc agtccgcaga   2460
aacggtgctg accccggatg aatgtcagct gggaggcaga ataaatgatc atatcgtcaa   2520
ttattacctc cacggggaga gcctgagcaa actggcctca ggcatttgag aagcacacgg   2580
tcacactgct tccggtagtc aataaaccgg taagtagcgt atgcgctcac gcaactggtc   2640
cagaaccttg accgaacgca gcggtggtaa cggcgcagtg gcggttttca tggcttgtta   2700
tgactgtttt tttggggtac agtctatgcc tcggcatcc aagcagcaag cgcgttacgc   2760
cgtgggtcga tgtttgatgt tatggagcag caacgatgtt acgcagcagg gcagtcgccc   2820
taaaacaaag ttaaacatc                                                2839
```

<210> SEQ ID NO 31  
<211> LENGTH: 330  
<212> TYPE: PRT  
<213> ORGANISM: Artificial Sequence  
<220> FEATURE:  
<223> OTHER INFORMATION: Rat gamma1_S315P

<400> SEQUENCE: 31

```
Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
    50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Asp Glu
    290                 295                 300

His Asp Val Val Lys Gly Ile Val Ser Leu Pro Asp Ile Leu Gln Ala
305                 310                 315                 320

Leu Val Leu Thr Gly Gly Glu Lys Lys Pro
                325                 330
```

<210> SEQ ID NO 32
<211> LENGTH: 2839
<212> TYPE: DNA
<213> ORGANISM: Artificial Sequence
<220> FEATURE:
<223> OTHER INFORMATION: Rat gamma1_V275G+L276G, pDS plasmid

<400> SEQUENCE: 32

```
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
```

```
ggcctgaagc cacacagtga tattgatttg ctggttacgg tgaccgtaag gcttgatgaa      180
acaacgcggc gagctttgat caacgacctt ttggaaactt cggcttcccc tggagagagc      240
gagattctcc gcgctgtaga agtcaccatt gttgtgcacg acgacatcat tccgtggcgt      300
tatccagcta agcgcgaact gcaatttgga gaatggcagc gcaatgacat tcttgcaggt      360
atcttcgagc cagccacgat cgacattgat ctggctatct tgctgacaaa agcaagagaa      420
catagcgttg ccttggtagg tccagcggcg gaggaactct ttgatccggt tcctgaacag      480
gatctatttg aggcgctaaa tgaaaaccta acgctatgga actcgccgcc cgactgggct      540
ggcgatgagc gaaatgtagt gcttacgttg tcccgcattt ggtacagcgc agtaaccggc      600
aaaatcgcgc cgaaggatgt cgctgccgac tgggcaatgg agcgcctgcc ggcccagtat      660
cagcccgtca tacttgaagc tagacaggct tatcttggac aagaagaaga tcgcttggcc      720
tcgcgcgcag atcagttgga agaatttgtc cactacgtga aaggcgagat caccaaggta      780
gtcggcaaat aatgtctaac aattcgttca agccgacgga tctatgtcgg gtgcggagaa      840
agaggtaatg aaatggcacc taggtatcga taatacgact cactataggg gaattgtgag      900
cggataacaa ttcccctcta gaaataattt tgtttaactt taagaaggag atatacatat      960
ggagtcggtt gctgcagaga gcgctccagc tccggagaat gaacactctc aagagacccc     1020
ggaatcgaac agtagtgtgt acaccacctt catgaagtct catcgctgct atgacctgat     1080
ccccacaagc tccaagctgg tggtatttga tacttcgctg caggtaaaga aagcttctt     1140 tgccctggtg actaacggtg ttcgtgctgc ccctttgtgg gatagtaaga agcagagctt     1200
tgtgggcatg ctgaccatca ctgacttcat caatattctg caccgatact acaagtcagc     1260
cctggtgcag atctatgaac tggaggagca caagatagag acttggagag aggtctacct     1320
gcaagactcc tttaagccac ttgtctgcat ttctccaaat gccagcttgt tcgatgctgt     1380
ctcttcatta attcgaaata agatccacag gcttccagtt attgacccgg agtcaggcaa     1440
caccttgtac attcttactc acaagcggat cctcaagttc ctcaagttgt ttatcactga     1500
gttccccaag ccggaattca tgtctaagtc tctggaagag ctacagattg caacctacgc     1560
caatattgcc atggtccgta ccactacacc tgtctatgtg gctctgggca tctttgtaca     1620
gcaccgagtc tccgccttgc ctgtggtgga tgagaaaggg cgtgtggtgg acatctactc     1680
caagtttgat gtgattaatt tggcagcaga aaagacatac aacaacctag atgtgtctgt     1740
gacaaaagcc ctacagcacc ggtcacacta cttcgagggt ggaggtaagt gctacctaca     1800
tgagactctc gaggcaatca tcaatagact ggtggaagca gaggttcacc gtctggtggt     1860
ggtggatgaa catgacgtgg tcaagggcat tgtatcgctg tctgacatct tacaggctct     1920
ggtgctcaca ggtggagaga agaagccctg ataactagtt ccgtttaaac ccatgtgcct     1980
ggcagataac ttcgtataat gtatgctata cgaagttatg gtacgtacta agctctcatg     2040
tttcacgtac taagctctca tgtttaacgt actaagctct catgtttaac gaactaaacc     2100
ctcatggcta acgtactaag ctctcatggc taacgtacta agctctcatg tttcacgtac     2160
taagctctca tgtttgaaca ataaaattaa tataaatcag caacttaaat agcctctaag     2220
gttttaagtt ttataagaaa aaaaagaata tataaggctt ttaaagcttt taaggtttaa     2280
cggttgtgga caacaagcca gggatgtaac gcactgagaa gcccttagag cctctcaaag     2340
caattttgag tgacacagga acacttaacg gctgacataa ttcagcttca cgctgccgca     2400
agcactcagg gcgcaagggc tgctaaagga agcggaacac gtagaaagcc agtccgcaga     2460
aacggtgctg accccggatg aatgtcagct gggaggcaga ataaatgatc atatcgtcaa     2520
```

```
ttattacctc cacgggaga gcctgagcaa actggcctca ggcatttgag aagcacacgg    2580
tcacactgct tccggtagtc aataaaccgg taagtagcgt atgcgctcac gcaactggtc    2640
cagaaccttg accgaacgca gcggtggtaa cggcgcagtg gcggttttca tggcttgtta    2700
tgactgtttt tttggggtac agtctatgcc tcgggcatcc aagcagcaag cgcgttacgc    2760
cgtgggtcga tgtttgatgt tatggagcag caacgatgtt acgcagcagg gcagtcgccc    2820
taaaacaaag ttaaacatc                                                 2839
```

<210> SEQ ID NO 33
<211> LENGTH: 330
<212> TYPE: PRT
<213> ORGANISM: Artificial Sequence
<220> FEATURE:
<223> OTHER INFORMATION: Rat gamma1_V275G+L276G

<400> SEQUENCE: 33

```
Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
                20                  25                  30

Lys Ser His Arg Cys Tyr Asp Leu Ile Pro Thr Ser Ser Lys Leu Val
            35                  40                  45

Val Phe Asp Thr Ser Leu Gln Val Lys Lys Ala Phe Phe Ala Leu Val
        50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Gly Gly Lys Cys Tyr Leu His Glu Thr Leu Glu Ala Ile Ile
        275                 280                 285

Asn Arg Leu Val Glu Ala Glu Val His Arg Leu Val Val Val Asp Glu
    290                 295                 300
```

His Asp Val Val Lys Gly Ile Val Ser Leu Ser Asp Ile Leu Gln Ala
305                 310                 315                 320

Leu Val Leu Thr Gly Gly Glu Lys Lys Pro
            325                 330

<210> SEQ ID NO 34
<211> LENGTH: 3640
<212> TYPE: DNA
<213> ORGANISM: Artificial Sequence
<220> FEATURE:
<223> OTHER INFORMATION: Rat gamma1-YFP_L128D+V129D, pDS plasmid

<400> SEQUENCE: 34

| | | | | | |
|---|---|---|---|---|---|
| atgagggaag | cggtgatcgc | cgaagtatcg | actcaactat | cagaggtagt | tggcgtcatc | 60 |
| gagcgccatc | tcgaaccgac | gttgctggcc | gtacatttgt | acggctccgc | agtggatggc | 120 |
| ggcctgaagc | cacacagtga | tattgatttg | ctggttacgg | tgaccgtaag | gcttgatgaa | 180 |
| acaacgcggc | gagctttgat | caacgacctt | ttggaaactt | cggcttcccc | tggagagagc | 240 |
| gagattctcc | gcgctgtaga | agtcaccatt | gttgtgcacg | acgacatcat | tccgtggcgt | 300 |
| tatccagcta | agcgcgaact | gcaatttgga | gaatggcagc | gcaatgacat | tcttgcaggt | 360 |
| atcttcgagc | cagccacgat | cgacattgat | ctggctatct | tgctgacaaa | agcaagagaa | 420 |
| catagcgttg | ccttggtagg | tccagcggcg | gaggaactct | tgatccggt | tcctgaacag | 480 |
| gatctatttg | aggcgctaaa | tgaaaccta | acgctatgga | actcgccgcc | cgactgggct | 540 |
| ggcgatgagc | gaaatgtagt | gcttacgttg | tcccgcattt | ggtacagcgc | agtaaccggc | 600 |
| aaaatcgcgc | cgaaggatgt | cgctgccgac | tgggcaatgg | agcgcctgcc | ggcccagtat | 660 |
| cagcccgtca | tacttgaagc | tagacaggct | tatcttggac | aagaagaaga | tcgcttggcc | 720 |
| tcgcgcgcag | atcagttgga | agaatttgtc | cactacgtga | aggcgagat | caccaaggta | 780 |
| gtcggcaaat | aatgtctaac | aattcgttca | agccgacgga | tctatgtcgg | gtgcggagaa | 840 |
| agaggtaatg | aaatggcacc | taggtatcga | taatacgact | cactataggg | gaattgtgag | 900 |
| cggataacaa | ttcccctcta | gaaataattt | tgtttaactt | taagaaggag | atatacatat | 960 |
| ggagtcggtt | gctgcagaga | gcgctccagc | tccggagaat | gaacactctc | aagagacccc | 1020 |
| ggaatcgaac | agtagtgtgt | acaccaccct | catgaagtct | catcgctgct | atgacctgat | 1080 |
| ccccacaagc | tccaagctgg | tggtatttga | tacttcgctg | caggtaaaga | aagccttctt | 1140 |
| tgccctggtg | actaacggtg | ttcgtgctgc | ccctttgtgg | gatagtaaga | agcagagctt | 1200 |
| tgtgggcatg | ctgaccatca | ctgacttcat | caatattctg | caccgatact | acaagtcagc | 1260 |
| cctggtgcag | atctatgaac | tggaggagca | caagatagag | acttggagag | aggtctacct | 1320 |
| gcaggactcc | tttaagccag | atgattgcat | ttctccaaat | gccagcttgt | tcgatgctgt | 1380 |
| ctcttcatta | attcgaaata | agatccacag | gcttccagtt | attgacccgg | agtcaggcaa | 1440 |
| caccttgtac | attcttactc | acaagcggat | cctcaagttc | ctcaagttgt | ttatcactga | 1500 |
| gttccccaag | ccggaattca | tgtctaagtc | tctggaagag | ctacagattg | gcacctacgc | 1560 |
| caatattgcc | atggtccgta | ccactacacc | tgtctatgtg | gctctgggca | tctttgtaca | 1620 |
| gcaccgagtc | tccgccttgc | ctgtggtgga | tgagaaaggg | cgtgtggtgg | acatctactc | 1680 |
| caagtttgat | gtgattaatt | tggcagcaga | aaagacatac | aacaacctag | atgtgtctgt | 1740 |
| gacaaaagcc | ctacagcacc | ggtcacacta | cttcgagggt | gttctcaagt | gctacctaca | 1800 |
| tgagactcta | gaagcaatca | tcaatagact | ggtggaagca | gaggttcacc | gtctggtggt | 1860 |

-continued

| | |
|---|---|
| ggtggatgaa catgacgtgg tcaagggcat tgtatcgctg tctgacatct acaggctct | 1920 |
| ggtgctcaca ggtggagaga agaagcccgc tagcatggtg agcaagggcg aggagctgtt | 1980 |
| caccggggtg gtgcccatcc tggtcgagct ggacggcgac gtaaacggcc acaagttcag | 2040 |
| cgtgtccggc gagggcgagg gcgatgccac ctacggcaag ctgaccctga agttcatctg | 2100 |
| caccaccggc aagctgcccg tgccctggcc cacccgtgt accaccttcg gctacggcct | 2160 |
| gcagtgcttc gcccgctacc ccgaccacat gaagcagcac gacttcttca gtccgccat | 2220 |
| gcccgaaggc tacgtccagg agcgcaccat cttcttcaag gacgacggca actacaagac | 2280 |
| ccgcgccgag gtgaagttcg agggcgacac cctggtgaac cgcatcgagc tgaagggcat | 2340 |
| cgacttcaag gaggacggca acatcctggg gcacaagctg gagtacaact acaacagcca | 2400 |
| caacgtctat atcatggccg acaagcagaa gaacggcatc aaggtgaact tcaagatccg | 2460 |
| ccacaacatc gaggacggca cgtgcagct cgccgaccac taccagcaga acacccccat | 2520 |
| cggcgacggc cccgtgctgc tgcccgacaa ccactacctg agctaccagt ccgcccctgag | 2580 |
| caaagacccc aacgagaagc gcgatcacat ggtcctgctg gagttcgtga ccgccgccgg | 2640 |
| gatcactctc ggcatggacg agctgtacaa gtccggactc agatctcgag ctcaagcttc | 2700 |
| gaattctgca gtcgacggta ccgcgggccc gggatccacc ggatctagat gataactagt | 2760 |
| tccgttaaaa cccatgtgcc tggcagataa cttcgtataa tgtatgctat acgaagttat | 2820 |
| ggtacgtact aagctctcat gtttcacgta ctaagctctc atgtttaacg tactaagctc | 2880 |
| tcatgtttaa cgaactaaac cctcatggct aacgtactaa gctctcatgg ctaacgtact | 2940 |
| aagctctcat gtttcacgta ctaagctctc atgtttgaac aataaaatta atataaatca | 3000 |
| gcaacttaaa tagcctctaa ggttttaagt tttataagaa aaaaagaat atataaggct | 3060 |
| tttaaagctt ttaaggttta acggttgtgg acaacaagcc agggatgtaa cgcactgaga | 3120 |
| agcccttaga gcctctcaaa gcaattttga gtgacacagg aacacttaac ggctgacata | 3180 |
| attcagcttc acgctgccgc aagcactcag ggcgcaaggg ctgctaaagg aagcggaaca | 3240 |
| cgtagaaagc cagtccgcag aaacggtgct gaccccggat gaatgtcagc tgggaggcag | 3300 |
| aataaatgat catatcgtca attattacct ccacggggag agcctgagca aactggcctc | 3360 |
| aggcatttga gaagcacacg gtcacactgc ttccggtagt caataaaccg gtaagtagcg | 3420 |
| tatgcgctca cgcaactggt ccagaacctt gaccgaacgc agcggtggta acggcgcagt | 3480 |
| ggcggttttc atggcttgtt atgactgttt ttttggggta cagtctatgc ctcgggcatc | 3540 |
| caagcagcaa gcgcgttacg ccgtgggtcg atgtttgatg ttatggagca gcaacgatgt | 3600 |
| tacgcagcag ggcagtcgcc ctaaaacaaa gttaaacatc | 3640 |

<210> SEQ ID NO 35
<211> LENGTH: 597
<212> TYPE: PRT
<213> ORGANISM: Artificial Sequence
<220> FEATURE:
<223> OTHER INFORMATION: Rat gamma1-YFP_L128D+V129D

<400> SEQUENCE: 35

Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

```
Val Phe Asp Thr Ser Leu Gln Val Lys Lys Ala Phe Phe Ala Leu Val
 50                  55                  60

Thr Asn Gly Val Arg Ala Ala Pro Leu Trp Asp Ser Lys Lys Gln Ser
 65                  70                  75                  80

Phe Val Gly Met Leu Thr Ile Thr Asp Phe Ile Asn Ile Leu His Arg
                 85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Asp
             115                 120                 125

Asp Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
            290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro Ala Ser Met Val Ser Lys
                325                 330                 335

Gly Glu Glu Leu Phe Thr Gly Val Val Pro Ile Leu Val Glu Leu Asp
            340                 345                 350

Gly Asp Val Asn Gly His Lys Phe Ser Val Ser Gly Glu Gly Glu Gly
        355                 360                 365

Asp Ala Thr Tyr Gly Lys Leu Thr Leu Lys Phe Ile Cys Thr Thr Gly
    370                 375                 380

Lys Leu Pro Val Pro Trp Pro Thr Leu Val Thr Thr Phe Gly Tyr Gly
385                 390                 395                 400

Leu Gln Cys Phe Ala Arg Tyr Pro Asp His Met Lys Gln His Asp Phe
                405                 410                 415

Phe Lys Ser Ala Met Pro Glu Gly Tyr Val Gln Glu Arg Thr Ile Phe
            420                 425                 430

Phe Lys Asp Asp Gly Asn Tyr Lys Thr Arg Ala Glu Val Lys Phe Glu
        435                 440                 445

Gly Asp Thr Leu Val Asn Arg Ile Glu Leu Lys Gly Ile Asp Phe Lys
    450                 455                 460

Glu Asp Gly Asn Ile Leu Gly His Lys Leu Glu Tyr Asn Tyr Asn Ser
```

```
                465                 470                 475                 480
            His Asn Val Tyr Ile Met Ala Asp Lys Gln Lys Asn Gly Ile Lys Val
                            485                 490                 495
            Asn Phe Lys Ile Arg His Asn Ile Glu Asp Gly Ser Val Gln Leu Ala
                            500                 505                 510
            Asp His Tyr Gln Gln Asn Thr Pro Ile Gly Asp Gly Pro Val Leu Leu
                            515                 520                 525
            Pro Asp Asn His Tyr Leu Ser Tyr Gln Ser Ala Leu Ser Lys Asp Pro
                            530                 535                 540
            Asn Glu Lys Arg Asp His Met Val Leu Leu Glu Phe Val Thr Ala Ala
            545                 550                 555                 560
            Gly Ile Thr Leu Gly Met Asp Glu Leu Tyr Lys Ser Gly Leu Arg Ser
                            565                 570                 575
            Arg Ala Gln Ala Ser Asn Ser Ala Val Asp Gly Thr Ala Gly Pro Gly
                            580                 585                 590
            Ser Thr Gly Ser Arg
                    595

<210> SEQ ID NO 36
<211> LENGTH: 3640
<212> TYPE: DNA
<213> ORGANISM: Artificial Sequence
<220> FEATURE:
<223> OTHER INFORMATION: Rat gamma1-YFP_V275G+L276G, pDS plasmid

<400> SEQUENCE: 36
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc cacacagtga tattgatttg ctggttacgg tgaccgtaag gcttgatgaa     180
acaacgcggc gagctttgat caacgacctt ttggaaactt cggcttcccc tggagagagc     240
gagattctcc gcgctgtaga agtcaccatt gttgtgcacg acgacatcat tccgtggcgt     300
tatccagcta agcgcgaact gcaatttgga gaatggcagc gcaatgacat tcttgcaggt     360
atcttcgagc cagccacgat cgacattgat ctggctatct tgctgacaaa agcaagagaa     420
catagcgttg ccttggtagg tccagcggcg gaggaactct ttgatccggt tcctgaacag     480
gatctatttg aggcgctaaa tgaaacctta acgctatgga actcgccgcc cgactgggct     540
ggcgatgagc gaaatgtagt gcttacgttg tcccgcattt ggtacagcgc agtaaccggc     600
aaaatcgcgc cgaaggatgt cgctgccgac tgggcaatgg agcgcctgcc ggcccagtat     660
cagcccgtca tacttgaagc tagacaggct tatcttggac aagaagaaga tcgcttggcc     720
tcgcgcgcag atcagttgga agaatttgtc cactacgtga aaggcgagat caccaaggta     780
gtcggcaaat aatgtctaac aattcgttca agccgacgga tctatgtcgg gtgcggagaa     840
agaggtaatg aaatggcacc taggtatcga taatacgact cactataggg aattgtgag     900
cggataacaa ttcccctcta gaaataattt tgtttaactt taagaaggag atatacatat     960
ggagtcggtt gctgcagaga gcgctccagc tccggagaat gaacactctc aagagacccc    1020
ggaatcgaac agtagtgtgt acaccacctt catgaagtct catcgctgct atgacctgat    1080
ccccacaagc tccaagctgg tggtatttga tacttcgctg caggtaaaga aagccttctt    1140
tgccctggtg actaacggtg ttcgtgctgc ccctttgtgg atagtaaga agcagagctt    1200
tgtgggcatg ctgaccatca ctgacttcat caatattctg caccgatact acaagtcagc    1260
cctggtgcag atctatgaac tggaggagca agatagag acttggagag aggtctacct    1320
```

-continued

```
gcaagactcc tttaagccac ttgtctgcat ttctccaaat gccagcttgt tcgatgctgt    1380
ctcttcatta attcgaaata agatccacag gcttccagtt attgacccgg agtcaggcaa    1440
caccttgtac attcttactc acaagcggat cctcaagttc ctcaagttgt ttatcactga    1500
gttccccaag ccggaattca tgtctaagtc tctggaagag ctacagattg gcacctacgc    1560
caatattgcc atggtccgta ccactacacc tgtctatgtg gctctgggca tctttgtaca    1620
gcaccgagtc tccgccttgc ctgtggtgga tgagaaaggg cgtgtggtgg acatctactc    1680
caagtttgat gtgattaatt tggcagcaga aaagacatac aacaacctag atgtgtctgt    1740
gacaaaagcc ctacagcacc ggtcacacta cttcgagggt ggaggtaagt gctacctaca    1800
tgagactctc gaggcaatca tcaatagact ggtggaagca gaggttcacc gtctggtggt    1860
ggtggatgaa catgacgtgg tcaagggcat tgtatcgctg tctgacatct acaggctct    1920 ggtgctcaca ggtggagaga agaagcccgc tagcatggtg agcaagggcg aggagctgtt    1980
caccggggtg gtgcccatcc tggtcgagct ggacggcgac gtaaacggcc acaagttcag    2040
cgtgtccggc gagggcgagg gcgatgccac ctacggcaag ctgaccctga agttcatctg    2100
caccaccggc aagctgcccg tgccctggcc caccctcgtg accaccttcg gctacggcct    2160
gcagtgcttc gcccgctacc ccgaccacat gaagcagcac gacttcttca agtccgccat    2220
gcccgaaggc tacgtccagg agcgcaccat cttcttcaag gacgacggca actacaagac    2280
ccgcgccgag gtgaagttcg agggcgacac cctggtgaac cgcatcgagc tgaagggcat    2340
cgacttcaag gaggacggca acatcctggg gcacaagctg gagtacaact acaacagcca    2400
caacgtctat atcatggccg acaagcagaa gaacggcatc aaggtgaact tcaagatccg    2460
ccacaacatc gaggacggca gcgtgcagct cgccgaccac taccagcaga cacccccat     2520 cggcgacggc cccgtgctgc tgcccgacaa ccactacctg agctaccagt ccgccctgag    2580
caaagacccc aacgagaagc gcgatcacat ggtcctgctg gagttcgtga ccgccgccgg    2640
gatcactctc ggcatggacg agctgtacaa gtccggactc agatctcgag ctcaagcttc    2700
gaattctgca gtcgacggta ccgcgggccc gggatccacc ggatctagat gataactagt    2760 tccgttttaaa cccatgtgcc tggcagataa cttcgtataa tgtatgctat acgaagttat    2820
ggtacgtact aagctctcat gtttcacgta ctaagctctc atgtttaacg tactaagctc    2880
tcatgtttaa cgaactaaac cctcatggct aacgtactaa gctctcatgg ctaacgtact    2940
aagctctcat gtttcacgta ctaagctctc atgtttgaac aataaaatta atataaatca    3000
gcaacttaaa tagcctctaa ggttttaagt tttataagaa aaaaagaat atataaggct    3060 tttaaagctt ttaaggttta acggttgtgg acaacaagcc agggatgtaa cgcactgaga    3120
agcccttaga gcctctcaaa gcaatttga gtgacacagg aacacttaac ggctgacata    3180
attcagcttc acgctgccgc aagcactcag ggcgcaaggg ctgctaaagg aagcggaaca    3240
cgtagaaagc cagtccgcag aaacggtgct gaccccggat gaatgtcagc tgggaggcag    3300
aataaatgat catatcgtca attattacct ccacggggag agcctgagca aactggcctc    3360
aggcatttga gaagcacacg gtcacactgc ttccggtagt caataaaccg gtaagtagcg    3420
tatgcgctca cgcaactggt ccagaacctt gaccgaacga gcggtggta acggcgcagt    3480 ggcggttttc atggcttgtt atgactgttt ttttggggta cagtctatgc ctcgggcatc    3540
caagcagcaa gcgcgttacg ccgtgggtcg atgtttgatg ttatggagca gcaacgatgt    3600
tacgcagcag ggcagtcgcc ctaaaacaaa gttaaacatc                           3640
```

<210> SEQ ID NO 37
<211> LENGTH: 597
<212> TYPE: PRT
<213> ORGANISM: Artificial Sequence
<220> FEATURE:
<223> OTHER INFORMATION: Rat gamma1-YFP_V275G+L276G

<400> SEQUENCE: 37

```
Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
    50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Gly Gly Lys Cys Tyr Leu His Glu Thr Leu Glu Ala Ile Ile
        275                 280                 285

Asn Arg Leu Val Glu Ala Glu Val His Arg Leu Val Val Val Asp Glu
    290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro Ala Ser Met Val Ser Lys
                325                 330                 335

Gly Glu Glu Leu Phe Thr Gly Val Val Pro Ile Leu Val Glu Leu Asp
            340                 345                 350

Gly Asp Val Asn Gly His Lys Phe Ser Val Ser Gly Glu Gly Glu Gly
        355                 360                 365
```

```
Asp Ala Thr Tyr Gly Lys Leu Thr Leu Lys Phe Ile Cys Thr Thr Gly
    370                 375                 380
Lys Leu Pro Val Pro Trp Pro Thr Leu Val Thr Thr Phe Gly Tyr Gly
385                 390                 395                 400
Leu Gln Cys Phe Ala Arg Tyr Pro Asp His Met Lys Gln His Asp Phe
                405                 410                 415
Phe Lys Ser Ala Met Pro Glu Gly Tyr Val Gln Glu Arg Thr Ile Phe
            420                 425                 430
Phe Lys Asp Asp Gly Asn Tyr Lys Thr Arg Ala Glu Val Lys Phe Glu
        435                 440                 445
Gly Asp Thr Leu Val Asn Arg Ile Glu Leu Lys Gly Ile Asp Phe Lys
450                 455                 460
Glu Asp Gly Asn Ile Leu Gly His Lys Leu Glu Tyr Asn Tyr Asn Ser
465                 470                 475                 480
His Asn Val Tyr Ile Met Ala Asp Lys Gln Lys Asn Gly Ile Lys Val
                485                 490                 495
Asn Phe Lys Ile Arg His Asn Ile Glu Asp Gly Ser Val Gln Leu Ala
            500                 505                 510
Asp His Tyr Gln Gln Asn Thr Pro Ile Gly Asp Gly Pro Val Leu Leu
        515                 520                 525
Pro Asp Asn His Tyr Leu Ser Tyr Gln Ser Ala Leu Ser Lys Asp Pro
530                 535                 540
Asn Glu Lys Arg Asp His Met Val Leu Leu Glu Phe Val Thr Ala Ala
545                 550                 555                 560
Gly Ile Thr Leu Gly Met Asp Glu Leu Tyr Lys Ser Gly Leu Arg Ser
                565                 570                 575
Arg Ala Gln Ala Ser Asn Ser Ala Val Asp Gly Thr Ala Gly Pro Gly
            580                 585                 590
Ser Thr Gly Ser Arg
        595

<210> SEQ ID NO 38
<211> LENGTH: 3640
<212> TYPE: DNA
<213> ORGANISM: Artificial Sequence
<220> FEATURE:
<223> OTHER INFORMATION: Rat gamma1-YFP_S315P, pDS plasmid

<400> SEQUENCE: 38
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc cacacagtga tattgatttg ctggttacgg tgaccgtaag gcttgatgaa     180
acaacgcggc gagctttgat caacgacctt ttggaaactt cggcttcccc tggagagagc     240
gagattctcc gcgctgtaga agtcaccatt gttgtgcacg acgacatcat tccgtggcgt     300
tatccagcta agcgcgaact gcaatttgga gaatggcagc gcaatgacat tcttgcaggt     360
atcttcgagc cagccacgat cgacattgat ctggctatct tgctgacaaa agcaagagaa     420
catagcgttg ccttggtagg tccagcggcg gaggaactct tgatccggtt cctgaacag      480 gatctatttg aggcgctaaa tgaaacctta acgctatgga actcgccgcc cgactgggct     540
ggcgatgagc gaaatgtagt gcttacgttg tcccgcattt ggtacagcgc agtaaccggc     600
aaaatcgcgc cgaaggatgt cgctgccgac tgggcaatgg agcgcctgcc ggcccagtat     660
cagcccgtca tacttgaagc tagacaggct tatcttggac aagaagaaga tcgcttggcc     720
```

```
tcgcgcgcag atcagttgga agaatttgtc cactacgtga aggcgagat caccaaggta    780
gtcggcaaat aatgtctaac aattcgttca agccgacgga tctatgtcgg gtgcggagaa    840
agaggtaatg aaatggcacc taggtatcga taatacgact cactataggg gaattgtgag    900
cggataacaa ttcccctcta gaaataattt tgtttaactt taagaaggag atatacatat    960
ggagtcggtt gctgcagaga gcgctccagc tccggagaat gaacactctc aagagacccc   1020
ggaatcgaac agtagtgtgt acaccacctt catgaagtct catcgctgct atgacctgat   1080
ccccacaagc tccaagctgg tggtatttga tacttcgctg caggtaaaga aagccttctt   1140
tgccctggtg actaacggtg ttcgtgctgc ccctttgtgg gatagtaaga agcagagctt   1200
tgtgggcatg ctgaccatca ctgacttcat caatattctg caccgatact acaagtcagc   1260
cctggtgcag atctatgaac tggaggagca aagatagag acttggagag aggtctacct    1320
gcaagactcc tttaagccac ttgtctgcat ttctccaaat gccagcttgt tcgatgctgt   1380
ctcttcatta attcgaaata agatccacag gcttccagtt attgacccgg agtcaggcaa   1440
caccttgtac attcttactc acaagcggat cctcaagttc ctcaagttgt ttatcactga   1500
gttccccaag ccggaattca tgtctaagtc tctggaagag ctacagattg gcacctacgc   1560
caatattgcc atggtccgta ccactacacc tgtctatgtg gctctgggca tctttgtaca   1620
gcaccgagtc tccgccttgc ctgtggtgga tgagaaaggg cgtgtggtgg acatctactc   1680
caagtttgat gtgattaatt tggcagcaga aaagacatac aacaacctag atgtgtctgt   1740
gacaaaagcc ctacagcacc ggtcacacta cttcgagggt gttctcaagt gctacctaca   1800
tgagactcta gaagcaatca tcaatagact ggtggaagca gaggttcacc gtctggtggt   1860
ggtggatgaa catgacgtgg tcaagggcat tgtatcgctg cccgatatct acaggctct    1920
ggtgctcaca ggtggagaga agaagcccgc tagcatggtg agcaagggcg aggagctgtt   1980
caccggggtg gtgcccatcc tggtcgagct ggacggcgac gtaaacggcc acaagttcag   2040
cgtgtccggc gagggcgagg gcgatgccac ctacggcaag ctgaccctga agttcatctg   2100
caccaccggc aagctgcccg tgccctggcc caccctcgtg accaccttcg gctacggcct   2160
gcagtgcttc gcccgctacc ccgaccacat gaagcagcac gacttcttca gtccgccat    2220
gcccgaaggc tacgtccagg agcgcaccat cttcttcaag gacgacggca actacaagac   2280
ccgcgccgag gtgaagttcg agggcgacac cctggtgaac cgcatcgagc tgaagggcat   2340
cgacttcaag gaggacggca acatcctggg gcacaagctg gagtacaact acaacagcca   2400
caacgtctat atcatggccg acaagcagaa gaacggcatc aaggtgaact tcaagatccg   2460
ccacaacatc gaggacggca gcgtgcagct cgccgaccac taccagcaga cacccccat    2520
cggcgacggc cccgtgctgc tgcccgacaa ccactacctg agctaccagt ccgccctgag   2580
caaagacccc aacgagaagc gcgatcacat ggtcctgctg gagttcgtga ccgccgccgg   2640
gatcactctc ggcatggacg agctgtacaa gtccggactc agatctcgag ctcaagcttc   2700
gaattctgca gtcgacggta ccgcgggccc gggatccacc ggatctagat gataactagt   2760
tccgtttaaa cccatgtgcc tggcagataa cttcgtataa tgtatgctat acgaagttat   2820
ggtacgtact aagctctcat gtttcacgta ctaagctctc atgtttaacg tactaagctc   2880
tcatgtttaa cgaactaaac cctcatggct aacgtactaa gctctcatgg ctaacgtact   2940
aagctctcat gtttcacgta ctaagctctc atgtttgaac aataaaatta atataaatca   3000
gcaacttaaa tagcctctaa ggttttaagt tttataagaa aaaaagaat atataaggct   3060
tttaaagctt ttaaggttta acggttgtgg acaacaagcc agggatgtaa cgcactgaga   3120
```

```
agcccttaga gcctctcaaa gcaattttga gtgacacagg aacacttaac ggctgacata   3180
attcagcttc acgctgccgc aagcactcag ggcgcaaggg ctgctaaagg aagcggaaca   3240
cgtagaaagc cagtccgcag aaacggtgct gaccccggat gaatgtcagc tgggaggcag   3300
aataaatgat catatcgtca attattacct ccacggggag agcctgagca aactggcctc   3360
aggcatttga gaagcacacg gtcacactgc ttccggtagt caataaaccg gtaagtagcg   3420
tatgcgctca cgcaactggt ccagaacctt gaccgaacgc agcggtggta acggcgcagt   3480
ggcggttttc atggcttgtt atgactgttt ttttggggta cagtctatgc ctcgggcatc   3540
caagcagcaa gcgcgttacg ccgtgggtcg atgtttgatg ttatggagca gcaacgatgt   3600
tacgcagcag ggcagtcgcc ctaaaacaaa gttaaacatc                         3640
```

<210> SEQ ID NO 39
<211> LENGTH: 597
<212> TYPE: PRT
<213> ORGANISM: Artificial Sequence
<220> FEATURE:
<223> OTHER INFORMATION: Rat gamma1-YFP_S315P

<400> SEQUENCE: 39

```
Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
    50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270
```

```
Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
290                 295                 300

His Asp Val Val Lys Gly Ile Val Ser Leu Pro Asp Ile Leu Gln Ala
305                 310                 315                 320

Leu Val Leu Thr Gly Gly Glu Lys Lys Pro Ala Ser Met Val Ser Lys
                325                 330                 335

Gly Glu Glu Leu Phe Thr Gly Val Val Pro Ile Leu Val Glu Leu Asp
                340                 345                 350

Gly Asp Val Asn Gly His Lys Phe Ser Val Ser Gly Glu Gly Glu Gly
                355                 360                 365

Asp Ala Thr Tyr Gly Lys Leu Thr Leu Lys Phe Ile Cys Thr Thr Gly
370                 375                 380

Lys Leu Pro Val Pro Trp Pro Thr Leu Val Thr Thr Phe Gly Tyr Gly
385                 390                 395                 400

Leu Gln Cys Phe Ala Arg Tyr Pro Asp His Met Lys Gln His Asp Phe
                405                 410                 415

Phe Lys Ser Ala Met Pro Glu Gly Tyr Val Gln Glu Arg Thr Ile Phe
                420                 425                 430

Phe Lys Asp Asp Gly Asn Tyr Lys Thr Arg Ala Glu Val Lys Phe Glu
                435                 440                 445

Gly Asp Thr Leu Val Asn Arg Ile Glu Leu Lys Gly Ile Asp Phe Lys
                450                 455                 460

Glu Asp Gly Asn Ile Leu Gly His Lys Leu Glu Tyr Asn Tyr Asn Ser
465                 470                 475                 480

His Asn Val Tyr Ile Met Ala Asp Lys Gln Lys Asn Gly Ile Lys Val
                485                 490                 495

Asn Phe Lys Ile Arg His Asn Ile Glu Asp Gly Ser Val Gln Leu Ala
                500                 505                 510

Asp His Tyr Gln Gln Asn Thr Pro Ile Gly Asp Gly Pro Val Leu Leu
                515                 520                 525

Pro Asp Asn His Tyr Leu Ser Tyr Gln Ser Ala Leu Ser Lys Asp Pro
530                 535                 540

Asn Glu Lys Arg Asp His Met Val Leu Leu Glu Phe Val Thr Ala Ala
545                 550                 555                 560

Gly Ile Thr Leu Gly Met Asp Glu Leu Tyr Lys Ser Gly Leu Arg Ser
                565                 570                 575

Arg Ala Gln Ala Ser Asn Ser Ala Val Asp Gly Thr Ala Gly Pro Gly
                580                 585                 590

Ser Thr Gly Ser Arg
        595

<210> SEQ ID NO 40
<211> LENGTH: 2839
<212> TYPE: DNA
<213> ORGANISM: Artificial Sequence
<220> FEATURE:
<223> OTHER INFORMATION: Rat gamma1, T7 Promoter

<400> SEQUENCE: 40
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc cacacagtga tattgatttg ctggttacgg tgaccgtaag gcttgatgaa     180
```

```
acaacgcggc gagctttgat caacgacctt ttggaaactt cggcttcccc tggagagagc    240
gagattctcc gcgctgtaga agtcaccatt gttgtgcacg acgacatcat tccgtggcgt    300
tatccagcta agcgcgaact gcaatttgga gaatggcagc gcaatgacat tcttgcaggt    360
atcttcgagc cagccacgat cgacattgat ctggctatct tgctgacaaa agcaagagaa    420
catagcgttg ccttggtagg tccagcggcg gaggaactct tgatccggt tcctgaacag     480
gatctatttg aggcgctaaa tgaaaccta acgctatgga actcgccgcc cgactgggct     540
ggcgatgagc gaaatgtagt gcttacgttg tcccgcattt ggtacagcgc agtaaccggc    600
aaaatcgcgc cgaaggatgt cgctgccgac tgggcaatgg agcgcctgcc ggcccagtat    660
cagcccgtca tacttgaagc tagacaggct tatcttggac aagaagaaga tcgcttggcc    720
tcgcgcgcag atcagttgga agaatttgtc cactacgtga aaggcgagat caccaaggta    780
gtcggcaaat aatgtctaac aattcgttca agccgacgga tctatgtcgg gtgcggagaa    840
agaggtaatg aaatggcacc taggtatcga taatacgact cactataggg gaattgtgag    900
cggataacaa ttcccctcta gaaataattt tgtttaactt taagaaggag atatacatat    960
ggagtcggtt gctgcagaga gcgctccagc tccggagaat gaacactctc aagagacccc   1020
ggaatcgaac agtagtgtgt acaccacctt catgaagtct catcgctgct atgacctgat   1080
ccccacaagc tccaagctgg tggtatttga tacttcgctg caggtaaaga aagccttctt   1140
tgccctggtg actaacggtg ttcgtgctgc ccctttgtgg gatagtaaga agcagagctt   1200
tgtgggcatg ctgaccatca ctgacttcat caatattctg caccgatact acaagtcagc   1260
cctggtgcag atctatgaac tggaggagca caagatagag acttggagag aggtctacct   1320
gcaagactcc tttaagccac ttgtctgcat ttctccaaat gccagcttgt tcgatgctgt   1380
ctcttcatta attcgaaata agatccacag gcttccagtt attgacccgg agtcaggcaa   1440
caccttgtac attcttactc acaagcggat cctcaagttc ctcaagttgt ttatcactga   1500
gttccccaag ccggaattca tgtctaagtc tctggaagag ctacagattg gcacctacgc   1560
caatattgcc atggtccgta ccactacacc tgtctatgtg gctctgggca tctttgtaca   1620
gcaccgagtc tccgccttgc ctgtggtgga tgagaaaggg cgtgtggtgg acatctactc   1680
caagtttgat gtgattaatt tggcagcaga aaagacatac aacaacctag atgtgtctgt   1740
gacaaaagcc ctacagcacc ggtcacacta cttcgagggt gttctcaagt gctacctaca   1800
tgagactcta gaagcaatca tcaatagact ggtggaagca gaggttcacc gtctggtggt   1860
ggtggatgaa catgacgtgg tcaagggcat tgtatcgctg tctgacatct acaggctct    1920
ggtgctcaca ggtggagaga agaagccctg ataactagtt ccgtttaaac ccatgtgcct   1980
ggcagataac ttcgtataat gtatgctata cgaagttatg gtacgtacta agctctcatg   2040
tttcacgtac taagctctca tgtttaacgt actaagctct catgtttaac gaactaaacc   2100
ctcatggcta cgtactaagc tctcatggct aacgtacta agctctcatg tttcacgtac    2160
taagctctca tgtttgaaca ataaaattaa tataaatcag caacttaaat agcctctaag   2220
gttttaagtt ttataagaaa aaaaagaata tataaggctt ttaaagcttt taaggtttaa   2280
cggttgtgga caacaagcca gggatgtaac gcactgagaa gcccttagag cctctcaaag   2340
caattttgag tgacacagga acacttaacg gctgacataa ttcagcttca cgctgccgca   2400
agcactcagg gcgcaagggc tgctaaagga agcggaacac gtagaaagcc agtccgcaga   2460
aacggtgctg accccggatg aatgtcagct gggaggcaga ataaatgatc atatcgtcaa   2520
```

```
ttattacctc cacggggaga gcctgagcaa actggcctca ggcatttgag aagcacacgg    2580
tcacactgct tccggtagtc aataaaccgg taagtagcgt atgcgctcac gcaactggtc    2640
cagaaccttg accgaacgca gcggtggtaa cggcgcagtg gcggttttca tggcttgtta    2700
tgactgtttt tttggggtac agtctatgcc tcgggcatcc aagcagcaag cgcgttacgc    2760
cgtgggtcga tgtttgatgt tatggagcag caacgatgtt acgcagcagg gcagtcgccc    2820
taaaacaaag ttaaacatc                                                 2839
```

<210> SEQ ID NO 41
<211> LENGTH: 330
<212> TYPE: PRT
<213> ORGANISM: Rattus norvegicus

<400> SEQUENCE: 41

```
Met Glu Ser Val Ala Ala Glu Ser Ala Pro Ala Glu Asn Glu His
1               5                   10                  15

Ser Gln Glu Thr Pro Glu Ser Asn Ser Ser Val Tyr Thr Thr Phe Met
                20                  25                  30

Lys Ser His Arg Cys Tyr Asp Leu Ile Pro Thr Ser Ser Lys Leu Val
            35                  40                  45

Val Phe Asp Thr Ser Leu Gln Val Lys Lys Ala Phe Phe Ala Leu Val
        50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
    290                 295                 300

His Asp Val Val Lys Gly Ile Val Ser Leu Ser Asp Ile Leu Gln Ala
305                 310                 315                 320
```

Leu Val Leu Thr Gly Gly Glu Lys Lys Pro
             325                 330

<210> SEQ ID NO 42
<211> LENGTH: 3589
<212> TYPE: DNA
<213> ORGANISM: Artificial Sequence
<220> FEATURE:
<223> OTHER INFORMATION: Rat gamma1-eCFP, pDS plasmid, T7 promoter

<400> SEQUENCE: 42

```
ccggtaagta gcgtatgcgc tcacgcaact ggtccagaac cttgaccgaa cgcagcggtg     60
gtaacggcgc agtggcggtt ttcatggctt gttatgactg ttttttttggg gtacagtcta    120
tgcctcgggc atccaagcag caagcgcgtt acgccgtggg tcgatgtttg atgttatgga    180
gcagcaacga tgttacgcag cagggcagtc gccctaaaac aaagttaaac atcatgaggg    240
aagcggtgat cgccgaagta tcgactcaac tatcagaggt agttggcgtc atcgagcgcc    300
atctcgaacc gacgttgctg gccgtacatt tgtacggctc cgcagtggat ggcggcctga    360
agccacacag tgatattgat ttgctggtta cggtgaccgt aaggcttgat gaaacaacgc    420
ggcgagcttt gatcaacgac cttttggaaa cttcggcttc cctggagag agcgagattc    480
tccgcgctgt agaagtcacc attgttgtgc acgacgacat cattccgtgg cgttatccag    540
ctaagcgcga actgcaattt ggagaatggc agcgcaatga cattcttgca ggtatcttcg    600
agccagccac gatcgacatt gatctggcta tcttgctgac aaaagcaaga gaacatagcg    660
ttgccttggt aggtccagcg gcggaggaac tctttgatcc ggttcctgaa caggatctat    720
ttgaggcgct aaatgaaacc ttaacgctat ggaactcgcc gcccgactgg gctggcgatg    780
agcgaaatgt agtgcttacg ttgtcccgca tttggtacag cgcagtaacc ggcaaaatcg    840
cgccgaagga tgtcgctgcc gactgggcaa tggagcgcct gccggcccag tatcagcccg    900
tcatacttga agctagacag gcttatcttg acaagaaga agatcgcttg gcctcgcgcg    960
cagatcagtt ggaagaattt gtccactacg tgaaggcga gatcaccaag gtagtcggca   1020
aataatgtct aacaattcgt tcaagccgac ggatctatgt cgggtgcgga gaaagaggta   1080
atgaaatggc acctaggtat cgataatacg actcactata ggggaattgt gagcggataa   1140
caattcccct ctagaaataa ttttgtttaa ctttaagaag gagatataca tatggagtcg   1200
gttgctgcag agagcgctcc agctccggag aatgaacact ctcaagagac cccggaatcg   1260
aacagtagtg tgtacaccac cttcatgaag tctcatcgct gctatgacct gatccccaca   1320
agctccaagc tggtggtatt tgatacttcg ctgcaggtaa agaaagcctt ctttgccctg   1380
gtgactaacg gtgttcgtgc tgccccttttg tgggatagta agagcagag ctttgtgggc   1440
atgctgacca tcactgactt catcaatatt ctgcaccgat actacaagtc agccctggtg   1500
cagatctatg aactggagga gcacaagata gagacttgga gagaggtcta cctgcaagac   1560
tcctttaagc cacttgtctg catttctcca aatgccagct tgttcgatgc tgtctcttca   1620
ttaattcgaa ataagatcca caggcttcca gttattgacc cggagtcagg caacaccttg   1680
tacattctta ctcacaagcg gatcctcaag ttcctcaagt tgtttatcac tgagttcccc   1740
aagccggaat tcatgtctaa gtctctggaa gagctacaga ttggcaccta cgccaatatt   1800
gccatggtcc gtaccactac acctgtctat gtggctctgg catctttgt acagcaccga   1860
gtctccgcct tgcctgtggt ggatgagaaa gggcgtgtgg tggacatcta ctccaagttt   1920
gatgtgatta atttggcagc agaaaagaca tacaacaacc tagatgtgtc tgtgacaaaa   1980
```

```
gccctacagc accggtcaca ctacttcgag ggtgttctca agtgctacct acatgagact    2040
ctagaagcaa tcatcaatag actggtggaa gcagaggttc accgtctggt ggtggtggat    2100
gaacatgacg tggtcaaggg cattgtatcg ctgtctgaca tcttacaggc tctggtgctc    2160
acaggtggag agaagaagcc cgctagcatg gtgagcaagg gcgaggagct gttcaccggg    2220
gtggtgccca tcctggtcga gctggacggc gacgtaaacg gccacaagtt cagcgtgtcc    2280
ggcgagggcg agggcgatgc cacctacggc aagctgaccc tgaagttcat ctgcaccacc    2340
ggcaagctgc ccgtgccctg gccaccctc gtgaccaccc tgacctgggg cgtgcagtgc    2400
ttcagccgct accccgacca catgaagcag cacgacttct tcaagtccgc catgcccgaa    2460
ggctacgtcc aggagcgcac catcttcttc aaggacgacg gcaactacaa gacccgcgcc    2520
gaggtgaagt tcgagggcga caccctggtg aaccgcatcg agctgaaggg catcgacttc    2580
aaggaggacg gcaacatcct ggggcacaag ctggagtaca actacatcag ccacaacgtc    2640
tatatcaccg ccgacaagca gaagaacggc atcaaggcca acttcaagat ccgccacaac    2700
atcgaggacg gcagcgtgca gctcgccgac cactaccagc agaacacccc catcggcgac    2760
ggccccgtgc tgctgcccga caaccactac ctgagcaccc agtccgccct gagcaaagac    2820
cccaacgaga gcgcgatca catggtcctg ctggagttcg tgaccgccgc cgggatcact    2880
ctcggcatgg acgagctgta caagtccgga ctcagatctc gacgagctca ctgataacta    2940
gttccgttta aacccatgtg cctggcagat aacttcgtat aatgtatgct atacgaagtt    3000
atggtacgta ctaagctctc atgtttcacg tactaagctc tcatgtttaa cgtactaagc    3060
tctcatgttt aacgaactaa accctcatgg ctaacgtact aagctctcat ggctaacgta    3120
ctaagctctc atgtttcacg tactaagctc tcatgtttga acaataaaat taatataaat    3180
cagcaactta aatagcctct aaggttttaa gttttataag aaaaaaaaga atatataagg    3240
cttttaaagc ttttaaggtt taacggttgt ggacaacaag ccaggatgt aacgcactga    3300 gaagcccta gagcctctca aagcaatttt gagtgacaca ggaacactta acggctgaca    3360
taattcagct tcacgctgcc gcaagcactc agggcgcaag ggctgctaaa ggaagcggaa    3420
cacgtagaaa gccagtccgc agaaacggtg ctgaccccgg atgaatgtca gctgggaggc    3480
agaataaatg atcatatcgt caattattac ctccacgggg agagcctgag caaactggcc    3540
tcaggcattt gagaagcaca cggtcacact gcttccggta gtcaataaa              3589
```

<210> SEQ ID NO 43
<211> LENGTH: 580
<212> TYPE: PRT
<213> ORGANISM: Artificial Sequence
<220> FEATURE:
<223> OTHER INFORMATION: Rat gamma1-eCFP, T7 promoter

<400> SEQUENCE: 43

```
Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
    50                  55                  60

Thr Asn Gly Val Arg Ala Ala Pro Leu Trp Asp Ser Lys Lys Gln Ser
65                  70                  75                  80
```

```
Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
    290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro Ala Ser Met Val Ser Lys
                325                 330                 335

Gly Glu Glu Leu Phe Thr Gly Val Val Pro Ile Leu Val Glu Leu Asp
            340                 345                 350

Gly Asp Val Asn Gly His Lys Phe Ser Val Ser Gly Glu Gly Glu Gly
        355                 360                 365

Asp Ala Thr Tyr Gly Lys Leu Thr Leu Lys Phe Ile Cys Thr Thr Gly
    370                 375                 380

Lys Leu Pro Val Pro Trp Pro Thr Leu Val Thr Thr Leu Thr Trp Gly
385                 390                 395                 400

Val Gln Cys Phe Ser Arg Tyr Pro Asp His Met Lys Gln His Asp Phe
                405                 410                 415

Phe Lys Ser Ala Met Pro Glu Gly Tyr Val Gln Glu Arg Thr Ile Phe
            420                 425                 430

Phe Lys Asp Asp Gly Asn Tyr Lys Thr Arg Ala Glu Val Lys Phe Glu
        435                 440                 445

Gly Asp Thr Leu Val Asn Arg Ile Glu Leu Lys Gly Ile Asp Phe Lys
    450                 455                 460

Glu Asp Gly Asn Ile Leu Gly His Lys Leu Glu Tyr Asn Tyr Ile Ser
465                 470                 475                 480

His Asn Val Tyr Ile Thr Ala Asp Lys Gln Lys Asn Gly Ile Lys Ala
                485                 490                 495
```

```
Asn Phe Lys Ile Arg His Asn Ile Glu Asp Gly Ser Val Gln Leu Ala
            500                 505                 510

Asp His Tyr Gln Gln Asn Thr Pro Ile Gly Asp Gly Pro Val Leu Leu
        515                 520                 525

Pro Asp Asn His Tyr Leu Ser Thr Gln Ser Ala Leu Ser Lys Asp Pro
    530                 535                 540

Asn Glu Lys Arg Asp His Met Val Leu Leu Glu Phe Val Thr Ala Ala
545                 550                 555                 560

Gly Ile Thr Leu Gly Met Asp Glu Leu Tyr Lys Ser Gly Leu Arg Ser
                565                 570                 575

Arg Arg Ala His
            580

<210> SEQ ID NO 44
<211> LENGTH: 3589
<212> TYPE: DNA
<213> ORGANISM: Artificial Sequence
<220> FEATURE:
<223> OTHER INFORMATION: Rat eCFP-gamma1, pDS plasmid, T7 promoter

<400> SEQUENCE: 44
tattacctcc acggggagag cctgagcaaa ctggcctcag gcatttgaga agcacacggt      60
cacactgctt ccggtagtca ataaaccggt aagtagcgta tgcgctcacg caactggtcc    120
agaaccttga ccgaacgcag cggtggtaac ggcgcagtgg cggttttcat ggcttgttat    180
gactgttttt ttggggtaca gtctatgcct cgggcatcca agcagcaagc gcgttacgcc    240
gtgggtcgat gtttgatgtt atggagcagc aacgatgtta cgcagcaggg cagtcgccct    300
aaaacaaagt taaacatcat gagggaagcg gtgatcgccg aagtatcgac tcaactatca    360
gaggtagttg gcgtcatcga gcgccatctc gaaccgacgt tgctggccgt acatttgtac    420
ggctccgcag tggatggcgg cctgaagcca cacagtgata ttgatttgct ggttacggtg    480
accgtaaggc ttgatgaaac aacgcggcga gctttgatca cgaccttttt ggaaacttcg    540
gcttcccctg gagagagcga gattctccgc gctgtagaag tcaccattgt tgtgcacgac    600
gacatcattc cgtggcgtta tccagctaag cgcgaactgc aatttggaga atggcagcgc    660
aatgacattc ttgcaggtat cttcgagcca gccacgatcg acattgatct ggctatcttg    720
ctgacaaaag caagagaaca tagcgttgcc ttggtaggtc cagcggcgga ggaactcttt    780
gatccggttc ctgaacagga tctatttgag gcgctaaatg aaaccttaac gctatggaac    840
tcgccgcccg actgggctgg cgatgagcga aatgtagtgc ttacgttgtc ccgcatttgg    900
tacagcgcag taaccggcaa aatcgcgccg aaggatgtcg ctgccgactg ggcaatggag    960
cgcctgccgg cccagtatca gcccgtcata cttgaagcta cagggcttac tcttggacaa   1020
gaagaagatc gcttggcctc gcgcgcagat cagttggaag aatttgtcca ctacgtgaaa   1080
ggcgagatca ccaaggtagt cggcaaataa tgtctaacaa ttcgttcaag ccgacggatc   1140
tatgtcgggt gcggagaaag aggtaatgaa atggcaccta ggtatcgata atacgactca   1200
ctatagggga attgtgagcg gataacaatt cccctctaga aataattttg tttaacttta   1260
agaaggagat atacatatgg tgagcaaggg cgaggagctg ttcaccgggg tggtgcccat   1320
cctggtcgag ctggacggcg acgtaaacgg ccacaagttc agcgtgtccg gcgagggcga   1380
gggcgatgcc acctacggca agctgaccct gaagttcatc tgcaccaccg gcaagctgcc   1440
cgtgccctgg cccaccctcg tgaccaccct gacctggggc gtgcagtgct tcagccgcta   1500
ccccgaccac atgaagcagc acgacttctt caagtccgcc atgcccgaag gctacgtcca   1560
```

| | |
|---|---|
| ggagcgcacc atcttcttca aggacgacgg caactacaag acccgcgccg aggtgaagtt | 1620 |
| cgagggcgac accctggtga accgcatcga gctgaagggc atcgacttca aggaggacgg | 1680 |
| caacatcctg gggcacaagc tggagtacaa ctacatcagc cacaacgtct atatcaccgc | 1740 |
| cgacaagcag aagaacggca tcaaggccaa cttcaagatc cgccacaaca tcgaggacgg | 1800 |
| cagcgtgcag ctcgccgacc actaccagca gaacacccccc atcggcgacg gccccgtgct | 1860 |
| gctgcccgac aaccactacc tgagcaccca gtccgccctg agcaaagacc caacgagaa | 1920 |
| gcgcgatcac atggtcctgc tggagttcgt gaccgccgcc gggatcactc tcggcatgga | 1980 |
| cgagctgtac aagtccggac tcagatctcg acgagctcac gctagcatgg agtcggttgc | 2040 |
| tgcagagagc gctccagctc cggagaatga acactctcaa gagacccccgg aatcgaacag | 2100 |
| tagtgtgtac accaccttca tgaagtctca tcgctgctat gacctgatcc ccacaagctc | 2160 |
| caagctggtg gtatttgata cttcgctgca ggtaaagaaa gccttctttg ccctggtgac | 2220 |
| taacggtgtt cgtgctgccc ctttgtggga tagtaagaag cagagctttg tgggcatgct | 2280 |
| gaccatcact gacttcatca atattctgca ccgatactac aagtcagccc tggtgcagat | 2340 |
| ctatgaactg gaggagcaca agatagagac ttggagagag gtctacctgc aagactcctt | 2400 |
| taagccactt gtctgcattt ctccaaatgc cagcttgttc gatgctgtct cttcattaat | 2460 |
| tcgaaataag atccacaggc ttccagttat tgacccggag tcaggcaaca ccttgtacat | 2520 |
| tcttactcac aagcggatcc tcaagttcct caagttgttt atcactgagt tccccaagcc | 2580 |
| ggaattcatg tctaagtctc tggaagagct acagattggc acctacgcca atattgccat | 2640 |
| ggtccgtacc actacacctg tctatgtggc tctgggcatc tttgtacagc accgagtctc | 2700 |
| cgccttgcct gtggtggatg agaaagggcg tgtggtggac atctactcca gtttgatgt | 2760 |
| gattaatttg gcagcagaaa agacatacaa caacctagat gtgtctgtga caaaagccct | 2820 |
| acagcaccgg tcacactact tcgagggtgt tctcaagtgc tacctacatg agactctaga | 2880 |
| agcaatcatc aatagactgg tggaagcaga ggttcaccgt ctggtggtgg tggatgaaca | 2940 |
| tgacgtggtc aagggcattg tatcgctgtc tgacatctta caggctctgg tgctcacagg | 3000 |
| tggagagaag aagccctgat aactagttcc gtttaaaccc atgtgcctgg cagataactt | 3060 |
| cgtataatgt atgctatacg aagttatggt acgtactaag ctctcatgtt tcacgtacta | 3120 |
| agctctcatg tttaacgtac taagctctca tgtttaacga actaaaccct catggctaac | 3180 |
| gtactaagct ctcatggcta acgtactaag ctctcatgtt tcacgtacta agctctcatg | 3240 |
| tttgaacaat aaaattaata taaatcagca acttaaatag cctctaaggt tttaagtttt | 3300 |
| ataagaaaaa aaagaatata taaggctttt aaagcttttta aggtttaacg gttgtggaca | 3360 |
| acaagccagg gatgtaacgc actgagaagc ccttagagcc tctcaaagca attttgagtg | 3420 |
| acacaggaac acttaacggc tgacataatt cagcttcacg ctgccgcaag cactcagggc | 3480 |
| gcaagggctg ctaaaggaag cggaacacgt agaaagccag tccgcagaaa cggtgctgac | 3540 |
| cccggatgaa tgtcagctgg gaggcagaat aaatgatcat atcgtcaat | 3589 |

<210> SEQ ID NO 45
<211> LENGTH: 580
<212> TYPE: PRT
<213> ORGANISM: Artificial Sequence
<220> FEATURE:
<223> OTHER INFORMATION: Rat eCFP-gamma1, T7 promoter

<400> SEQUENCE: 45

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
    115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Ser
225                 230                 235                 240

Gly Leu Arg Ser Arg Arg Ala His Ala Ser Met Glu Ser Val Ala Ala
                245                 250                 255

Glu Ser Ala Pro Ala Pro Glu Asn Glu His Ser Gln Glu Thr Pro Glu
            260                 265                 270

Ser Asn Ser Ser Val Tyr Thr Thr Phe Met Lys Ser His Arg Cys Tyr
    275                 280                 285

Asp Leu Ile Pro Thr Ser Ser Lys Leu Val Val Phe Asp Thr Ser Leu
290                 295                 300

Gln Val Lys Lys Ala Phe Phe Ala Leu Val Thr Asn Gly Val Arg Ala
305                 310                 315                 320

Ala Pro Leu Trp Asp Ser Lys Lys Gln Ser Phe Val Gly Met Leu Thr
                325                 330                 335

Ile Thr Asp Phe Ile Asn Ile Leu His Arg Tyr Tyr Lys Ser Ala Leu
            340                 345                 350

Val Gln Ile Tyr Glu Leu Glu Glu His Lys Ile Glu Thr Trp Arg Glu
    355                 360                 365

Val Tyr Leu Gln Asp Ser Phe Lys Pro Leu Val Cys Ile Ser Pro Asn
370                 375                 380

Ala Ser Leu Phe Asp Ala Val Ser Ser Leu Ile Arg Asn Lys Ile His
385                 390                 395                 400

Arg Leu Pro Val Ile Asp Pro Glu Ser Gly Asn Thr Leu Tyr Ile Leu
                405                 410                 415

Thr His Lys Arg Ile Leu Lys Phe Leu Lys Leu Phe Ile Thr Glu Phe
```

```
            420             425             430
Pro Lys Pro Glu Phe Met Ser Lys Ser Leu Glu Glu Leu Gln Ile Gly
            435                     440                 445

Thr Tyr Ala Asn Ile Ala Met Val Arg Thr Thr Thr Pro Val Tyr Val
        450                     455             460

Ala Leu Gly Ile Phe Val Gln His Arg Val Ser Ala Leu Pro Val Val
465                 470                 475                 480

Asp Glu Lys Gly Arg Val Val Asp Ile Tyr Ser Lys Phe Asp Val Ile
                485                 490                 495

Asn Leu Ala Ala Glu Lys Thr Tyr Asn Asn Leu Asp Val Ser Val Thr
            500                 505                 510

Lys Ala Leu Gln His Arg Ser His Tyr Phe Glu Gly Val Leu Lys Cys
        515                 520                 525

Tyr Leu His Glu Thr Leu Glu Ala Ile Ile Asn Arg Leu Val Glu Ala
        530                 535                 540

Glu Val His Arg Leu Val Val Val Asp Glu His Asp Val Val Lys Gly
545                 550                 555                 560

Ile Val Ser Leu Ser Asp Ile Leu Gln Ala Leu Val Leu Thr Gly Gly
                565                 570                 575

Glu Lys Lys Pro
            580

<210> SEQ ID NO 46
<211> LENGTH: 3640
<212> TYPE: DNA
<213> ORGANISM: Artificial Sequence
<220> FEATURE:
<223> OTHER INFORMATION: Rat gamma1-YFP, pDS plasmid, T7 promoter

<400> SEQUENCE: 46
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc cacacagtga tattgatttg ctggttacgg tgaccgtaag gcttgatgaa     180
acaacgcggc gagctttgat caacgacctt ttggaaactt cggcttcccc tggagagagc     240
gagattctcc gcgctgtaga agtcaccatt gttgtgcacg acgacatcat tccgtggcgt     300
tatccagcta agcgcgaact gcaatttgga gaatggcagc gcaatgacat tcttgcaggt     360
atcttcgagc cagccacgat cgacattgat ctggctatct tgctgacaaa agcaagagaa     420
catagcgttg ccttggtagg tccagcggcg gaggaactct tgatccggt tcctgaacag     480
gatctatttg aggcgctaaa tgaaacctta acgctatgga actcgccgcc cgactgggct     540
ggcgatgagc gaaatgtagt gcttacgttg tcccgcattt ggtacagcgc agtaaccggc     600
aaaatcgcgc cgaaggatgt cgctgccgac tgggcaatgg agcgcctgcc ggcccagtat     660
cagcccgtca tacttgaagc tagacaggct tatcttggac aagaagaa tcgcttggcc     720
tcgcgcgcag atcagttgga agaatttgtc cactacgtga aggcgagat caccaaggta     780
gtcggcaaat aatgtctaac aattcgttca agccgacgga tctatgtcgg gtgcggagaa     840
agaggtaatg aaatggcacc taggtatcga taatacgact cactataggg aattgtgag     900
cggataacaa ttcccctcta gaaataattt tgtttaactt taagaaggag atatacatat     960
ggagtcggtt gctgcagaga gcgctccagc tccggagaat gaacactctc aagagacccc    1020
ggaatcgaac agtagtgtgt acaccacctt catgaagtct catcgctgct atgacctgat    1080
ccccacaagc tccaagctgg tggtatttga tacttcgctg caggtaaaga aagccttctt    1140
```

```
tgccctggtg actaacggtg ttcgtgctgc cccttttgtgg gatagtaaga agcagagctt   1200
tgtgggcatg ctgaccatca ctgacttcat caatattctg caccgatact acaagtcagc   1260
cctggtgcag atctatgaac tggaggagca caagatagag acttggagag aggtctacct   1320
gcaagactcc tttaagccac ttgtctgcat ttctccaaat gccagcttgt tcgatgctgt   1380
ctcttcatta attcgaaata agatccacag gcttccagtt attgacccgg agtcaggcaa   1440
caccttgtac attcttactc acaagcggat cctcaagttc ctcaagttgt ttatcactga   1500
gttccccaag ccggaattca tgtctaagtc tctggaagag ctacagattg gcacctacgc   1560
caatattgcc atggtccgta ccactacacc tgtctatgtg gctctgggca tctttgtaca   1620
gcaccgagtc tccgccttgc ctgtggtgga tgagaaaggg cgtgtggtgg acatctactc   1680
caagtttgat gtgattaatt tggcagcaga aaagacatac aacaacctag atgtgtctgt   1740
gacaaaagcc ctacagcacc ggtcacacta cttcgagggt gttctcaagt gctacctaca   1800
tgagactcta gaagcaatca tcaatagact ggtggaagca gaggttcacc gtctggtggt   1860
ggtggatgaa catgacgtgg tcaagggcat tgtatcgctg tctgacatct acaggctct   1920 ggtgctcaca ggtggagaga agaagcccgc tagcatggtg agcaagggcg aggagctgtt   1980 caccgggggtg gtgcccatcc tggtcgagct ggacggcgac gtaaacggcc acaagttcag   2040
cgtgtccggc gagggcgagg gcgatgccac ctacggcaag ctgaccctga agttcatctg   2100
caccaccggc aagctgcccg tgccctggcc caccctcgtg accaccttcg gctacggcct   2160
gcagtgcttc gcccgctacc ccgaccacat gaagcagcac gacttcttca agtccgccat   2220
gcccgaaggc tacgtccagg agcgcaccat cttcttcaag gacgacggca actacaagac   2280
ccgcgccgag gtgaagttcg agggcgacac cctggtgaac cgcatcgagc tgaagggcat   2340
cgacttcaag gaggacggca acatcctggg gcacaagctg gagtacaact acaacagcca   2400
caacgtctat atcatggccg acaagcagaa gaacggcatc aaggtgaact tcaagatccg   2460
ccacaacatc gaggacggca gcgtgcagct cgccgaccac taccagcaga caccccat    2520 cggcgacggc cccgtgctgc tgcccgacaa ccactacctg agctaccagt ccgccctgag   2580
caaagacccc aacgagaagc gcgatcacat ggtcctgctg gagttcgtga ccgccgccgg   2640
gatcactctc ggcatggacg agctgtacaa gtccggactc agatctcgag ctcaagcttc   2700
gaattctgca gtcgacggta ccgcgggccc gggatccacc ggatctagat gataactagt   2760
tccgtttaaa cccatgtgcc tggcagataa cttcgtataa tgtatgctat acgaagttat   2820
ggtacgtact aagctctcat gtttcacgta ctaagctctc atgtttaacg tactaagctc   2880
tcatgtttaa cgaactaaac cctcatggct aacgtactaa gctctcatgg ctaacgtact   2940
aagctctcat gtttcacgta ctaagctctc atgtttgaac aataaaatta atataaatca   3000
gcaacttaaa tagcctctaa ggttttaagt tttataagaa aaaaagaat atataaggct   3060 tttaaagctt ttaaggttta acggttgtgg acaacaagcc agggatgtaa cgcactgaga   3120
agcccttaga gcctctcaaa gcaattttga gtgacacagg aacacttaac ggctgacata   3180
attcagcttc acgctgccgc aagcactcag ggcgcaaggg ctgctaaagg aagcggaaca   3240
cgtagaaagc cagtccgcag aaacggtgct gaccccggat gaatgtcagc tgggaggcag   3300
aataaatgat catatcgtca attattacct ccacggggag agcctgagca aactggcctc   3360
aggcatttga gaagcacacg gtcacactgc ttccggtagt caataaaccg gtaagtagcg   3420
tatgcgctca cgcaactggt ccagaacctt gaccgaacgc agcggtggta acggcgcagt   3480
```

```
ggcggttttc atggcttgtt atgactgttt ttttggggta cagtctatgc ctcgggcatc    3540
caagcagcaa gcgcgttacg ccgtgggtcg atgtttgatg ttatggagca gcaacgatgt    3600
tacgcagcag ggcagtcgcc ctaaaacaaa gttaaacatc                          3640
```

<210> SEQ ID NO 47
<211> LENGTH: 597
<212> TYPE: PRT
<213> ORGANISM: Artificial Sequence
<220> FEATURE:
<223> OTHER INFORMATION: Rat gamma1-YFP, T7 promoter

<400> SEQUENCE: 47

```
Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
    50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
    290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro Ala Ser Met Val Ser Lys
                325                 330                 335
```

-continued

```
Gly Glu Glu Leu Phe Thr Gly Val Val Pro Ile Leu Val Glu Leu Asp
            340                 345                 350

Gly Asp Val Asn Gly His Lys Phe Ser Val Ser Gly Glu Gly Glu Gly
        355                 360                 365

Asp Ala Thr Tyr Gly Lys Leu Thr Leu Lys Phe Ile Cys Thr Thr Gly
    370                 375                 380

Lys Leu Pro Val Pro Trp Pro Thr Leu Val Thr Thr Phe Gly Tyr Gly
385                 390                 395                 400

Leu Gln Cys Phe Ala Arg Tyr Pro Asp His Met Lys Gln His Asp Phe
                405                 410                 415

Phe Lys Ser Ala Met Pro Glu Gly Tyr Val Gln Glu Arg Thr Ile Phe
            420                 425                 430

Phe Lys Asp Asp Gly Asn Tyr Lys Thr Arg Ala Glu Val Lys Phe Glu
        435                 440                 445

Gly Asp Thr Leu Val Asn Arg Ile Glu Leu Lys Gly Ile Asp Phe Lys
    450                 455                 460

Glu Asp Gly Asn Ile Leu Gly His Lys Leu Glu Tyr Asn Tyr Asn Ser
465                 470                 475                 480

His Asn Val Tyr Ile Met Ala Asp Lys Gln Lys Asn Gly Ile Lys Val
                485                 490                 495

Asn Phe Lys Ile Arg His Asn Ile Glu Asp Gly Ser Val Gln Leu Ala
            500                 505                 510

Asp His Tyr Gln Gln Asn Thr Pro Ile Gly Asp Gly Pro Val Leu Leu
        515                 520                 525

Pro Asp Asn His Tyr Leu Ser Tyr Gln Ser Ala Leu Ser Lys Asp Pro
    530                 535                 540

Asn Glu Lys Arg Asp His Met Val Leu Leu Glu Phe Val Thr Ala Ala
545                 550                 555                 560

Gly Ile Thr Leu Gly Met Asp Glu Leu Tyr Lys Ser Gly Leu Arg Ser
                565                 570                 575

Arg Ala Gln Ala Ser Asn Ser Ala Val Asp Gly Thr Ala Gly Pro Gly
            580                 585                 590

Ser Thr Gly Ser Arg
        595
```

<210> SEQ ID NO 48
<211> LENGTH: 3640
<212> TYPE: DNA
<213> ORGANISM: Artificial Sequence
<220> FEATURE:
<223> OTHER INFORMATION: Rat YFP-gamma1, pDS plasmid, T7 promoter

<400> SEQUENCE: 48

```
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc acacagtga tattgatttg ctggttacgg tgaccgtaag gcttgatgaa      180
acaacgcggc gagctttgat caacgacctt ttggaaactt cggcttcccc tggagagagc     240
gagattctcc gcgctgtaga agtcaccatt gttgtgcacg acgacatcat tccgtggcgt     300
tatccagcta agcgcgaact gcaatttgga gaatggcagc gcaatgacat tcttgcaggt     360
atcttcgagc cagccacgat cgacattgat ctggctatct tgctgacaaa agcaagagaa     420
catagcgttg ccttggtagg tccagcggcg gaggaactct ttgatccggt tcctgaacag     480
gatctatttg aggcgctaaa tgaaacctta acgctatgga actcgccgcc cgactgggct     540
```

```
ggcgatgagc gaaatgtagt gcttacgttg tcccgcattt ggtacagcgc agtaaccggc      600
aaaatcgcgc cgaaggatgt cgctgccgac tgggcaatgg agcgcctgcc ggcccagtat      660
cagcccgtca tacttgaagc tagacaggct tatcttggac aagaagaaga tcgcttggcc      720
tcgcgcgcag atcagttgga agaatttgtc cactacgtga aaggcgagat caccaaggta      780
gtcggcaaat aatgtctaac aattcgttca agccgacgga tctatgtcgg gtgcggagaa      840
agaggtaatg aaatggcacc taggtatcga taatacgact cactataggg gaattgtgag      900
cggataacaa ttcccctcta gaaataattt tgtttaactt taagaaggag atatacatat      960
ggtgagcaag ggcgaggagc tgttcaccgg ggtggtgccc atcctggtcg agctggacgg     1020
cgacgtaaac ggccacaagt tcagcgtgtc cggcgagggc gagggcgatg ccacctacgg     1080
caagctgacc ctgaagttca tctgcaccac cggcaagctg cccgtgccct ggcccaccct     1140
cgtgaccacc ttcggctacg gcctgcagtg cttcgcccgc taccccgacc acatgaagca     1200
gcacgacttc ttcaagtccg ccatgcccga aggctacgtc caggagcgca ccatcttctt     1260
caaggacgac ggcaactaca agacccgcgc cgaggtgaag ttcgagggcg acaccctggt     1320
gaaccgcatc gagctgaagg gcatcgactt caaggaggac ggcaacatcc tggggcacaa     1380
gctggagtac aactacaaca gccacaacgt ctatatcatg gccgacaagc agaagaacgg     1440
catcaaggtg aacttcaaga tccgccacaa catcgaggac ggcagcgtgc agctcgccga     1500
ccactaccag cagaacaccc ccatcggcga cggccccgtg ctgctgcccg acaaccacta     1560
cctgagctac cagtccgccc tgagcaaaga ccccaacgag aagcgcgatc acatggtcct     1620
gctggagttc gtgaccgccg ccgggatcac tctcggcatg gacgagctgt acaagtccgg     1680
actcagatct cgagctcaag cttcgaattc tgcagtcgac ggtaccgcgg gcccgggatc     1740
caccggatct agagctagca tggagtcggt tgctgcagag agcgctccag ctccggagaa     1800
tgaacactct caagagaccc cggaatcgaa cagtagtgtg tacaccacct tcatgaagtc     1860
tcatcgctgc tatgacctga tccccacaag ctccaagctg gtggtatttg atacttcgct     1920
gcaggtaaag aaagccttct tgccctggt gactaacggt gttcgtgctg cccctttgtg      1980
ggatagtaag aagcagagct tgtgggcat gctgaccatc actgacttca tcaatattct      2040
gcaccgatac tacaagtcag ccctggtgca gatctatgaa ctggaggagc acaagataga     2100
gacttggaga gaggtctacc tgcaagactc ctttaagcca cttgtctgca tttctccaaa     2160
tgccagcttg ttcgatgctg tctcttcatt aattcgaaat aagatccaca ggcttccagt     2220
tattgacccg gagtcaggca acaccttgta cattcttact cacaagcgga tcctcaagtt     2280
cctcaagttg tttatcactg agttccccaa gccggaattc atgtctaagt ctctggaaga     2340
gctacagatt ggcaccctacg ccaatattgc catggtccgt accactacac ctgtctatgt     2400
ggctctgggc atctttgtac agcaccgagt ctccgccttg cctgtggtgg atgagaaagg     2460
gcgtgtggtg gacatctact ccaagtttga tgtgattaat ttggcagcag aaaagacata     2520
caacaaccta gatgtgtctg tgacaaaagc cctacagcac cggtcacact acttcgaggg     2580
tgttctcaag tgctacctac atgagactct agaagcaatc atcaatagac tggtggaagc     2640
agaggttcac cgtctggtgg tggtggatga acatgacgtg tcaagggca ttgtatcgct      2700 gtctgacatc ttacaggctc tggtgctcac aggtggagag aagaagccct gataactagt     2760
tccgtttaaa cccatgtgcc tggcagataa cttcgtataa tgtatgctat acgaagttat     2820
ggtacgtact aagctctcat gtttcacgta ctaagctctc atgtttaacg tactaagctc     2880
tcatgtttaa cgaactaaac cctcatggct aacgtactaa gctctcatgg ctaacgtact     2940
```

```
aagctctcat gtttcacgta ctaagctctc atgtttgaac aataaaatta atataaatca   3000
gcaacttaaa tagcctctaa ggttttaagt tttataagaa aaaaaagaat atataaggct   3060
tttaaagctt ttaaggttta acggttgtgg acaacaagcc agggatgtaa cgcactgaga   3120
agcccttaga gcctctcaaa gcaattttga gtgacacagg aacacttaac ggctgacata   3180
attcagcttc acgctgccgc aagcactcag ggcgcaaggg ctgctaaagg aagcggaaca   3240
cgtagaaagc cagtccgcag aaacggtgct gacccggat gaatgtcagc tgggaggcag    3300
aataaatgat catatcgtca attattacct ccacggggag agcctgagca aactggcctc   3360
aggcatttga gaagcacacg gtcacactgc ttccggtagt caataaaccg gtaagtagcg   3420
tatgcgctca cgcaactggt ccagaacctt gaccgaacgc agcggtggta acggcgcagt   3480
ggcggttttc atggcttgtt atgactgttt ttttggggta cagtctatgc ctcgggcatc   3540
caagcagcaa gcgcgttacg ccgtgggtcg atgtttgatg ttatggagca gcaacgatgt   3600
tacgcagcag ggcagtcgcc ctaaaacaaa gttaaacatc                         3640
```

<210> SEQ ID NO 49
<211> LENGTH: 597
<212> TYPE: PRT
<213> ORGANISM: Artificial Sequence
<220> FEATURE:
<223> OTHER INFORMATION: Rat YFP-gamma1

<400> SEQUENCE: 49

```
Met Val Ser Lys Gly Glu Glu Leu Phe Thr Gly Val Val Pro Ile Leu
1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240
```

Gly Leu Arg Ser Arg Ala Gln Ala Ser Asn Ser Ala Val Asp Gly Thr
            245                 250                 255

Ala Gly Pro Gly Ser Thr Gly Ser Arg Ala Ser Met Glu Ser Val Ala
        260                 265                 270

Ala Glu Ser Ala Pro Ala Pro Glu Asn Glu His Ser Gln Glu Thr Pro
    275                 280                 285

Glu Ser Asn Ser Ser Val Tyr Thr Thr Phe Met Lys Ser His Arg Cys
290                 295                 300

Tyr Asp Leu Ile Pro Thr Ser Ser Lys Leu Val Val Phe Asp Thr Ser
305                 310                 315                 320

Leu Gln Val Lys Lys Ala Phe Phe Ala Leu Val Thr Asn Gly Val Arg
                325                 330                 335

Ala Ala Pro Leu Trp Asp Ser Lys Lys Gln Ser Phe Val Gly Met Leu
            340                 345                 350

Thr Ile Thr Asp Phe Ile Asn Ile Leu His Arg Tyr Tyr Lys Ser Ala
        355                 360                 365

Leu Val Gln Ile Tyr Glu Leu Glu Glu His Lys Ile Glu Thr Trp Arg
    370                 375                 380

Glu Val Tyr Leu Gln Asp Ser Phe Lys Pro Leu Val Cys Ile Ser Pro
385                 390                 395                 400

Asn Ala Ser Leu Phe Asp Ala Val Ser Ser Leu Ile Arg Asn Lys Ile
                405                 410                 415

His Arg Leu Pro Val Ile Asp Pro Glu Ser Gly Asn Thr Leu Tyr Ile
            420                 425                 430

Leu Thr His Lys Arg Ile Leu Lys Phe Leu Lys Leu Phe Ile Thr Glu
        435                 440                 445

Phe Pro Lys Pro Glu Phe Met Ser Lys Ser Leu Glu Glu Leu Gln Ile
    450                 455                 460

Gly Thr Tyr Ala Asn Ile Ala Met Val Arg Thr Thr Thr Pro Val Tyr
465                 470                 475                 480

Val Ala Leu Gly Ile Phe Val Gln His Arg Val Ser Ala Leu Pro Val
                485                 490                 495

Val Asp Glu Lys Gly Arg Val Val Asp Ile Tyr Ser Lys Phe Asp Val
            500                 505                 510

Ile Asn Leu Ala Ala Glu Lys Thr Tyr Asn Asn Leu Asp Val Ser Val
        515                 520                 525

Thr Lys Ala Leu Gln His Arg Ser His Tyr Phe Glu Gly Val Leu Lys
    530                 535                 540

Cys Tyr Leu His Glu Thr Leu Glu Ala Ile Ile Asn Arg Leu Val Glu
545                 550                 555                 560

Ala Glu Val His Arg Leu Val Val Asp Glu His Asp Val Val Lys
                565                 570                 575

Gly Ile Val Ser Leu Ser Asp Ile Leu Gln Ala Leu Val Leu Thr Gly
            580                 585                 590

Gly Glu Lys Lys Pro
        595

<210> SEQ ID NO 50
<211> LENGTH: 795
<212> TYPE: DNA
<213> ORGANISM: Artificial Sequence
<220> FEATURE:
<223> OTHER INFORMATION: eYFP

<400> SEQUENCE: 50

-continued

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcggcta cggcctgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggccac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagct accagtccgc cctgagcaaa gaccccaacg agaagcgcga tcacatggtc     660
ctgctggagt tcgtgaccgc cgccgggatc actctcggca tggacgagct gtacaagtcc     720
ggactcagat ctcgagctca agcttcgaat tctgcagtcg acggtaccgc gggcccggga     780
tccaccggat ctaga                                                      795
```

<210> SEQ ID NO 51
<211> LENGTH: 265
<212> TYPE: PRT
<213> ORGANISM: Artificial Sequence
<220> FEATURE:
<223> OTHER INFORMATION: eYFP

<400> SEQUENCE: 51

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
```

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Ala Val Asp Gly Thr
            245                 250                 255

Ala Gly Pro Gly Ser Thr Gly Ser Arg
            260                 265

<210> SEQ ID NO 52
<211> LENGTH: 687
<212> TYPE: DNA
<213> ORGANISM: Artificial Sequence
<220> FEATURE:
<223> OTHER INFORMATION: mseCFP

<400> SEQUENCE: 52
atggtgagca agggcgagga gctgttcacc ggggtggtgc ccatcctggt cgagctggac      60
ggcgacgtaa acggccacag gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcgccc gctaccccga ccacatgaag     240
cagcacgact tcttcaagtc cgccatgccc gaaggctacg tccaggagcg taccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg cccacttcaa gatccgccac aacatcgagg acggcggcgt gcagctcgcc     540
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgcctaa                                         687

<210> SEQ ID NO 53
<211> LENGTH: 228
<212> TYPE: PRT
<213> ORGANISM: Artificial Sequence
<220> FEATURE:
<223> OTHER INFORMATION: mseCFP

<400> SEQUENCE: 53

Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

-continued

```
Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
210                 215                 220

Val Thr Ala Ala
225

<210> SEQ ID NO 54
<211> LENGTH: 738
<212> TYPE: DNA
<213> ORGANISM: Artificial Sequence
<220> FEATURE:
<223> OTHER INFORMATION: cpVenus

<400> SEQUENCE: 54
atgggcggcg tgcagctcgc cgaccactac cagcagaaca cccccatcgg cgacggcccc      60
gtgctgctgc ccgacaacca ctacctgagc taccagtcca agctgagcaa agaccccaac     120
gagaagcgcg atcacatggt cctgctggag ttcgtgaccg ccgccgggat cactctcggc     180
atggacgagc tgtacaaggg tggcagcggt ggcatggtga gcaagggcga ggagctgttc     240
accggggtgg tgcccatcct ggtcgagctg gacggcgacg taaacggcca caagttcagc     300
gtgtccggcg agggcgaggg cgatgccacc tacggcaagc tgaccctgaa gctgatctgc     360
accaccggca agctgcccgt gccctggccc accctcgtga ccaccctggg ctacggcctg     420
cagtgcttcg cccgctaccc cgaccacatg aagcagcacg acttcttcaa gtccgccatg     480
cccgaaggct acgtccagga gcgcaccatc ttcttcaagg acgacggcaa ctacaagacc     540
cgcgccgagg tgaagttcga gggcgacacc ctggtgaacc gcatcgagct gaagggcatc     600
gacttcaagg aggacggcaa catcctgggg cacaagctgg agtacaacta caacagccac     660
aacgtctata tcaccgccga caagcagaag aacggcatca aggccaactt caagatccgc     720
cacaacatcg agtaatga                                                    738

<210> SEQ ID NO 55
<211> LENGTH: 244
<212> TYPE: PRT
<213> ORGANISM: Artificial Sequence
<220> FEATURE:
<223> OTHER INFORMATION: cpVenus

<400> SEQUENCE: 55

Met Gly Gly Val Gln Leu Ala Asp His Tyr Gln Gln Asn Thr Pro Ile
1               5                   10                  15

Gly Asp Gly Pro Val Leu Leu Pro Asp Asn His Tyr Leu Ser Tyr Gln
            20                  25                  30

Ser Lys Leu Ser Lys Asp Pro Asn Glu Lys Arg Asp His Met Val Leu
        35                  40                  45

Leu Glu Phe Val Thr Ala Ala Gly Ile Thr Leu Gly Met Asp Glu Leu
    50                  55                  60
```

```
Tyr Lys Gly Gly Ser Gly Gly Met Val Ser Lys Gly Glu Glu Leu Phe
 65                  70                  75                  80

Thr Gly Val Val Pro Ile Leu Val Glu Leu Asp Gly Asp Val Asn Gly
                 85                  90                  95

His Lys Phe Ser Val Ser Gly Glu Gly Glu Gly Asp Ala Thr Tyr Gly
            100                 105                 110

Lys Leu Thr Leu Lys Leu Ile Cys Thr Thr Gly Lys Leu Pro Val Pro
        115                 120                 125

Trp Pro Thr Leu Val Thr Thr Leu Gly Tyr Gly Leu Gln Cys Phe Ala
    130                 135                 140

Arg Tyr Pro Asp His Met Lys Gln His Asp Phe Phe Lys Ser Ala Met
145                 150                 155                 160

Pro Glu Gly Tyr Val Gln Glu Arg Thr Ile Phe Phe Lys Asp Asp Gly
                165                 170                 175

Asn Tyr Lys Thr Arg Ala Glu Val Lys Phe Glu Gly Asp Thr Leu Val
            180                 185                 190

Asn Arg Ile Glu Leu Lys Gly Ile Asp Phe Lys Glu Asp Gly Asn Ile
        195                 200                 205

Leu Gly His Lys Leu Glu Tyr Asn Tyr Asn Ser His Asn Val Tyr Ile
    210                 215                 220

Thr Ala Asp Lys Gln Lys Asn Gly Ile Lys Ala Asn Phe Lys Ile Arg
225                 230                 235                 240

His Asn Ile Glu

<210> SEQ ID NO 56
<211> LENGTH: 3445
<212> TYPE: DNA
<213> ORGANISM: Artificial Sequence
<220> FEATURE:
<223> OTHER INFORMATION: Human beta2-cpVenus, pDC plasmid

<400> SEQUENCE: 56
cgccccgccc tgccactcat cgcagtactg ttgtaattca ttaagcattc tgccgacatg      60
gaagccatca caaacggcat gatgaacctg aatcgccagc ggcatcagca ccttgtcgcc    120
ttgcgtataa tatttgccca tggtgaaaac ggggcgaag aagttgtcca tattggccac     180
gtttaaatca aaactggtga aactcaccca gggattggct gagacgaaaa acatattctc    240
aataaaccct ttagggaaat aggccaggtt ttcaccgtaa cacgccacat cttgcgaata    300
tatgtgtaga aactgccgga atcgtcgtg gtattcactc cagagcgatg aaaacgtttc     360
agtttgctca tggaaaacgg tgtaacaagg gtgaacacta tcccatatca ccagctcacc    420
gtctttcatt gccatacgga attccggatg agcattcatc aggcgggcaa gaatgtgaat    480
aaaggccgga taaaacttgt gcttattttt ctttacggtc tttaaaaagg ccgtaatatc    540
cagctgaacg gtctggttat aggtacattg agcaactgac tgaaatgcct caaaatgttc    600
tttacgatgc cattgggata tatcaacggt ggtatatcca gtgatttttt tctccatttt    660
agcttcctta gctcctgaaa atctcgataa ctcaaaaaat acgcccggta gtgatcttat    720
ttcattatgg tgaaagttgg accctcttac gtgccgatca acgtctcatt ttcgccaaaa    780
gttggcccag atcaacgtct cattttcgcc aaaagttggc ccagatctat gtcgggtgcg    840
gagaaagagg taatgaaatg gcacctaggt atcgataata cgactcacta gggggaatt    900 gtgagcggat aacaattccc ctctagaaat aattttgttt aactttaaga aggagatata    960
catatgaggc ctatgggaaa caccaccagc gaccgggtgt ccggggagcg ccacggcgcc    1020
```

```
aaggctgcac gctccgaggg cgcaggcggc catgccccgg ggaaggagca caagatcatg    1080
gtggggagta cggacgaccc cagcgtgttc agcctccctg actccaagct ccctggggac    1140
aaagagtttg tatcatggca gcaggatttg gaggactccg taaagcccac acagcaggcc    1200
cggcccactg ttatccgctg gtctgaagga ggcaaggagg tcttcatctc tgggtccttc    1260
aacaattgga gcgccaagat tccactgatt aagagccata atgactttgt tgccatcctg    1320
gacctccctg agggagagca ccaatacaag ttctttgtgg atggacagtg ggttcatgat    1380
ccatcagagc ctgtggttac cagtcagctt ggcacaatta acaatttgat ccatgtcaag    1440
aaatctgatt ttgaggtgtt cgatgcttta aagttagatt ctatggaaag ttctgagaca    1500
tcttgtagag acctttccag ctcacccca gggccttatg gtcaagaaat gtatgcgttt     1560
cgatctgagg aaagattcaa atccccaccc atccttcctc ctcatctact tcaagttatt    1620
cttaacaaag acactaatat ttcttgtgac ccagccttac tccctgagcc caaccatgtt    1680
atgctgaacc atctctatgc attgtccatt aaggacagtg tgatggtcct tagcgcaacc    1740
catcgctaca agaagaagta tgttactact ctgctataca agcccattgt gcacatgggc    1800
ggcgtgcagc tcgccgacca ctaccagcag aacaccccca tcggcgacgg ccccgtgctg    1860
ctgcccgaca ccactaccct gagctaccag tccaagctga gcaaagaccc caacgagaag    1920
cgcgatcaca tggtcctgct ggagttcgtg accgccgccg ggatcactct cggcatggac    1980
gagctgtaca agggtggcag cggtggcatg gtgagcaagg gcgaggagct gttcaccggg    2040
gtggtgccca tcctggtcga gctggacggc gacgtaaacg gccacaagtt cagcgtgtcc    2100
ggcgagggcg agggcgatgc cacctacggc aagctgaccc tgaagctgat ctgcaccacc    2160
ggcaagctgc ccgtgccctg gcccaccctc gtgaccaccc tgggctacgg cctgcagtgc    2220
ttcgcccgct accccgacca catgaagcag cacgacttct tcaagtccgc catgcccgaa    2280
ggctacgtcc aggagcgcac catcttcttc aaggacgacg gcaactacaa gacccgcgcc    2340
gaggtgaagt tcgagggcga caccctggtg aaccgcatcg agctgaaggg catcgacttc    2400
aaggaggacg gcaacatcct ggggcacaag ctggagtaca actacaacag ccacaacgtc    2460
tatatcaccg ccgacaagca gaagaacggc atcaaggcca acttcaagat ccgccacaac    2520
atcgagtaat gagcatgcta gcataacccc ttggggcctc taaacgggtc ttgaggggtt    2580
ttttggttta aacccatgtg cctggcagat aacttcgtat aatgtatgct atacgaagtt    2640
atggtaccgc ggccgcgtag aggatctgtt gatcagcagt tcaacctgtt gatagtacgt    2700
actaagctct catgtttcac gtactaagct ctcatgttta cgtactaagc tctcatgttt    2760
taacgaacta accctcatg gctaacgtac taagctctca tggctaacgt actaagctct    2820
catgtttcac gtactaagct ctcatgtttg aacaataaaa ttaatataaa tcagcaactt    2880
aaatagcctc taaggtttta agttttataa gaaaaaaaag aatatataag gcttttaaag    2940
cttttaaggt ttaacggttg tggacaacaa gccaggatg taacgcactg agaagccctt     3000
agagcctctc aaagcaattt tgagtgacac aggaacactt aacggctgac agaattagct    3060
tcacgctgcc gcaagcactc agggcgcaag gctgctaaa ggaagcggaa cacgtagaaa     3120
gccagtccgc agaaacggtg ctgaccccgg atgaatgtca gctgggaggc agaataaatg    3180
atcatatcgt caattattac ctccacgggg agagcctgag caaactggcc tcaggcattt    3240
gagaagcaca cggtcacact gcttccggta gtcaataaac cggtaaacca gcaatagaca    3300
taagcggcta tttaacgacc ctgccctgaa ccgacgaccg ggtcgaattt gctttcgaat    3360
ttctgccatt catccgctta ttatcactta ttcaggcgta gcaaccaggc gtttaagggc    3420
```
accaataact gccttaaaaa aatta 3445

<210> SEQ ID NO 57
<211> LENGTH: 518
<212> TYPE: PRT
<213> ORGANISM: Artificial Sequence
<220> FEATURE:
<223> OTHER INFORMATION: Human beta2-cpVenus

<400> SEQUENCE: 57

```
Met Gly Asn Thr Thr Ser Asp Arg Val Ser Gly Glu Arg His Gly Ala
1               5                   10                  15

Lys Ala Ala Arg Ser Glu Gly Ala Gly Gly His Ala Pro Gly Lys Glu
            20                  25                  30

His Lys Ile Met Val Gly Ser Thr Asp Asp Pro Ser Val Phe Ser Leu
        35                  40                  45

Pro Asp Ser Lys Leu Pro Gly Asp Lys Glu Phe Val Ser Trp Gln Gln
    50                  55                  60

Asp Leu Glu Asp Ser Val Lys Pro Thr Gln Gln Ala Arg Pro Thr Val
65                  70                  75                  80

Ile Arg Trp Ser Glu Gly Gly Lys Glu Val Phe Ile Ser Gly Ser Phe
                85                  90                  95

Asn Asn Trp Ser Ala Lys Ile Pro Leu Ile Lys Ser His Asn Asp Phe
            100                 105                 110

Val Ala Ile Leu Asp Leu Pro Glu Gly Glu His Gln Tyr Lys Phe Phe
        115                 120                 125

Val Asp Gly Gln Trp Val His Asp Pro Ser Glu Pro Val Val Thr Ser
    130                 135                 140

Gln Leu Gly Thr Ile Asn Asn Leu Ile His Val Lys Lys Ser Asp Phe
145                 150                 155                 160

Glu Val Phe Asp Ala Leu Lys Leu Asp Ser Met Glu Ser Ser Glu Thr
                165                 170                 175

Ser Cys Arg Asp Leu Ser Ser Ser Pro Pro Gly Pro Tyr Gly Gln Glu
            180                 185                 190

Met Tyr Ala Phe Arg Ser Glu Glu Arg Phe Lys Ser Pro Pro Ile Leu
        195                 200                 205

Pro Pro His Leu Leu Gln Val Ile Leu Asn Lys Asp Thr Asn Ile Ser
    210                 215                 220

Cys Asp Pro Ala Leu Leu Pro Glu Pro Asn His Val Met Leu Asn His
225                 230                 235                 240

Leu Tyr Ala Leu Ser Ile Lys Asp Ser Val Met Val Leu Ser Ala Thr
                245                 250                 255

His Arg Tyr Lys Lys Lys Tyr Val Thr Thr Leu Leu Tyr Lys Pro Ile
            260                 265                 270

Val His Met Gly Gly Val Gln Leu Ala Asp His Tyr Gln Gln Asn Thr
        275                 280                 285

Pro Ile Gly Asp Gly Pro Val Leu Leu Pro Asp Asn His Tyr Leu Ser
    290                 295                 300

Tyr Gln Ser Lys Leu Ser Lys Asp Pro Asn Glu Lys Arg Asp His Met
305                 310                 315                 320

Val Leu Leu Glu Phe Val Thr Ala Ala Gly Ile Thr Leu Gly Met Asp
                325                 330                 335

Glu Leu Tyr Lys Gly Gly Ser Gly Gly Met Val Ser Lys Gly Glu Glu
            340                 345                 350
```

```
Leu Phe Thr Gly Val Val Pro Ile Leu Val Glu Leu Asp Gly Asp Val
            355                 360                 365

Asn Gly His Lys Phe Ser Val Ser Gly Glu Gly Glu Gly Asp Ala Thr
        370                 375                 380

Tyr Gly Lys Leu Thr Leu Lys Leu Ile Cys Thr Thr Gly Lys Leu Pro
385                 390                 395                 400

Val Pro Trp Pro Thr Leu Val Thr Thr Leu Gly Tyr Gly Leu Gln Cys
                405                 410                 415

Phe Ala Arg Tyr Pro Asp His Met Lys Gln His Asp Phe Phe Lys Ser
            420                 425                 430

Ala Met Pro Glu Gly Tyr Val Gln Glu Arg Thr Ile Phe Phe Lys Asp
        435                 440                 445

Asp Gly Asn Tyr Lys Thr Arg Ala Glu Val Lys Phe Glu Gly Asp Thr
    450                 455                 460

Leu Val Asn Arg Ile Glu Leu Lys Gly Ile Asp Phe Lys Glu Asp Gly
465                 470                 475                 480

Asn Ile Leu Gly His Lys Leu Glu Tyr Asn Tyr Asn Ser His Asn Val
                485                 490                 495

Tyr Ile Thr Ala Asp Lys Gln Lys Asn Gly Ile Lys Ala Asn Phe Lys
            500                 505                 510

Ile Arg His Asn Ile Glu
        515

<210> SEQ ID NO 58
<211> LENGTH: 3536
<212> TYPE: DNA
<213> ORGANISM: Artificial Sequence
<220> FEATURE:
<223> OTHER INFORMATION: Human cpVenus-beta2, pDC plasmid

<400> SEQUENCE: 58
cgccaaaagt tggcccagat caacgtctca ttttcgccaa agttggccc  agatctatgt     60 cgggtgcgga gaaagaggta atgaaatggc acctaggtat cgataatacg actcactata    120
ggggaattgt gagcggataa caattcccct ctagaaataa ttttgtttaa ctttaagaag    180
gagatataca tatgggcggc gtgcagctcg ccgaccacta ccagcagaac cccccatcg    240 gcgacggccc cgtgctgctg cccgacaacc actacctgag ctaccagtcc aagctgagca    300 aagacccccaa cgagaagcgc gatcacatgg tcctgctgga gttcgtgacc gccgccggga    360
tcactctcgg catggacgag ctgtacaagg gtggcagcgg tggcatggtg agcaagggcg    420
aggagctgtt caccggggtg gtgcccatcc tggtcgagct ggacggcgac gtaaacggcc    480
acaagttcag cgtgtccggc gagggcgagg gcgatgccac ctacggcaag ctgaccctga    540
agctgatctg caccaccggc aagctgcccg tgccctggcc cacccccgtg accaccctgg    600
gctacggcct gcagtgcttc gcccgctacc ccgaccacat gaagcagcac gacttcttca    660
agtccgccat gcccgaaggc tacgtccagg agcgcaccat cttcttcaag gacgacggca    720
actacaagac ccgcgccgag gtgaagttcg agggcgacac cctggtgaac cgcatcgagc    780
tgaagggcat cgacttcaag gaggacggca acatcctggg gcacaagctg gagtacaact    840
acaacagcca caacgtctat atcaccgccg acaagcagaa gaacggcatc aaggccaact    900
tcaagatccg ccacaacatc gagaggccta tgggaaacac caccagcgac cgggtgtccg    960
gggagcgcca cggcgccaag gctgcacgct ccgaggcgc  aggcggccat gccccggga    1020 aggagcacaa gatcatggtg gggagtacgg acgaccccag cgtgttcagc ctccctgact   1080
```

```
ccaagctccc tgggacaaa gagtttgtat catggcagca ggatttggag gactccgtaa    1140
agcccacaca gcaggcccgg cccactgtta tccgctggtc tgaaggaggc aaggaggtct    1200
tcatctctgg gtccttcaac aattggagcg ccaagattcc actgattaag agccataatg    1260
actttgttgc catcctggac ctccctgagg gagagcacca atacaagttc tttgtggatg    1320
gacagtgggt tcatgatcca tcagagcctg tggttaccag tcagcttggc acaattaaca    1380
atttgatcca tgtcaagaaa tctgattttg aggtgttcga tgctttaaag ttagattcta    1440
tggaaagttc tgagacatct tgtagagacc tttccagctc accccaggg ccttatggtc     1500 aagaaatgta tgcgtttcga tctgaggaaa gattcaaatc cccacccatc cttcctcctc    1560
atctacttca agttattctt aacaaagaca ctaatatttc ttgtgaccca gccttactcc    1620
ctgagcccaa ccatgttatg ctgaaccatc tctatgcatt gtccattaag acagtgtga     1680 tggtccttag cgcaacccat cgctacaaga agaagtatgt tactactctg ctatacaagc    1740
ccattgtgca ctaagcatgc tagcataacc ccttggggcc tctaaacggg tcttgagggg    1800
ttttttggtt taaacccatg tgcctggcag ataacttcgt ataatgtatg ctatacgaag    1860
ttatggtacc gcggccgcgt agaggatctg ttgatcagca gttcaacctg ttgatagtac    1920
gtactaagct ctcatgtttc acgtactaag ctctcatgtt taacgtacta agctctcatg    1980
tttaacgaac taaaccctca tggctaacgt actaagctct catggctaac gtactaagct    2040
ctcatgtttc acgtactaag ctctcatgtt tgaacaataa aattaatata aatcagcaac    2100
ttaaatagcc tctaaggttt taagttttat aagaaaaaaa agaatatata aggcttttaa    2160
agcttttaag gttaacggt tgtggacaac aagccaggga tgtaacgcac tgagaagccc     2220
ttagagcctc tcaaagcaat tttgagtgac acaggaacac ttaacggctg acagaattag    2280
cttcacgctg ccgcaagcac tcagggcgca agggctgcta aaggaagcgg aacacgtaga    2340
aagccagtcc gcagaaacgg tgctgacccc ggatgaatgt cagctgggag gcagaataaa    2400
tgatcatatc gtcaattatt acctccacgg ggagagcctg agcaaactgg cctcaggcat    2460
ttgagaagca cacggtcaca ctgcttccgg tagtcaataa accggtaaac cagcaataga    2520
cataagcggc tatttaacga ccctgccctg aaccgacgac cgggtcgaat tgctttcga    2580 atttctgcca ttcatccgct tattatcact tattcaggcg tagcaaccag gcgtttaagg    2640
gcaccaataa ctgccttaaa aaaattacgc cccgccctgc cactcatcgc agtactgttg    2700
taattcatta agcattctgc cgacatggaa gccatcacaa acggcatgat gaacctgaat    2760
cgccagcggc atcagcacct gtcgccttg cgtataatat ttgcccatgg tgaaaacggg    2820
ggcgaagaag ttgtccatat tggccacgtt taaatcaaaa ctggtgaaac tcacccaggg    2880
attggctgag acgaaaaaca tattctcaat aaaccctta gggaaatagg ccaggttttc     2940
accgtaacac gccacatctt gcgaatatat gtgtagaaac tgccggaaat cgtcgtggta    3000
ttcactccag agcgatgaaa acgtttcagt ttgctcatgg aaaacggtgt aacaagggtg    3060
aacactatcc catatcacca gctcaccgtc tttcattgcc atacgaatt ccggatgagc     3120 attcatcagg cgggcaagaa tgtgaataaa ggccggataa aacttgtgct tatttttctt    3180
tacggtcttt aaaaaggccg taatatccag ctgaacggtc tggttatagg tacattgagc    3240
aactgactga aatgcctcaa aatgttcttt acgatgccat gggatatat caacggtggt     3300 atatccagtg atttttttct ccatttagc ttccttagct cctgaaaatc tcgataactc     3360
aaaaaatacg cccggtagtg atcttatttc attatgtgta aagttggacc ctcttacgtg    3420
ccgatcaacg tctcatttc gccaaaagtt ggcccagatc aacgtctcat tttcgccaaa     3480
```
agttggccca gatctatgtc gggtgcggag aaagaggtaa tgaaatggca cctagg        3536

<210> SEQ ID NO 59
<211> LENGTH: 520
<212> TYPE: PRT
<213> ORGANISM: Artificial Sequence
<220> FEATURE:
<223> OTHER INFORMATION: Human cpVenus-beta2

<400> SEQUENCE: 59

```
Met Gly Gly Val Gln Leu Ala Asp His Tyr Gln Gln Asn Thr Pro Ile
1               5                   10                  15

Gly Asp Gly Pro Val Leu Leu Pro Asp Asn His Tyr Leu Ser Tyr Gln
            20                  25                  30

Ser Lys Leu Ser Lys Asp Pro Asn Glu Lys Arg Asp His Met Val Leu
        35                  40                  45

Leu Glu Phe Val Thr Ala Ala Gly Ile Thr Leu Gly Met Asp Glu Leu
    50                  55                  60

Tyr Lys Gly Gly Ser Gly Gly Met Val Ser Lys Gly Glu Glu Leu Phe
65                  70                  75                  80

Thr Gly Val Val Pro Ile Leu Val Glu Leu Asp Gly Asp Val Asn Gly
                85                  90                  95

His Lys Phe Ser Val Ser Gly Glu Gly Glu Gly Asp Ala Thr Tyr Gly
            100                 105                 110

Lys Leu Thr Leu Lys Leu Ile Cys Thr Thr Gly Lys Leu Pro Val Pro
        115                 120                 125

Trp Pro Thr Leu Val Thr Thr Leu Gly Tyr Gly Leu Gln Cys Phe Ala
    130                 135                 140

Arg Tyr Pro Asp His Met Lys Gln His Asp Phe Phe Lys Ser Ala Met
145                 150                 155                 160

Pro Glu Gly Tyr Val Gln Glu Arg Thr Ile Phe Phe Lys Asp Asp Gly
                165                 170                 175

Asn Tyr Lys Thr Arg Ala Glu Val Lys Phe Glu Gly Asp Thr Leu Val
            180                 185                 190

Asn Arg Ile Glu Leu Lys Gly Ile Asp Phe Lys Glu Asp Gly Asn Ile
        195                 200                 205

Leu Gly His Lys Leu Glu Tyr Asn Tyr Asn Ser His Asn Val Tyr Ile
    210                 215                 220

Thr Ala Asp Lys Gln Lys Asn Gly Ile Lys Ala Asn Phe Lys Ile Arg
225                 230                 235                 240

His Asn Ile Glu Arg Pro Met Gly Asn Thr Thr Ser Asp Arg Val Ser
                245                 250                 255

Gly Glu Arg His Gly Ala Lys Ala Ala Arg Ser Glu Gly Ala Gly Gly
            260                 265                 270

His Ala Pro Gly Lys Glu His Lys Ile Met Val Gly Ser Thr Asp Asp
        275                 280                 285

Pro Ser Val Phe Ser Leu Pro Asp Ser Lys Leu Pro Gly Asp Lys Glu
    290                 295                 300

Phe Val Ser Trp Gln Gln Asp Leu Glu Asp Ser Val Lys Pro Thr Gln
305                 310                 315                 320

Gln Ala Arg Pro Thr Val Ile Arg Trp Ser Glu Gly Gly Lys Glu Val
                325                 330                 335

Phe Ile Ser Gly Ser Phe Asn Asn Trp Ser Ala Lys Ile Pro Leu Ile
            340                 345                 350
```

```
Lys Ser His Asn Asp Phe Val Ala Ile Leu Asp Leu Pro Glu Gly Glu
            355                 360                 365

His Gln Tyr Lys Phe Phe Val Asp Gly Gln Trp Val His Asp Pro Ser
        370                 375                 380

Glu Pro Val Val Thr Ser Gln Leu Gly Thr Ile Asn Asn Leu Ile His
385                 390                 395                 400

Val Lys Lys Ser Asp Phe Glu Val Phe Asp Ala Leu Lys Leu Asp Ser
                405                 410                 415

Met Glu Ser Ser Glu Thr Ser Cys Arg Asp Leu Ser Ser Pro Pro
                420                 425                 430

Gly Pro Tyr Gly Gln Glu Met Tyr Ala Phe Arg Ser Glu Glu Arg Phe
            435                 440                 445

Lys Ser Pro Pro Ile Leu Pro Pro His Leu Leu Gln Val Ile Leu Asn
    450                 455                 460

Lys Asp Thr Asn Ile Ser Cys Asp Pro Ala Leu Leu Pro Glu Pro Asn
465                 470                 475                 480

His Val Met Leu Asn His Leu Tyr Ala Leu Ser Ile Lys Asp Ser Val
                485                 490                 495

Met Val Leu Ser Ala Thr His Arg Tyr Lys Lys Lys Tyr Val Thr Thr
                500                 505                 510

Leu Leu Tyr Lys Pro Ile Val His
            515                 520

<210> SEQ ID NO 60
<211> LENGTH: 3569
<212> TYPE: DNA
<213> ORGANISM: Artificial Sequence
<220> FEATURE:
<223> OTHER INFORMATION: Rat gamma1-cpVenus, pDS plasmid

<400> SEQUENCE: 60
tgtctaacaa ttcgttcaag ccgacggatc tatgtcgggt gcggagaaag aggtaatgaa      60
atggcaccta ggtatcgata atacgactca ctatagggga attgtgagcg ataacaatt     120 cccctctaga aataattttg tttaacttta agaaggagat atacatatgg agtcggttgc     180
tgcagagagc gctccagctc ggagaatga acactctcaa gagacccccgg aatcgaacag     240 tagtgtgtac accaccttca tgaagtctca tcgctgctat gacctgatcc ccacaagctc     300
caagctggtg gtatttgata cttcgctgca ggtaaagaaa gccttctttg ccctggtgac     360
taacggtgtt cgtgctgccc ctttgtggga tagtaagaag cagagctttg tgggcatgct     420
gaccatcact gacttcatca atattctgca ccgatactac aagtcagccc tggtgcagat     480
ctatgaactg gaggagcaca agatagagac ttggagagag gtctacctgc aagactcctt     540
taagccactt gtctgcattt ctccaaatgc cagcttgttc gatgctgtct cttcattaat     600
tcgaaataag atccacaggc ttccagttat tgacccggag tcaggcaaca ccttgtacat     660
tcttactcac aagcggatcc tcaagttcct caagttgttt atcactgagt tccccaagcc     720
ggaattcatg tctaagtctc tggaagagct acagattggc acctacgcca atattgccat     780
ggtccgtacc actacacctg tctatgtggc tctgggcatc tttgtacagc accgagtctc     840
cgccttgcct gtggtggatg agaaaagggcg tgtggtggac atctactcca gtttgatgt     900 gattaatttg gcagcagaaa agacatacaa caacctagat gtgtctgtga caaaagccct     960
acagcaccgg tcacactact tcgagggtgt tctcaagtgc tacctacatg agactctaga    1020
agcaatcatc aatagactgg tggaagcaga ggttcaccgt ctggtggtgg tggatgaaca    1080
```

```
tgacgtggtc aagggcattg tatcgctgtc tgacatctta caggctctgg tgctcacagg    1140
tggagagaag aagcccgcta gcatgggcgg cgtgcagctc gccgaccact accagcagaa    1200 caccccatc ggcgacggcc ccgtgctgct gcccgacaac cactacctga gctaccagtc     1260
caagctgagc aaagacccca acgagaagcg cgatcacatg gtcctgctgg agttcgtgac    1320
cgccgccggg atcactctcg gcatggacga gctgtacaag ggtggcagcg gtggcatggt    1380
gagcaagggc gaggagctgt tcaccggggt ggtgcccatc ctggtcgagc tggacggcga    1440
cgtaaacggc cacaagttca gcgtgtccgg cgagggcgag ggcgatgcca cctacggcaa    1500
gctgaccctg aagctgatct gcaccaccgg caagctgccc gtgccctggc ccaccctcgt    1560
gaccaccctg ggctacggcc tgcagtgctt cgcccgctac cccgaccaca tgaagcagca    1620
cgacttcttc aagtccgcca tgcccgaagg ctacgtccag gagcgcacca tcttcttcaa    1680
ggacgacggc aactacaaga cccgcgccga ggtgaagttc gagggcgaca ccctggtgaa    1740
ccgcatcgag ctgaagggca tcgacttcaa ggaggacggc aacatcctgg ggcacaagct    1800
ggagtacaac tacaacagcc acaacgtcta tatcaccgcc gacaagcaga agaacggcat    1860
caaggccaac ttcaagatcc gccacaacat cgagtaatag gtttaaaccc atgtgcctgg    1920
cagataactt cgtataatgt atgctatacg aagttatggt acgtactaag ctctcatgtt    1980
tcacgtacta agctctcatg tttaacgtac taagctctca tgtttaacga actaaaccct    2040
catggctaac gtactaagct ctcatggcta acgtactaag ctctcatgtt tcacgtacta    2100
agctctcatg tttgaacaat aaaattaata taaatcagca acttaaatag cctctaaggt    2160
tttaagtttt ataagaaaaa aaagaatata taaggctttt aaagctttta aggtttaacg    2220
gttgtggaca acaagccagg gatgtaacgc actgagaagc ccttagagcc tctcaaagca    2280
attttgagtg acacaggaac acttaacggc tgacataatt cagcttcacg ctgccgcaag    2340
cactcagggc gcaagggctg ctaaaggaag cggaacacgt agaaagccag tccgcagaaa    2400
cggtgctgac cccggatgaa tgtcagctgg gaggcagaat aaatgatcat atcgtcaatt    2460
attacctcca cggggagagc ctgagcaaac tggcctcagg catttgagaa gcacacggtc    2520
acactgcttc cggtagtcaa taaaccggta agtagcgtat gcgctcacgc aactggtcca    2580
gaaccttgac cgaacgcagc ggtggtaacg gcgcagtggc ggttttcatg gcttgttatg    2640
actgtttttt tggggtacag tctatgcctc gggcatccaa gcagcaagcg cgttacgccg    2700
tgggtcgatg tttgatgtta tggagcagca acgatgttac gcagcagggc agtcgcccta    2760
aaacaaagtt aaacatcatg agggaagcgg tgatcgccga agtatcgact caactatcag    2820
aggtagttgg cgtcatcgag cgccatctcg aaccgacgtt gctggccgta catttgtacg    2880
gctccgcagt ggatggcggc ctgaagccac acagtgatat tgatttgctg gttacggtga    2940
ccgtaaggct tgatgaaaca acgcggcgag cttt gatcaa cgaccttttg gaaacttcgg    3000
cttcccctgg agagagcgag attctccgcg ctgtagaagt caccattgtt gtgcacgacg    3060
acatcattcc gtggcgttat ccagctaagc gcgaactgca atttggagaa tggcagcgca    3120
atgacattct gcaggtatc ttcgagccag ccacgatcga cattgatctg ctatcttgc     3180 tgacaaaagc aagagaacat agcgttgcct tggtaggtcc agcggcggag gaactctttg    3240
atccggttcc tgaacaggat ctatttgagg cgctaaatga aaccttaacg ctatggaact    3300
cgccgcccga ctgggctggc gatgagcgaa atgtagtgct tacgttgtcc cgcatttggt    3360
acagcgcagt aaccggcaaa atcgcgccga aggatgtcgc tgccgactgg gcaatggagc    3420
gcctgccggc ccagtatcag cccgtcatac ttgaagctag acaggcttat cttggacaag    3480
```

-continued

```
aagaagatcg cttggcctcg cgcgcagatc agttggaaga atttgtccac tacgtgaaag    3540
gcgagatcac caaggtagtc ggcaaataa                                       3569
```

<210> SEQ ID NO 61
<211> LENGTH: 576
<212> TYPE: PRT
<213> ORGANISM: Artificial Sequence
<220> FEATURE:
<223> OTHER INFORMATION: Rat gamma1-cpVenus

<400> SEQUENCE: 61

```
Met Glu Ser Val Ala Ala Glu Ser Ala Pro Ala Pro Glu Asn Glu His
 1               5                  10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
    50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
    290                 295                 300

His Asp Val Val Lys Gly Ile Val Ser Leu Asp Ile Leu Gln Ala
305                 310                 315                 320

Leu Val Leu Thr Gly Gly Glu Lys Lys Pro Ala Ser Met Gly Gly Val
                325                 330                 335

Gln Leu Ala Asp His Tyr Gln Gln Asn Thr Pro Ile Gly Asp Gly Pro
```

```
                340              345              350
Val Leu Leu Pro Asp Asn His Tyr Leu Ser Tyr Gln Ser Lys Leu Ser
            355                  360                  365

Lys Asp Pro Asn Glu Lys Arg Asp His Met Val Leu Leu Glu Phe Val
        370                  375                  380

Thr Ala Ala Gly Ile Thr Leu Gly Met Asp Glu Leu Tyr Lys Gly Gly
385                  390                  395                 400

Ser Gly Gly Met Val Ser Lys Gly Glu Glu Leu Phe Thr Gly Val Val
                405                  410                  415

Pro Ile Leu Val Glu Leu Asp Gly Asp Val Asn Gly His Lys Phe Ser
                420                  425                  430

Val Ser Gly Glu Gly Glu Gly Asp Ala Thr Tyr Gly Lys Leu Thr Leu
            435                  440                  445

Lys Leu Ile Cys Thr Thr Gly Lys Leu Pro Val Pro Trp Pro Thr Leu
        450                  455                  460

Val Thr Thr Leu Gly Tyr Gly Leu Gln Cys Phe Ala Arg Tyr Pro Asp
465                  470                  475                 480

His Met Lys Gln His Asp Phe Phe Lys Ser Ala Met Pro Glu Gly Tyr
                485                  490                  495

Val Gln Glu Arg Thr Ile Phe Phe Lys Asp Asp Gly Asn Tyr Lys Thr
                500                  505                  510

Arg Ala Glu Val Lys Phe Glu Gly Asp Thr Leu Val Asn Arg Ile Glu
            515                  520                  525

Leu Lys Gly Ile Asp Phe Lys Glu Asp Gly Asn Ile Leu Gly His Lys
        530                  535                  540

Leu Glu Tyr Asn Tyr Asn Ser His Asn Val Tyr Ile Thr Ala Asp Lys
545                  550                  555                 560

Gln Lys Asn Gly Ile Lys Ala Asn Phe Lys Ile Arg His Asn Ile Glu
                565                  570                  575
```

<210> SEQ ID NO 62
<211> LENGTH: 3577
<212> TYPE: DNA
<213> ORGANISM: Artificial Sequence
<220> FEATURE:
<223> OTHER INFORMATION: Rat cpVenus-gamma1, pDS plasmid

<400> SEQUENCE: 62

```
atgagggaag cggtgatcgc cgaagtatcg actcaactat cagaggtagt tggcgtcatc      60
gagcgccatc tcgaaccgac gttgctggcc gtacatttgt acggctccgc agtggatggc    120
ggcctgaagc cacacagtga tattgatttg ctggttacgg tgaccgtaag gcttgatgaa    180
acaacgcggc gagctttgat caacgacctt ttggaaactt cggcttcccc tggagagagc    240
gagattctcc gcgctgtaga agtcaccatt gttgtgcacg acgacatcat tccgtggcgt    300
tatccagcta agcgcgaact gcaatttgga gaatggcagc gcaatgacat tcttgcaggt    360
atcttcgagc cagccacgat cgacattgat ctggctatct tgctgacaaa agcaagagaa    420
catagcgttg ccttggtagg tccagcggcg gaggaactct tgatccggt tcctgaacag    480
gatctatttg aggcgctaaa tgaaacctta cgctatggaa ctcgccgcc cgactgggct    540
ggcgatgagc gaaatgtagt gcttacgttg tcccgcattt ggtacagcgc agtaaccggc    600
aaaatcgcgc cgaaggatgt cgctgccgac tgggcaatgg agcgcctgcc ggcccagtat    660
cagcccgtca tacttgaagc tagacaggct tatcttggac aagaagaaga tcgcttggcc    720
tcgcgcgcag atcagttgga agaatttgtc cactacgtga aaggcgagat caccaaggta    780
```

-continued

```
gtcggcaaat aatgtctaac aattcgttca agccgacgga tctatgtcgg gtgcggagaa      840
agaggtaatg aaatggcacc taggtatcga taatacgact cactataggg gaattgtgag      900
cggataacaa ttcccctcta gaaataattt tgtttaactt taagaaggag atatacatat      960
gggcggcgtg cagctcgccg accactacca gcagaacacc cccatcggcg acggcccgt      1020 gctgctgccc gacaaccact acctgagcta ccagtccaag ctgagcaaag accccaacga     1080
gaagcgcgat cacatggtcc tgctggagtt cgtgaccgcc gccgggatca ctctcggcat     1140
ggacgagctg tacaagggtg gcagcggtgg catggtgagc aagggcgagg agctgttcac     1200
cggggtggtg cccatcctgg tcgagctgga cggcgacgta acggccaca agttcagcgt      1260 gtccggcgag ggcgagggcg atgccaccta cggcaagctg accctgaagc tgatctgcac     1320
caccggcaag ctgcccgtgc cctggcccac cctcgtgacc accctgggct acggcctgca     1380
gtgcttcgcc cgctaccccg accacatgaa gcagcacgac ttcttcaagt ccgccatgcc     1440
cgaaggctac gtccaggagc gcaccatctt cttcaaggac gacggcaact acaagacccg     1500
cgccgaggtg aagttcgagg gcgacaccct ggtgaaccgc atcgagctga agggcatcga     1560
cttcaaggag gacggcaaca tcctggggca caagctggag tacaactaca acagccacaa     1620
cgtctatatc accgccgaca gcagaagaa cggcatcaag ccaacttca agatccgcca      1680 caacatcgag gctagcatgg agtcggttgc tgcagagagc gctccagctc cggagaatga     1740
acactctcaa gagacccegg aatcgaacag tagtgtgtac accaccttca tgaagtctca     1800
tcgctgctat gacctgatcc ccacaagctc aagctggtg gtatttgata cttcgctgca      1860
ggtaaagaaa gccttctttg ccctggtgac taacggtgtt cgtgctgccc ctttgtggga     1920
tagtaagaag cagagctttg tgggcatgct gaccatcact gacttcatca atattctgca     1980
ccgatactac aagtcagccc tggtgcagat ctatgaactg gaggagcaca agatagagac     2040
ttggagagag gtctacctgc aagactcctt taagccactt gtctgcattt ctccaaatgc     2100
cagcttgttc gatgctgtct cttcattaat tcgaaataag atccacaggc ttccagttat     2160
tgacccggag tcaggcaaca ccttgtacat tcttactcac aagcggatcc tcaagttcct     2220
caagttgttt atcactgagt tccccaagcc ggaattcatg tctaagtctc tggaagagct     2280
acagattggc acctacgcca atattgccat ggtccgtacc actacacctg tctatgtggc     2340
tctgggcatc tttgtacagc accgagtctc cgccttgcct gtggtggatg agaaagggcg     2400
tgtggtggac atctactcca gtttgatgt gattaatttg gcagcagaaa agacatacaa     2460
caacctagat gtgtctgtga caaaagcccc acagcaccgg tcacactact cgagggtgt      2520 tctcaagtgc tacctacatg agactctaga agcaatcatc aatagactgg tggaagcaga     2580
ggttcaccgt ctggtggtgg tggatgaaca tgacgtggtc aagggcattg tatcgctgtc     2640
tgacatctta caggctctgg tgctcacagg tggagagaag aagccctgat aactagttcc     2700
gtttaaaccc atgtgcctgg cagataactt cgtataatgt atgctatacg aagttatggt     2760
acgtactaag ctctcatgtt tcacgtacta agctctcatg tttaacgtac taagctctca     2820
tgtttaacga actaaaccct catggctaac gtactaagct ctcatggcta acgtactaag     2880
ctctcatgtt tcacgtacta agctctcatg tttaacaat aaaattaata taaatcagca      2940
acttaaatag cctctaaggt tttaagtttt ataagaaaaa aagaatata taaggcttt       3000 aaagctttta aggtttaacg gttgtggaca caagccagg gatgtaacgc actgagaagc      3060
ccttagagcc tctcaaagca attttgagtg acacaggaac acttaacggc tgacataatt     3120
```

```
cagcttcacg ctgccgcaag cactcagggc gcaagggctg ctaaaggaag cggaacacgt    3180
agaaagccag tccgcagaaa cggtgctgac cccggatgaa tgtcagctgg gaggcagaat    3240
aaatgatcat atcgtcaatt attacctcca cggggagagc ctgagcaaac tggcctcagg    3300
catttgagaa gcacacggtc acactgcttc cggtagtcaa taaaccggta agtagcgtat    3360
gcgctcacgc aactggtcca gaaccttgac cgaacgcagc ggtggtaacg gcgcagtggc    3420
ggttttcatg gcttgttatg actgtttttt tggggtacag tctatgcctc gggcatccaa    3480
gcagcaagcg cgttacgccg tgggtcgatg tttgatgtta tggagcagca acgatgttac    3540
gcagcagggc agtcgcccta aacaaagtt aaacatc    3577
```

<210> SEQ ID NO 63
<211> LENGTH: 576
<212> TYPE: PRT
<213> ORGANISM: Artificial Sequence
<220> FEATURE:
<223> OTHER INFORMATION: Rat pVenus-gamma1

<400> SEQUENCE: 63

```
Met Gly Gly Val Gln Leu Ala Asp His Tyr Gln Gln Asn Thr Pro Ile
1               5                   10                  15

Gly Asp Gly Pro Val Leu Leu Pro Asp Asn His Tyr Leu Ser Tyr Gln
            20                  25                  30

Ser Lys Leu Ser Lys Asp Pro Asn Glu Lys Arg Asp His Met Val Leu
        35                  40                  45

Leu Glu Phe Val Thr Ala Ala Gly Ile Thr Leu Gly Met Asp Glu Leu
    50                  55                  60

Tyr Lys Gly Gly Ser Gly Gly Met Val Ser Lys Gly Glu Glu Leu Phe
65                  70                  75                  80

Thr Gly Val Val Pro Ile Leu Val Glu Leu Asp Gly Asp Val Asn Gly
                85                  90                  95

His Lys Phe Ser Val Ser Gly Glu Gly Glu Gly Asp Ala Thr Tyr Gly
            100                 105                 110

Lys Leu Thr Leu Lys Leu Ile Cys Thr Thr Gly Lys Leu Pro Val Pro
        115                 120                 125

Trp Pro Thr Leu Val Thr Thr Leu Gly Tyr Gly Leu Gln Cys Phe Ala
    130                 135                 140

Arg Tyr Pro Asp His Met Lys Gln His Asp Phe Phe Lys Ser Ala Met
145                 150                 155                 160

Pro Glu Gly Tyr Val Gln Glu Arg Thr Ile Phe Phe Lys Asp Asp Gly
                165                 170                 175

Asn Tyr Lys Thr Arg Ala Glu Val Lys Phe Glu Gly Asp Thr Leu Val
            180                 185                 190

Asn Arg Ile Glu Leu Lys Gly Ile Asp Phe Lys Glu Asp Gly Asn Ile
        195                 200                 205

Leu Gly His Lys Leu Glu Tyr Asn Tyr Asn Ser His Asn Val Tyr Ile
    210                 215                 220

Thr Ala Asp Lys Gln Lys Asn Gly Ile Lys Ala Asn Phe Lys Ile Arg
225                 230                 235                 240

His Asn Ile Glu Ala Ser Met Glu Ser Val Ala Glu Ser Ala Pro
                245                 250                 255

Ala Pro Glu Asn Glu His Ser Gln Gln Thr Pro Glu Ser Asn Ser Ser
            260                 265                 270

Val Tyr Thr Thr Phe Met Lys Ser His Arg Cys Tyr Asp Leu Ile Pro
        275                 280                 285
```

```
Thr Ser Ser Lys Leu Val Val Phe Asp Thr Ser Leu Gln Val Lys Lys
    290                 295                 300

Ala Phe Phe Ala Leu Val Thr Asn Gly Val Arg Ala Ala Pro Leu Trp
305                 310                 315                 320

Asp Ser Lys Lys Gln Ser Phe Val Gly Met Leu Thr Ile Thr Asp Phe
                325                 330                 335

Ile Asn Ile Leu His Arg Tyr Tyr Lys Ser Ala Leu Val Gln Ile Tyr
                340                 345                 350

Glu Leu Glu Glu His Lys Ile Glu Thr Trp Arg Glu Val Tyr Leu Gln
                355                 360                 365

Asp Ser Phe Lys Pro Leu Val Cys Ile Ser Pro Asn Ala Ser Leu Phe
    370                 375                 380

Asp Ala Val Ser Ser Leu Ile Arg Asn Lys Ile His Arg Leu Pro Val
385                 390                 395                 400

Ile Asp Pro Glu Ser Gly Asn Thr Leu Tyr Ile Leu Thr His Lys Arg
                405                 410                 415

Ile Leu Lys Phe Leu Lys Leu Phe Ile Thr Glu Phe Pro Lys Pro Glu
                420                 425                 430

Phe Met Ser Lys Ser Leu Glu Glu Leu Gln Ile Gly Thr Tyr Ala Asn
                435                 440                 445

Ile Ala Met Val Arg Thr Thr Thr Pro Val Tyr Val Ala Leu Gly Ile
                450                 455                 460

Phe Val Gln His Arg Val Ser Ala Leu Pro Val Val Asp Glu Lys Gly
465                 470                 475                 480

Arg Val Val Asp Ile Tyr Ser Lys Phe Asp Val Ile Asn Leu Ala Ala
                485                 490                 495

Glu Lys Thr Tyr Asn Asn Leu Asp Val Ser Val Thr Lys Ala Leu Gln
                500                 505                 510

His Arg Ser His Tyr Phe Glu Gly Val Leu Lys Cys Tyr Leu His Glu
                515                 520                 525

Thr Leu Glu Ala Ile Ile Asn Arg Leu Val Glu Ala Glu Val His Arg
    530                 535                 540

Leu Val Val Val Asp Glu His Asp Val Val Lys Gly Ile Val Ser Leu
545                 550                 555                 560

Ser Asp Ile Leu Gln Ala Leu Val Leu Thr Gly Gly Glu Lys Lys Pro
                565                 570                 575

<210> SEQ ID NO 64
<211> LENGTH: 4947
<212> TYPE: DNA
<213> ORGANISM: Artificial Sequence
<220> FEATURE:
<223> OTHER INFORMATION: Rat alpha2-mseCFP-11, pACE plasmid

<400> SEQUENCE: 64
ttgagatcct ttttttctgc gcgtaatctg ctgcttgcaa acaaaaaaac caccgctacc      60
agcggtggtt tgtttgccgg atcaagagct accaactctt tttccgaagg taactggctt    120
cagcagagcg cagataccaa atactgtcct tctagtgtag ccgtagttag gccaccactt    180
caagaactct gtagcaccgc ctacatacct cgctctgcta atcctgttac cagtggctgc    240
tgccagtggc gataagtcgt gtcttaccgg gttggactca agacgatagt taccggataa    300
ggcgcagcgg tcgggctgaa cggggggttc gtgcacacag cccagcttgg agcgaacgac    360
ctacaccgaa ctgagatacc tacagcgtga gctatgagaa agcgccacgc ttcccgaagg    420
```

```
gagaaaggcg acaggtatc cggtaagcgg cagggtcgga acaggagagc gcacgaggga    480
gcttccaggg ggaaacgcct ggtatctttta tagtcctgtc gggtttcgcc acctctgact   540
tgagcgtcga ttttttgtgat gctcgtcagg ggggcggagc ctatggaaaa acgccagcaa  600
cgcggccttt ttacggttcc tggccttttg ctggcctttt gctcacatgt tctttcctgc   660
gttatcccct gattctgtgg ataaccgtat taccgccttt gagtgagctg ataccgctcg   720
ccgcagccga acgaccgagc gcagcgagtc agtgagcgag gaagcggaag agcgcctgat   780
gcggtatttt ctccttacgc atctgtgcgg tatttcacac cgcaatggtg cactctcagt   840
acaatctgct ctgatgccgc atagttaagc cagtatacac tccgctatcg ctacgtgact   900
gggtcatggc tgcgccccga cacccgccaa cacccgctga cgcgccctga cgggcttgtc   960
tgctcccggc atccgcttac agacaagctg tgaccgtctc cgggagctgc atgtgtcaga  1020
ggttttcacc gtcatcaccg aaacgcgcga ggcaggggga attccagata acttcgtata  1080
atgtatgcta tacgaagtta tggtaccgcg gccgcgtaga ggatctgttg atcagcagtt  1140
caacctgttg atagtacttc gttaatacag atgtaggtgt tggcaccatg cataactata  1200
acggtcctaa ggtagcgacc taggtatcga taatacgact cactataggg gaattgtgag  1260
cggataacaa ttcccctcta gaaataattt tgtttaactt taagaaggag atataatggg  1320
cagtagtcac catcaccacc accatcatca ccatcatagt agtgaaaacc tgtattttca  1380
ggggcatatg gctgagaagc agaagcacga cgggcgtgtg aagatcggac actacgtgct  1440
gggggacacc ctgggcgtcg gcaccttcgg caaagtgaag attggagaac atcaattgac  1500
aggccataaa gtggcagtta agatcttaaa tagacagaag attcgcagtt tagatgttgt  1560
tggaaaaata aaacgagaaa ttcaaaatct taaactcttt cgtcatcctc atattatcaa  1620
actctaccaa gtgatcagca ctccaacaga cttttttatg gtaatggaat atgtgtctgg  1680
aggtgaattg ttcgactaca tctgtaaaca cgggagggtt gaagaggtgg aagctcgccg  1740
gctcttccag cagattctgt ctgccgtgga ctactgtcac aggcacatgg ttgtccacag  1800
ggacctgaag ccagagaacg tgttgctgga cgcccagatg aatgctaaga tagctgactt  1860
cggactctct aatatgatgt cagatggtga atttctacga actagctgtg gatcgccaaa  1920
ttatgcagca ccggaggtca tctcaggaag gctgtatgcg ggtcctgagg ttgatatctg  1980
gagctgtggt gttatcctgt atgcccttct ctgtggcacc ctcccgttcg acgatgagca  2040
cgtgcctacg ctctttaaga agatccgagg gggtgtgttc tacatcccgg agtatctcaa  2100
ccgttctatt gccactctgc tgatgcacat gctgcaggtg gacccttga agcgagcaac  2160
tatcaaagac atacgagagc atgaatggtt taaacaggat ttgcccagtt acctctttcc  2220
tgaagacccc tcctatgatg ctaacgtcat tgatgatgag gctgtgaaag aagtatgtga  2280
aaaatttgag tgtacagaat cagaagtgat gaacagttta tacagtggtg accctcaaga  2340
ccagctcgca gtggcttatc atctcatcat tgacaatcgg agaataatga accaagccag  2400
tgagttctac ctcgcctcca gtcctccaac gggttccttc atggacgata gtgccatgca  2460
tattcccccc ggcctgaaac acatcctga aaggatgcca cctctcatag cagacagccc  2520
caaagcacgc tgtccactgg atgcactcaa cacaactaag cccaaatctt tagctgtgaa  2580
aaaagccaag tggcaccttg ggatccgaag ccagagcaaa ccatacgaca ttatggcgga  2640
ggtgtaccga gctatgaagc agctggactt tgaatggaag gtagtgaatg cataccatct  2700
tcgagtaaga agaaaaaacc cagtgactgg caattacgtg aaaatgagct tacagctttta 2760
cctggttgac aatcggagct atctgctgga cttttaaaagc atcgatgatg aggtggtgga  2820
```

```
gcagaggtct ggttcttcaa cacctcagcg ctcctgttct gctgccggcc tccacagacc   2880
tcggtcaagt gtcgattcca gcacagccga gaaccattca ctgtctggct ctctcactgg   2940
ttctttgact ggcagcactt tgtcctccgc ttccccgcgc ctgggcagtc ataccatgga   3000
ttttttgaa atgtgcgcca gtcttatcac tgctttagcc cgtaagctta tggtgagcaa    3060
gggcgaggag ctgttcaccg gggtggtgcc catcctggtc gagctggacg gcgacgtaaa   3120
cggccacagg ttcagcgtgt ccggcgaggg cgagggcgat gccacctacg gcaagctgac   3180
cctgaagttc atctgcacca ccggcaagct gcccgtgccc tggcccaccc tcgtgaccac   3240
cctgacctgg ggcgtgcagt gcttcgcccg ctacccgac cacatgaagc agcacgactt    3300
cttcaagtcc gccatgcccg aaggctacgt ccaggagcgt accatcttct caaggacga    3360
cggcaactac aagacccgcg ccgaggtgaa gttcgagggc gacaccctgg tgaaccgcat   3420
cgagctgaag ggcatcgact tcaaggagga cggcaacatc ctggggcaca agctggagta   3480
caactacatc agccacaacg tctatatcac cgccgacaag cagaagaacg gcatcaaggc   3540
ccacttcaag atccgccaca acatcgagga cggcggcgtg cagctcgccg accactacca   3600
gcagaacacc cccatcggcg acggccccgt gctgctgccc gacaaccact acctgagcac   3660
ccagtccaag ctgagcaaag accccaacga gaagcgcgat cacatggtcc tgctggagtt   3720
cgtgaccgcc gcctaatagc tcgagagatc cggctgctaa caaagcccga aggaagctg    3780
agttggctgc tgccaccgct gagcaataac tagcataacc ccttgggcc tctaaacggg     3840
tcttgagggg ttttttggtt taaacccatc taattggact agtagcccgc ctaatgagcg   3900
ggcttttttt taattcccct atttgtttat tttctaaat acattcaaat atgtatccgc     3960
tcatgagaca ataaccctga taatgcttc aataatattg aaaaggaag agtatgagta      4020
ttcaacattt ccgtgtcgcc cttattccct tttttgcggc attttgcctt cctgtttttg    4080
ctcacccaga aacgctcgtg aaagtaaaag acgcagagga ccaattgggg gcacgagtgg   4140
gatacataga actggacttg aatagcggta aaatccttga gagttttcgc cctgaagagc    4200
gttttccaat gatgagcact ttcaaagttc tgctatgtgg agcagtatta tcccgtgtag    4260
atgcggggca agagcaactc ggacgacgaa tacactattc gcagaatgac ttggttgaat    4320
actcccagt gacagaaaag caccttacgg acggaatgac ggtaagagaa ttatgtagtg     4380
ccgccataac gatgagtgat aacactgcgg cgaacttact tctgacaacc atcggtggac    4440
cgaaggaatt aaccgctttt ttgcacaata tgggagacca tgtaactcgc cttgaccgtt    4500
gggaaccaga actgaatgaa gccataccaa acgacgagcg agacaccaca atgcctgcgg    4560
caatggcaac aacattacgc aaactattaa ctggcgaact acttactctg gcttcacggc    4620
aacaattaat agactggctt gaagcggata agttgcagg accactactg cgttcggcac    4680
ttcctgctgg ctggtttatt gctgataaat ctggggcagg agagcgtggt tcacggggta   4740
tcattgccgc acttggacca gatggtaagc cttcccgtat cgtagttatc tacacgacgg   4800
gtagtcaggc aactatggac gaacgaaata gacagattgc tgaaataggg gcttcactga   4860
ttaagcattg gtaaaccgat acaattaaag gctccttttg gagcctttt ttttggacgg     4920
accggtagaa aagatcaaag gatcttc                                      4947
```

<210> SEQ ID NO 65
<211> LENGTH: 806
<212> TYPE: PRT
<213> ORGANISM: Artificial Sequence
<220> FEATURE:

<223> OTHER INFORMATION: Rat alpha2-mseCFP-11

<400> SEQUENCE: 65

```
Met Gly Ser Ser His His His His His His Ser Ser
1               5                   10              15

Glu Asn Leu Tyr Phe Gln Gly Met Ala Glu Lys Gln Lys His Asp
            20                  25                  30

Gly Arg Val Lys Ile Gly His Tyr Val Leu Gly Asp Thr Leu Gly
            35                  40                  45

Gly Thr Phe Gly Lys Val Lys Ile Gly Glu His Gln Leu Thr Gly His
    50                  55                  60

Lys Val Ala Val Lys Ile Leu Asn Arg Gln Lys Ile Arg Ser Leu Asp
65                  70                  75                  80

Val Val Gly Lys Ile Lys Arg Glu Ile Gln Asn Leu Lys Leu Phe Arg
                85                  90                  95

His Pro His Ile Ile Lys Leu Tyr Gln Val Ile Ser Thr Pro Thr Asp
                100                 105                 110

Phe Phe Met Val Met Glu Tyr Val Ser Gly Gly Glu Leu Phe Asp Tyr
                115                 120                 125

Ile Cys Lys His Gly Arg Val Glu Glu Val Ala Arg Arg Leu Phe
130                 135                 140

Gln Gln Ile Leu Ser Ala Val Asp Tyr Cys His Arg His Met Val Val
145                 150                 155                 160

His Arg Asp Leu Lys Pro Glu Asn Val Leu Leu Asp Ala Gln Met Asn
                165                 170                 175

Ala Lys Ile Ala Asp Phe Gly Leu Ser Asn Met Met Ser Asp Gly Glu
                180                 185                 190

Phe Leu Arg Thr Ser Cys Gly Ser Pro Asn Tyr Ala Ala Pro Glu Val
                195                 200                 205

Ile Ser Gly Arg Leu Tyr Ala Gly Pro Glu Val Asp Ile Trp Ser Cys
                210                 215                 220

Gly Val Ile Leu Tyr Ala Leu Leu Cys Gly Thr Leu Pro Phe Asp Asp
225                 230                 235                 240

Glu His Val Pro Thr Leu Phe Lys Lys Ile Arg Gly Gly Val Phe Tyr
                245                 250                 255

Ile Pro Glu Tyr Leu Asn Arg Ser Ile Ala Thr Leu Leu Met His Met
                260                 265                 270

Leu Gln Val Asp Pro Leu Lys Arg Ala Thr Ile Lys Asp Ile Arg Glu
                275                 280                 285

His Glu Trp Phe Lys Gln Asp Leu Pro Ser Tyr Leu Phe Pro Glu Asp
                290                 295                 300

Pro Ser Tyr Asp Ala Asn Val Ile Asp Glu Ala Val Lys Glu Val
305                 310                 315                 320

Cys Glu Lys Phe Glu Cys Thr Glu Ser Glu Val Met Asn Ser Leu Tyr
                325                 330                 335

Ser Gly Asp Pro Gln Asp Gln Leu Ala Val Ala Tyr His Leu Ile Ile
                340                 345                 350

Asp Asn Arg Arg Ile Met Asn Gln Ala Ser Glu Phe Tyr Leu Ala Ser
                355                 360                 365

Ser Pro Pro Thr Gly Ser Phe Met Asp Asp Ser Ala Met His Ile Pro
                370                 375                 380

Pro Gly Leu Lys Pro His Pro Glu Arg Met Pro Pro Leu Ile Ala Asp
385                 390                 395                 400
```

```
Ser Pro Lys Ala Arg Cys Pro Leu Asp Ala Leu Asn Thr Thr Lys Pro
                405                 410                 415
Lys Ser Leu Ala Val Lys Ala Lys Trp His Leu Gly Ile Arg Ser
    420                 425                 430
Gln Ser Lys Pro Tyr Asp Ile Met Ala Glu Val Tyr Arg Ala Met Lys
        435                 440                 445
Gln Leu Asp Phe Glu Trp Lys Val Val Asn Ala Tyr His Leu Arg Val
450                 455                 460
Arg Arg Lys Asn Pro Val Thr Gly Asn Tyr Val Lys Met Ser Leu Gln
465                 470                 475                 480
Leu Tyr Leu Val Asp Asn Arg Ser Tyr Leu Leu Asp Phe Lys Ser Ile
                485                 490                 495
Asp Asp Glu Val Val Glu Gln Arg Ser Gly Ser Ser Thr Pro Gln Arg
                500                 505                 510
Ser Cys Ser Ala Ala Gly Leu His Arg Pro Arg Ser Ser Val Asp Ser
            515                 520                 525
Ser Thr Ala Glu Asn His Ser Leu Ser Gly Ser Leu Thr Gly Ser Leu
            530                 535                 540
Thr Gly Ser Thr Leu Ser Ser Ala Ser Pro Arg Leu Gly Ser His Thr
545                 550                 555                 560
Met Asp Phe Phe Glu Met Cys Ala Ser Leu Ile Thr Ala Leu Ala Arg
                565                 570                 575
Lys Leu Met Val Ser Lys Gly Glu Glu Leu Phe Thr Gly Val Val Pro
            580                 585                 590
Ile Leu Val Glu Leu Asp Gly Asp Val Asn Gly His Arg Phe Ser Val
            595                 600                 605
Ser Gly Glu Gly Glu Gly Asp Ala Thr Tyr Gly Lys Leu Thr Leu Lys
    610                 615                 620
Phe Ile Cys Thr Thr Gly Lys Leu Pro Val Pro Trp Pro Thr Leu Val
625                 630                 635                 640
Thr Thr Leu Thr Trp Gly Val Gln Cys Phe Ala Arg Tyr Pro Asp His
                645                 650                 655
Met Lys Gln His Asp Phe Phe Lys Ser Ala Met Pro Glu Gly Tyr Val
            660                 665                 670
Gln Glu Arg Thr Ile Phe Phe Lys Asp Asp Gly Asn Tyr Lys Thr Arg
        675                 680                 685
Ala Glu Val Lys Phe Glu Gly Asp Thr Leu Val Asn Arg Ile Glu Leu
        690                 695                 700
Lys Gly Ile Asp Phe Lys Glu Asp Gly Asn Ile Leu Gly His Lys Leu
705                 710                 715                 720
Glu Tyr Asn Tyr Ile Ser His Asn Val Tyr Ile Thr Ala Asp Lys Gln
                725                 730                 735
Lys Asn Gly Ile Lys Ala His Phe Lys Ile Arg His Asn Ile Glu Asp
            740                 745                 750
Gly Gly Val Gln Leu Ala Asp His Tyr Gln Gln Asn Thr Pro Ile Gly
            755                 760                 765
Asp Gly Pro Val Leu Leu Pro Asp Asn His Tyr Leu Ser Thr Gln Ser
    770                 775                 780
Lys Leu Ser Lys Asp Pro Asn Glu Lys Arg Asp His Met Val Leu Leu
785                 790                 795                 800
Glu Phe Val Thr Ala Ala
                805
```

<210> SEQ ID NO 66
<211> LENGTH: 687
<212> TYPE: DNA
<213> ORGANISM: Artificial Sequence
<220> FEATURE:
<223> OTHER INFORMATION: mseCFP-11

<400> SEQUENCE: 66

```
atggtgagca agggcgagga gctgttcacc ggggtggtgc ccatcctggt cgagctggac    60
ggcgacgtaa acggccacag gttcagcgtg tccggcgagg gcgagggcga tgccacctac   120
ggcaagctga ccctgaagtt catctgcacc accggcaagc tgcccgtgcc ctggcccacc   180
ctcgtgacca ccctgacctg gggcgtgcag tgcttcgccc gctaccccga ccacatgaag   240
cagcacgact tcttcaagtc cgccatgccc gaaggctacg tccaggagcg taccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctgggccac   420
aagctggagt acaactacat cagccacaac gtctatatca ccgccgacaa gcagaagaac   480
ggcatcaagg cccacttcaa gatccgccac aacatcgagg acggcggcgt gcagctcgcc   540
gaccactacc agcagaacac ccccatcggc gacggccccg tgctgctgcc cgacaaccac   600
tacctgagca cccagtccaa gctgagcaaa gaccccaacg agaagcgcga tcacatggtc   660
ctgctggagt tcgtgaccgc cgcctaa                                       687
```

<210> SEQ ID NO 67
<211> LENGTH: 228
<212> TYPE: PRT
<213> ORGANISM: Artificial Sequence
<220> FEATURE:
<223> OTHER INFORMATION: mseCFP-11

<400> SEQUENCE: 67

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190
```

Pro Val Leu Leu Pro Asp Asn His Tyr Leu Ser Thr Gln Ser Lys Leu
    195                 200                 205

Ser Lys Asp Pro Asn Glu Lys Arg Asp His Met Val Leu Leu Glu Phe
    210                 215                 220

Val Thr Ala Ala
225

<210> SEQ ID NO 68
<211> LENGTH: 4950
<212> TYPE: DNA
<213> ORGANISM: Artificial Sequence
<220> FEATURE:
<223> OTHER INFORMATION: Rat mseCFP-11-alpha2, pACE plasmid

<400> SEQUENCE: 68

| | | | | | |
|---|---|---|---|---|---|
| ggaattccag | ataacttcgt | ataatgtatg | ctatacgaag | ttatggtacc | gcggccgcgt | 60 |
| agaggatctg | ttgatcagca | gttcaacctg | ttgatagtac | ttcgttaata | cagatgtagg | 120 |
| tgttggcacc | atgcataact | ataacggtcc | taaggtagcg | acctaggtat | cgataatacg | 180 |
| actcactata | ggggaattgt | gagcggataa | caattcccct | ctagaaataa | ttttgtttaa | 240 |
| ctttaagaag | gagatataat | gggcagtagt | caccatcacc | accaccatca | tcaccatcat | 300 |
| agtagtgaaa | acctgtattt | tcaggggcat | atggtgagca | agggcgagga | gctgttcacc | 360 |
| ggggtggtgc | ccatcctggt | cgagctggac | ggcgacgtaa | acggccacag | gttcagcgtg | 420 |
| tccggcgagg | gcgagggcga | tgccacctac | ggcaagctga | ccctgaagtt | catctgcacc | 480 |
| accggcaagc | tgcccgtgcc | ctggcccacc | ctcgtgacca | ccctgacctg | gggcgtgcag | 540 |
| tgcttcgccc | gctaccccga | ccacatgaag | cagcacgact | tcttcaagtc | cgccatgccc | 600 |
| gaaggctacg | tccaggagcg | taccatcttc | ttcaaggacg | acggcaacta | caagacccgc | 660 |
| gccgaggtga | agttcgaggg | cgacaccctg | gtgaaccgca | tcgagctgaa | gggcatcgac | 720 |
| ttcaaggagg | acggcaacat | cctggggcac | aagctggagt | acaactacat | cagccacaac | 780 |
| gtctatatca | ccgccgacaa | gcagaagaac | ggcatcaagg | cccacttcaa | gatccgccac | 840 |
| aacatcgagg | acggcggcgt | gcagctcgcc | gaccactacc | agcagaacac | ccccatcggc | 900 |
| gacggccccg | tgctgctgcc | cgacaaccac | tacctgagca | cccagtccaa | gctgagcaaa | 960 |
| gaccccaacg | agaagcgcga | tcacatggtc | ctgctggagt | tcgtgaccgc | cgccggcggt | 1020 |
| atggctgaga | agcagaagca | cgacgggcgt | gtgaagatcg | acactacgt | gctggggac | 1080 |
| accctgggcg | tcggcacctt | cggcaaagtg | aagattggag | aacatcaatt | gacaggccat | 1140 |
| aaagtggcag | ttaagatctt | aaatagacag | aagattcgca | gtttagatgt | tgttggaaaa | 1200 |
| ataaaacgag | aaattcaaaa | tcttaaactc | tttcgtcatc | ctcatattat | caaactctac | 1260 |
| caagtgatca | gcactccaac | agactttttt | atggtaatgg | aatatgtgtc | tggaggtgaa | 1320 |
| ttgttcgact | acatctgtaa | acacgggagg | gttgaagagg | tggaagctcg | ccggctcttc | 1380 |
| cagcagattc | tgtctgccgt | ggactactgt | cacaggcaca | tggttgtcca | cagggacctg | 1440 |
| aagccagaga | acgtgttgct | ggacgcccag | atgaatgcta | agatagctga | cttcggactc | 1500 |
| tctaatatga | tgtcagatgg | tgaatttcta | cgaactagct | gtggatcgcc | aaattatgca | 1560 |
| gcaccggagg | tcatctcagg | aaggctgtat | gcgggtcctg | aggttgatat | ctggagctgt | 1620 |
| ggtgttatcc | tgtatgccct | tctctgtggc | accctcccgt | tcgacgatga | gcacgtgcct | 1680 |
| acgctcttta | agaagatccg | aggggtgtg | ttctacatcc | cggagtatct | caaccgttct | 1740 |
| attgccactc | tgctgatgca | catgctgcag | gtggaccccc | tgaagcgagc | aactatcaaa | 1800 |

```
gacatacgag agcatgaatg gtttaaacag gatttgccca gttacctctt tcctgaagac   1860
ccctcctatg atgctaacgt cattgatgat gaggctgtga agaagtatg tgaaaaattt    1920
gagtgtacag aatcagaagt gatgaacagt ttatacagtg gtgaccctca agaccagctc   1980
gcagtggctt atcatctcat cattgacaat cggagaataa tgaaccaagc cagtgagttc   2040
tacctcgcct ccagtcctcc aacgggttcc ttcatggacg atatggccat gcacattccc   2100
cccggcctga aaccacatcc tgaaaggatg ccacctctca tagcagacag ccccaaagca   2160
cgctgtccac tggatgcact caacacaact aagcccaaat ctttagctgt gaaaaaagcc   2220
aagtggcacc ttgggatccg aagccagagc aaaccatacg acattatggc ggaggtgtac   2280
cgagctatga agcagctgga ctttgaatgg aaggtagtga atgcatacca tcttcgagta   2340
agaagaaaaa acccagtgac tggcaattac gtgaaaatga gcttacagct ttacctggtt   2400
gacaatcgga gctatctgct ggactttaaa agcatcgatg atgaggtggt ggagcagagg   2460
tctggttctt caacacctca gcgctcctgt tctgctgccg gcctccacag acctcggtca   2520
agtgtcgatt ccagcacagc cgagaaccat tcactgtctg gctctctcac tggttctttg   2580
actggcagca ctttgtcctc gcttccccg cgcctgggca gtcataccat ggattttttt    2640
gaaatgtgcg ccagtcttat cactgcttta gcccgtaagc tttaactcga gagatccggc   2700
tgctaacaaa gcccgaaagg aagctgagtt ggctgctgcc accgctgagc aataactagc   2760
ataacccctt ggggcctcta acgggtctt gaggggtttt ttggtttaaa cccatctaat    2820
tggactagta gcccgcctaa tgagcgggct ttttttttaat tcccctattt gtttatttt    2880
ctaaatacat tcaaatatgt atccgctcat gagacaataa ccctgataaa tgcttcaata   2940
atattgaaaa aggaagagta tgagtattca acatttccgt gtcgccctta ttcccttttt   3000
tgcggcattt tgccttcctg ttttgctca cccagaaacg ctcgtgaaag taaaagacgc    3060
agaggaccaa ttggggcac gagtgggata catagaactg gacttgaata gcggtaaaat    3120
ccttgagagt tttcgccctg aagagcgttt tccaatgatg agcactttca aagttctgct   3180
atgtggagca gtattatccc gtgtagatgc ggggcaagag caactcggac gacgaataca   3240
ctattcgcag aatgacttgg ttgaatactc cccagtgaca gaaaagcacc ttacggacgg   3300
aatgacggta agagaattat gtagtgccgc cataacgatg agtgataaca ctgcggcgaa   3360
cttacttctg acaaccatcg gtggaccgaa ggaattaacc gctttttgc acaatatggg    3420
agaccatgta actcgccttg accgttggga accagaactg aatgaagcca taccaaacga   3480
cgagcgagac accacaatgc ctgcggcaat ggcaacaaca ttacgcaaac tattaactgg   3540
cgaactactt actctggctt cacggcaaca attaatagac tggcttgaag cggataaagt   3600
tgcaggacca ctactgcgtt cggcacttcc tgctggctgg tttattgctg ataaatctgg   3660
ggcaggagag cgtggttcac ggggtatcat tgccgcactt ggaccagatg gtaagccttc   3720
ccgtatcgta gttatctaca cgacgggtag tcaggcaact atggacgaac gaaatagaca   3780
gattgctgaa atagggggctt cactgattaa gcattggtaa accgatacaa ttaaaggctc   3840
cttttggagc cttttttttt ggacggaccg gtagaaaaga tcaaaggatc ttcttgagat   3900
cctttttttc tgcgcgtaat ctgctgcttg caaacaaaaa aaccaccgct accagcggtg   3960
gtttgtttgc cggatcaaga gctaccaact cttttttccga aggtaactgg cttcagcaga   4020
gcgcagatac caaatactgt ccttctagtg tagccgtagt taggccacca cttcaagaac   4080
tctgtagcac cgcctacata cctcgctctg ctaatcctgt taccagtggc tgctgccagt   4140
ggcgataagt cgtgtcttac cgggttggac tcaagacgat agttaccgga taaggcgcag   4200
```

```
cggtcgggct gaacgggggg ttcgtgcaca cagcccagct tggagcgaac gacctacacc    4260
gaactgagat acctacagcg tgagctatga gaaagcgcca cgcttcccga agggagaaag    4320
gcggacaggt atccggtaag cggcagggtc ggaacaggag agcgcacgag ggagcttcca    4380
gggggaaacg cctggtatct ttatagtcct gtcgggtttc gccacctctg acttgagcgt    4440 cgattttttgt gatgctcgtc agggggggcgg agcctatgga aaaacgccag caacgcggcc    4500
tttttacggt tcctggcctt ttgctggcct tttgctcaca tgttctttcc tgcgttatcc    4560
cctgattctg tggataaccg tattaccgcc tttgagtgag ctgataccgc tcgccgcagc    4620
cgaacgaccg agcgcagcga gtcagtgagc gaggaagcgg aagagcgcct gatgcggtat    4680
tttctcctta cgcatctgtg cggtatttca caccgcaatg gtgcactctc agtacaatct    4740
gctctgatgc cgcatagtta agccagtata cactccgcta tcgctacgtg actgggtcat    4800
ggctgcgccc cgacacccgc caacacccgc tgacgcgccc tgacgggctt gtctgctccc    4860
ggcatccgct tacagacaag ctgtgaccgt ctccgggagc tgcatgtgtc agaggttttc    4920
accgtcatca ccgaaacgcg cgaggcaggg                                     4950
```

<210> SEQ ID NO 69
<211> LENGTH: 808
<212> TYPE: PRT
<213> ORGANISM: Artificial Sequence
<220> FEATURE:
<223> OTHER INFORMATION: Rat mseCFP-11-alpha2

<400> SEQUENCE: 69

```
Met Gly Ser Ser His His His His His His His His Ser Ser
1               5                   10                  15

Glu Asn Leu Tyr Phe Gln Gly His Met Val Ser Lys Gly Glu Glu Leu
            20                  25                  30

Phe Thr Gly Val Val Pro Ile Leu Val Glu Leu Asp Gly Asp Val Asn
        35                  40                  45

Gly His Arg Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Trp Gly Val Gln Cys Phe
                85                  90                  95

Ala Arg Tyr Pro Asp His Met Lys Gln His Asp Phe Lys Ser Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Ile Ser His Asn Val Tyr
                165                 170                 175

Ile Thr Ala Asp Lys Gln Lys Asn Gly Ile Lys Ala His Phe Lys Ile
            180                 185                 190

Arg His Asn Ile Glu Asp Gly Gly Val Gln Leu Ala Asp His Tyr Gln
        195                 200                 205

Gln Asn Thr Pro Ile Gly Asp Gly Pro Val Leu Leu Pro Asp Asn His
    210                 215                 220
```

```
Tyr Leu Ser Thr Gln Ser Lys Leu Ser Lys Asp Pro Asn Glu Lys Arg
225                 230                 235                 240

Asp His Met Val Leu Leu Glu Phe Val Thr Ala Ala Gly Gly Met Ala
            245                 250                 255

Glu Lys Gln Lys His Asp Gly Arg Val Lys Ile Gly His Tyr Val Leu
        260                 265                 270

Gly Asp Thr Leu Gly Val Gly Thr Phe Gly Lys Val Lys Ile Gly Glu
    275                 280                 285

His Gln Leu Thr Gly His Lys Val Ala Val Lys Ile Leu Asn Arg Gln
290                 295                 300

Lys Ile Arg Ser Leu Asp Val Val Gly Lys Ile Lys Arg Glu Ile Gln
305                 310                 315                 320

Asn Leu Lys Leu Phe Arg His Pro His Ile Ile Lys Leu Tyr Gln Val
                325                 330                 335

Ile Ser Thr Pro Thr Asp Phe Phe Met Val Met Glu Tyr Val Ser Gly
            340                 345                 350

Gly Glu Leu Phe Asp Tyr Ile Cys Lys His Gly Arg Val Glu Glu Val
        355                 360                 365

Glu Ala Arg Arg Leu Phe Gln Gln Ile Leu Ser Ala Val Asp Tyr Cys
370                 375                 380

His Arg His Met Val Val His Arg Asp Leu Lys Pro Glu Asn Val Leu
385                 390                 395                 400

Leu Asp Ala Gln Met Asn Ala Lys Ile Ala Asp Phe Gly Leu Ser Asn
                405                 410                 415

Met Met Ser Asp Gly Glu Phe Leu Arg Thr Ser Cys Gly Ser Pro Asn
            420                 425                 430

Tyr Ala Ala Pro Glu Val Ile Ser Gly Arg Leu Tyr Ala Gly Pro Glu
        435                 440                 445

Val Asp Ile Trp Ser Cys Gly Val Ile Leu Tyr Ala Leu Leu Cys Gly
    450                 455                 460

Thr Leu Pro Phe Asp Asp Glu His Val Pro Thr Leu Phe Lys Lys Ile
465                 470                 475                 480

Arg Gly Gly Val Phe Tyr Ile Pro Glu Tyr Leu Asn Arg Ser Ile Ala
                485                 490                 495

Thr Leu Leu Met His Met Leu Gln Val Asp Pro Leu Lys Arg Ala Thr
            500                 505                 510

Ile Lys Asp Ile Arg Glu His Glu Trp Phe Lys Gln Asp Leu Pro Ser
        515                 520                 525

Tyr Leu Phe Pro Glu Asp Pro Ser Tyr Asp Ala Asn Val Ile Asp Asp
    530                 535                 540

Glu Ala Val Lys Glu Val Cys Glu Lys Phe Glu Cys Thr Glu Ser Glu
545                 550                 555                 560

Val Met Asn Ser Leu Tyr Ser Gly Asp Pro Gln Asp Gln Leu Ala Val
                565                 570                 575

Ala Tyr His Leu Ile Ile Asp Asn Arg Arg Ile Met Asn Gln Ala Ser
            580                 585                 590

Glu Phe Tyr Leu Ala Ser Ser Pro Pro Thr Gly Ser Phe Met Asp Asp
        595                 600                 605

Met Ala Met His Ile Pro Pro Gly Leu Lys Pro His Pro Glu Arg Met
    610                 615                 620

Pro Pro Leu Ile Ala Asp Ser Pro Lys Ala Arg Cys Pro Leu Asp Ala
625                 630                 635                 640

Leu Asn Thr Thr Lys Pro Lys Ser Leu Ala Val Lys Lys Ala Lys Trp
```

His Leu Gly Ile Arg Ser Gln Ser Lys Pro Tyr Asp Ile Met Ala Glu
              660                 665                 670

Val Tyr Arg Ala Met Lys Gln Leu Asp Phe Glu Trp Lys Val Val Asn
        675                 680                 685

Ala Tyr His Leu Arg Val Arg Arg Lys Asn Pro Val Thr Gly Asn Tyr
    690                 695                 700

Val Lys Met Ser Leu Gln Leu Tyr Leu Val Asp Asn Arg Ser Tyr Leu
705                 710                 715                 720

Leu Asp Phe Lys Ser Ile Asp Asp Glu Val Val Glu Gln Arg Ser Gly
                725                 730                 735

Ser Ser Thr Pro Gln Arg Ser Cys Ser Ala Ala Gly Leu His Arg Pro
            740                 745                 750

Arg Ser Ser Val Asp Ser Ser Thr Ala Glu Asn His Ser Leu Ser Gly
        755                 760                 765

Ser Leu Thr Gly Ser Leu Thr Gly Ser Thr Leu Ser Ser Ala Ser Pro
770                 775                 780

Arg Leu Gly Ser His Thr Met Asp Phe Phe Glu Met Cys Ala Ser Leu
785                 790                 795                 800

Ile Thr Ala Leu Ala Arg Lys Leu
                805

```
<210> SEQ ID NO 70
<211> LENGTH: 3520
<212> TYPE: DNA
<213> ORGANISM: Artificial Sequence
<220> FEATURE:
<223> OTHER INFORMATION: Rat gamma1-mseCFP-11, pDS plasmid

<400> SEQUENCE: 70
atgagggaag cggtgatcgc cgaagtatcg actcaactat cagaggtagt tggcgtcatc      60
gagcgccatc tcgaaccgac gttgctggcc gtacatttgt acggctccgc agtggatggc     120
ggcctgaagc acacagtga tattgatttg ctggttacgg tgaccgtaag gcttgatgaa      180
acaacgcggc gagctttgat caacgacctt ttggaaactt cggcttcccc tggagagagc     240
gagattctcc gcgctgtaga agtcaccatt gttgtgcacg acgacatcat tccgtggcgt     300
tatccagcta agcgcgaact gcaatttgga gaatggcagc gcaatgacat tcttgcaggt     360
atcttcgagc cagccacgat cgacattgat ctggctatct tgctgacaaa agcaagagaa     420
catagcgttg ccttggtagg tccagcggcg gaggaactct tgatccggt tcctgaacag      480 gatctatttg aggcgctaaa tgaaacctta acgctatgga actcgccgcc cgactgggct     540
ggcgatgagc gaaatgtagt gcttacgttg tcccgcattt ggtacagcgc agtaaccggc     600
aaaatcgcgc cgaaggatgt cgctgccgac tgggcaatgg agcgcctgcc ggcccagtat     660
cagcccgtca tacttgaagc tagacaggct tatcttggac aagaagaa tcgcttggcc       720 tcgcgcgcag atcagttgga agaatttgtc cactacgtga aaggcgagat caccaaggta     780
gtcggcaaat aatgtctaac aattcgttca agccgacgga tctatgtcgg gtgcggagaa     840
agaggtaatg aaatggcacc taggtatcga taatacgact cactataggg gaattgtgag     900
cggataacaa ttcccctcta gaaataattt tgtttaactt taagaaggag atatacatat     960
ggagtcggtt gctgcagaga gcgctccagc tccggagaat gaacactctc aagagccccc    1020
ggaatcgaac agtagtgtgt acaccacctt catgaagtct catcgctgct atgacctgat    1080
ccccacaagc tccaagctgg tggtatttga tacttcgctg caggtaaaga aagccttctt    1140
```

```
tgccctggtg actaacggtg ttcgtgctgc cccttttgtgg gatagtaaga agcagagctt    1200
tgtgggcatg ctgaccatca ctgacttcat caatattctg caccgatact acaagtcagc    1260
cctggtgcag atctatgaac tggaggagca caagatagag acttggagag aggtctacct    1320
gcaagactcc tttaagccac ttgtctgcat ttctccaaat gccagcttgt tcgatgctgt    1380
ctcttcatta attcgaaata agatccacag gcttccagtt attgacccgg agtcaggcaa    1440
caccttgtac attcttactc acaagcggat cctcaagttc ctcaagttgt ttatcactga    1500
gttccccaag ccggaattca tgtctaagtc tctggaagag ctacagattg cacctacgc    1560
caatattgcc atggtccgta ccactacacc tgtctatgtg gctctgggca tctttgtaca    1620
gcaccgagtc tccgccttgc ctgtggtgga tgagaaaggg cgtgtggtgg acatctactc    1680
caagtttgat gtgattaatt tggcagcaga aaagacatac aacaacctag atgtgtctgt    1740
gacaaaagcc ctacagcacc ggtcacacta cttcgagggt gttctcaagt gctacctaca    1800
tgagactcta gaagcaatca tcaatagact ggtggaagca gaggttcacc gtctggtggt    1860
ggtggatgaa catgacgtgg tcaagggcat tgtatcgctg tctgacatct acaggctct    1920
ggtgctcaca ggtggagaga agaagcccgc tagcatggtg agcaagggcg aggagctgtt    1980
caccggggtg gtgcccatcc tggtcgagct ggacggcgac gtaaacggcc acaggttcag    2040
cgtgtccggc gagggcgagg gcgatgccac ctacggcaag ctgaccctga agttcatctg    2100
caccaccggc aagctgcccg tgccctggcc caccctcgtg accaccctga cctggggcgt    2160
gcagtgcttc gcccgctacc ccgaccacat gaagcagcac gacttcttca gtccgccat    2220
gcccgaaggc tacgtccagg agcgtaccat cttcttcaag gacgacggca actacaagac    2280
ccgcgccgag gtgaagttcg agggcgacac cctggtgaac cgcatcgagc tgaagggcat    2340
cgacttcaag gaggacggca acatcctggg gcacaagctg gagtacaact acatcagcca    2400
caacgtctat atcaccgccg acaagcagaa gaacggcatc aaggcccact tcaagatccg    2460
ccacaacatc gaggacggcg gcgtgcagct cgccgaccac taccagcaga cacccccat    2520
cggcgacggc cccgtgctgc tgcccgacaa ccactacctg agcacccagt ccaagctgag    2580
caaagacccc aacgagaagc gcgatcacat ggtcctgctg gagttcgtga ccgccgccta    2640
ataggtttaa accatgtgcc tggcagataa cttcgtataa tgtatgctat acgaagttat    2700
ggtacgtact aagctctcat gtttcacgta ctaagctctc atgtttaacg tactaagctc    2760
tcatgtttaa cgaactaaac cctcatggct aacgtactaa gctctcatgg ctaacgtact    2820
aagctctcat gtttcacgta ctaagctctc atgtttgaac aataaaatta atataaatca    2880
gcaacttaaa tagcctctaa ggttttaagt tttataagaa aaaaagaat atataaggct    2940
tttaagctt ttaaggttta acggttgtgg acaacaagcc agggatgtaa cgcactgaga    3000
agcccttaga gcctctcaaa gcaattttga gtgacacagg aacacttaac ggctgacata    3060
attcagcttc acgctgccgc aagcactcag ggcgcaaggg ctgctaaagg aagcggaaca    3120
cgtagaaagc cagtccgcag aaacggtgct gaccccggat gaatgtcagc tgggaggcag    3180
aataaatgat catatcgtca attattacct ccacggggag agcctgagca aactggcctc    3240
aggcatttga gaagcacacg gtcacactgc ttccggtagt caataaaccg gtaagtagcg    3300
tatgcgctca cgcaactggt ccagaacctt gaccgaacgc agcggtggta acggcgcagt    3360
ggcggttttc atggcttgtt atgactgttt ttttggggta cagtctatgc ctcgggcatc    3420
caagcagcaa gcgcgttacg ccgtgggtcg atgtttgatg ttatggagca gcaacgatgt    3480
```
tacgcagcag ggcagtcgcc ctaaaacaaa gttaaacatc        3520

<210> SEQ ID NO 71
<211> LENGTH: 560
<212> TYPE: PRT
<213> ORGANISM: Artificial Sequence
<220> FEATURE:
<223> OTHER INFORMATION: Rat gamma1-mseCFP-11

<400> SEQUENCE: 71

Met Glu Ser Val Ala Ala Glu Ser Ala Pro Ala Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
    50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
    290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro Ala Ser Met Val Ser Lys
                325                 330                 335

Gly Glu Glu Leu Phe Thr Gly Val Val Pro Ile Leu Val Glu Leu Asp
            340                 345                 350

Gly Asp Val Asn Gly His Arg Phe Ser Val Ser Gly Glu Gly Glu Gly

```
                355            360            365
Asp Ala Thr Tyr Gly Lys Leu Thr Leu Lys Phe Ile Cys Thr Thr Gly
    370                375                380
Lys Leu Pro Val Pro Trp Pro Thr Leu Val Thr Thr Leu Thr Trp Gly
385                390                395                400
Val Gln Cys Phe Ala Arg Tyr Pro Asp His Met Lys Gln His Asp Phe
                405                410                415
Phe Lys Ser Ala Met Pro Glu Gly Tyr Val Gln Glu Arg Thr Ile Phe
            420                425                430
Phe Lys Asp Asp Gly Asn Tyr Lys Thr Arg Ala Glu Val Lys Phe Glu
        435                440                445
Gly Asp Thr Leu Val Asn Arg Ile Glu Leu Lys Gly Ile Asp Phe Lys
    450                455                460
Glu Asp Gly Asn Ile Leu Gly His Lys Leu Glu Tyr Asn Tyr Ile Ser
465                470                475                480
His Asn Val Tyr Ile Thr Ala Asp Lys Gln Lys Asn Gly Ile Lys Ala
                485                490                495
His Phe Lys Ile Arg His Asn Ile Glu Asp Gly Gly Val Gln Leu Ala
            500                505                510
Asp His Tyr Gln Gln Asn Thr Pro Ile Gly Asp Gly Pro Val Leu Leu
        515                520                525
Pro Asp Asn His Tyr Leu Ser Thr Gln Ser Lys Leu Ser Lys Asp Pro
    530                535                540
Asn Glu Lys Arg Asp His Met Val Leu Leu Glu Phe Val Thr Ala Ala
545                550                555                560

<210> SEQ ID NO 72
<211> LENGTH: 3529
<212> TYPE: DNA
<213> ORGANISM: Artificial Sequence
<220> FEATURE:
<223> OTHER INFORMATION: Rat eCFP-11-gamma1, pDS plasmid

<400> SEQUENCE: 72
atgagggaag cggtgatcgc cgaagtatcg actcaactat cagaggtagt tggcgtcatc     60
gagcgccatc tcgaaccgac gttgctggcc gtacatttgt acggctccgc agtggatggc    120
ggcctgaagc cacacagtga tattgatttg ctggttacgg tgaccgtaag gcttgatgaa    180
acaacgcggc gagctttgat caacgacctt ttggaaactt cggcttcccc tggagagagc    240
gagattctcc gcgctgtaga agtcaccatt gttgtgcacg acgacatcat tccgtggcgt    300
tatccagcta agcgcgaact gcaatttgga gaatggcagc gcaatgacat tcttgcaggt    360
atcttcgagc cagccacgat cgacattgat ctggctatct tgctgacaaa agcaagagaa    420
catagcgttg ccttggtagg tccagcggcg gaggaactct ttgatccggt tcctgaacag    480
gatctatttg aggcgctaaa tgaaaccttaa cgctatgga actcgccgcc cgactgggct    540
ggcgatgagc gaaatgtagt gcttacgttg tcccgcattt ggtacagcgc agtaaccggc    600
aaaatcgcgc cgaaggatgt cgctgccgac tgggcaatgg agcgcctgcc ggcccagtat    660
cagcccgtca tacttgaagc tagacaggct tatcttggac aagaagaaga tcgcttggcc    720
tcgcgcgcag atcagttgga agaatttgtc cactacgtga aggcgagat caccaaggta    780
gtcggcaaat aatgtctaac aattcgttca agccgacgga tctatgtcgg gtgcggagaa    840
agaggtaatg aaatggcacc taggtatcga taatacgact cactataggg gaattgtgag    900
cggataacaa ttcccctcta gaaataattt tgtttaactt taagaaggag atatacatat    960
```

```
ggtgagcaag ggcgaggagc tgttcaccgg ggtggtgccc atcctggtcg agctggacgg   1020
cgacgtaaac ggccacaggt tcagcgtgtc cggcgagggc gagggcgatg ccacctacgg   1080
caagctgacc ctgaagttca tctgcaccac cggcaagctg cccgtgccct ggcccaccct   1140
cgtgaccacc ctgacctggg gcgtgcagtg cttcgcccgc taccccgacc acatgaagca   1200
gcacgacttc ttcaagtccg ccatgcccga aggctacgtc caggagcgta ccatcttctt   1260
caaggacgac ggcaactaca agacccgcgc cgaggtgaag ttcgagggcg acaccctggt   1320
gaaccgcatc gagctgaagg gcatcgactt caaggaggac ggcaacatcc tggggcacaa   1380
gctggagtac aactacatca gccacaacgt ctatatcacc gccgacaagc agaagaacgg   1440
catcaaggcc cacttcaaga tccgccacaa catcgaggac ggcggcgtgc agctcgccga   1500
ccactaccag cagaacaccc ccatcggcga cggccccgtg ctgctgcccg acaaccacta   1560
cctgagcacc cagtccaagc tgagcaaaga ccccaacgag aagcgcgatc acatggtcct   1620
gctggagttc gtgaccgccg ccgctagcat ggagtcggtt gctgcagaga cgctccagc   1680 tccggagaat gaacactctc aagagacccc ggaatcgaac agtagtgtgt acaccacctt   1740
catgaagtct catcgctgct atgacctgat ccccacaagc tccaagctgg tggtatttga   1800
tacttcgctg caggtaaaga aagccttctt tgccctggtg actaacggtg ttcgtgctgc   1860
ccctttgtgg gatagtaaga agcagagctt tgtgggcatg ctgaccatca ctgacttcat   1920
caatattctg caccgatact acaagtcagc cctggtgcag atctatgaac tggaggagca   1980
caagatagag acttggagag aggtctacct gcaagactcc tttaagccac ttgtctgcat   2040
ttctccaaat gccagcttgt tcgatgctgt ctcttcatta attcgaaata agatccacag   2100
gcttccagtt attgacccgg agtcaggcaa caccttgtac attcttactc acaagcggat   2160
cctcaagttc ctcaagttgt ttatcactga gttccccaag ccggaattca tgtctaagtc   2220
tctggaagag ctacagattg gcacctacgc caatattgcc atggtccgta ccactacacc   2280
tgtctatgtg gctctgggca tctttgtaca gcaccgagtc tccgccttgc ctgtggtgga   2340
tgagaagggg cgtgtggtgg acatctactc caagtttgat gtgattaatt ggcagcaga   2400 aaagacatac aacaacctag atgtgtctgt gacaaaagcc ctacagcacc ggtcacacta   2460
cttcgagggt gttctcaagt gctacctaca tgagactcta gaagcaatca tcaatagact   2520
ggtgaagcca gaggttcacc gtctggtggt ggtggatgaa catgacgtgg tcaagggcat   2580
tgtatcgctg tctgacatct acaggctct ggtgctcaca ggtggagaga agaagccctg   2640
ataactagtt ccgtttaaac ccatgtgcct ggcagataac ttcgtataat gtatgctata   2700
cgaagttatg gtacgtacta agctctcatg tttcacgtac taagctctca tgtttaacgt   2760
actaagctct catgtttaac gaactaaacc ctcatggcta acgtactaag ctctcatggc   2820
taacgtacta agctctcatg tttcacgtac taagctctca tgtttgaaca ataaaattaa   2880
tataaatcag caacttaaat agcctctaag gttttaagtt ttataagaaa aaaagaata   2940 tataaggctt ttaaagcttt taaggtttaa cggttgtgga caacaagcca gggatgtaac   3000
gcactgagaa gcccttagag cctctcaaag caattttgag tgacacagga acacttaacg   3060
gctgacataa ttcagcttca cgctgccgca agcactcagg gcgcaagggc tgctaaagga   3120
agcggaacac gtagaaagcc agtccgcaga aacggtgctg accccggatg aatgtcagct   3180
gggaggcaga ataaatgatc atatcgtcaa ttattacctc cacggggaga gcctgagcaa   3240
actggcctca ggcatttgag aagcacacgg tcacactgct tccggtagtc aataaaccgg   3300
```

```
taagtagcgt atgcgctcac gcaactggtc cagaaccttg accgaacgca gcggtggtaa    3360
cggcgcagtg gcggtttcca tggcttgtta tgactgtttt tttggggtac agtctatgcc    3420
tcgggcatcc aagcagcaag cgcgttacgc cgtgggtcga tgtttgatgt tatggagcag    3480
caacgatgtt acgcagcagg gcagtcgccc taaaacaaag ttaaacatc                3529
```

<210> SEQ ID NO 73
<211> LENGTH: 560
<212> TYPE: PRT
<213> ORGANISM: Artificial Sequence
<220> FEATURE:
<223> OTHER INFORMATION: Rat eCFP-11-gamma1

<400> SEQUENCE: 73

```
Met Val Ser Lys Gly Glu Glu Leu Phe Thr Gly Val Val Pro Ile Leu
1               5                   10                  15

Val Glu Leu Asp Gly Asp Val Asn Gly His Arg Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Trp Gly Val Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
210                 215                 220

Val Thr Ala Ala Ala Ser Met Glu Ser Val Ala Ala Glu Ser Ala Pro
225                 230                 235                 240

Ala Pro Glu Asn Glu His Ser Gln Glu Thr Pro Glu Ser Asn Ser Ser
                245                 250                 255

Val Tyr Thr Thr Phe Met Lys Ser His Arg Cys Tyr Asp Leu Ile Pro
            260                 265                 270

Thr Ser Ser Lys Leu Val Val Phe Asp Thr Ser Leu Gln Val Lys Lys
        275                 280                 285

Ala Phe Phe Ala Leu Val Thr Asn Gly Val Arg Ala Ala Pro Leu Trp
290                 295                 300

Asp Ser Lys Lys Gln Ser Phe Val Gly Met Leu Thr Ile Thr Asp Phe
305                 310                 315                 320

Ile Asn Ile Leu His Arg Tyr Tyr Lys Ser Ala Leu Val Gln Ile Tyr
```

```
                    325                 330                 335
Glu Leu Glu Glu His Lys Ile Glu Thr Trp Arg Glu Val Tyr Leu Gln
                340                 345                 350

Asp Ser Phe Lys Pro Leu Val Cys Ile Ser Pro Asn Ala Ser Leu Phe
            355                 360                 365

Asp Ala Val Ser Ser Leu Ile Arg Asn Lys Ile His Arg Leu Pro Val
        370                 375                 380

Ile Asp Pro Glu Ser Gly Asn Thr Leu Tyr Ile Leu Thr His Lys Arg
385                 390                 395                 400

Ile Leu Lys Phe Leu Lys Leu Phe Ile Thr Glu Phe Pro Lys Pro Glu
                405                 410                 415

Phe Met Ser Lys Ser Leu Glu Glu Leu Gln Ile Gly Thr Tyr Ala Asn
            420                 425                 430

Ile Ala Met Val Arg Thr Thr Thr Pro Val Tyr Val Ala Leu Gly Ile
        435                 440                 445

Phe Val Gln His Arg Val Ser Ala Leu Pro Val Val Asp Glu Lys Gly
    450                 455                 460

Arg Val Val Asp Ile Tyr Ser Lys Phe Asp Val Ile Asn Leu Ala Ala
465                 470                 475                 480

Glu Lys Thr Tyr Asn Asn Leu Asp Val Ser Val Thr Lys Ala Leu Gln
                485                 490                 495

His Arg Ser His Tyr Phe Glu Gly Val Leu Lys Cys Tyr Leu His Glu
            500                 505                 510

Thr Leu Glu Ala Ile Ile Asn Arg Leu Val Glu Ala Glu Val His Arg
        515                 520                 525

Leu Val Val Asp Glu His Asp Val Lys Gly Ile Val Ser Leu
    530                 535                 540

Ser Asp Ile Leu Gln Ala Leu Val Leu Thr Gly Gly Glu Lys Lys Pro
545                 550                 555                 560

<210> SEQ ID NO 74
<211> LENGTH: 4995
<212> TYPE: DNA
<213> ORGANISM: Artificial Sequence
<220> FEATURE:
<223> OTHER INFORMATION: Rat alpha2-AR-eCFP_deletion, pACE plasmid

<400> SEQUENCE: 74
ttgagatcct ttttttctgc gcgtaatctg ctgcttgcaa acaaaaaaac caccgctacc    60
agcggtggtt tgtttgccgg atcaagagct accaactctt tttccgaagg taactggctt   120
cagcagagcg cagataccaa atactgtcct tctagtgtag ccgtagttag gccaccactt   180
caagaactct gtagcaccgc ctacatacct cgctctgcta atcctgttac cagtggctgc   240
tgccagtggc gataagtcgt gtcttaccgg gttggactca agacgatagt taccggataa   300
ggcgcagcgg tcgggctgaa cggggggttc gtgcacacag cccagcttgg agcgaacgac   360
ctacaccgaa ctgagatacc tacagcgtga gctatgagaa agcgccacgc ttcccgaagg   420
gagaaaggcg gacaggtatc cggtaagcgg cagggtcgga acaggagagc gcacgaggga   480
gcttccaggg ggaaacgcct ggtatcttta tagtcctgtc gggtttcgcc acctctgact   540
tgagcgtcga ttttgtgat gctcgtcagg ggggcggagc ctatggaaaa acgccagcaa   600
cgcggccttt ttacggttcc tggccttttg ctggcctttt gctcacatgt tctttcctgc   660
gttatcccct gattctgtgg ataaccgtat taccgccttt gagtgagctg ataccgctcg   720
ccgcagccga acgaccgagc gcagcgagtc agtgagcgag gaagcggaag agcgcctgat   780
```

```
gcggtatttt ctccttacgc atctgtgcgg tatttcacac cgcaatggtg cactctcagt    840
acaatctgct ctgatgccgc atagttaagc cagtatacac tccgctatcg ctacgtgact    900
gggtcatggc tgcgcccga cacccgccaa cacccgctga cgcgccctga cgggcttgtc    960
tgctcccggc atccgcttac agacaagctg tgaccgtctc cgggagctgc atgtgtcaga   1020
ggttttcacc gtcatcaccg aaacgcgcga ggcaggggga attccagata acttcgtata   1080
atgtatgcta tacgaagtta tggtaccgcg gccgcgtaga ggatctgttg atcagcagtt   1140
caacctgttg atagtacttc gttaatacag atgtaggtgt tggcaccatg cataactata   1200
acggtcctaa ggtagcgacc taggtatcga taatacgact cactataggg gaattgtgag   1260
cggataacaa ttcccctcta gaaataattt tgtttaactt taagaaggag atataatggg   1320
cagtagtcac catcaccacc accatcatca ccatcatagt agtgaaaacc tgtattttca   1380
ggggcatatg gctgagaagc agaagcacga cgggcgtgtg aagatcggac actacgtgct   1440
gggggacacc ctgggcgtcg gcaccttcgg caaagtgaag attggagaac atcaattgac   1500
aggccataaa gtggcagtta agatcttaaa tagacagaag attcgcagtt tagatgttgt   1560
tggaaaaata aaacgagaaa ttcaaaatct taaactcttt cgtcatcctc atattatcaa   1620
actctaccaa gtgatcagca ctccaacaga cttttttatg gtaatggaat atgtgtctgg   1680
aggtgaattg ttcgactaca tctgtaaaca cgggagggtt gaagaggtgg aagctcgccg   1740
gctcttccag cagattctgt ctgccgtgga ctactgtcac aggcacatgg ttgtccacag   1800
ggacctgaag ccagagaacg tgttgctgga cgcccagatg aatgctaaga tagctgactt   1860
cggactctct aatatgatgt cagatggtga atttctacga actagctgtg gatcgccaaa   1920
ttatgcagca ccggaggtca tctcaggaag gctgtatgcg ggtcctgagg ttgatatctg   1980
gagctgtggt gttatcctgt atgcccttct ctgtggcacc ctcccgttcg acgatgagca   2040
cgtgcctacg ctctttaaga gatccgaggg ggtgtgttc tacatcccgg agtatctcaa   2100
ccgttctatt gccactctgc tgatgcacat gctgcaggtg gaccccttga agcgagcaac   2160
tatcaaagac atacgagagc atgaatggtt taaacaggat ttgcccagtt acctctttcc   2220
tgaagacccc tcctatgatg ctaacgtcat tgatgatgag gctgtgaaag aagtatgtga   2280
aaaatttgag tgtacagaat cagaagtgat gaacagttta tacagtggtg accctcaaga   2340
ccagctcgca gtggcttatc atctcatcat tgacaatcgg agaataatga accaagccag   2400
tgagttctac ctcgcctcca gtcctccaac gggttccttc atggacgata tggccatgca   2460
cattcccccc ggcctgaaac cacatcctga aaggatgcca cctctcatag cagacagccc   2520
caaagcacgc tgtccactgg atgcactcaa cacaactaag cccaaatctt tagctgtgaa   2580
aaaagccaag tggcaccttg ggatccgaag ccagagcaaa ccatacgaca ttatggcgga   2640
ggtgtaccga gctatgaagc agctggactt tgaatggaag gtagtgaatg cataccatct   2700
tcgagtaaga agaaaaaacc cagtgactgg caattacgtg aaaatgagct acagctttta   2760
cctggttgac aatcggagct atctgctgga ctttaaaagc atcgatgatg aggtggtgga   2820
gcagaggtct ggttcttcaa cacctcagcg ctcctgttct gctgccggcc tccacagacc   2880
tcggtcaagt gtcgattcca gcacagccga gaaccattca ctgtctggct ctctcactgg   2940
ttctttgact ggcagcactt tgtcctccgc ttccccgcgc ctgggcagtc ataccatgga   3000
tttttttgaa atgtgcgcca gtcttatcac tgctttaatg gtgagcaagg gcgaggagct   3060
gttcaccggg gtggtgccca tcctggtcga gctggacggc gacgtaaacg gccacaagtt   3120
```

| | |
|---|---|
| cagcgtgtcc ggcgagggcg agggcgatgc cacctacggc aagctgaccc tgaagttcat | 3180 |
| ctgcaccacc ggcaagctgc ccgtgccctg gcccaccctc gtgaccaccc tgacctgggg | 3240 |
| cgtgcagtgc ttcagccgct accccgacca catgaagcag cacgacttct tcaagtccgc | 3300 |
| catgcccgaa ggctacgtcc aggagcgcac catcttcttc aaggacgacg gcaactacaa | 3360 |
| gacccgcgcc gaggtgaagt tcgagggcga caccctggtg aaccgcatcg agctgaaggg | 3420 |
| catcgacttc aaggaggacg gcaacatcct ggggcacaag ctggagtaca actacatcag | 3480 |
| ccacaacgtc tatatcaccg ccgacaagca gaagaacggc atcaaggcca acttcaagat | 3540 |
| ccgccacaac atcgaggacg gcagcgtgca gctcgccgac cactaccagc agaacacccc | 3600 |
| catcggcgac ggccccgtgc tgctgcccga caaccactac ctgagcaccc agtccgccct | 3660 |
| gagcaaagac cccaacgaga gcgcgatca catggtcctg ctggagttcg tgaccgccgc | 3720 |
| cgggatcact ctcggcatgg acgagctgta caagtccgga ctcagatctc gacgagctca | 3780 |
| ctgataactc gagagatccg gctgctaaca aagcccgaaa ggaagctgag ttggctgctg | 3840 |
| ccaccgctga gcaataacta gcataacccc ttggggcctc taaacgggtc ttgaggggtt | 3900 |
| ttttggttta aacccatcta attggactag tagcccgcct aatgagcggg cttttttta | 3960 |
| attccctat ttgtttattt ttctaaatac attcaaatat gtatccgctc atgagacaat | 4020 |
| aaccctgata aatgcttcaa taatattgaa aaaggaagag tatgagtatt caacatttcc | 4080 |
| gtgtcgccct tattccctttt tttgcggcat tttgccttcc tgtttttgct cacccagaaa | 4140 |
| cgctcgtgaa agtaaaagac gcagaggacc aattgggggc acgagtggga tacatagaac | 4200 |
| tggacttgaa tagcggtaaa atccttgaga gttttcgccc tgaagagcgt tttccaatga | 4260 |
| tgagcacttt caaagttctg ctatgtggag cagtattatc ccgtgtagat gcgggcaag | 4320 |
| agcaactcgg acgacgaata cactattcgc agaatgactt ggttgaatac tccccagtga | 4380 |
| cagaaaagca ccttacggac ggaatgacgg taagagaatt atgtagtgcc gccataacga | 4440 |
| tgagtgataa cactgcggcg aacttacttc tgacaaccat cggtggaccg aaggaattaa | 4500 |
| ccgcttttt gcacaatatg ggagaccatg taactcgcct tgaccgttgg gaaccagaac | 4560 |
| tgaatgaagc cataccaaac gacgagcgag acaccacaat gcctgcggca atggcaacaa | 4620 |
| cattacgcaa actattaact ggcgaactac ttactctggc ttcacggcaa caattaatag | 4680 |
| actggcttga agcggataaa gttgcaggac cactactgcg ttcggcactt cctgctggct | 4740 |
| ggtttattgc tgataaatct ggggcaggag agcgtggttc acggggtatc attgccgcac | 4800 |
| ttggaccaga tggtaagcct tcccgtatcg tagttatcta cacgacgggt agtcaggcaa | 4860 |
| ctatggacga acgaaataga cagattgctg aaataggggc ttcactgatt aagcattggt | 4920 |
| aaaccgatac aattaaaggc tccttttgga gccttttttt ttggacggac cggtagaaaa | 4980 |
| gatcaaagga tcttc | 4995 |

<210> SEQ ID NO 75
<211> LENGTH: 822
<212> TYPE: PRT
<213> ORGANISM: Artificial Sequence
<220> FEATURE:
<223> OTHER INFORMATION: Rat alpha2-AR-eCFP_deletion

<400> SEQUENCE: 75

```
Met Gly Ser Ser His His His His His His His His Ser Ser
1               5                   10                  15

Glu Asn Leu Tyr Phe Gln Gly His Met Ala Glu Lys Gln Lys His Asp
            20                  25                  30
```

```
Gly Arg Val Lys Ile Gly His Tyr Val Leu Gly Asp Thr Leu Gly Val
            35                  40                  45

Gly Thr Phe Gly Lys Val Lys Ile Gly Glu His Gln Leu Thr Gly His
        50                  55                  60

Lys Val Ala Val Lys Ile Leu Asn Arg Gln Lys Ile Arg Ser Leu Asp
 65                  70                  75                  80

Val Val Gly Lys Ile Lys Arg Glu Ile Gln Asn Leu Lys Leu Phe Arg
                85                  90                  95

His Pro His Ile Ile Lys Leu Tyr Gln Val Ile Ser Thr Pro Thr Asp
            100                 105                 110

Phe Phe Met Val Met Glu Tyr Val Ser Gly Gly Glu Leu Phe Asp Tyr
        115                 120                 125

Ile Cys Lys His Gly Arg Val Glu Glu Val Glu Ala Arg Arg Leu Phe
    130                 135                 140

Gln Gln Ile Leu Ser Ala Val Asp Tyr Cys His Arg His Met Val Val
145                 150                 155                 160

His Arg Asp Leu Lys Pro Glu Asn Val Leu Leu Asp Ala Gln Met Asn
                165                 170                 175

Ala Lys Ile Ala Asp Phe Gly Leu Ser Asn Met Met Ser Asp Gly Glu
            180                 185                 190

Phe Leu Arg Thr Ser Cys Gly Ser Pro Asn Tyr Ala Ala Pro Glu Val
        195                 200                 205

Ile Ser Gly Arg Leu Tyr Ala Gly Pro Glu Val Asp Ile Trp Ser Cys
    210                 215                 220

Gly Val Ile Leu Tyr Ala Leu Leu Cys Gly Thr Leu Pro Phe Asp Asp
225                 230                 235                 240

Glu His Val Pro Thr Leu Phe Lys Lys Ile Arg Gly Gly Val Phe Tyr
                245                 250                 255

Ile Pro Glu Tyr Leu Asn Arg Ser Ile Ala Thr Leu Leu Met His Met
            260                 265                 270

Leu Gln Val Asp Pro Leu Lys Arg Ala Thr Ile Lys Asp Ile Arg Glu
        275                 280                 285

His Glu Trp Phe Lys Gln Asp Leu Pro Ser Tyr Leu Phe Pro Glu Asp
    290                 295                 300

Pro Ser Tyr Asp Ala Asn Val Ile Asp Asp Glu Ala Val Lys Glu Val
305                 310                 315                 320

Cys Glu Lys Phe Glu Cys Thr Glu Ser Glu Val Met Asn Ser Leu Tyr
                325                 330                 335

Ser Gly Asp Pro Gln Asp Gln Leu Ala Val Ala Tyr His Leu Ile Ile
            340                 345                 350

Asp Asn Arg Arg Ile Met Asn Gln Ala Ser Glu Phe Tyr Leu Ala Ser
        355                 360                 365

Ser Pro Pro Thr Gly Ser Phe Met Asp Asp Met Ala Met His Ile Pro
    370                 375                 380

Pro Gly Leu Lys Pro His Pro Glu Arg Met Pro Pro Leu Ile Ala Asp
385                 390                 395                 400

Ser Pro Lys Ala Arg Cys Pro Leu Asp Ala Leu Asn Thr Thr Lys Pro
                405                 410                 415

Lys Ser Leu Ala Val Lys Lys Ala Lys Trp His Leu Gly Ile Arg Ser
            420                 425                 430

Gln Ser Lys Pro Tyr Asp Ile Met Ala Glu Val Tyr Arg Ala Met Lys
        435                 440                 445
```

```
Gln Leu Asp Phe Glu Trp Lys Val Val Asn Ala Tyr His Leu Arg Val
450                 455                 460

Arg Arg Lys Asn Pro Val Thr Gly Asn Tyr Val Lys Met Ser Leu Gln
465                 470                 475                 480

Leu Tyr Leu Val Asp Asn Arg Ser Tyr Leu Leu Asp Phe Lys Ser Ile
                485                 490                 495

Asp Asp Glu Val Val Glu Gln Arg Ser Gly Ser Ser Thr Pro Gln Arg
                500                 505                 510

Ser Cys Ser Ala Ala Gly Leu His Arg Pro Arg Ser Ser Val Asp Ser
                515                 520                 525

Ser Thr Ala Glu Asn His Ser Leu Ser Gly Ser Leu Thr Gly Ser Leu
530                 535                 540

Thr Gly Ser Thr Leu Ser Ser Ala Ser Pro Arg Leu Gly Ser His Thr
545                 550                 555                 560

Met Asp Phe Phe Glu Met Cys Ala Ser Leu Ile Thr Ala Leu Met Val
                565                 570                 575

Ser Lys Gly Glu Glu Leu Phe Thr Gly Val Val Pro Ile Leu Val Glu
                580                 585                 590

Leu Asp Gly Asp Val Asn Gly His Lys Phe Ser Val Ser Gly Glu Gly
                595                 600                 605

Glu Gly Asp Ala Thr Tyr Gly Lys Leu Thr Leu Lys Phe Ile Cys Thr
                610                 615                 620

Thr Gly Lys Leu Pro Val Pro Trp Pro Thr Leu Val Thr Thr Leu Thr
625                 630                 635                 640

Trp Gly Val Gln Cys Phe Ser Arg Tyr Pro Asp His Met Lys Gln His
                645                 650                 655

Asp Phe Phe Lys Ser Ala Met Pro Glu Gly Tyr Val Gln Glu Arg Thr
                660                 665                 670

Ile Phe Phe Lys Asp Asp Gly Asn Tyr Lys Thr Arg Ala Glu Val Lys
                675                 680                 685

Phe Glu Gly Asp Thr Leu Val Asn Arg Ile Glu Leu Lys Gly Ile Asp
690                 695                 700

Phe Lys Glu Asp Gly Asn Ile Leu Gly His Lys Leu Glu Tyr Asn Tyr
705                 710                 715                 720

Ile Ser His Asn Val Tyr Ile Thr Ala Asp Lys Gln Lys Asn Gly Ile
                725                 730                 735

Lys Ala Asn Phe Lys Ile Arg His Asn Ile Glu Asp Gly Ser Val Gln
                740                 745                 750

Leu Ala Asp His Tyr Gln Gln Asn Thr Pro Ile Gly Asp Gly Pro Val
                755                 760                 765

Leu Leu Pro Asp Asn His Tyr Leu Ser Thr Gln Ser Ala Leu Ser Lys
770                 775                 780

Asp Pro Asn Glu Lys Arg Asp His Met Val Leu Leu Glu Phe Val Thr
785                 790                 795                 800

Ala Ala Gly Ile Thr Leu Gly Met Asp Glu Leu Tyr Lys Ser Gly Leu
                805                 810                 815

Arg Ser Arg Arg Ala His
                820
```

<210> SEQ ID NO 76
<211> LENGTH: 5007
<212> TYPE: DNA
<213> ORGANISM: Artificial Sequence
<220> FEATURE:
<223> OTHER INFORMATION: Rat alpha2-AR_helix_-MVSKeCFP_deletion+alpha helix, pACE plasmid

<400> SEQUENCE: 76

```
ttgagatcct ttttttctgc gcgtaatctg ctgcttgcaa acaaaaaaac caccgctacc      60
agcggtggtt tgtttgccgg atcaagagct accaactctt tttccgaagg taactggctt     120
cagcagagcg cagataccaa atactgtcct tctagtgtag ccgtagttag gccaccactt     180
caagaactct gtagcaccgc ctacatacct cgctctgcta atcctgttac cagtggctgc     240
tgccagtggc gataagtcgt gtcttaccgg gttggactca agacgatagt taccggataa     300
ggcgcagcgg tcgggctgaa cggggggttc gtgcacacag cccagcttgg agcgaacgac     360
ctacaccgaa ctgagatacc tacagcgtga gctatgagaa agcgccacgc ttcccgaagg     420
gagaaaggcg gacaggtatc cggtaagcgg cagggtcgga acaggagagc gcacgaggga     480
gcttccaggg ggaaacgcct ggtatcttta tagtcctgtc gggtttcgcc acctctgact     540
tgagcgtcga tttttgtgat gctcgtcagg gggcggagc ctatggaaaa acgccagcaa     600
cgcggccttt ttacggttcc tggccttttg ctggcctttt gctcacatgt tctttcctgc     660
gttatcccct gattctgtgg ataaccgtat taccgccttt gagtgagctg ataccgctcg     720
ccgcagccga acgaccgagc gcagcgagtc agtgagcgag gaagcggaag agcgcctgat     780
gcggtatttt ctccttacgc atctgtgcgg tatttcacac cgcaatggtg cactctcagt     840
acaatctgct ctgatgccgc atagttaagc cagtatacac tccgctatcg ctacgtgact     900
gggtcatggc tgcgccccga cacccgccaa cacccgctga cgcgccctga cgggcttgtc     960
tgctcccggc atccgcttac agacaagctg tgaccgtctc cgggagctgc atgtgtcaga    1020
ggttttcacc gtcatcaccg aaacgcgcga ggcaggggga attccagata acttcgtata    1080
atgtatgcta tacgaagtta tggtaccgcg gccgcgtaga ggatctgttg atcagcagtt    1140
caacctgttg atagtacttc gttaatacag atgtaggtgt tggcaccatg cataactata    1200
acggtcctaa ggtagcgacc taggtatcga taatacgact cactataggg gaattgtgag    1260
cggataacaa ttcccctcta gaaataattt tgtttaactt taagaaggag atataatggg    1320
cagtagtcac catcaccacc accatcatca ccatcatagt agtgaaaacc tgtatttca     1380
ggggcatatg gctgagaagc agaagcacga cgggcgtgtg aagatcggac actacgtgct    1440
gggggacacc ctgggcgtcg gcaccttcgg caaagtgaag attggagaac atcaattgac    1500
aggccataaa gtgcagtta agatcttaaa tagacagaag attcgcagtt tagatgttgt     1560
tggaaaaata aaacgagaaa ttcaaaatct taaactcttt cgtcatcctc atattatcaa    1620
actctaccaa gtgatcagca ctccaacaga cttttttatg gtaatggaat atgtgtctgg    1680
aggtgaattg ttcgactaca tctgtaaaca cgggagggtt gaagaggtgg aagctcgccg    1740
gctcttccag cagattctgt ctgccgtgga ctactgtcac aggcacatgg ttgtccacag    1800
ggacctgaag ccagagaacg tgttgctgga cgcccagatg aatgctaaga tagctgactt    1860
cggactctct aatatgatgt cagatggtga atttctacga actagctgtg gatcgccaaa    1920
ttatgcagca ccggaggtca tctcaggaag gctgtatgcg ggtcctgagg ttgatatctg    1980
gagctgtggt gttatcctgt atgcccttct ctgtggcacc ctcccgttcg acatgagcag    2040
cgtgcctacg ctctttaaga agatccgagg gggtgtgttc tacatcccgg agtatctcaa    2100
ccgttctatt gccactctgc tgatgcacat gctgcaggtg gacccttga agcgagcaac    2160
tatcaaagac atacgagagc atgaatggtt taaacaggat ttgcccagtt acctctttcc    2220
tgaagacccc tcctatgatg ctaacgtcat tgatgatgag gctgtgaaag aagtatgtga    2280
```

```
aaaatttgag tgtacagaat cagaagtgat gaacagttta tacagtggtg accctcaaga    2340
ccagctcgca gtggcttatc atctcatcat tgacaatcgg agaataatga accaagccag    2400
tgagttctac ctcgcctcca gtcctccaac gggttccttc atggacgata tggccatgca    2460 cattccccccc ggcctgaaac cacatcctga aaggatgcca cctctcatag cagacagccc   2520
caaagcacgc tgtccactgg atgcactcaa cacaactaag cccaaatctt tagctgtgaa    2580
aaaagccaag tggcaccttg ggatccgaag ccagagcaaa ccatacgaca ttatggcgga    2640
ggtgtaccga gctatgaagc agctggactt tgaatggaag gtagtgaatg cataccatct    2700
tcgagtaaga agaaaaaacc cagtgactgg caattacgtg aaaatgagct acagctttta    2760
cctggttgac aatcggagct atctgctgga ctttaaaagc atcgatgatg aggtggtgga    2820
gcagaggtct ggttcttcaa cacctcagcg ctcctgttct gctgccggcc tccacagacc    2880
tcggtcaagt gtcgattcca gcacagccga gaaccattca ctgtctggct ctctcactgg    2940
ttctttgact ggcagcactt tgtcctccgc ttccccgcgc ctgggcagtc ataccatgga    3000 ttttttttgaa atgtgcgcca gtcttatcac tgctttagag gaggaagaga agaaaaagaa    3060
aggcgaggag ctgttcaccg gggtggtgcc catcctggtc gagctggacg gcgacgtaaa    3120
cggccacaag ttcagcgtgt ccggcgaggg cgagggcgat gccacctacg gcaagctgac    3180
cctgaagttc atctgcacca ccggcaagct gcccgtgccc tggcccaccc tcgtgaccac    3240
cctgacctgg ggcgtgcagt gcttcagccg ctaccccgac cacatgaagc agcacgactt    3300
cttcaagtcc gccatgcccg aaggctacgt ccaggagcgc accatcttct tcaaggacga    3360
cggcaactac aagacccgcg ccgaggtgaa gttcgagggc gacaccctgg tgaaccgcat    3420
cgagctgaag ggcatcgact tcaaggagga cggcaacatc ctggggcaca gctggagta    3480 caactacatc agccacaacg tctatatcac cgccgacaag cagaagaacg gcatcaaggc    3540
caacttcaag atccgccaca acatcgagga cggcagcgtg cagctcgccg accactacca    3600
gcagaacacc cccatcggcg acggccccgt gctgctgccc gacaaccact acctgagcac    3660
ccagtccgcc ctgagcaaag accccaacga gaagcgcgat cacatggtcc tgctggagtt    3720
cgtgaccgcc gccgggatca ctctcggcat ggacgagctg tacaagtccg gactcagatc    3780
tcgacgagct cactgataac tcgagagatc cggctgctaa caaagcccga aggaagctg    3840 agttggctgc tgccaccgct gagcaataac tagcataacc ccttgggggcc tctaaacggg    3900 tcttgagggg ttttttggtt taaacccatc taattggact agtagcccgc ctaatgagcg    3960
ggcttttttt taattccccct atttgtttat ttttctaaat acattcaaat atgtatccgc    4020
tcatgagaca ataaccctga taaatgcttc aataatattg aaaaaggaag agtatgagta    4080
ttcaacattt ccgtgtcgcc cttattccct tttttgcggc attttgcctt cctgtttttg    4140
ctcacccaga aacgctcgtg aaagtaaaag acgcagagga ccaattgggg gcacgagtgg    4200
gatacataga actggacttg aatagcggta aaatccttga gagttttcgc cctgaagagc    4260
gttttccaat gatgagcact ttcaaagttc tgctatgtgg agcagtatta tcccgtgtag    4320
atgcggggca agagcaactc ggacgacgaa tacactattc gcagaatgac ttggttgaat    4380
actccccagt gacagaaaag caccttacgg acggaatgac ggtaagagaa ttatgtagtg    4440
ccgccataac gatgagtgat aacactgcgg cgaacttact tctgacaacc atcggtggac    4500
cgaaggaatt aaccgctttt ttgcacaata tgggagacca tgtaactcgc cttgaccgtt    4560
gggaaccaga actgaatgaa gccataccaa acgacgagcg agacaccaca atgcctgcgg    4620
```

```
caatggcaac aacattacgc aaactattaa ctggcgaact acttactctg gcttcacggc    4680
aacaattaat agactggctt gaagcggata aagttgcagg accactactg cgttcggcac    4740
ttcctgctgg ctggtttatt gctgataaat ctggggcagg agagcgtggt tcacggggta    4800
tcattgccgc acttggacca gatggtaagc cttcccgtat cgtagttatc tacacgacgg    4860
gtagtcaggc aactatggac gaacgaaata gacagattgc tgaaataggg gcttcactga    4920
ttaagcattg gtaaaccgat acaattaaag gctccttttg gagcctttttt ttttggacgg    4980 accggtagaa aagatcaaag gatcttc                                         5007

<210> SEQ ID NO 77
<211> LENGTH: 3493
<212> TYPE: DNA
<213> ORGANISM: Artificial Sequence
<220> FEATURE:
<223> OTHER INFORMATION: Human beta2-KPI-YFP_deletion, pDC plasmid

<400> SEQUENCE: 77
cgccccgccc tgccactcat cgcagtactg ttgtaattca ttaagcattc tgccgacatg      60
gaagccatca caaacggcat gatgaacctg aatcgccagc ggcatcagca ccttgtcgcc     120
ttgcgtataa tatttgccca tggtgaaaac gggggcgaag aagttgtcca tattggccac     180
gtttaaatca aaactggtga aactcaccca gggattggct gagacgaaaa acatattctc     240
aataaaccct ttagggaaat aggccaggtt ttccaccgta aacgccacat cttgcgaata     300
tatgtgtaga aactgccgga atcgtcgtg gtattcactc cagagcgatg aaaacgtttc     360
agtttgctca tggaaaacgg tgtaacaagg gtgaacacta tcccatatca ccagctcacc     420
gtctttcatt gccatacgga attccggatg agcattcatc aggcgggcaa gaatgtgaat     480
aaaggccgga taaaacttgt gcttattttt ctttacggtc tttaaaaagg ccgtaatatc     540
cagctgaacg gtctggttat aggtacattg agcaactgac tgaaatgcct caaaatgttc     600
tttacgatgc cattgggata tatcaacggt ggtatatcca gtgattttt tctccatttt     660 agcttcctta gctcctgaaa atctcgataa ctcaaaaaat acgcccggta gtgatcttat     720
ttcattatgg tgaaagttgg accctcttac gtgccgatca acgtctcatt tcgccaaaa     780 gttggcccag atcaacgtct catttttcgcc aaaagttggc ccagatctat gtcgggtgcg     840
gagaaagagg taatgaaatg gcacctaggt atcgataata cgactcacta tagggggaatt     900 gtgagcggat aacaattccc ctctagaaat aattttgttt aactttaaga aggagatata     960
catatgaggc ctatgggaaa caccaccagc gaccgggtgt ccggggagcg ccacggcgcc    1020
aaggctgcac gctccgaggg cgcaggcggc catgccccgg ggaaggagca agatcatg     1080 gtggggagta cggacgaccc cagcgtgttc agcctccctg actccaagct ccctgggac     1140 aaagagtttg tatcatggca gcaggatttg gaggactccg taaagcccac acagcaggcc    1200
cggcccactg ttatccgctg gtctgaagga ggcaaggagg tcttcatctc tgggtctttc     1260
aacaattgga gcaccaagat tccactgatt aagagccata tgactttgt tgccatcctg    1320 gacctccctg agggagagca ccaatacaag ttctttgtgg atggacagtg ggttcatgat    1380
ccatcagagc ctgtggttac cagtcagctt ggcacaatta caatttgat ccatgtcaag    1440 aaatctgatt ttgaggtgtt cgatgcttta agttagatt ctatggaaag ttctgagaca    1500
tcttgtagag acctttccag ctcacccca gggccttatg gtcaagaaat gtatgcgttt    1560
cgatctgagg aaagattcaa atccccaccc atccttcctc ctcatctact tcaagttatt    1620
cttaacaaag acactaatat ttcttgtgac ccagccttac tccctgagcc caaccatgtt    1680
```

```
atgctgaacc atctctatgc attgtccatt aaggacagtg tgatggtcct tagcgcaacc    1740
catcgctaca agaagaagta tgttactact ctgctataca tggtgagcaa gggcgaggag    1800
ctgttcaccg gggtggtgcc catcctggtc gagctggacg gcgacgtaaa cggccacaag    1860
ttcagcgtgt ccggcgaggg cgagggcgat gccacctacg gcaagctgac cctgaagttc    1920
atctgcacca ccggcaagct gcccgtgccc tggcccaccc tcgtgaccac cttcggctac    1980
ggcctgcagt gcttcgcccg ctaccccgac cacatgaagc agcacgactt cttcaagtcc    2040
gccatgcccg aaggctacgt ccaggagcgc accatcttct tcaaggacga cggcaactac    2100
aagacccgcg ccgaggtgaa gttcgagggc gacaccctgg tgaaccgcat cgagctgaag    2160
ggcatcgact tcaaggagga cggcaacatc ctggggcaca agctggagta caactacaac    2220
agccacaacg tctatatcat ggccgacaag cagaagaacg gcatcaaggt gaacttcaag    2280
atccgccaca acatcgagga cggcagcgtg cagctcgccg accactacca gcagaacacc    2340
cccatcggcg acggccccgt gctgctgccc gacaaccact acctgagcta ccagtccgcc    2400
ctgagcaaag accccaacga aaagcgcgat cacatggtcc tgctggagtt cgtgaccgcc    2460
gccgggatca ctctcggcat ggacgagctg tacaagtccg gactcagatc tcgagctcaa    2520
gcttcgaatt ctgcagtcga cggtaccgcg ggcccgggat ccaccggatc tagatgataa    2580
gcatgctagc ataacccctt ggggcctcta acgggtctt gaggggtttt ttggtttaaa    2640
cccatgtgcc tggcagataa cttcgtataa tgtatgctat acgaagttat ggtaccgcgg    2700
ccgcgtagag gatctgttga tcagcagttc aacctgttga tagtacgtac taagctctca    2760
tgtttcacgt actaagctct catgtttaac gtactaagct ctcatgttta cgaactaaa    2820
ccctcatggc taacgtacta agctctcatg gctaacgtac taagctctca tgtttcacgt    2880
actaagctct catgtttgaa caataaaatt aatataaatc agcaacttaa atagcctcta    2940
aggttttaag ttttataaga aaaaaagaa tatataaggc ttttaaagct tttaaggttt    3000
aacggttgtg gacaacaagc cagggatgta acgcactgag aagcccttag agcctctcaa    3060
agcaattttg agtgacacag gaacacttaa cggctgacag aattagcttc acgctgccgc    3120
aagcactcag ggcgcaaggg ctgctaaagg aagcggaaca cgtagaaagc cagtccgcag    3180
aaacggtgct gaccccggat gaatgtcagc tgggaggcag aataaatgat catatcgtca    3240
attattacct ccacggggag agcctgagca aactggcctc aggcatttga aagcacacg    3300
gtcacactgc ttccggtagt caataaaccg gtaaaccagc aatagacata agcggctatt    3360
taacgaccct gccctgaacc gacgaccggg tcgaatttgc tttcgaattt ctgccattca    3420
tccgcttatt atcacttatt caggcgtagc aaccaggcgt ttaagggcac aataactgc    3480
cttaaaaaaa tta                                                      3493

<210> SEQ ID NO 78
<211> LENGTH: 534
<212> TYPE: PRT
<213> ORGANISM: Artificial Sequence
<220> FEATURE:
<223> OTHER INFORMATION: Human beta2-KPI-YFP_deletion

<400> SEQUENCE: 78

Met Gly Asn Thr Thr Ser Asp Arg Val Ser Gly Glu Arg His Gly Ala
1               5                   10                  15

Lys Ala Ala Arg Ser Glu Gly Ala Gly Gly His Ala Pro Gly Lys Glu
            20                  25                  30
```

His Lys Ile Met Val Gly Ser Thr Asp Asp Pro Ser Val Phe Ser Leu
 35              40              45

Pro Asp Ser Lys Leu Pro Gly Asp Lys Glu Phe Val Ser Trp Gln Gln
 50              55              60

Asp Leu Glu Asp Ser Val Lys Pro Thr Gln Gln Ala Arg Pro Thr Val
 65              70              75              80

Ile Arg Trp Ser Glu Gly Gly Lys Glu Val Phe Ile Ser Gly Ser Phe
                 85              90              95

Asn Asn Trp Ser Thr Lys Ile Pro Leu Ile Lys Ser His Asn Asp Phe
             100             105             110

Val Ala Ile Leu Asp Leu Pro Glu Gly Glu His Gln Tyr Lys Phe Phe
         115             120             125

Val Asp Gly Gln Trp Val His Asp Pro Ser Glu Pro Val Val Thr Ser
 130             135             140

Gln Leu Gly Thr Ile Asn Asn Leu Ile His Val Lys Lys Ser Asp Phe
 145             150             155             160

Glu Val Phe Asp Ala Leu Lys Leu Asp Ser Met Glu Ser Ser Glu Thr
                 165             170             175

Ser Cys Arg Asp Leu Ser Ser Pro Pro Gly Pro Tyr Gly Gln Glu
             180             185             190

Met Tyr Ala Phe Arg Ser Glu Glu Arg Phe Lys Ser Pro Pro Ile Leu
         195             200             205

Pro Pro His Leu Leu Gln Val Ile Leu Asn Lys Asp Thr Asn Ile Ser
     210             215             220

Cys Asp Pro Ala Leu Leu Pro Glu Pro Asn His Val Met Leu Asn His
 225             230             235             240

Leu Tyr Ala Leu Ser Ile Lys Asp Ser Val Met Val Leu Ser Ala Thr
                 245             250             255

His Arg Tyr Lys Lys Tyr Val Thr Thr Leu Leu Tyr Met Val Ser
             260             265             270

Lys Gly Glu Glu Leu Phe Thr Gly Val Val Pro Ile Leu Val Glu Leu
         275             280             285

Asp Gly Asp Val Asn Gly His Lys Phe Ser Val Ser Gly Glu Gly Glu
 290             295             300

Gly Asp Ala Thr Tyr Gly Lys Leu Thr Leu Lys Phe Ile Cys Thr Thr
 305             310             315             320

Gly Lys Leu Pro Val Pro Trp Pro Thr Leu Val Thr Thr Phe Gly Tyr
                 325             330             335

Gly Leu Gln Cys Phe Ala Arg Tyr Pro Asp His Met Lys Gln His Asp
             340             345             350

Phe Phe Lys Ser Ala Met Pro Glu Gly Tyr Val Gln Glu Arg Thr Ile
         355             360             365

Phe Phe Lys Asp Asp Gly Asn Tyr Lys Thr Arg Ala Glu Val Lys Phe
 370             375             380

Glu Gly Asp Thr Leu Val Asn Arg Ile Glu Leu Lys Gly Ile Asp Phe
 385             390             395             400

Lys Glu Asp Gly Asn Ile Leu Gly His Lys Leu Glu Tyr Asn Tyr Asn
                 405             410             415

Ser His Asn Val Tyr Ile Met Ala Asp Lys Gln Lys Asn Gly Ile Lys
             420             425             430

Val Asn Phe Lys Ile Arg His Asn Ile Glu Asp Gly Ser Val Gln Leu
         435             440             445

Ala Asp His Tyr Gln Gln Asn Thr Pro Ile Gly Asp Gly Pro Val Leu

```
                450             455             460
Leu Pro Asp Asn His Tyr Leu Ser Tyr Gln Ser Ala Leu Ser Lys Asp
465                 470                 475                 480

Pro Asn Glu Lys Arg Asp His Met Val Leu Leu Glu Phe Val Thr Ala
                485                 490                 495

Ala Gly Ile Thr Leu Gly Met Asp Glu Leu Tyr Lys Ser Gly Leu Arg
            500                 505                 510

Ser Arg Ala Gln Ala Ser Asn Ser Ala Val Asp Gly Thr Ala Gly Pro
        515                 520                 525

Gly Ser Thr Gly Ser Arg
    530

<210> SEQ ID NO 79
<211> LENGTH: 3610
<212> TYPE: DNA
<213> ORGANISM: Artificial Sequence
<220> FEATURE:
<223> OTHER INFORMATION: Rat gamma1-LTGGEKKP-YFP_deletion, pDS plasmid

<400> SEQUENCE: 79
```

| | | | | | |
|---|---|---|---|---|---|
| atgagggaag | cggtgatcgc | cgaagtatcg | actcaactat | cagaggtagt | tggcgtcatc | 60 |
| gagcgccatc | tcgaaccgac | gttgctggcc | gtacatttgt | acggctccgc | agtggatggc | 120 |
| ggcctgaagc | cacacagtga | tattgatttg | ctggttacgg | tgaccgtaag | gcttgatgaa | 180 |
| acaacgcggc | gagctttgat | caacgacctt | ttggaaactt | cggcttcccc | tggagagagc | 240 |
| gagattctcc | gcgctgtaga | agtcaccatt | gttgtgcacg | acgacatcat | tccgtggcgt | 300 |
| tatccagcta | agcgcgaact | gcaatttgga | gaatggcagc | gcaatgacat | tcttgcaggt | 360 |
| atcttcgagc | cagccacgat | cgacattgat | ctggctatct | tgctgacaaa | agcaagagaa | 420 |
| catagcgttg | ccttggtagg | tccagcggcg | gaggaactct | ttgatccggt | tcctgaacag | 480 |
| gatctatttg | aggcgctaaa | tgaaacctta | acgctatgga | actcgccgcc | cgactgggct | 540 |
| ggcgatgagc | gaaatgtagt | gcttacgttg | tcccgcattt | ggtacagcgc | agtaaccggc | 600 |
| aaaatcgcgc | cgaaggatgt | cgctgccgac | tgggcaatgg | agcgcctgcc | ggcccagtat | 660 |
| cagcccgtca | tacttgaagc | tagacaggct | tatcttggac | aagaagaaga | tcgcttggcc | 720 |
| tcgcgcgcag | atcagttgga | agaatttgtc | cactacgtga | aaggcgagat | caccaaggta | 780 |
| gtcggcaaat | aatgtctaac | aattcgttca | agccgacgga | tctatgtcgg | gtgcggagaa | 840 |
| agaggtaatg | aaatggcacc | taggtatcga | taatacgact | cactataggg | aattgtgag | 900 |
| cggataacaa | ttcccctcta | gaaataattt | tgtttaactt | taagaaggag | atatacatat | 960 |
| ggagtcggtt | gctgcagaga | gcgctccagc | tccggagaat | gaacactctc | aagagacccc | 1020 |
| ggaatcgaac | agtagtgtgt | acaccacctt | catgaagtct | catcgctgct | atgacctgat | 1080 |
| ccccacaagc | tccaagctgg | tggtatttga | tacttcgctg | caggtaaaga | aagccttctt | 1140 |
| tgccctggtg | actaacggtg | ttcgtgctgc | ccctttgtgg | gatagtaaga | agcagagctt | 1200 |
| tgtgggcatg | ctgaccatca | ctgacttcat | caatattctg | caccgatact | acaagtcagc | 1260 |
| cctggtgcag | atctatgaac | tggaggagca | caagatagag | acttggagag | aggtctacct | 1320 |
| gcaagactcc | tttaagccac | ttgtctgcat | ttctccaaat | gccagcttgt | tcgatgctgt | 1380 |
| ctcttcatta | attcgaaata | agatccacag | gcttccagtt | attgacccgg | agtcaggcaa | 1440 |
| caccttgtac | attcttactc | acaagcggat | cctcaagttc | ctcaagttgt | ttatcactga | 1500 |
| gttccccaag | ccggaattca | tgtctaagtc | tctggaagag | ctacagattg | gcacctacgc | 1560 |

```
caatattgcc atggtccgta ccactacacc tgtctatgtg gctctgggca tctttgtaca   1620
gcaccgagtc tccgccttgc ctgtggtgga tgagaaaggg cgtgtggtgg acatctactc   1680
caagtttgat gtgattaatt tggcagcaga aaagacatac aacaacctag atgtgtctgt   1740
gacaaaagcc ctacagcacc ggtcacacta cttcgagggt gttctcaagt gctacctaca   1800
tgagactcta gaagcaatca tcaatagact ggtggaagca gaggttcacc gtctggtggt   1860
ggtggatgaa catgacgtgg tcaagggcat tgtatcgctg tctgacatct tacaggctct   1920
ggtgatggtg agcaagggcg aggagctgtt caccggggtg gtgcccatcc tggtcgagct   1980
ggacggcgac gtaaacggcc acaagttcag cgtgtccggc gagggcgagg gcgatgccac   2040
ctacggcaag ctgaccctga agttcatctg caccaccggc aagctgcccg tgccctggcc   2100
caccctcgtg accaccttcg gctacggcct gcagtgcttc gcccgctacc ccgaccacat   2160
gaagcagcac gacttcttca gtccgccat gcccgaaggc tacgtccagg agcgcaccat   2220
cttcttcaag gacgacggca actacaagac ccgcgccgag gtgaagttcg agggcgacac   2280
cctggtgaac cgcatcgagc tgaagggcat cgacttcaag gaggacggca acatcctggg   2340
gcacaagctg gagtacaact acaacagcca caacgtctat atcatggccg acaagcagaa   2400
gaacggcatc aaggtgaact tcaagatccg ccacaacatc gaggacggca gcgtgcagct   2460
cgccgaccac taccagcaga cacccccat cggcgacggc cccgtgctgc tgcccgacaa   2520
ccactacctg agctaccagt ccgcctgag caaagacccc aacgagaagc gcgatcacat   2580
ggtcctgctg gagttcgtga ccgccgccgg gatcactctc ggcatggacg agctgtacaa   2640
gtccggactc agatctcgag ctcaagcttc gaattctgca gtcgacggta ccgcgggccc   2700
gggatccacc ggatctagat gataactagt ccgtttaaa cccatgtgcc tggcagataa   2760
cttcgtataa tgtatgctat acgaagttat ggtacgtact aagctctcat gtttcacgta   2820
ctaagctctc atgtttaacg tactaagctc tcatgtttaa cgaactaaac cctcatggct   2880
aacgtactaa gctctcatgg ctaacgtact aagctctcat gtttcacgta ctaagctctc   2940
atgtttgaac aataaaatta atataaatca gcaacttaaa tagcctctaa ggttttaagt   3000
tttataagaa aaaaagaat atataaggct tttaaagctt ttaaggttta acggttgtgg   3060
acaacaagcc agggatgtaa cgcactgaga agcccttaga gcctctcaaa gcaattttga   3120
gtgacacagg aacacttaac ggctgacata attcagcttc acgctgccgc aagcactcag   3180
ggcgcaaggg ctgctaaagg aagcggaaca cgtagaaagc cagtccgcag aaacggtgct   3240
gaccccggat gaatgtcagc tgggaggcag aataaatgat catatcgtca attattacct   3300
ccacggggag agcctgagca aactggcctc aggcatttga gaagcacacg gtcacactgc   3360
ttccggtagt caataaaccg gtaagtagcg tatgcgctca cgcaactggt ccagaacctt   3420
gaccgaacgc agcggtggta acggcgcagt ggcggttttc atggcttgtt atgactgttt   3480 tttggggta cagtctatgc ctcgggcatc caagcagcaa gcgcgttacg ccgtgggtcg   3540
atgtttgatg ttatggagca gcaacgatgt tacgcagcag ggcagtcgcc ctaaaacaaa   3600
gttaaacatc                                                         3610
```

<210> SEQ ID NO 80
<211> LENGTH: 587
<212> TYPE: PRT
<213> ORGANISM: Artificial sequence
<220> FEATURE:
<223> OTHER INFORMATION: Rat gamma1-YFP, LTGGEKKP deletion

<400> SEQUENCE: 80

```
Met Glu Ser Val Ala Ala Glu Ser Ala Pro Ala Glu Asn Glu His
 1               5                  10                  15

Ser Gln Glu Thr Pro Glu Ser Asn Ser Ser Val Tyr Thr Thr Phe Met
             20                  25                  30

Lys Ser His Arg Cys Tyr Asp Leu Ile Pro Thr Ser Ser Lys Leu Val
         35                  40                  45

Val Phe Asp Thr Ser Leu Gln Val Lys Lys Ala Phe Phe Ala Leu Val
     50                  55                  60

Thr Asn Gly Val Arg Ala Ala Pro Leu Trp Asp Ser Lys Lys Gln Ser
 65                  70                  75                  80

Phe Val Gly Met Leu Thr Ile Thr Asp Phe Ile Asn Ile Leu His Arg
                 85                  90                  95

Tyr Tyr Lys Ser Ala Leu Val Gln Ile Tyr Glu Leu Glu Glu His Lys
             100                 105                 110

Ile Glu Thr Trp Arg Glu Val Tyr Leu Gln Asp Ser Phe Lys Pro Leu
         115                 120                 125

Val Cys Ile Ser Pro Asn Ala Ser Leu Phe Asp Ala Val Ser Ser Leu
     130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                 165                 170                 175

Leu Phe Ile Thr Glu Phe Pro Lys Pro Glu Phe Met Ser Lys Ser Leu
             180                 185                 190

Glu Glu Leu Gln Ile Gly Thr Tyr Ala Asn Ile Ala Met Val Arg Thr
         195                 200                 205

Thr Thr Pro Val Tyr Val Ala Leu Gly Ile Phe Val Gln His Arg Val
     210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                 245                 250                 255

Leu Asp Val Ser Val Thr Lys Ala Leu Gln His Arg Ser His Tyr Phe
             260                 265                 270

Glu Gly Val Leu Lys Cys Tyr Leu His Glu Thr Leu Glu Ala Ile Ile
         275                 280                 285

Asn Arg Leu Val Glu Ala Glu Val His Arg Leu Val Val Asp Glu
     290                 295                 300

His Asp Val Val Lys Gly Ile Val Ser Leu Ser Asp Ile Leu Gln Ala
305                 310                 315                 320

Leu Val Met Val Ser Lys Gly Glu Glu Leu Phe Thr Gly Val Val Pro
                 325                 330                 335

Ile Leu Val Glu Leu Asp Gly Asp Val Asn Gly His Lys Phe Ser Val
             340                 345                 350

Ser Gly Glu Gly Glu Gly Asp Ala Thr Tyr Gly Lys Leu Thr Leu Lys
         355                 360                 365

Phe Ile Cys Thr Thr Gly Lys Leu Pro Val Pro Trp Pro Thr Leu Val
     370                 375                 380

Thr Thr Phe Gly Tyr Gly Leu Gln Cys Phe Ala Arg Tyr Pro Asp His
385                 390                 395                 400

Met Lys Gln His Asp Phe Phe Lys Ser Ala Met Pro Glu Gly Tyr Val
                 405                 410                 415
```

```
Gln Glu Arg Thr Ile Phe Phe Lys Asp Asp Gly Asn Tyr Lys Thr Arg
            420                 425                 430

Ala Glu Val Lys Phe Glu Gly Asp Thr Leu Val Asn Arg Ile Glu Leu
        435                 440                 445

Lys Gly Ile Asp Phe Lys Glu Asp Gly Asn Ile Leu Gly His Lys Leu
    450                 455                 460

Glu Tyr Asn Tyr Asn Ser His Asn Val Tyr Ile Met Ala Asp Lys Gln
465                 470                 475                 480

Lys Asn Gly Ile Lys Val Asn Phe Lys Ile Arg His Asn Ile Glu Asp
                485                 490                 495

Gly Ser Val Gln Leu Ala Asp His Tyr Gln Gln Asn Thr Pro Ile Gly
            500                 505                 510

Asp Gly Pro Val Leu Leu Pro Asp Asn His Tyr Leu Ser Tyr Gln Ser
        515                 520                 525

Ala Leu Ser Lys Asp Pro Asn Glu Lys Arg Asp His Met Val Leu Leu
    530                 535                 540

Glu Phe Val Thr Ala Ala Gly Ile Thr Leu Gly Met Asp Glu Leu Tyr
545                 550                 555                 560

Lys Ser Gly Leu Arg Ser Arg Ala Gln Ala Ser Asn Ser Ala Val Asp
                565                 570                 575

Gly Thr Ala Gly Pro Gly Ser Thr Gly Ser Arg
            580                 585
```

<210> SEQ ID NO 81
<211> LENGTH: 6958
<212> TYPE: DNA
<213> ORGANISM: Artificial Sequence
<220> FEATURE:
<223> OTHER INFORMATION: Rat alpha2-AR-mseCFP-11_deletion, pACEMam2 plasmid

<400> SEQUENCE: 81

```
tcgagccatg gtgctagcag ctgatgcata gcatgcggta cctaattcac tcctcaggtg    60
caggctgcct atcagaaggt ggtggctggt gtggctaatg ccctggctca caaataccac   120
tgagatcttt ttccctctgc caaaaattat ggggacatca tgaagcccct tgagcatctg   180
acttctggct aataaaggaa atttattttc attgcaatag tgtgttggaa ttttttgtgt   240
ctctcactcg gaaggacata tgggagggca aatcatttaa acatcagaat gagtatttg    300
gtttagagtt tggcaacata tgccatatgc tggctgccat gaacaaaggt ggctataaag   360
aggtcatcag tatatgaaac agccccctgc tgtccattcc ttattccata gaaaagcctt   420
gacttgaggt tagatttttt ttatattttg ttttgtgtta ttttttttctt taacatccct   480
aaaattttcc ttacatgttt tactagccag atttttcctc ctctcctgac tactcccagt   540
catagctgtc cctcttctct tatgaagatc cctcgacgtt taaactcgct accttaggac   600
cgttatagtt acagataact tcgtataatg tatgctatac gaagttatgg cgacttcgct   660
gctgcccaag gttgccgggt gacgcacacc gtggaaacgg atgaaggcac gaacccagtt   720
gacataagcc tgttcggttc gtaaactgta atgcaagtag cgtatgcgct cacgcaactg   780
gtccagaacc ttgaccgaac gcagcggtgg taacggcgca gtggcggttt catggcttg   840
ttatgactgt ttttttgtac agtctatgcc tcggcatcc aagcagcaag cgcgttacgc   900
cgtgggtcga tgtttgatgt tatggagcag caacgatgtt acgcagcagc aacgatgtta   960
cgcagcaggg cagtcgccct aaaacaaagt taggtggctc aagtatgggc atcattcgca  1020
catgtaggct cggccctgac caagtcaaat ccatgcgggc tgctcttgat cttttcggtc  1080
```

```
gtgagttcgg agacgtagcc acctactccc aacatcagcc ggactccgat tacctcggga   1140
acttgctccg tagtaagaca ttcatcgcgc ttgctgcctt cgaccaagaa gcggttgttg   1200
gcgctctcgc ggcttacgtt ctgcccaagt ttgagcagcc gcgtagtgag atctatatct   1260
atgatctcgc agtctccggc gagcaccgga ggcagggcat tgccaccgcg ctcatcaatc   1320
tcctcaagca tgaggccaac gcgcttggtg cttatgtgat ctacgtgcaa gcagattacg   1380
gtgacgatcc cgcagtggct ctctatacaa agttgggcat acgggaagaa gtgatgcact   1440
ttgatatcga cccaagtacc gccacctaac aattcgttca agccgagatc ggcttcccgg   1500
ccgcggagtt gttcggtaaa ttgtcacaac gccgcgaata tagtctttac atgcccttgg   1560
ccacgcccct ctttaatacg acgggcaatt tgcacttcag aaaatgaaga gtttgcttta   1620
gccataacaa aagtccagta tgcttttttca cagcataact ggactgattt cagtttacaa   1680
ctattctgtc tagtttaaga ctttattgtc atagtttaga tctattttgt tcagtttaag   1740
acttattgt ccgcccacac ccgcttacgc agggcatctg cgcatccaca ggaagagcga   1800
cccaagtcaa tcagggata acgcaggaaa gaacatgtga gcaaaaggcc agcaaaaggc   1860
caggaaccgt aaaaaggccg cgttgctggc gttttttccat aggctccgcc ccctgacga   1920
gcatcacaaa aatcgacgct caagtcagag gtggcgaaac ccgacaggac tataaagata   1980
ccaggcgttt ccccctggaa gctccctcgt gcgctctcct gttccgaccc tgccgcttac   2040
cggatacctg tccgcctttc tcccttcggg aagcgtggcg ctttctcata gctcacgctg   2100
taggtatctc agttcggtgt aggtcgttcg ctccaagctg ggctgtgtgc acgaaccccc   2160
cgttcagccc gaccgctgcg ccttatccgg taactatcgt cttgagtcca acccggtaag   2220
acacgactta tcgccactgg cagcagccac tggtaacagg attagcagag cgaggtatgt   2280
aggcggtgct acagagttct tgaagtggtg gcctaactac ggctacacta agaacagt   2340
atttggtatc tgcgctctgc tgaagccagt taccttcgga aaaagagttg gtagctcttg   2400
atccggcaaa caaaccaccg ctggtagcgg tggtttttttt gtttgcaagc agcagattac   2460
gcgcagaaaa aaaggatctc aagaagatcc tttgatcttt tctacggggt ctgacgctca   2520
gtggaacgaa aactcacgtt aagggatttt ggtcatgaga ttatcaaaaa ggatcttcac   2580
ctagatcctt ttaaattaaa aatgaagttt taaatcaatc taaagtatat atgagtaaac   2640
ttggtctgac agttgaccca agtcaaccgg ttgtgggcgg acaaaatagt tgggaactgg   2700
gaggggtgga aatggagttt ttaaggatta tttagggaag agtgacaaaa tagatgggaa   2760
ctgggtgtag cgtcgtaagc taatacgaaa attaaaaatg acaaaatagt ttggaactag   2820
atttcactta tctggttcca attagatgga tcgatactac gatactagta tacgttatta   2880
atagtaatca attacggggt cattagttca tagcccatat atggagttcc gcgttacata   2940
acttacggta aatggcccgc ctggctgacc gcccaacgac ccccgcccat tgacgtcaat   3000
aatgacgtat gttcccatag taacgccaat agggactttc cattgacgtc aatgggtgga   3060
ctatttacgg taaactgccc acttggcagt acatcaagtg tatcatatgc caagtacgcc   3120
ccctattgac gtcaatgacg gtaaatggcc cgcctggcat tatgcccagt acatgacctt   3180
atgggacttt cctacttggc agtacatcta cgtattagtc atcgctatta ctcatgggtc   3240
gaggtgagcc ccacgttctg cttcactctc cccatctccc ccccctcccc accccaatt   3300
ttgtatttat ttattttta attatttgt gcagcgatgg gggcgggggg gggggggcg   3360
cgcgccaggc gggggcggggc ggggcgaggg gcggggcggg gcgaggcgga gaggtgcggc   3420
```

```
ggcagccaat cagagcggcg cgctccgaaa gtttccttt atggcgaggc ggcggcggcg    3480
gcggccctat aaaaagcgaa gcgcgcggcg ggcgggagtc gctgcgttgc cttcgccccg    3540
tgccccgctc cgcgccgcct cgcgccgccc gccccggctc tgactgaccg cgttactccc    3600
acaggtgagc gggcgggacg gcccttctcc tccgggctgt aattagcgct tggtttaatg    3660
acggctcgtt tcttttctgt ggctgcgtga aagccttaaa gggctccggg agggcccttt    3720
gtgcgggggg gagcggctcg gggggtgcgt gcgtgtgtgt gtgcgtgggg agcgccgcgt    3780
gcggcccgcg ctgcccggcg gctgtgagcg ctgcgggcgc ggcgcggggc tttgtgcgct    3840
ccgcgtgtgc gcgaggggag cgcggccggg ggcggtgccc cgcggtgcgg ggggctgcg    3900
agggaacaa aggctgcgtg cggggtgtgt gcgtgggggg gtgagcaggg ggtgtgggcg    3960
cggcggtcgg gctgtaaccc ccccctgcac cccctcccc gagttgctga gcacggcccg    4020
gcttcgggtg cggggctccg tgcggggcgt ggcgcggggc tcgccgtgcc gggcgggggg    4080
tggcggcagg tggggtgcc gggcggggcg ggccgcctc gggccgggga gggctcgggg    4140
gaggggcgcg gcggccccgg agcgccggcg gctgtcgagg cgcggcgagc cgcagccatt    4200
gccttttatg gtaatcgtgc gagagggcgc agggacttcc tttgtcccaa atctggcgga    4260
gccgaaatct gggaggcgcc gccgcacccc ctctagcggg cgcgggcgaa gcggtgcggc    4320
gccggcagga aggaaatggg cggggagggc cttcgtgcgt cgccgcgccg ccgtcccctt    4380
ctccatctcc agcctcgggg ctgccgcagg gggacggctg ccttcggggg ggacggggca    4440
gggcggggtt cggcttctgg cgtgtgaccg gcggctgcta gagcctctgc taaccatgtt    4500
catgccttct tctttttcct acagctcctg ggcaacgtgc tggttgttgt gctgtctcat    4560
cattttggca aagaattgcg gccgtctcag gccaccgaag acttgatcac ccgggatcat    4620
ggctgagaag cagaagcacg acgggcgtgt gaagatcgga cactacgtgc tggggggacac    4680
cctgggcgtc ggcaccttcg gcaaagtgaa gattggagaa catcaattga caggccataa    4740
agtggcagtt aagatcttaa atagacagaa gattcgcagt ttagatgttg ttggaaaaat    4800
aaaacgagaa attcaaaatc ttaaactctt tcgtcatcct catattatca aactctacca    4860
agtgatcagc actccaacag actttttat ggtaatggaa tatgtgtctg gaggtgaatt    4920
gttcgactac atctgtaaac acgggagggt tgaagaggtg gaagctcgcc ggctcttcca    4980
gcagattctg tctgccgtgg actactgtca caggcacatg gttgtccaca gggacctgaa    5040
gccagagaac gtgttgctgg acgcccagat gaatgctaag atagctgact tcggactctc    5100
taatatgatg tcagatggtg aatttctacg aactagctgt ggatcgccaa attatgcagc    5160
accggaggtc atctcaggaa ggctgtatgc gggtcctgag gttgatatct ggagctgtgg    5220
tgttatcctg tatgccccttc tctgtggcac cctcccgttc gacgatgagc acgtgcctac    5280
gctctttaag aagatccgag ggggtgtgtt ctacatcccg gagtatctca accgttctat    5340
tgccactctg ctgatgcaca tgctgcaggt ggacccttg aagcgagcaa ctatcaaaga    5400
catacgagag catgaatggt ttaaacagga tttgcccagt tacctctttc ctgaagaccc    5460
ctcctatgat gctaacgtca ttgatgatga ggctgtgaaa gaagtatgtg aaaaatttga    5520
gtgtacagaa tcagaagtga tgaacagttt atacagtggt gaccctcaag accagctcgc    5580
agtggcttat catctcatca ttgacaatcg gagaataatg aaccaagcca gtgagttcta    5640
cctcgcctcc agtcctccaa cgggttcctt catggacgat atggccatgc acattccccc    5700
cggcctgaaa ccacatcctg aaaggatgcc acctctcata gcagacagcc ccaaagcacg    5760
ctgtccactg gatgcactca acacaactaa gcccaaatct ttagctgtga aaaaagccaa    5820
```

```
gtggcacctt gggatccgaa gccagagcaa accatacgac attatggcgg aggtgtaccg    5880
agctatgaag cagctggact ttgaatggaa ggtagtgaat gcataccatc ttcgagtaag    5940
aagaaaaaac ccagtgactg gcaattacgt gaaaatgagc ttacagcttt acctggttga    6000
caatcggagc tatctgctgg actttaaaag catcgatgat gaggtggtgg agcagaggtc    6060
tggttcttca cacctcagc gctcctgttc tgctgccggc ctccacagac ctcggtcaag    6120
tgtcgattcc agcacagccg agaaccattc actgtctggc tctctcactg gttctttgac    6180
tggcagcact ttgtcctccg cttccccgcg cctgggcagt cataccatgg attttttga    6240 aatgtgcgcc agtcttatca ctgctttaat ggtgagcaag ggcgaggagc tgttcaccgg    6300
ggtggtgccc atcctggtcg agctggacgg cgacgtaaac ggccacaggt tcagcgtgtc    6360
cggcgagggc gagggcgatg ccacctacgg caagctgacc ctgaagttca tctgcaccac    6420
cggcaagctg cccgtgccct ggcccaccct cgtgaccacc ctgacctggg cgtgcagtg    6480 cttcgcccgc tacccgacc acatgaagca gcacgacttc ttcaagtccg ccatgcccga    6540
aggctacgtc caggagcgta ccatcttctt caaggacgac ggcaactaca agacccgcgc    6600
cgaggtgaag ttcgagggcg acaccctggt gaaccgcatc gagctgaagg gcatcgactt    6660
caaggaggac ggcaacatcc tggggcacaa gctggagtac aactacatca gccacaacgt    6720
ctatatcacc gccgacaagc agaagaacgg catcaaggcc cacttcaaga tccgccacaa    6780
catcgaggac ggcggcgtgc agctcgccga ccactaccag cagaacaccc ccatcggcga    6840
cggccccgtg ctgctgcccg acaaccacta cctgagcacc cagtccaagc tgagcaaaga    6900
ccccaacgag aagcgcgatc acatggtcct gctggagttc gtgaccgccg cctaatag      6958
```

<210> SEQ ID NO 82  
<211> LENGTH: 778  
<212> TYPE: PRT  
<213> ORGANISM: Artificial Sequence  
<220> FEATURE:  
<223> OTHER INFORMATION: Rat alpha2-AR-mseCFP-11_deletion

<400> SEQUENCE: 82

```
Met Ala Glu Lys Gln Lys His Asp Gly Arg Val Lys Ile Gly His Tyr
1               5                   10                  15

Val Leu Gly Asp Thr Leu Gly Val Gly Thr Phe Gly Lys Val Lys Ile
                20                  25                  30

Gly Glu His Gln Leu Thr Gly His Lys Val Ala Val Lys Ile Leu Asn
            35                  40                  45

Arg Gln Lys Ile Arg Ser Leu Asp Val Val Gly Lys Ile Lys Arg Glu
        50                  55                  60

Ile Gln Asn Leu Lys Leu Phe Arg His Pro His Ile Ile Lys Leu Tyr
65                  70                  75                  80

Gln Val Ile Ser Thr Pro Thr Asp Phe Phe Met Val Met Glu Tyr Val
                85                  90                  95

Ser Gly Gly Glu Leu Phe Asp Tyr Ile Cys Lys His Gly Arg Val Glu
                100                 105                 110

Glu Val Glu Ala Arg Arg Leu Phe Gln Gln Ile Leu Ser Ala Val Asp
            115                 120                 125

Tyr Cys His Arg His Met Val Val His Arg Asp Leu Lys Pro Glu Asn
        130                 135                 140

Val Leu Leu Asp Ala Gln Met Asn Ala Lys Ile Ala Asp Phe Gly Leu
145                 150                 155                 160
```

-continued

```
Ser Asn Met Met Ser Asp Gly Glu Phe Leu Arg Thr Ser Cys Gly Ser
            165                 170                 175
Pro Asn Tyr Ala Ala Pro Glu Val Ile Ser Gly Arg Leu Tyr Ala Gly
            180                 185                 190
Pro Glu Val Asp Ile Trp Ser Cys Gly Val Ile Leu Tyr Ala Leu Leu
            195                 200                 205
Cys Gly Thr Leu Pro Phe Asp Asp Glu His Val Pro Thr Leu Phe Lys
        210                 215                 220
Lys Ile Arg Gly Gly Val Phe Tyr Ile Pro Glu Tyr Leu Asn Arg Ser
225                 230                 235                 240
Ile Ala Thr Leu Leu Met His Met Leu Gln Val Asp Pro Leu Lys Arg
                245                 250                 255
Ala Thr Ile Lys Asp Ile Arg Glu His Glu Trp Phe Lys Gln Asp Leu
            260                 265                 270
Pro Ser Tyr Leu Phe Pro Glu Asp Pro Ser Tyr Asp Ala Asn Val Ile
            275                 280                 285
Asp Asp Glu Ala Val Lys Glu Val Cys Glu Lys Phe Glu Cys Thr Glu
        290                 295                 300
Ser Glu Val Met Asn Ser Leu Tyr Ser Gly Asp Pro Gln Asp Gln Leu
305                 310                 315                 320
Ala Val Ala Tyr His Leu Ile Ile Asp Asn Arg Arg Ile Met Asn Gln
                325                 330                 335
Ala Ser Glu Phe Tyr Leu Ala Ser Ser Pro Pro Thr Gly Ser Phe Met
            340                 345                 350
Asp Asp Met Ala Met His Ile Pro Pro Gly Leu Lys Pro His Pro Glu
            355                 360                 365
Arg Met Pro Pro Leu Ile Ala Asp Ser Pro Lys Ala Arg Cys Pro Leu
        370                 375                 380
Asp Ala Leu Asn Thr Thr Lys Pro Lys Ser Leu Ala Val Lys Lys Ala
385                 390                 395                 400
Lys Trp His Leu Gly Ile Arg Ser Gln Ser Lys Pro Tyr Asp Ile Met
                405                 410                 415
Ala Glu Val Tyr Arg Ala Met Lys Gln Leu Asp Phe Glu Trp Lys Val
            420                 425                 430
Val Asn Ala Tyr His Leu Arg Val Arg Arg Lys Asn Pro Val Thr Gly
            435                 440                 445
Asn Tyr Val Lys Met Ser Leu Gln Leu Tyr Leu Val Asp Asn Arg Ser
        450                 455                 460
Tyr Leu Leu Asp Phe Lys Ser Ile Asp Asp Glu Val Val Glu Gln Arg
465                 470                 475                 480
Ser Gly Ser Ser Thr Pro Gln Arg Ser Cys Ser Ala Ala Gly Leu His
                485                 490                 495
Arg Pro Arg Ser Ser Val Asp Ser Ser Thr Ala Glu Asn His Ser Leu
            500                 505                 510
Ser Gly Ser Leu Thr Gly Ser Leu Thr Gly Ser Thr Leu Ser Ser Ala
            515                 520                 525
Ser Pro Arg Leu Gly Ser His Thr Met Asp Phe Phe Glu Met Cys Ala
        530                 535                 540
Ser Leu Ile Thr Ala Leu Met Val Ser Lys Gly Glu Glu Leu Phe Thr
545                 550                 555                 560
Gly Val Val Pro Ile Leu Val Glu Leu Asp Gly Asp Val Asn Gly His
                565                 570                 575
Arg Phe Ser Val Ser Gly Glu Gly Glu Gly Asp Ala Thr Tyr Gly Lys
```

```
              580               585               590
Leu Thr Leu Lys Phe Ile Cys Thr Thr Gly Lys Leu Pro Val Pro Trp
            595               600               605

Pro Thr Leu Val Thr Thr Leu Thr Trp Gly Val Gln Cys Phe Ala Arg
            610               615               620

Tyr Pro Asp His Met Lys Gln His Asp Phe Phe Lys Ser Ala Met Pro
625             630              635              640

Glu Gly Tyr Val Gln Glu Arg Thr Ile Phe Phe Lys Asp Asp Gly Asn
                645              650              655

Tyr Lys Thr Arg Ala Glu Val Lys Phe Glu Gly Asp Thr Leu Val Asn
                660              665              670

Arg Ile Glu Leu Lys Gly Ile Asp Phe Lys Glu Asp Gly Asn Ile Leu
            675              680              685

Gly His Lys Leu Glu Tyr Asn Tyr Ile Ser His Asn Val Tyr Ile Thr
            690              695              700

Ala Asp Lys Gln Lys Asn Gly Ile Lys Ala His Phe Lys Ile Arg His
705              710              715              720

Asn Ile Glu Asp Gly Gly Val Gln Leu Ala Asp His Tyr Gln Gln Asn
                725              730              735

Thr Pro Ile Gly Asp Gly Pro Val Leu Leu Pro Asp Asn His Tyr Leu
            740              745              750

Ser Thr Gln Ser Lys Leu Ser Lys Asp Pro Asn Glu Lys Arg Asp His
            755              760              765

Met Val Leu Leu Glu Phe Val Thr Ala Ala
770              775
```

<210> SEQ ID NO 83
<211> LENGTH: 6970
<212> TYPE: DNA
<213> ORGANISM: Artificial Sequence
<220> FEATURE:
<223> OTHER INFORMATION: Rat
   alpha2-AR_helix_-MVSKmseCFPll_deletion+helix, pACEMam2 plasmid

<400> SEQUENCE: 83

```
tcgagccatg gtgctagcag ctgatgcata gcatgcggta cctaattcac tcctcaggtg    60
caggctgcct atcagaaggt ggtggctggt gtggctaatg ccctggctca caaataccac   120
tgagatcttt ttccctctgc caaaaattat ggggacatca tgaagcccct tgagcatctg   180
acttctggct aataaaggaa atttattttc attgcaatag tgtgttggaa ttttttgtgt   240
ctctcactcg gaaggacata tgggagggca aatcatttaa aacatcagaa tgagtatttg   300
gtttagagtt tggcaacata tgccatatgc tggctgccat gaacaaaggt ggctataaag   360
aggtcatcag tatatgaaac agcccccctgc tgtccattcc ttattccata gaaaagcctt   420
gacttgaggt tagattttt ttatattttg ttttgtgtta ttttttttctt taacatccct   480
aaaatttttcc ttacatgttt tactagccag attttttcctc ctctcctgac tactcccagt   540
catagctgtc cctcttctct tatgaagatc cctcgacgtt taaactcgct accttaggac   600
cgttatagtt acagataact tcgtataatg tatgctatac gaagttatgg cgacttcgct   660
gctgcccaag gttccgggt gacgcacacc gtggaaacgg atgaaggcac gaacccagtt   720
gacataagcc tgttcggttc gtaaactgta atgcaagtag cgtatgcgct cacgcaactg   780
gtccagaacc ttgaccgaac gcagcggtgg taacggcgca gtggcggttt tcatggcttg   840
ttatgactgt ttttttgtac agtctatgcc tcgggcatcc aagcagcaag cgcgttacgc   900
```

```
cgtgggtcga tgtttgatgt tatggagcag caacgatgtt acgcagcagc aacgatgtta    960
cgcagcaggg cagtcgccct aaaacaaagt taggtggctc aagtatgggc atcattcgca   1020
catgtaggct cggccctgac caagtcaaat ccatgcgggc tgctcttgat cttttcggtc   1080
gtgagttcgg agacgtagcc acctactccc aacatcagcc ggactccgat tacctcggga   1140
acttgctccg tagtaagaca ttcatcgcgc ttgctgcctt cgaccaagaa gcggttgttg   1200
gcgctctcgc ggcttacgtt ctgcccaagt ttgagcagcc gcgtagtgag atctatatct   1260
atgatctcgc agtctccggc gagcaccgga ggcagggcat tgccaccgcg ctcatcaatc   1320
tcctcaagca tgaggccaac gcgcttggtg cttatgtgat ctacgtgcaa gcagattacg   1380
gtgacgatcc cgcagtggct ctctatacaa agttgggcat acgggaagaa gtgatgcact   1440
ttgatatcga cccaagtacc gccacctaac aattcgttca agccgagatc ggcttcccgg   1500
ccgcggagtt gttcggtaaa ttgtcacaac gccgcgaata tagtctttac atgcccttgg   1560
ccacgcccct ctttaatacg acgggcaatt tgcacttcag aaaatgaaga gtttgcttta   1620
gccataacaa aagtccagta tgcttttcca cagcataact ggactgattt cagtttacaa   1680
ctattctgtc tagtttaaga ctttattgtc atagtttaga tctattttgt tcagtttaag   1740
actttattgt ccgcccacac ccgcttacgc agggcatctg cgcatccaca ggaagagcga   1800
cccaagtcaa tcaggggata acgcaggaaa gaacatgtga gcaaaaggcc agcaaaaggc   1860
caggaaccgt aaaaaggccg cgttgctggc gttttccat aggctccgcc cccctgacga   1920
gcatcacaaa aatcgacgct caagtcagag gtggcgaaac ccgacaggac tataaagata   1980
ccaggcgttt ccccctggaa gctccctcgt gcgctctcct gttccgaccc tgccgcttac   2040
cggatacctg tccgcctttc tcccttcggg aagcgtggcg ctttctcata gctcacgctg   2100
taggtatctc agttcggtgt aggtcgttcg ctccaagctg gctgtgtgc acgaaccccc   2160 cgttcagccc gaccgctgcg ccttatccgg taactatcgt cttgagtcca acccggtaag   2220
acacgactta tcgccactgg cagcagccac tggtaacagg attagcagag cgaggtatgt   2280
aggcggtgct acagagttct tgaagtggtg cctaactac ggctacacta gaagaacagt   2340
atttggtatc tgcgctctgc tgaagccagt taccttcgga aaagagttg gtagctcttg   2400 atccggcaaa caaaccaccg ctggtagcgg tggttttttt gtttgcaagc agcagattac   2460
gcgcagaaaa aaggatctc aagaagatcc tttgatcttt tctacggggt ctgacgctca   2520
gtggaacgaa aactcacgtt aagggatttt ggtcatgaga ttatcaaaaa ggatcttcac   2580
ctagatcctt ttaaattaaa aatgaagttt taaatcaatc taaagtatat atgagtaaac   2640
ttggtctgac agttgaccca agtcaaccgg ttgtgggcgg acaaaatagt tgggaactgg   2700 gagggggtgga aatggagttt ttaaggatta tttagggaag agtgacaaaa tagatgggaa   2760
ctgggtgtag cgtcgtaagc taatacgaaa attaaaaatg acaaaatagt ttggaactag   2820
atttcactta tctggttcca attagatgga tcgatactac gatactagta tacgttatta   2880
atagtaatca attacggggt cattagttca tagcccatat atggagttcc gcgttacata   2940
acttacggta aatggcccgc ctggctgacc gcccaacgac ccccgcccat tgacgtcaat   3000
aatgacgtat gttcccatag taacgccaat agggactttc cattgacgtc aatgggtgga   3060
ctatttacgg taaactgccc acttggcagt acatcaagtg tatcatatgc caagtacgcc   3120
ccctattgac gtcaatgacg gtaaatggcc cgcctggcat tatgcccagt acatgacctt   3180
atgggacttt cctacttggc agtacatcta cgtattagtc atcgctatta ctcatgggtc   3240
gaggtgagcc ccacgttctg cttcactctc cccatctccc cccctcccc accccccaatt   3300
```

```
ttgtatttat ttattttta attattttgt gcagcgatgg gggcgggggg ggggggggcg    3360
cgcgccaggc ggggcggggc ggggcgaggg cggggcggg gcgaggcgga gaggtgcggc    3420
ggcagccaat cagagcggcg cgctccgaaa gtttcctttt atggcgaggc ggcggcggcg    3480
gcggccctat aaaaagcgaa gcgcgcgcg ggcgggagtc gctgcgttgc cttcgcccg    3540
tgccccgctc cgcgccgcct cgcgccgccc gccccggctc tgactgaccg cgttactccc    3600
acaggtgagc gggcgggacg gcccttctcc tccgggctgt aattagcgct tggtttaatg    3660
acggctcgtt tcttttctgt ggctgcgtga aagccttaaa gggctccggg agggcccttt    3720
gtgcgggggg gagcggctcg gggggtgcgt gcgtgtgtgt gtgcgtgggg agcgccgcgt    3780
gcggcccgcg ctgcccggcg gctgtgagcg ctgcgggcgc ggcgcggggc tttgtgcgct    3840
ccgcgtgtgc gcgaggggag gcgggccggg ggcggtgccc cgcggtgcgg ggggctgcg    3900
agggggaacaa aggctgcgtg cggggtgtgt gcgtgggggg gtgagcaggg ggtgtgggcg    3960
cggcggtcgg gctgtaaccc ccccctgcac cccctcccc gagttgctga gcacggcccg    4020
gcttcgggtg cggggctccg tgcggggcgt ggcgcggggc tcgccgtgcc gggcgggggg    4080
tggcggcagg tgggggtgcc gggcggggcg gggccgcctc gggccgggga gggctcgggg    4140
gaggggcgcg gcggccccgg agcgccggcg gctgtcgagg gcgcggcgagc cgcagccatt    4200
gccttttatg gtaatcgtgc gagagggcgc agggacttcc tttgtcccaa atctggcgga    4260
gccgaaatct gggaggcgcc gccgcacccc ctctagcggg cgcgggcgaa gcggtgcggc    4320
gccggcagga aggaaatggg cggggagggc cttcgtgcgt cgccgcgccg ccgtcccctt    4380
ctccatctcc agcctcgggg ctgccgcagg gggacggctg ccttcggggg ggacggggca    4440
gggcggggtt cggcttctgg cgtgtgaccg gcggctgcta gagcctctgc taaccatgtt    4500
catgccttct tcttttcct acagctcctg ggcaacgtgc tggttgttgt gctgtctcat    4560
cattttggca aagaattgcg gccgtctcag gccaccgaag acttgatcac ccgggatcat    4620
ggctgagaag cagaagcacg acgggcgtgt gaagatcgga cactacgtgc tggggggacac    4680
cctgggcgtc ggcaccttcg gcaaagtgaa gattggagaa catcaattga caggccataa    4740
agtggcagtt aagatcttaa atagacagaa gattcgcagt ttagatgttg ttggaaaaat    4800
aaaacgagaa attcaaaatc ttaaactctt tcgtcatcct catattatca aactctacca    4860
agtgatcagc actccaacag acttttttat ggtaatggaa tatgtgtctg gaggtgaatt    4920
gttcgactac atctgtaaac acgggagggt tgaagaggtg aagctcgcc ggctcttcca    4980
gcagattctg tctgccgtgg actactgtca caggcacatg gttgtccaca gggacctgaa    5040
gccagagaac gtgttgctgg acgcccagat gaatgctaag atagctgact tcggactctc    5100
taatatgatg tcagatggtg aatttctacg aactagctgt ggatcgccaa attatgcagc    5160
accggaggtc atctcaggaa ggctgtatgc gggtcctgag gttgatatct ggagctgtgg    5220
tgttatcctg tatgcccttc tctgtggcac cctcccgttc gacgatgagc acgtgcctac    5280
gctctttaag aagatccgag ggggtgtgtt ctacatcccg gagtatctca ccgttctat    5340
tgccactctg ctgatgcaca tgctgcaggt ggacccttg aagcgagcaa ctatcaaaga    5400
catacgagag catgaatggt ttaaacagga tttgcccagt tacctctttc ctgaagaccc    5460
ctcctatgat gctaacgtca ttgatgatga ggctgtgaaa gaagtatgtg aaaaatttga    5520
gtgtacagaa tcagaagtga tgaacagttt atacagtggt gaccctcaag accagctcgc    5580
agtggcttat catctcatca ttgacaatcg gagaataatg aaccaagcca gtgagttcta    5640
```

```
cctcgcctcc agtcctccaa cgggttcctt catggacgat atggccatgc acattccccc    5700
cggcctgaaa ccacatcctg aaaggatgcc acctctcata gcagacagcc caaagcacg     5760
ctgtccactg gatgcactca acacaactaa gcccaaatct ttagctgtga aaaagccaa     5820
gtggcacctt gggatccgaa gccagagcaa accatacgac attatggcgg aggtgtaccg    5880
agctatgaag cagctggact tgaatggaa  ggtagtgaat gcataccatc ttcgagtaag    5940
aagaaaaaac ccagtgactg caattacgt  gaaaatgagc ttacagcttt acctggttga    6000
caatcggagc tatctgctgg actttaaaag catcgatgat gaggtggtgg agcagaggtc    6060
tggttcttca cacctcagc  gctcctgttc tgctgccggc ctccacagac ctcggtcaag    6120
tgtcgattcc agcacagccg agaaccattc actgtctggc tctctcactg gttctttgac    6180
tggcagcact ttgtcctccg cttccccgcg cctgggcagt cataccatgg attttttga    6240
aatgtgcgcc agtcttatca ctgctttaga ggaggaagag aagaaaaaga aaggcgagga    6300
gctgttcacc ggggtggtgc ccatcctggt cgagctggac ggcgacgtaa acggccacag    6360
gttcagcgtg tccggcgagg gcgagggcga tgccacctac ggcaagctga ccctgaagtt    6420
catctgcacc accggcaagc tgcccgtgcc ctggcccacc ctcgtgacca ccctgacctg    6480
gggcgtgcag tgcttcgccc gctaccccga ccacatgaag cagcacgact tcttcaagtc    6540
cgccatgccc gaaggctacg tccaggagcg taccatcttc ttcaaggacg acggcaacta    6600
caagacccgc gccgaggtga agttcgaggg cgacaccctg gtgaaccgca tcgagctgaa    6660
gggcatcgac ttcaaggagg acggcaacat cctggggcac aagctggagt acaactacat    6720
cagccacaac gtctatatca ccgccgacaa gcagaagaac ggcatcaagg cccacttcaa    6780
gatccgccac aacatcgagg acggcggcgt gcagctcgcc gaccactacc agcagaacac    6840
ccccatcggc gacggccccg tgctgctgcc cgacaaccac tacctgagca cccagtccaa    6900
gctgagcaaa gaccccaacg agaagcgcga tcacatggtc ctgctggagt tcgtgaccgc    6960
cgcctaatag                                                          6970
```

<210> SEQ ID NO 84
<211> LENGTH: 782
<212> TYPE: PRT
<213> ORGANISM: Artificial Sequence
<220> FEATURE:
<223> OTHER INFORMATION: Rat
    alpha2-AR_helix_-MVSKmseCFPll_deletion+helix

<400> SEQUENCE: 84

Met Ala Glu Lys Gln Lys His Asp Gly Arg Val Lys Ile Gly His Tyr
1               5                   10                  15

Val Leu Gly Asp Thr Leu Gly Val Gly Thr Phe Gly Lys Val Lys Ile
            20                  25                  30

Gly Glu His Gln Leu Thr Gly His Lys Val Ala Val Lys Ile Leu Asn
        35                  40                  45

Arg Gln Lys Ile Arg Ser Leu Asp Val Val Gly Lys Ile Lys Arg Glu
    50                  55                  60

Ile Gln Asn Leu Lys Leu Phe Arg His Pro His Ile Ile Lys Leu Tyr
65                  70                  75                  80

Gln Val Ile Ser Thr Pro Thr Asp Phe Phe Met Val Met Glu Tyr Val
                85                  90                  95

Ser Gly Gly Glu Leu Phe Asp Tyr Ile Cys Lys His Gly Arg Val Glu
            100                 105                 110

Glu Val Glu Ala Arg Arg Leu Phe Gln Gln Ile Leu Ser Ala Val Asp

-continued

```
            115                 120                 125
Tyr Cys His Arg His Met Val His Arg Asp Leu Lys Pro Glu Asn
            130                 135                 140
Val Leu Leu Asp Ala Gln Met Asn Ala Lys Ile Ala Asp Phe Gly Leu
145                 150                 155                 160
Ser Asn Met Met Ser Asp Gly Glu Phe Leu Arg Thr Ser Cys Gly Ser
                165                 170                 175
Pro Asn Tyr Ala Ala Pro Glu Val Ile Ser Gly Arg Leu Tyr Ala Gly
                180                 185                 190
Pro Glu Val Asp Ile Trp Ser Cys Gly Val Ile Leu Tyr Ala Leu Leu
                195                 200                 205
Cys Gly Thr Leu Pro Phe Asp Asp Glu His Val Pro Thr Leu Phe Lys
            210                 215                 220
Lys Ile Arg Gly Gly Val Phe Tyr Ile Pro Glu Tyr Leu Asn Arg Ser
225                 230                 235                 240
Ile Ala Thr Leu Leu Met His Met Leu Gln Val Asp Pro Leu Lys Arg
                245                 250                 255
Ala Thr Ile Lys Asp Ile Arg Glu His Glu Trp Phe Lys Gln Asp Leu
            260                 265                 270
Pro Ser Tyr Leu Phe Pro Glu Asp Pro Ser Tyr Asp Ala Asn Val Ile
                275                 280                 285
Asp Asp Glu Ala Val Lys Glu Val Cys Glu Lys Phe Glu Cys Thr Glu
            290                 295                 300
Ser Glu Val Met Asn Ser Leu Tyr Ser Gly Asp Pro Gln Asp Gln Leu
305                 310                 315                 320
Ala Val Ala Tyr His Leu Ile Ile Asp Asn Arg Arg Ile Met Asn Gln
                325                 330                 335
Ala Ser Glu Phe Tyr Leu Ala Ser Pro Pro Thr Gly Ser Phe Met
                340                 345                 350
Asp Asp Met Ala Met His Ile Pro Pro Gly Leu Lys Pro His Pro Glu
            355                 360                 365
Arg Met Pro Pro Leu Ile Ala Asp Ser Pro Lys Ala Arg Cys Pro Leu
            370                 375                 380
Asp Ala Leu Asn Thr Thr Lys Pro Lys Ser Leu Ala Val Lys Lys Ala
385                 390                 395                 400
Lys Trp His Leu Gly Ile Arg Ser Gln Ser Lys Pro Tyr Asp Ile Met
                405                 410                 415
Ala Glu Val Tyr Arg Ala Met Lys Gln Leu Asp Phe Glu Trp Lys Val
            420                 425                 430
Val Asn Ala Tyr His Leu Arg Val Arg Arg Lys Asn Pro Val Thr Gly
            435                 440                 445
Asn Tyr Val Lys Met Ser Leu Gln Leu Tyr Leu Val Asp Asn Arg Ser
            450                 455                 460
Tyr Leu Leu Asp Phe Lys Ser Ile Asp Asp Glu Val Val Glu Gln Arg
465                 470                 475                 480
Ser Gly Ser Ser Thr Pro Gln Arg Ser Cys Ser Ala Ala Gly Leu His
                485                 490                 495
Arg Pro Arg Ser Ser Val Asp Ser Ser Thr Ala Glu Asn His Ser Leu
                500                 505                 510
Ser Gly Ser Leu Thr Gly Ser Leu Thr Gly Ser Thr Leu Ser Ser Ala
            515                 520                 525
Ser Pro Arg Leu Gly Ser His Thr Met Asp Phe Phe Glu Met Cys Ala
            530                 535                 540
```

```
Ser Leu Ile Thr Ala Leu Glu Glu Glu Lys Lys Lys Gly Glu
545                 550                 555                 560

Glu Leu Phe Thr Gly Val Val Pro Ile Leu Val Glu Leu Asp Gly Asp
                565                 570                 575

Val Asn Gly His Arg Phe Ser Val Ser Gly Glu Gly Glu Gly Asp Ala
            580                 585                 590

Thr Tyr Gly Lys Leu Thr Leu Lys Phe Ile Cys Thr Thr Gly Lys Leu
        595                 600                 605

Pro Val Pro Trp Pro Thr Leu Val Thr Thr Leu Thr Trp Gly Val Gln
    610                 615                 620

Cys Phe Ala Arg Tyr Pro Asp His Met Lys Gln His Asp Phe Phe Lys
625                 630                 635                 640

Ser Ala Met Pro Glu Gly Tyr Val Gln Glu Arg Thr Ile Phe Phe Lys
                645                 650                 655

Asp Asp Gly Asn Tyr Lys Thr Arg Ala Glu Val Lys Phe Glu Gly Asp
            660                 665                 670

Thr Leu Val Asn Arg Ile Glu Leu Lys Gly Ile Asp Phe Lys Glu Asp
        675                 680                 685

Gly Asn Ile Leu Gly His Lys Leu Glu Tyr Asn Tyr Ile Ser His Asn
    690                 695                 700

Val Tyr Ile Thr Ala Asp Lys Gln Lys Asn Gly Ile Lys Ala His Phe
705                 710                 715                 720

Lys Ile Arg His Asn Ile Glu Asp Gly Gly Val Gln Leu Ala Asp His
                725                 730                 735

Tyr Gln Gln Asn Thr Pro Ile Gly Asp Gly Pro Val Leu Leu Pro Asp
            740                 745                 750

Asn His Tyr Leu Ser Thr Gln Ser Lys Leu Ser Lys Asp Pro Asn Glu
        755                 760                 765

Lys Arg Asp His Met Val Leu Leu Glu Phe Val Thr Ala Ala
    770                 775                 780

<210> SEQ ID NO 85
<211> LENGTH: 826
<212> TYPE: PRT
<213> ORGANISM: Artificial Sequence
<220> FEATURE:
<223> OTHER INFORMATION: Rat a2-AR_helix_-MVSKeCFP_deletion+helix

<400> SEQUENCE: 85

Met Gly Ser Ser His His His His His His His His Ser Ser
1               5                   10                  15

Glu Asn Leu Tyr Phe Gln Gly His Met Ala Glu Lys Gln Lys His Asp
                20                  25                  30

Gly Arg Val Lys Ile Gly His Tyr Val Leu Gly Asp Thr Leu Gly Val
            35                  40                  45

Gly Thr Phe Gly Lys Val Lys Ile Gly Glu His Gln Leu Thr Gly His
        50                  55                  60

Lys Val Ala Val Lys Ile Leu Asn Arg Gln Lys Ile Arg Ser Leu Asp
65                  70                  75                  80

Val Val Gly Lys Ile Lys Arg Glu Ile Gln Asn Leu Lys Leu Phe Arg
                85                  90                  95

His Pro His Ile Ile Lys Leu Tyr Gln Val Ile Ser Thr Pro Thr Asp
            100                 105                 110

Phe Phe Met Val Met Glu Tyr Val Ser Gly Gly Glu Leu Phe Asp Tyr
        115                 120                 125
```

Ile Cys Lys His Gly Arg Val Glu Val Glu Ala Arg Leu Phe
130                 135             140

Gln Gln Ile Leu Ser Ala Val Asp Tyr Cys His Arg His Met Val Val
145                 150             155             160

His Arg Asp Leu Lys Pro Glu Asn Val Leu Leu Asp Ala Gln Met Asn
                165             170             175

Ala Lys Ile Ala Asp Phe Gly Leu Ser Asn Met Met Ser Asp Gly Glu
            180             185             190

Phe Leu Arg Thr Ser Cys Gly Ser Pro Asn Tyr Ala Ala Pro Glu Val
        195             200             205

Ile Ser Gly Arg Leu Tyr Ala Gly Pro Glu Val Asp Ile Trp Ser Cys
210             215             220

Gly Val Ile Leu Tyr Ala Leu Leu Cys Gly Thr Leu Pro Phe Asp Asp
225             230             235             240

Glu His Val Pro Thr Leu Phe Lys Lys Ile Arg Gly Gly Val Phe Tyr
                245             250             255

Ile Pro Glu Tyr Leu Asn Arg Ser Ile Ala Thr Leu Leu Met His Met
                260             265             270

Leu Gln Val Asp Pro Leu Lys Arg Ala Thr Ile Lys Asp Ile Arg Glu
        275             280             285

His Glu Trp Phe Lys Gln Asp Leu Pro Ser Tyr Leu Phe Pro Glu Asp
        290             295             300

Pro Ser Tyr Asp Ala Asn Val Ile Asp Asp Glu Ala Val Lys Glu Val
305             310             315             320

Cys Glu Lys Phe Glu Cys Thr Glu Ser Glu Val Met Asn Ser Leu Tyr
                325             330             335

Ser Gly Asp Pro Gln Asp Gln Leu Ala Val Ala Tyr His Leu Ile Ile
                340             345             350

Asp Asn Arg Arg Ile Met Asn Gln Ala Ser Glu Phe Tyr Leu Ala Ser
            355             360             365

Ser Pro Pro Thr Gly Ser Phe Met Asp Asp Met Ala Met His Ile Pro
370             375             380

Pro Gly Leu Lys Pro His Pro Glu Arg Met Pro Pro Leu Ile Ala Asp
385             390             395             400

Ser Pro Lys Ala Arg Cys Pro Leu Asp Ala Leu Asn Thr Thr Lys Pro
                405             410             415

Lys Ser Leu Ala Val Lys Lys Ala Lys Trp His Leu Gly Ile Arg Ser
            420             425             430

Gln Ser Lys Pro Tyr Asp Ile Met Ala Glu Val Tyr Arg Ala Met Lys
        435             440             445

Gln Leu Asp Phe Glu Trp Lys Val Val Asn Ala Tyr His Leu Arg Val
    450             455             460

Arg Arg Lys Asn Pro Val Thr Gly Asn Tyr Val Lys Met Ser Leu Gln
465             470             475             480

Leu Tyr Leu Val Asp Asn Arg Ser Tyr Leu Leu Asp Phe Lys Ser Ile
                485             490             495

Asp Asp Glu Val Val Glu Gln Arg Ser Gly Ser Ser Thr Pro Gln Arg
                500             505             510

Ser Cys Ser Ala Ala Gly Leu His Arg Pro Arg Ser Ser Val Asp Ser
            515             520             525

Ser Thr Ala Glu Asn His Ser Leu Ser Gly Ser Leu Thr Gly Ser Leu
530             535             540

-continued

```
Thr Gly Ser Thr Leu Ser Ser Ala Ser Pro Arg Leu Gly Ser His Thr
545                 550                 555                 560

Met Asp Phe Phe Glu Met Cys Ala Ser Leu Ile Thr Ala Leu Glu Glu
                565                 570                 575

Glu Glu Lys Lys Lys Lys Gly Glu Glu Leu Phe Thr Gly Val Val Pro
            580                 585                 590

Ile Leu Val Glu Leu Asp Gly Asp Val Asn Gly His Lys Phe Ser Val
                595                 600                 605

Ser Gly Glu Gly Glu Gly Asp Ala Thr Tyr Gly Lys Leu Thr Leu Lys
            610                 615                 620

Phe Ile Cys Thr Thr Gly Lys Leu Pro Val Pro Trp Pro Thr Leu Val
625                 630                 635                 640

Thr Thr Leu Thr Trp Gly Val Gln Cys Phe Ser Arg Tyr Pro Asp His
                645                 650                 655

Met Lys Gln His Asp Phe Phe Lys Ser Ala Met Pro Glu Gly Tyr Val
            660                 665                 670

Gln Glu Arg Thr Ile Phe Phe Lys Asp Asp Gly Asn Tyr Lys Thr Arg
                675                 680                 685

Ala Glu Val Lys Phe Glu Gly Asp Thr Leu Val Asn Arg Ile Glu Leu
            690                 695                 700

Lys Gly Ile Asp Phe Lys Glu Asp Gly Asn Ile Leu Gly His Lys Leu
705                 710                 715                 720

Glu Tyr Asn Tyr Ile Ser His Asn Val Tyr Ile Thr Ala Asp Lys Gln
                725                 730                 735

Lys Asn Gly Ile Lys Ala Asn Phe Lys Ile Arg His Asn Ile Glu Asp
            740                 745                 750

Gly Ser Val Gln Leu Ala Asp His Tyr Gln Gln Asn Thr Pro Ile Gly
                755                 760                 765

Asp Gly Pro Val Leu Leu Pro Asp Asn His Tyr Leu Ser Thr Gln Ser
            770                 775                 780

Ala Leu Ser Lys Asp Pro Asn Glu Lys Arg Asp His Met Val Leu Leu
785                 790                 795                 800

Glu Phe Val Thr Ala Ala Gly Ile Thr Leu Gly Met Asp Glu Leu Tyr
                805                 810                 815

Lys Ser Gly Leu Arg Ser Arg Arg Ala His
            820                 825
```

<210> SEQ ID NO 86
<211> LENGTH: 4949
<212> TYPE: DNA
<213> ORGANISM: Artificial Sequence
<220> FEATURE:
<223> OTHER INFORMATION: Human beta2, pMDK plasmid

<400> SEQUENCE: 86

```
tcgagccatg gtgctagcag ctgatgcata gcatgcggta cctaattcac tcctcaggtg    60
caggctgcct atcagaaggt ggtggctggt gtggctaatg ccctggctca caaataccac   120
tgagatcttt ttccctctgc caaaaattat ggggacatca tgaagcccct tgagcatctg   180
acttctggct aataaaggaa atttatttc attgcaatag tgtgttggaa ttttttgtgt    240
ctctcactcg gaaggacata tgggagggca aatcatttaa acatcagaa tgagtatttg    300 gtttagagtt tggcaacata tgccatatgc tggctgccat gaacaaaggt ggctataaag   360
aggtcatcag tatatgaaac agcccccctgc tgtccattcc ttattccata gaaaagcctt   420
gacttgaggt tagatttttt ttatatttg ttttgtgtta ttttttttctt taacatccct    480
```

```
aaaatttttcc ttacatgttt tactagccag attttcctc ctctcctgac tactcccagt    540
catagctgtc cctcttctct tatgaagatc cctcgacgtt taaacccatg tgcctggcag    600
ataacttcgt ataatgtatg ctatacgaag ttatggtacg tactaagctc tcatgtttca    660
cgtactaagc tctcatgttt aacgtactaa gctctcatgt ttaacgaact aaaccctcat    720
ggctaacgta ctaagctctc atggctaacg tactaagctc tcatgtttca cgtactaagc    780
tctcatgttt gaacaataaa attaatataa atcagcaact taaatagcct ctaaggtttt    840
aagttttata agaaaaaaaa gaatatataa ggcttttaaa gcttttaagg tttaacggtt    900
gtggacaaca agccagggat gtaacgcact gagaagccct tagagcctct caaagcaatt    960
ttcagtgaca caggaacact taacggctga cagaattagc ttcacgctgc cgcaagcact   1020
cagggcgcaa gggctgctaa aggaagcgga acacgtagaa agccagtccg cagaaacggt   1080
gctgaccccg gatgaatgtc agctactggg ctatctggac aagggaaaac gcaagcgcaa   1140
agagaaagca ggtagcttgc agtgggctta catggcgata gctagactgg gcggttttat   1200
ggacagcaag cgaaccggaa ttgccagctg gggcgccctc tggtaaggtt gggaagccct   1260
gcaaagtaaa ctggatggct tcttgccgc caaggatctg atggcgcagg ggatcaagat    1320
ctgatcaaga gacaggatga ggatcgtttc gcatgattga acaagatgga ttgcacgcag   1380
gttctccggc cgcttgggtg gagaggctat tcggctatga ctgggcacaa cagacaatcg   1440
gctgctctga tgccgccgtg ttccggctgt cagcgcaggg gcgcccggtt cttttgtca   1500 agaccgacct gtccggtgcc ctgaatgaac tgcaggacga ggcagcgcgg ctatcgtggc   1560
tggccacgac gggcgttcct tgcgcagctg tgctcgacgt tgtcactgaa gcgggaaggg   1620
actggctgct attgggcgaa gtgccggggc aggatctcct gtcatctcac cttgctcctg   1680
ccgagaaagt atccatcatg gctgatgcaa tgcggcggct gcatacgctt gatccggcta   1740
cctgcccatt cgaccaccaa gcgaaacatc gcatcgagcg agcacgtact cggatggaag   1800
ccggtcttgt cgatcaggat gatctggacg aagagcatca ggggctcgcg ccagccgaac   1860
tgttcgccag gctcaaggcg cgcatgcccg acggcgagga tctcgtcgtg acacatggcg   1920
atgcctgctt gccgaatatc atggtggaaa atggccgctt tctggattc atcgactgtg   1980 gccggctggg tgtggcggac cgctatcagg acatagcgtt ggctacccgt gatattgctg   2040
aagagcttgg cggcgaatgg gctgaccgct tcctcgtgct ttacggtatc gccgctcccg   2100
attcgcagcg catcgccttc tatcgccttc ttgacgagtt cttctgagcg ggactctggg   2160
gttcgaaatg accgaccaag cgacgcccaa cctgccatca cgagatttcg attccaccgc   2220
cgccttctat gaaaggttgg gcttcggaat cgtttccgg gacgccggct ggatgatcct    2280
ccagcgcggg gatctcatgc tggagttctt cgcccacccc gggatctatg tcgggtgcgg   2340
agaaagaggt aatgaaatgg cacctaggta tcgatactag tatacgttat taatagtaat   2400
caattacggg gtcattagtt catagcccat atatggagtt ccgcgttaca taacttacgg   2460
taaatggccc gcctggctga ccgcccaacg acccccgccc attgacgtca ataatgacgt   2520
atgttcccat agtaacgcca atagggactt tccattgacg tcaatgggtg gactatttac   2580
ggtaaactgc ccacttggca gtacatcaag tgtatcatat gccaagtacg ccccctattg   2640
acgtcaatga cggtaaatgg cccgcctggc attatgccca gtacatgacc ttatgggact   2700
ttcctacttg gcagtacatc tacgtattag tcatcgctat tactcatggg tcgaggtgag   2760
ccccacgttc tgcttcactc tccccatctc cccccctcc ccaccccaa ttttgtattt    2820
```

```
atttattttt taattattttt gtgcagcgat gggggcgggg ggggggggggg cgcgcgccag    2880 gcggggcggg gcggggcgag gggcggggcg gggcgaggcg gagaggtgcg gcggcagcca    2940
atcagagcgg cgcgctccga aagtttcctt ttatggcgag gcggcggcgg cggcggccct    3000
ataaaaagcg aagcgcgcgg cgggcgggag tcgctgcgtt gccttcgccc cgtgccccgc    3060
tccgcgccgc ctcgcgccgc ccgccccggc tctgactgac cgcgttactc ccacaggtga    3120
gcgggcggga cggcccttct cctccgggct gtaattagcg cttggtttaa tgacggctcg    3180
tttcttttct gtggctgcgt gaaagcctta aagggctccg ggagggccct ttgtgcgggg    3240
gggagcggct cggggggtgc gtgcgtgtgt gtgtgcgtgg ggagcgccgc gtgcggcccg    3300
cgctgcccgg cggctgtgag cgctgcgggc gcggcgcggg gctttgtgcg ctccgcgtgt    3360 gcgcagggg agcgcggccg ggggcggtgc cccgcggtgc ggggggggctg cgaggggaac    3420 aaaggctgcg tgcggggtgt gtgcgtgggg gggtgagcag ggggtgtggg cgcggcggtc    3480
gggctgtaac ccccccctgc accccccctcc ccgagttgct gagcacggcc cggcttcggg    3540 tgcgggctc cgtgcggggc gtggcgcggg gctcgccgtg ccgggcgggg ggtggcggca    3600 ggtggggggtg ccgggcgggg cggggccgcc tcgggccggg gagggctcgg ggaggggcg    3660 cggcggcccc ggagcgccgg cggctgtcga ggcgcggcga ccgcagcca ttgccttta    3720 tggtaatcgt gcgagagggc gcagggactt cctttgtccc aaatctggcg gagccgaaat    3780
ctgggaggcg ccgccgcacc ccctctagcg ggcgcgggcg aagcggtgcg gcgccggcag    3840
gaaggaaatg gcggggagg gccttcgtgc gtcgccgcgc cgccgtcccc ttctccatct    3900
ccagcctcgg ggctgccgca gggggacggc tgccttcggg ggggacgggg cagggcgggg    3960
ttcggcttct ggcgtgtgac cggcggctgc tagagcctct gctaaccatg ttcatgcctt    4020 cttcttttc ctacagctcc tgggcaacgt gctggttgtt gtgctgtctc atcatttgg    4080 caaagaattg cggccgtctc aggccaccga agacttgatc acccgggatc atgggaaaca    4140
ccaccagcga ccgggtgtcc ggggagcgcc acggcgccaa ggctgcacgc tccgagggcg    4200
caggcggcca tgccccgggg aaggagcaca agatcatggt ggggagtacg gacgacccca    4260
gcgtgttcag cctccctgac tccaagctcc ctggggacaa agagtttgta tcatggcagc    4320 aggattttgga ggactccgta aagcccacac agcaggcccg gcccactgtt atccgctggt    4380
ctgaaggagg caaggaggtc ttcatctctg ggtccttcaa caattggagc gccaagattc    4440
cactgattaa gagccataat gactttgttg ccatcctgga cctccctgag ggagagcacc    4500
aatacaagtt ctttgtggat ggacagtggg ttcatgatcc atcagagcct gtggttacca    4560
gtcagcttgg cacaattaac aatttgatcc atgtcaagaa atctgatttt gaggtgttcg    4620
atgctttaaa gttagattct atggaaagtt ctgagacatc ttgtagagac ctttccagct    4680
cacccccagg gccttatggt caagaaatgt atgcgtttcg atctgaggaa agattcaaat    4740
ccccacccat ccttcctcct catctacttc aagttattct taacaaagac actaatattt    4800
cttgtgaccc agccttactc cctgagccca accatgttat gctgaaccat ctctatgcat    4860
tgtccattaa ggacagtgtg atggtcctta gcgcaaccca tcgctacaag aagaagtatg    4920
ttactactct gctatacaag cccatttaa                                      4949
```

<210> SEQ ID NO 87
<211> LENGTH: 272
<212> TYPE: PRT
<213> ORGANISM: Homo sapiens

<400> SEQUENCE: 87

```
Met Gly Asn Thr Thr Ser Asp Arg Val Ser Gly Glu Arg His Gly Ala
1               5                   10                  15

Lys Ala Ala Arg Ser Glu Gly Ala Gly Gly His Ala Pro Gly Lys Glu
            20                  25                  30

His Lys Ile Met Val Gly Ser Thr Asp Asp Pro Ser Val Phe Ser Leu
            35                  40                  45

Pro Asp Ser Lys Leu Pro Gly Asp Lys Glu Phe Val Ser Trp Gln Gln
50                  55                  60

Asp Leu Glu Asp Ser Val Lys Pro Thr Gln Gln Ala Arg Pro Thr Val
65                  70                  75                  80

Ile Arg Trp Ser Glu Gly Gly Lys Glu Val Phe Ile Ser Gly Ser Phe
                85                  90                  95

Asn Asn Trp Ser Ala Lys Ile Pro Leu Ile Lys Ser His Asn Asp Phe
                100                 105                 110

Val Ala Ile Leu Asp Leu Pro Glu Gly Glu His Gln Tyr Lys Phe Phe
            115                 120                 125

Val Asp Gly Gln Trp Val His Asp Pro Ser Glu Pro Val Val Thr Ser
130                 135                 140

Gln Leu Gly Thr Ile Asn Asn Leu Ile His Val Lys Lys Ser Asp Phe
145                 150                 155                 160

Glu Val Phe Asp Ala Leu Lys Leu Asp Ser Met Glu Ser Ser Glu Thr
                165                 170                 175

Ser Cys Arg Asp Leu Ser Ser Ser Pro Pro Gly Pro Tyr Gly Gln Glu
            180                 185                 190

Met Tyr Ala Phe Arg Ser Glu Glu Arg Phe Lys Ser Pro Pro Ile Leu
            195                 200                 205

Pro Pro His Leu Leu Gln Val Ile Leu Asn Lys Asp Thr Asn Ile Ser
210                 215                 220

Cys Asp Pro Ala Leu Leu Pro Glu Pro Asn His Val Met Leu Asn His
225                 230                 235                 240

Leu Tyr Ala Leu Ser Ile Lys Asp Ser Val Met Val Leu Ser Ala Thr
                245                 250                 255

His Arg Tyr Lys Lys Lys Tyr Val Thr Thr Leu Leu Tyr Lys Pro Ile
            260                 265                 270
```

<210> SEQ ID NO 88
<211> LENGTH: 5675
<212> TYPE: DNA
<213> ORGANISM: Artificial Sequence
<220> FEATURE:
<223> OTHER INFORMATION: Human beta2-KPI-cpVenus_deletion, pMDK plasmid

<400> SEQUENCE: 88

```
tcgagccatg gtgctagcag ctgatgcata gcatgcggta cctaattcac tcctcaggtg      60
caggctgcct atcagaaggt ggtggctggt gtggctaatg ccctggctca caataccac     120 tgagatcttt ttccctctgc caaaaattat ggggacatca tgaagcccct gagcatctg     180 acttctggct aataaaggaa atttattttc attgcaatag tgtgttggaa ttttttgtgt    240
ctctcactcg gaaggacata tgggagggca aatcatttaa acatcagaa tgagtatttg     300 gtttagagtt tggcaacata tgccatatgc tggctgccat gaacaaaggt ggctataaag    360
aggtcatcag tatatgaaac agcccctgc tgtccattcc ttattccata gaaaagcctt     420
gacttgaggt tagattttt ttatattttg ttttgtgtta ttttttttctt taacatccct    480 aaaattttcc ttacatgttt tactagccag attttcctc ctctcctgac tactcccagt     540
```

```
catagctgtc cctcttctct tatgaagatc cctcgacgtt taaacccatg tgcctggcag      600
ataacttcgt ataatgtatg ctatacgaag ttatggtacg tactaagctc tcatgtttca      660
cgtactaagc tctcatgttt aacgtactaa gctctcatgt ttaacgaact aaaccctcat      720
ggctaacgta ctaagctctc atggctaacg tactaagctc tcatgtttca cgtactaagc      780
tctcatgttt gaacaataaa attaatataa atcagcaact taaatagcct ctaaggtttt      840
aagttttata agaaaaaaaa gaatatataa ggcttttaaa gcttttaagg tttaacggtt      900
gtggacaaca agccagggat gtaacgcact gagaagccct tagagcctct caaagcaatt      960
ttcagtgaca caggaacact taacggctga cagaattagc ttcacgctgc cgcaagcact     1020
cagggcgcaa gggctgctaa aggaagcgga acacgtagaa agccagtccg cagaaacggt     1080
gctgaccccg gatgaatgtc agctactggg ctatctggac aagggaaaac gcaagcgcaa     1140
agagaaagca ggtagcttgc agtgggctta catggcgata gctagactgg gcggttttat     1200
ggacagcaag cgaaccggaa ttgccagctg gggcgccctc tggtaaggtt gggaagccct     1260
gcaaagtaaa ctggatggct ttcttgccgc caaggatctg atggcgcagg ggatcaagat     1320
ctgatcaaga gacaggatga ggatcgtttc gcatgattga acaagatgga ttgcacgcag     1380
gttctccggc cgcttgggtg gagaggctat tcggctatga ctgggcacaa cagacaatcg     1440
gctgctctga tgccgccgtg ttccggctgt cagcgcaggg gcgcccggtt ctttttgtca     1500
agaccgacct gtccggtgcc ctgaatgaac tgcaggacga ggcagcgcgg ctatcgtggc     1560
tggccacgac gggcgttcct tgcgcagctg tgctcgacgt tgtcactgaa gcgggaaggg     1620
actggctgct attgggcgaa gtgccggggc aggatctcct gtcatctcac cttgctcctg     1680
ccgagaaagt atccatcatg gctgatgcaa tgcggcggct gcatacgctt gatccggcta     1740
cctgcccatt cgaccaccaa gcgaaacatc gcatcgagcg agcacgtact cggatggaag     1800
ccggtcttgt cgatcaggat gatctggacg aagagcatca ggggctcgcg ccagccgaac     1860
tgttcgccag gctcaaggcg cgcatgcccg acggcgagga tctcgtcgtg acacatggcg     1920
atgcctgctt gccgaatatc atggtggaaa atggccgctt ttctggattc atcgactgtg     1980
gccggctggg tgtggcggac cgctatcagg acatagcgtt ggctacccgt gatattgctg     2040
aagagcttgg cggcgaatgg gctgaccgct tcctcgtgct ttacggtatc gccgctcccg     2100
attcgcagcg catcgccttc tatcgccttc ttgacgagtt cttctgagcg ggactctggg     2160
gttcgaaatg accgaccaag cgacgcccaa cctgccatca cgagatttcg attccaccgc     2220
cgccttctat gaaaggttgg gcttcggaat cgttttccgg gacgccggct ggatgatcct     2280
ccagcgcggg gatctcatgc tggagttctt cgcccacccc gggatctatg tcgggtgcgg     2340
agaaagaggt aatgaaatgg cacctaggta tcgatactag tatacgttat taatagtaat     2400
caattacggg gtcattagtt catagcccat atatggagtt ccgcgttaca taacttacgg     2460
taaatggccc gcctggctga ccgcccaacg acccccgccc attgacgtca ataatgacgt     2520
atgttcccat agtaacgcca atagggactt tccattgacg tcaatgggtg gactatttac     2580
ggtaaactgc ccacttggca gtacatcaag tgtatcatat gccaagtacg cccctattg      2640
acgtcaatga cggtaaatgg cccgcctggc attatgccca gtacatgacc ttatgggact     2700
ttcctacttg gcagtacatc tacgtattag tcatcgctat tactcatggg tcgaggtgag     2760
ccccacgttc tgcttcactc tccccatctc cccccctcc ccaccccaa ttttgtattt       2820
atttattttt taattatttt gtgcagcgat ggggcggg ggggggggg cgcgcgccag        2880
```

```
gcggggcggg gcggggcgag gggcggggcg gggcgaggcg gagaggtgcg gcggcagcca  2940
atcagagcgg cgcgctccga aagtttcctt ttatggcgag gcggcggcgg cggcggccct  3000
ataaaagcg aagcgcgcgg cgggcgggag tcgctgcgtt gccttcgccc cgtgccccgc   3060
tccgcgccgc ctcgcgccgc ccgccccggc tctgactgac cgcgttactc ccacaggtga  3120
gcgggcggga cggcccttct cctccgggct gtaattagcg cttggtttaa tgacggctcg  3180
tttctttttct gtggctgcgt gaaagcctta aagggctccg ggagggccct ttgtgcgggg 3240
gggagcggct cggggggtgc gtgcgtgtgt gtgtgcgtgg ggagcgccgc gtgcggcccg  3300
cgctgcccgg cggctgtgag cgctgcgggc gcggcgcggg gctttgtgcg ctccgcgtgt  3360
gcgcgagggg agcgcggccg ggggcggtgc cccgcggtgc ggggggggctg cgagggggaac 3420
aaaggctgcg tgcggggtgt gtgcgtgggg gggtgagcag ggggtgtggg cgcggcggtc   3480
gggctgtaac cccccctgc acccccctcc ccgagttgct gagcacggcc cggcttcggg   3540
tgcggggctc cgtgcggggc gtggcgcggg gctcgccgtg ccgggcgggg ggtggcggca  3600
ggtggggggtg ccgggcgggg cggggccgcc tcggccgggg gagggctcgg gggaggggcg  3660
cggcggcccc ggagcgccgg cggctgtcga ggcgcggcga ccgcagcca ttgccttta    3720
tggtaatcgt gcgagagggc gcagggactt cctttgtccc aaatctggcg gagccgaaat  3780
ctggaggcg ccgccgcacc ccctctagcg ggcgcgggcg aagcggtgcg gcgccggcag   3840
gaaggaaatg ggcgggagg gccttcgtgc gtcgccgcgc cgccgtcccc ttctccatct   3900
ccagcctcgg ggctgccgca gggggacggc tgccttcggg ggggacgggg cagggcgggg  3960
ttcggcttct ggcgtgtgac cggcggctgc tagagcctct gctaaccatg ttcatgcctt  4020
cttctttttc ctacagctcc tgggcaacgt gctggttgtt gtgctgtctc atcattttgg  4080
caaagaattg cggccgtctc aggccaccga agacttgatc acccgggatc atgggaaaca  4140
ccaccagcga ccgggtgtcc ggggagcgcc acggcgccaa ggctgcacgc tccgagggcg  4200
caggcggcca tgccccgggg aaggagcaca agatcatggt ggggagtacg gacgaccca   4260
gcgtgttcag cctccctgac tccaagctcc ctggggacaa agagtttgta tcatggcagc  4320
aggatttgga ggactccgta aagcccacac agcaggcccg gcccactgtt atccgctggt  4380
ctgaaggagg caaggaggtc ttcatctctg ggtccttcaa caattggagc gccaagattc  4440
cactgattaa gagccataat gactttgttg ccatcctgga cctccctgag ggagagcacc  4500
aatacaagtt ctttgtggat ggacagtggg ttcatgatcc atcagagcct gtggttacca  4560
gtcagcttgg cacaattaac aatttgatcc atgtcaagaa atctgatttt gaggtgttcg  4620
atgctttaaa gttagattct atggaaagtt ctgagacatc ttgtagagac ctttccagct  4680
cacccccagg gccttatggt caagaaatgt atgcgtttcg atctgaggaa agattccaaat 4740
ccccacccat ccttcctcct catctacttc aagttattct taacaaagac actaatattt  4800
cttgtgaccc agccttactc cctgagccca accatgttat gctgaaccat ctctatgcat  4860
tgtccattaa ggacagtgtg atggtcctta gcgcaaccca tcgctacaag aagaagtatg  4920
ttactactct gctatacatg ggcggcgtgc agctcgccga ccactaccag cagaacaccc  4980
ccatcggcga cggcccgtg ctgctgcccg acaaccacta cctgagctac cagtccaagc   5040
tgagcaaaga ccccaacgag aagcgcgatc acatggtcct gctggagttc gtgaccgccg  5100
ccgggatcac tctcggcatg gacgagctgt acaagggtgg cagcggtggc atggtgagca  5160
agggcgagga gctgttcacc ggggtggtgc ccatcctggt cgagctggac ggcgacgtaa  5220
acggccacaa gttcagcgtg tccggcgagg gcgagggcga tgccacctac ggcaagctga  5280
```

```
ccctgaagct gatctgcacc accggcaagc tgcccgtgcc ctggcccacc ctcgtgacca    5340
ccctgggcta cggcctgcag tgcttcgccc gctaccccga ccacatgaag cagcacgact    5400
tcttcaagtc cgccatgccc gaaggctacg tccaggagcg caccatcttc ttcaaggacg    5460
acggcaacta caagacccgc gccgaggtga agttcgaggg cgacaccctg gtgaaccgca    5520
tcgagctgaa gggcatcgac ttcaaggagg acggcaacat cctggggcac aagctggagt    5580
acaactacaa cagccacaac gtctatatca ccgccgacaa gcagaagaac ggcatcaagg    5640
ccaacttcaa gatccgccac aacatcgagt aatga                               5675
```

<210> SEQ ID NO 89
<211> LENGTH: 513
<212> TYPE: PRT
<213> ORGANISM: Artificial Sequence
<220> FEATURE:
<223> OTHER INFORMATION: Human beta2-KPI-cpVenus_deletion

<400> SEQUENCE: 89

```
Met Gly Asn Thr Thr Ser Asp Arg Val Ser Gly Glu Arg His Gly Ala
1               5                   10                  15

Lys Ala Ala Arg Ser Glu Gly Ala Gly Gly His Ala Pro Gly Lys Glu
            20                  25                  30

His Lys Ile Met Val Gly Ser Thr Asp Asp Pro Ser Val Phe Ser Leu
        35                  40                  45

Pro Asp Ser Lys Leu Pro Gly Asp Lys Glu Phe Val Ser Trp Gln Gln
    50                  55                  60

Asp Leu Glu Asp Ser Val Lys Pro Thr Gln Gln Ala Arg Pro Thr Val
65                  70                  75                  80

Ile Arg Trp Ser Glu Gly Gly Lys Glu Val Phe Ile Ser Gly Ser Phe
                85                  90                  95

Asn Asn Trp Ser Ala Lys Ile Pro Leu Ile Lys Ser His Asn Asp Phe
            100                 105                 110

Val Ala Ile Leu Asp Leu Pro Glu Gly Glu His Gln Tyr Lys Phe Phe
        115                 120                 125

Val Asp Gly Gln Trp Val His Asp Pro Ser Glu Pro Val Val Thr Ser
    130                 135                 140

Gln Leu Gly Thr Ile Asn Asn Leu Ile His Val Lys Lys Ser Asp Phe
145                 150                 155                 160

Glu Val Phe Asp Ala Leu Lys Leu Asp Ser Met Glu Ser Ser Glu Thr
                165                 170                 175

Ser Cys Arg Asp Leu Ser Ser Ser Pro Pro Gly Pro Tyr Gly Gln Glu
            180                 185                 190

Met Tyr Ala Phe Arg Ser Glu Glu Arg Phe Lys Ser Pro Pro Ile Leu
        195                 200                 205

Pro His Leu Leu Gln Val Ile Leu Asn Lys Asp Thr Asn Ile Ser
    210                 215                 220

Cys Asp Pro Ala Leu Leu Pro Glu Pro Asn His Val Met Leu Asn His
225                 230                 235                 240

Leu Tyr Ala Leu Ser Ile Lys Asp Ser Val Met Val Leu Ser Ala Thr
                245                 250                 255

His Arg Tyr Lys Lys Lys Tyr Val Thr Thr Leu Leu Tyr Met Gly Gly
            260                 265                 270

Val Gln Leu Ala Asp His Tyr Gln Gln Asn Thr Pro Ile Gly Asp Gly
        275                 280                 285
```

Pro Val Leu Leu Pro Asp Asn His Tyr Leu Ser Tyr Gln Ser Lys Leu
290                 295                 300

Ser Lys Asp Pro Asn Glu Lys Arg Asp His Met Val Leu Leu Glu Phe
305                 310                 315                 320

Val Thr Ala Ala Gly Ile Thr Leu Gly Met Asp Glu Leu Tyr Lys Gly
                325                 330                 335

Gly Ser Gly Gly Met Val Ser Lys Gly Glu Glu Leu Phe Thr Gly Val
            340                 345                 350

Val Pro Ile Leu Val Glu Leu Asp Gly Asp Val Asn Gly His Lys Phe
                355                 360                 365

Ser Val Ser Gly Glu Gly Glu Gly Asp Ala Thr Tyr Gly Lys Leu Thr
370                 375                 380

Leu Lys Leu Ile Cys Thr Thr Gly Lys Leu Pro Val Pro Trp Pro Thr
385                 390                 395                 400

Leu Val Thr Thr Leu Gly Tyr Gly Leu Gln Cys Phe Ala Arg Tyr Pro
                405                 410                 415

Asp His Met Lys Gln His Asp Phe Phe Lys Ser Ala Met Pro Glu Gly
                420                 425                 430

Tyr Val Gln Glu Arg Thr Ile Phe Phe Lys Asp Asp Gly Asn Tyr Lys
                435                 440                 445

Thr Arg Ala Glu Val Lys Phe Glu Gly Asp Thr Leu Val Asn Arg Ile
450                 455                 460

Glu Leu Lys Gly Ile Asp Phe Lys Glu Asp Gly Asn Ile Leu Gly His
465                 470                 475                 480

Lys Leu Glu Tyr Asn Tyr Asn Ser His Asn Val Tyr Ile Thr Ala Asp
                485                 490                 495

Lys Gln Lys Asn Gly Ile Lys Ala Asn Phe Lys Ile Arg His Asn Ile
                500                 505                 510

Glu

<210> SEQ ID NO 90
<211> LENGTH: 5081
<212> TYPE: DNA
<213> ORGANISM: Artificial Sequence
<220> FEATURE:
<223> OTHER INFORMATION: Rat gamma1, pMDS plasmid

<400> SEQUENCE: 90
tcgagccatg gtgctagcag ctgatgcata gcatgcggta cctaattcac tcctcaggtg      60
caggctgcct atcagaaggt ggtggctggt gtggctaatg ccctggctca caaataccac     120
tgagatcttt ttccctctgc caaaaattat ggggacatca tgaagcccct tgagcatctg     180
acttctggct aataaaggaa atttattttc attgcaatag tgtgttggaa ttttttgtgt     240
ctctcactcg gaaggacata tgggagggca aatcatttaa acatcagaa tgagtatttg      300 gtttagagtt tggcaacata tgccatatgc tggctgccat gaacaaaggt ggctataaag     360
aggtcatcag tatatgaaac agcccctgc tgtccattcc ttattccata gaaaagcctt      420
gacttgaggt tagatttttt ttatattttg ttttgtgtta ttttttttctt taacatccct    480 aaaattttcc ttcatgtttt tactagccag atttttcctc ctctcctgac tactcccagt     540
catagctgtc cctcttctct tatgaagatc cctcgacgtt taaacccatg tgcctggcag     600
ataacttcgt ataatgtatg ctatacgaag ttatggtacg tactaagctc tcatgtttca     660
cgtactaagc tctcatgttt aacgtactaa gctctcatgt ttaacgaact aaaccctcat     720
ggctaacgta ctaagctctc atggctaacg tactaagctc tcatgtttca cgtactaagc     780

| | |
|---|---|
| tctcatgttt gaacaataaa attaatataa atcagcaact taaatagcct ctaaggtttt | 840 |
| aagttttata agaaaaaaaa gaatatataa ggcttttaaa gcttttaagg tttaacggtt | 900 |
| gtggacaaca agccagggat gtaacgcact gagaagccct tagagcctct caaagcaatt | 960 |
| ttgagtgaca caggaacact taacggctga cataattcag cttcacgctg ccgcaagcac | 1020 |
| tcagggcgca agggctgcta aaggaagcgg aacacgtaga aagccagtcc gcagaaacgg | 1080 |
| tgctgacccc ggatgaatgt cagctgggag gcagaataaa tgatcatatc gtcaattatt | 1140 |
| acctccacgg ggagagcctg agcaaactgg cctcaggcat ttgagaagca cacggtcaca | 1200 |
| ctgcttccgg tagtcaataa accggtaagt agcgtatgcg ctcacgcaac tggtccagaa | 1260 |
| ccttgaccga acgcagcggt ggtaacggcg cagtggcggt tttcatggct tgttatgact | 1320 |
| gtttttttgg ggtacagtct atgcctcggg catccaagca gcaagcgcgt tacgccgtgg | 1380 |
| gtcgatgttt gatgttatgg agcagcaacg atgttacgca gcagggcagt cgccctaaaa | 1440 |
| caaagttaaa catcatgagg gaagcggtga tcgccgaagt atcgactcaa ctatcagagg | 1500 |
| tagttggcgt catcgagcgc catctcgaac cgacgttgct ggccgtacat ttgtacggct | 1560 |
| ccgcagtgga tggcggcctg aagccacaca gtgatattga tttgctggtt acggtgaccg | 1620 |
| taaggcttga tgaaacaacg cggcgagctt tgatcaacga cctttggaa acttcggctt | 1680 |
| cccctggaga gagcgagatt ctccgcgctg tagaagtcac cattgttgtg cacgacgaca | 1740 |
| tcattccgtg gcgttatcca gctaagcgcg aactgcaatt tggagaatgg cagcgcaatg | 1800 |
| acattcttgc aggtatcttc gagccagcca cgatcgacat tgatctggct atcttgctga | 1860 |
| caaaagcaag agaacatagc gttgccttgg taggtccagc ggcggaggaa ctctttgatc | 1920 |
| cggttcctga acaggatcta tttgaggcgc taaatgaaac cttaacgcta tggaactcgc | 1980 |
| cgcccgactg ggctggcgat gagcgaaatg tagtgcttac gttgtcccgc atttggtaca | 2040 |
| gcgcagtaac cggcaaaatc gcgccgaagg atgtcgctgc cgactgggca atggagcgcc | 2100 |
| tgccggccca gtatcagccc gtcatacttg aagctagaca ggcttatctt ggacaagaag | 2160 |
| aagatcgctt ggcctcgcgc gcagatcagt tggaagaatt tgtccactac gtgaaaggcg | 2220 |
| agatcaccaa ggtagtcggc aaataatgtc taacaattcg ttcaagccga cggatctatg | 2280 |
| tcgggtgcgg agaaagaggt aatgaaatgg cacctaggta tcgatactac gatactagta | 2340 |
| tacgttatta atagtaatca attacggggt cattagttca tagcccatat atggagttcc | 2400 |
| gcgttacata acttacggta aatggcccgc ctggctgacc gcccaacgac ccccgcccat | 2460 |
| tgacgtcaat aatgacgtat gttcccatag taacgccaat agggactttc cattgacgtc | 2520 |
| aatgggtgga ctatttacgg taaactgccc acttggcagt acatcaagtg tatcatatgc | 2580 |
| caagtacgcc ccctattgac gtcaatgacg gtaaatggcc cgcctggcat tatgcccagt | 2640 |
| acatgacctt atgggacttt cctacttggc agtacatcta cgtattagtc atcgctatta | 2700 |
| ctcatgggtc gaggtgagcc ccacgttctg cttcactctc cccatctccc ccccctcccc | 2760 |
| accccccaatt ttgtatttat ttattttta attatttgt gcagcgatgg gggcgggggg | 2820 |
| ggggggggcg cgcgccaggc ggggcggggc ggggcgaggg gcgggcggg gcgaggcgga | 2880 |
| gaggtgcggc ggcagccaat cagagcgcg cgctccgaaa gtttccttt atggcgaggc | 2940 |
| ggcggcggcg gcggccctat aaaaagcgaa gcgcgcggcg gcgggagtc gctgcgttgc | 3000 |
| cttcgccccg tgccccgctc cgcgccgcct cgcgccgccc gccccggctc tgactgaccg | 3060 |
| cgttactccc acaggtgagc gggcgggacg gcccttctcc tccgggctgt aattagcgct | 3120 |

-continued

| | |
|---|---|
| tggtttaatg acggctcgtt tctttcctgt ggctgcgtga agccttaaa gggctccggg | 3180 |
| agggcccttt gtgcgggggg gagcggctcg ggggtgcgt gcgtgtgtgt gtgcgtgggg | 3240 |
| agcgccgcgt gcggcccgcg ctgcccggcg gctgtgagcg ctgcgggcgc ggcgcggggc | 3300 |
| tttgtgcgct ccgcgtgtgc gcgaggggag cgcggccggg ggcggtgccc cgcggtgcgg | 3360 |
| gggggctgcg aggggaacaa aggctgcgtg cggggtgtgt gcgtgggggg gtgagcaggg | 3420 |
| ggtgtgggcg cggcggtcgg gctgtaaccc ccccctgcac cccctcccc gagttgctga | 3480 |
| gcacggcccg gcttcgggtg cggggctccg tgcggggcgt ggcgcggggc tcgccgtgcc | 3540 |
| gggcgggggg tggcggcagg tggggtgcc gggcggggcg gggccgcctc gggccggga | 3600 |
| gggctcgggg gaggggcgcg gcggcccgg agcgccggcg gctgtcgagg cgcggcgagc | 3660 |
| cgcagccatt gccttttatg gtaatcgtgc gagagggcgc agggacttcc tttgtcccaa | 3720 |
| atctggcgga gccgaaatct gggaggcgcc gccgcacccc ctctagcggg cgcgggcgaa | 3780 |
| gcggtgcggc gccggcagga aggaaatggg cggggagggc cttcgtgcgt cgccgcgccg | 3840 |
| ccgtccccctt ctccatctcc agcctcgggg ctgccgcagg gggacggctg ccttcggggg | 3900 |
| ggacggggca gggcggggtt cggcttctgg cgtgtgaccg gcggctgcta gagcctctgc | 3960 |
| taaccatgtt catgccttct ctttttcct acagctcctg ggcaacgtgc tggttgttgt | 4020 |
| gctgtctcat cattttggca aagaattgcg gccgtctcag gccaccgaag acttgatcac | 4080 |
| ccgggatcat ggagtcggtt gctgcagaga gcgctccagc tccggagaat gaacactctc | 4140 |
| aagagacccc ggaatcgaac agtagtgtgt acaccacctt catgaagtct catcgctgct | 4200 |
| atgacctgat ccccacaagc tccaagctgg tggtatttga tacttcgctg caggtaaaga | 4260 |
| aagccttctt tgccctggtg actaacggtg ttcgtgctgc ccctttgtgg gatagtaaga | 4320 |
| agcagagctt tgtgggcatg ctgaccatca ctgacttcat caatattctg caccgatact | 4380 |
| acaagtcagc cctggtgcag atctatgaac tggaggagca caagatagag acttggagag | 4440 |
| aggtctacct gcaagactcc tttaagccac ttgtctgcat ttctccaaat gccagcttgt | 4500 |
| tcgatgctgt ctcttcatta attcgaaata agatccacag gcttccagtt attgacccgg | 4560 |
| agtcaggcaa caccttgtac attcttactc acaagcggat cctcaagttc ctcaagttgt | 4620 |
| ttatcactga gttccccaag ccggaattca tgtctaagtc tctggaagag ctacagattg | 4680 |
| gcacctacgc caatattgcc atggtccgta ccactacacc tgtctatgtg gctctgggca | 4740 |
| tctttgtaca gcaccgagtc tccgccttgc ctgtggtgga tgagaaaggg cgtgtggtgg | 4800 |
| acatctactc caagtttgat gtgattaatt tggcagcaga aaagacatac aacaacctag | 4860 |
| atgtgtctgt gacaaaagcc ctacagcacc ggtcacacta cttcgagggt gttctcaagt | 4920 |
| gctacctaca tgagactcta gaagcaatca tcaatagact ggtggaagca gaggttcacc | 4980 |
| gtctggtggt ggtggatgaa catgacgtgg tcaagggcat tgtatcgctg tctgacatct | 5040 |
| tacaggctct ggtgctcaca ggtggagaga agaagccctg a | 5081 |

<210> SEQ ID NO 91
<211> LENGTH: 330
<212> TYPE: PRT
<213> ORGANISM: Rattus norvegicus

<400> SEQUENCE: 91

Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
 50                  55                  60

Thr Asn Gly Val Arg Ala Ala Pro Leu Trp Asp Ser Lys Lys Gln Ser
 65                  70                  75                  80

Phe Val Gly Met Leu Thr Ile Thr Asp Phe Ile Asn Ile Leu His Arg
                 85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
        275                 280                 285

Asn Arg Leu Val Glu Ala Glu Val His Arg Leu Val Val Val Asp Glu
290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro
                325                 330

<210> SEQ ID NO 92
<211> LENGTH: 5792
<212> TYPE: DNA
<213> ORGANISM: Artificial Sequence
<220> FEATURE:
<223> OTHER INFORMATION: Rat gamma1-LTGGEKKP-cpVenus_deletion, pMDS
      plasmid

<400> SEQUENCE: 92
tcgagccatg gtgctagcag ctgatgcata gcatgcggta cctaattcac tcctcaggtg    60
caggctgcct atcagaaggt ggtggctggt gtggctaatg ccctggctca caaataccac   120
tgagatcttt ttccctctgc caaaaattat ggggacatca tgaagcccct gagcatctg    180 acttctggct aataaaggaa atttatttc attgcaatag tgtgttggaa ttttttgtgt    240
ctctcactcg gaaggacata tgggagggca aatcatttaa aacatcagaa tgagtatttg    300

```
gtttagagtt tggcaacata tgccatatgc tggctgccat gaacaaaggt ggctataaag    360
aggtcatcag tatatgaaac agcccctgc tgtccattcc ttattccata gaaaagcctt    420
gacttgaggt tagattttt ttatattttg ttttgtgtta ttttttctt taacatccct    480 aaaattttcc ttacatgttt tactagccag attttcctc ctctcctgac tactcccagt    540
catagctgtc cctcttctct tatgaagatc cctcgacgtt taaacccatg tgcctggcag    600
ataacttcgt ataatgtatg ctatacgaag ttatggtacg tactaagctc tcatgtttca    660
cgtactaagc tctcatgttt aacgtactaa gctctcatgt ttaacgaact aaaccctcat    720
ggctaacgta ctaagctctc atggctaacg tactaagctc tcatgtttca cgtactaagc    780
tctcatgttt gaacaataaa attaatataa atcagcaact taaatagcct ctaaggtttt    840
aagttttata agaaaaaaaa gaatatataa ggcttttaaa gcttttaagg tttaacggtt    900
gtggacaaca agccagggat gtaacgcact gagaagccct tagagcctct caaagcaatt    960
ttgagtgaca caggaacact taacggctga cataattcag cttcacgctg ccgcaagcac   1020
tcagggcgca agggctgcta aggaagcgg aacacgtaga aagccagtcc gcagaaacgg   1080 tgctgaccc ggatgaatgt cagctgggag gcagaataaa tgatcatatc gtcaattatt   1140
acctccacgg ggagagcctg agcaaactgg cctcaggcat ttgagaagca cacggtcaca   1200
ctgcttccgg tagtcaataa accggtaagt agcgtatgcg ctcacgcaac tggtccagaa   1260
ccttgaccga acgcagcggt ggtaacgcg cagtggcgt tttcatggct tgttatgact   1320
gtttttttgg ggtacagtct atgcctcggg catccaagca gcaagcgcgt tacgccgtgg   1380
gtcgatgttt gatgttatgg agcagcaacg atgttacgca gcagggcagt cgccctaaaa   1440
caaagttaaa catcatgagg gaagcggtga tcgccgaagt atcgactcaa ctatcagagg   1500
tagttggcgt catcgagcgc catctcgaac cgacgttgct ggccgtacat ttgtacggct   1560
ccgcagtgga tggcggcctg aagccacaca gtgatattga tttgctggtt acggtgaccg   1620
taaggcttga tgaaacaacg cggcgagctt tgatcaacga ccttttggaa acttcggctt   1680
cccctggaga gagcgagatt ctccgcgctg tagaagtcac cattgttgtg cacgacgaca   1740
tcattccgtg gcgttatcca gctaagcgcg aactgcaatt tggagaatgg cagcgcaatg   1800
acattcttgc aggtatcttc gagccagcca cgatcgacat tgatctggct atcttgctga   1860
caaaagcaag agaacatagc gttgccttgg taggtccagc ggcggaggaa ctctttgatc   1920
cggttcctga acaggatcta tttgaggcgc taaatgaaac cttaacgcta tggaactcgc   1980
cgcccgactg ggctggcgat gagcgaaatg tagtgcttac gttgtcccgc atttggtaca   2040
gcgcagtaac cggcaaaatc gcgccgaagg atgtcgctgc cgactgggca atggagcgcc   2100
tgccggccca gtatcagccc gtcatacttg aagctagaca ggcttatctt ggacaagaag   2160
aagatcgctt ggcctcgcgc gcagatcagt tggaagaatt tgtccactac gtgaaaggcg   2220
agatcaccaa ggtagtcggc aaataatgtc taacaattcg ttcaagccga cggatctatg   2280
tcgggtgcgg agaaagaggt aatgaaatgg cacctaggta tcgatactac gatactagta   2340
tacgttatta atagtaatca attacgggt cattagttca tagcccatat atggagttcc   2400
gcgttacata acttacggta aatggcccgc ctggctgacc gcccaacgac ccccgcccat   2460
tgacgtcaat aatgacgtat gttcccatag taacgccaat agggactttc cattgacgtc   2520
aatgggtgga ctatttacgg taaactgccc acttggcagt acatcaagtg tatcatatgc   2580
caagtacgcc ccctattgac gtcaatgacg gtaaatggcc cgcctggcat tatgcccagt   2640
acatgacctt atgggacttt cctacttggc agtacatcta cgtattagtc atcgctatta   2700
```

```
ctcatgggtc gaggtgagcc ccacgttctg ctttcactctc cccatctccc ccccctcccc   2760
accccccaatt ttgtatttat ttatttttta attattttgt gcagcgatgg gggcgggggg   2820
ggggggggcg cgcgccaggc ggggcggggc ggggcgaggg gcgggcgggg gcgaggcgga   2880
gaggtgcggc ggcagccaat cagagcggcg cgctccgaaa gtttccttt atggcgaggc   2940
ggcggcggcg gcggccctat aaaaagcgaa gcgcgcggcg ggcgggagtc gctgcgttgc   3000
cttcgccccg tgcccgctc cgcgccgcct cgcgccgccc gccccggctc tgactgaccg   3060
cgttactccc acaggtgagc gggcgggacg gcccttctcc tccgggctgt aattagcgct   3120
tggtttaatg acggctcgtt tcttttctgt ggctgcgtga aagccttaaa gggctccggg   3180
agggcccttt gtgcgggggg gagcggctcg gggggtgcgt gcgtgtgtgt gtgcgtgggg   3240
agcgccgcgt gcgcccgcg ctgcccggcg gctgtgagcg ctgcgggcgc ggcgcggggc   3300
tttgtgcgct ccgcgtgtgc gcgaggggag cgcggccggg ggcggtgccc cgcggtgcgg   3360
gggggctgcg agggggaacaa aggctgcgtg cggggtgtgt gcgtgggggg gtgagcaggg   3420
ggtgtgggcg cggcggtcgg gctgtaaccc ccccctgcac ccccctcccc gagttgctga   3480
gcacggcccg gcttcgggtg cggggctccg tgcggggcgt ggcgcggggc tcgccgtgcc   3540
gggcggggg tggcggcagg tgggggtgcc gggcggggcg gggccgcctc gggccgggga   3600
gggctcgggg gaggggcgcg gcggcccgg agcgccggcg gctgtcgagg cgcggcgagc   3660
cgcagccatt gccttttatg gtaatcgtgc gagagggcgc agggacttcc tttgtcccaa   3720
atctggcgga gccgaaatct gggaggcgcc gccgcacccc ctctagcggg cgcgggcgaa   3780
gcggtgcggc gccggcagga aggaaatggg cggggagggc cttcgtgcgt cgccgcgccg   3840
ccgtccccct ctccatctcc agcctcgggg ctgccgcagg gggacggctg ccttcggggg   3900
ggacgggca gggcggggtt cggcttctgg cgtgtgaccg gcggctgcta gagcctctgc   3960
taaccatgtt catgccttct tctttttcct acagctcctg ggcaacgtgc tggttgttgt   4020
gctgtctcat cattttggca aagaattgcg gccgtctcag gccaccgaag acttgatcac   4080
ccgggatcat ggagtcggtt gctgcagaga gcgctccagc tccggagaat gaacactctc   4140
aagagacccc ggaatcgaac agtagtgtgt acaccaccttt catgaagtct catcgctgct   4200
atgacctgat ccccacaagc tccaagctgg tggtatttga tacttcgctg caggtaaaga   4260
aagccttctt tgccctggtg actaacggtg ttcgtgctgc cccttgtgg gatagtaaga   4320
agcagagctt tgtgggcatg ctgaccatca ctgacttcat caatattctg caccgatact   4380
acaagtcagc cctggtgcag atctatgaac tggaggagca caagatagag acttggagag   4440
aggtctacct gcaagactcc tttaagccac ttgtctgcat ttctccaaat gccagcttgt   4500
tcgatgctgt ctcttcatta attcgaaata agatccacag gcttccagtt attgacccgg   4560
agtcaggcaa caccttgtac attcttactc acaagcggat cctcaagttc ctcaagttgt   4620
ttatcactga gttccccaag ccggaattca tgtctaagtc tctggaagag ctacagattg   4680
gcacctacgc caatattgcc atggtccgta ccactacacc tgtctatgtg gctctgggca   4740
tctttgtaca gcaccgagtc tccgccttgc ctgtggtgga tgagaaaggg cgtgtggtgg   4800
acatctactc caagttgat gtgattaatt tggcagcaga aaagacatac aacaacctag   4860
atgtgtctgt gacaaaagcc ctacagcacc ggtcacacta cttcgagggt gttctcaagt   4920
gctacctaca tgagactcta gaagcaatca tcaatagact ggtggaagca gaggttcacc   4980
gtctggtggt ggtggatgaa catgacgtgg tcaagggcat tgtatcgctg tctgacatct   5040
```

```
tacaggctct ggtgatgggc ggcgtgcagc tcgccgacca ctaccagcag aacaccccca      5100
tcggcgacgg ccccgtgctg ctgcccgaca accactacct gagctaccag tccaagctga      5160
gcaaagaccc caacgagaag cgcgatcaca tggtcctgct ggagttcgtg accgccgccg      5220
ggatcactct cggcatggac gagctgtaca agggtggcag cggtggcatg gtgagcaagg      5280
gcgaggagct gttcaccggg gtggtgccca tcctggtcga gctggacggc gacgtaaacg      5340
gccacaagtt cagcgtgtcc ggcgagggcg agggcgatgc cacctacggc aagctgaccc      5400
tgaagctgat ctgcaccacc ggcaagctgc ccgtgccctg gcccaccctc gtgaccaccc      5460
tgggctacgg cctgcagtgc ttcgcccgct accccgacca catgaagcag cacgacttct      5520
tcaagtccgc catgcccgaa ggctacgtcc aggagcgcac catcttcttc aaggacgacg      5580
gcaactacaa gacccgcgcc gaggtgaagt tcgagggcga caccctggtg aaccgcatcg      5640
agctgaaggg catcgacttc aaggaggacg gcaacatcct ggggcacaag ctggagtaca      5700
actacaacag ccacaacgtc tatatcaccg ccgacaagca gaagaacggc atcaaggcca      5760
acttcaagat ccgccacaac atcgagtaat ga                                    5792
```

<210> SEQ ID NO 93
<211> LENGTH: 566
<212> TYPE: PRT
<213> ORGANISM: Artificial Sequence
<220> FEATURE:
<223> OTHER INFORMATION: Rat gamma1-LTGGEKKP-cpVenus_deletion

<400> SEQUENCE: 93

```
Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
    50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
```

|       |       |       |       |       |       |       |       |       |       |       |       |
|-------|-------|-------|-------|-------|-------|-------|-------|-------|-------|-------|-------|
|       | 225   |       |       |       | 230   |       |       |       | 235   |       | 240   |
| Ser   | Lys   | Phe   | Asp   | Val   | Ile   | Asn   | Leu   | Ala   | Ala   | Glu   | Lys   |
|       |       |       |       | 245   |       |       |       |       | 250   |       |       |
| Thr   | Tyr   | Asn   | Asn   |       |       |       |       |       |       |       |       |
|       |       |       | 255   |       |       |       |       |       |       |       |       |

Leu Asp Val Ser Val Thr Lys Ala Leu Gln His Arg Ser His Tyr Phe
            260                 265                 270

Glu Gly Val Leu Lys Cys Tyr Leu His Glu Thr Leu Glu Ala Ile Ile
            275                 280                 285

Asn Arg Leu Val Glu Ala Glu Val His Arg Leu Val Val Asp Glu
290                 295                 300

His Asp Val Val Lys Gly Ile Val Ser Leu Ser Asp Ile Leu Gln Ala
305                 310                 315                 320

Leu Val Met Gly Gly Val Gln Leu Ala Asp His Tyr Gln Gln Asn Thr
                325                 330                 335

Pro Ile Gly Asp Gly Pro Val Leu Leu Pro Asn His Tyr Leu Ser
            340                 345                 350

Tyr Gln Ser Lys Leu Ser Lys Asp Pro Asn Glu Lys Arg Asp His Met
            355                 360                 365

Val Leu Leu Glu Phe Val Thr Ala Ala Gly Ile Thr Leu Gly Met Asp
370                 375                 380

Glu Leu Tyr Lys Gly Gly Ser Gly Gly Met Val Ser Lys Gly Glu Glu
385                 390                 395                 400

Leu Phe Thr Gly Val Val Pro Ile Leu Val Glu Leu Asp Gly Asp Val
                405                 410                 415

Asn Gly His Lys Phe Ser Val Ser Gly Glu Gly Glu Gly Asp Ala Thr
            420                 425                 430

Tyr Gly Lys Leu Thr Leu Lys Leu Ile Cys Thr Thr Gly Lys Leu Pro
            435                 440                 445

Val Pro Trp Pro Thr Leu Val Thr Thr Leu Gly Tyr Gly Leu Gln Cys
            450                 455                 460

Phe Ala Arg Tyr Pro Asp His Met Lys Gln His Asp Phe Phe Lys Ser
465                 470                 475                 480

Ala Met Pro Glu Gly Tyr Val Gln Glu Arg Thr Ile Phe Phe Lys Asp
                485                 490                 495

Asp Gly Asn Tyr Lys Thr Arg Ala Glu Val Lys Phe Glu Gly Asp Thr
            500                 505                 510

Leu Val Asn Arg Ile Glu Leu Lys Gly Ile Asp Phe Lys Glu Asp Gly
            515                 520                 525

Asn Ile Leu Gly His Lys Leu Glu Tyr Asn Tyr Asn Ser His Asn Val
530                 535                 540

Tyr Ile Thr Ala Asp Lys Gln Lys Asn Gly Ile Lys Ala Asn Phe Lys
545                 550                 555                 560

Ile Arg His Asn Ile Glu
                565

<210> SEQ ID NO 94
<211> LENGTH: 5125
<212> TYPE: DNA
<213> ORGANISM: Artificial sequence
<220> FEATURE:
<223> OTHER INFORMATION: Rat gamma1 subunit, V275G and L276G mutation,
    pMDS plasmid

<400> SEQUENCE: 94
cgatactacg atactagtat acgttattaa tagtaatcaa ttacggggtc attagttcat     60
agcccatata tggagttccg cgttacataa cttacggtaa atggcccgcc tggctgaccg    120

```
cccaacgacc cccgcccatt gacgtcaata atgacgtatg ttcccatagt aacgccaata    180
gggactttcc attgacgtca atgggtggac tatttacggt aaactgccca cttggcagta    240
catcaagtgt atcatatgcc aagtacgccc cctattgacg tcaatgacgg taaatggccc    300
gcctggcatt atgcccagta catgacctta tgggactttc ctacttggca gtacatctac    360
gtattagtca tcgctattac tcatgggtcg aggtgagccc cacgttctgc ttcactctcc    420
ccatctcccc cccctcccca ccccaatttt gtatttatt tatttttaa ttattttgtg     480 cagcgatggg ggcggggggg ggggggcgc gcgccaggcg gggcggggcg gggcgagggg     540
cggggcgggg cgaggcggag aggtgcggcg gcagccaatc agagcggcgc gctccgaaag    600 tttccttta tggcgaggcg gcggcggcgg cggccctata aaaagcgaag cgcgcggcgg     660
gcgggagtcg ctgcgttgcc ttcgcccgt gccccgctcc gcgccgcctc gcgccgcccg     720
ccccggctct gactgaccgc gttactccca caggtgagcg ggcgggacgg cccttctcct    780
ccgggctgta attagcgctt ggtttaatga cggctcgttt cttttctgtg gctgcgtgaa    840
agccttaaag ggctccggga gggcccttttg tgcgggggg agcggctcgg ggggtgcgtg    900
cgtgtgtgtg tgcgtgggga gcgccgcgtg cggcccgcgc tgcccggcgg ctgtgagcgc    960
tgcgggcgcg gcgcggggct tgtgcgctc cgcgtgtgcg cgagggagc gcggccgggg    1020 gcggtgcccc gcggtgcggg ggggctgcga ggggaacaaa ggctgcgtgc ggggtgtgtg    1080 cgtgggggg tgagcagggg gtgtgggcgc ggcggtcggg ctgtaacccc ccctgcacc    1140 ccctccccg agttgctgag cacggccegg cttcgggtgc ggggctccgt gcggggcgtg    1200
gcgcggggct cgccgtgccg ggcgggggt ggcggcaggt ggggggtgccg ggcggggcgg    1260 ggccgcctcg ggccggggag ggctcggggg aggggcgcgg cggccccgga gcgccggcgg    1320
ctgtcgaggc gcggcgagcc gcagccattg cctttatgg taatcgtgcg agagggcgca    1380
gggacttcct ttgtcccaaa tctggcggag ccgaaatctg ggaggcgccg ccgcaccccc    1440
tctagcgggc gcggcgaag cggtgcgcg ccggcaggaa ggaaatgggc ggggagggcc    1500
ttcgtgcgtc gccgcgccgc cgtcccctt tccatctcca gcctcggggc tgccgcaggg    1560
ggacggctgc cttcggggg gacggggcag ggcgggtttc ggcttctggc gtgtgaccgg    1620
cggctgctag agcctctgct aaccatgttc atgccttctt cttttcccta cagctcctgg    1680
gcaacgtgct ggttgttgtg ctgtctcatc attttggcaa agaattgcgg ccgtctcagg    1740
ccaccgaaga cttgatcacc cgggatctcg agccatggtg ctagaaataa ttttgtttaa    1800 cttaagaag gagatataca tatggagtcg gttgctgcag agagcgctcc agctccggag    1860
aatgaacact ctcaagagac cccggaatcg aacagtagtg tgtacaccac cttcatgaag    1920
tctcatcgct gctatgacct gatccccaca agctccaagc tggtggtatt tgatacttcg    1980
ctgcaggtaa agaaagcctt ctttgccctg tgactaacg gtgttcgtgc tgccccttg    2040 tgggatagta agaagcagag ctttgtgggc atgctgacca tcactgactt catcaatatt    2100
ctgcaccgat actacaagtc agccctggtg cagatctatg aactggagga gcacaagata    2160
gagacttgga gagaggtcta cctgcaagac tcctttaagc cacttgtctg catttctcca    2220
aatgccagct tgttcgatgc tgtctcttca ttaattcgaa ataagatcca caggcttcca    2280
gttattgacc cggagtcagg caacaccttg tacattctta ctcacaagcg atcctcaag    2340 ttcctcaagt tgtttatcac tgagttcccc aagccggaat tcatgtctaa gtctctggaa    2400
gagctacaga ttggcaccta cgccaatatt gccatggtcc gtaccactac acctgtctat    2460
```

```
gtggctctgg gcatctttgt acagcaccga gtctccgcct tgcctgtggt ggatgagaaa    2520
gggcgtgtgg tggacatcta ctccaagttt gatgtgatta atttggcagc agaaaagaca    2580
tacaacaacc tagatgtgtc tgtgacaaaa gccctacagc accggtcaca ctacttcgag    2640
ggtggaggta agtgctacct acatgagact ctcgaggcaa tcatcaatag actggtggaa    2700
gcagaggttc accgtctggt ggtggtggat gaacatgacg tggtcaaggg cattgtatcg    2760
ctgtctgaca tcttacaggc tctggtgctc acaggtggag agaagaagcc ctgataacta    2820
gcagctgatg catagcatgc ggtacctaat tcactcctca ggtgcaggct gcctatcaga    2880
aggtggtggc tggtgtggct aatgccctgg ctcacaaata ccactgagat cttttttccct    2940
ctgccaaaaa ttatggggac atcatgaagc cccttgagca tctgacttct ggctaataaa    3000
ggaaatttat tttcattgca atagtgtgtt ggaattttttt gtgtctctca ctcggaagga    3060
catatgggag ggcaaatcat ttaaaacatc agaatgagta tttggtttag agtttggcaa    3120
catatgccat atgctggctg ccatgaacaa aggtggctat aaagaggtca tcagtatatg    3180
aaacagcccc ctgctgtcca ttccttattc catagaaaag ccttgacttg aggttagatt    3240
tttttttatat tttgttttgt gttattttttt tctttaacat ccctaaaatt ttccttacat    3300
gttttactag ccagattttt cctcctctcc tgactactcc cagtcatagc tgtccctctt    3360
ctcttatgaa gatccctcga cgtttaaacc catgtgcctg gcagataact tcgtataatg    3420
tatgctatac gaagttatgg tacgtactaa gctctcatgt ttcacgtact aagctctcat    3480
gtttaacgta ctaagctctc atgtttaacg aactaaaccc tcatggctaa cgtactaagc    3540
tctcatggct aacgtactaa gctctcatgt ttcacgtact aagctctcat gtttgaacaa    3600
taaaattaat ataatcagc aacttaaata gcctctaagg ttttaagttt tataagaaaa    3660
aaagaatat ataaggcttt taagctttt aaggtttaac ggttgtggac aacaagccag    3720
ggatgtaacg cactgagaag cccttagagc ctctcaaagc aattttgagt gacacaggaa    3780
cacttaacgg ctgacataat tcagcttcac gctgccgcaa gcactcaggg cgcaagggct    3840
gctaaaggaa gcggaacacg tagaaagcca gtccgcagaa acggtgctga ccccggatga    3900
atgtcagctg ggaggcagaa taaatgatca tatcgtcaat tattacctcc acggggagag    3960
cctgagcaaa ctggcctcag gcatttgaga agcacacggt cacactgctt ccggtagtca    4020
ataaaccggt aagtagcgta tgcgctcacg caactggtcc agaaccttga ccgaacgcag    4080
cggtggtaac ggcgcagtgg cggttttcat ggcttgttat gactgttttt ttggggtaca    4140
gtctatgcct cggcatcca agcagcaagc gcgttacgcc gtgggtcgat gtttgatgtt    4200
atggagcagc aacgatgtta cgcagcaggg cagtcgccct aaaacaaagt taaacatcat    4260
gagggaagcg gtgatcgccg aagtatcgac tcaactatca gaggtagttg gcgtcatcga    4320
gcgccatctc gaaccgacgt tgctggccgt acatttgtac ggctccgcag tggatggcgg    4380
cctgaagcca cacagtgata ttgatttgct ggttacggtg accgtaaggc ttgatgaaac    4440
aacgcggcga gctttgatca cgacctttt ggaaacttcg gcttcccctg agagagcga    4500
gattctccgc gctgtagaag tcaccattgt tgtgcacgac gacatcattc cgtggcgtta    4560
tccagctaag cgcgaactgc aatttggaga atggcagcgc aatgacattc ttgcaggtat    4620
cttcgagcca gccacgatcg acattgatct ggctatcttg ctgacaaaag caagagaaca    4680
tagcgttgcc ttggtaggtc cagcggcgga ggaactcttt gatccggttc ctgaacagga    4740
tctatttgag gcgctaaatg aaaccttaac gctatggaac tcgccgcccg actgggctgg    4800
cgatgagcga aatgtagtgc ttacgttgtc ccgcatttgg tacagcgcag taaccggcaa    4860
```

```
aatcgcgccg aaggatgtcg ctgccgactg ggcaatggag cgcctgccgg cccagtatca    4920
gcccgtcata cttgaagcta gacaggctta tcttggacaa gaagaagatc gcttggcctc    4980
gcgcgcagat cagttggaag aatttgtcca ctacgtgaaa ggcgagatca ccaaggtagt    5040
cggcaaataa tgtctaacaa ttcgttcaag ccgacggatc tatgtcgggt gcggagaaag    5100
aggtaatgaa atggcaccta ggtat                                         5125
```

<210> SEQ ID NO 95
<211> LENGTH: 330
<212> TYPE: PRT
<213> ORGANISM: Artificial sequence
<220> FEATURE:
<223> OTHER INFORMATION: Rat gamma 1 subunit, V275G and L276G mutation

<400> SEQUENCE: 95

```
Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
    50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
        195                 200                 205

Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
            260                 265                 270

Glu Gly Gly Gly Lys Cys Tyr Leu His Glu Thr Leu Glu Ala Ile Ile
        275                 280                 285

Asn Arg Leu Val Glu Ala Glu Val His Arg Leu Val Val Val Asp Glu
    290                 295                 300

His Asp Val Val Lys Gly Ile Val Ser Leu Ser Asp Ile Leu Gln Ala
```

```
                    305                 310                 315                 320
Leu Val Leu Thr Gly Gly Glu Lys Lys Pro
                    325                 330

<210> SEQ ID NO 96
<211> LENGTH: 3566
<212> TYPE: DNA
<213> ORGANISM: Artificial sequence
<220> FEATURE:
<223> OTHER INFORMATION: Human beta1 subunit-YFP, KPI deletion, pDC
      plasmid

<400> SEQUENCE: 96
attcatccgc ttattatcac ttattcaggc gtagcaacca ggcgtttaag ggcaccaata      60
actgccttaa aaaaattacg ccccgccctg ccactcatcg cagtactgtt gtaattcatt     120
aagcattctg ccgacatgga agccatcaca acggcatga tgaacctgaa tcgccagcgg      180
catcagcacc ttgtcgcctt gcgtataata tttgcccatg gtgaaaacgg gggcgaagaa     240
gttgtccata ttggccacgt ttaaatcaaa actggtgaaa ctcacccagg gattggctga     300
gacgaaaaac atattctcaa taaacccttt agggaaatag gccaggtttt caccgtaaca     360
cgccacatct tgcgaatata tgtgtagaaa ctgccgaaaa tcgtcgtggt attcactcca     420
gagcgatgaa aacgtttcag tttgctcatg gaaaacggtg taacagggt gaacactatc      480 ccatatcacc agctcaccgt ctttcattgc catacggaat tccggatgag cattcatcag     540
gcgggcaaga atgtgaataa aggccggata aaacttgtgc ttattttct ttacggtctt      600 taaaaaggcc gtaatatcca gctgaacggt ctggttatag gtacattgag caactgactg     660
aaatgcctca aaatgttctt tacgatgcca tgggatata tcaacggtgg tatatccagt      720
gatttttttc tccattttag cttccttagc tcctgaaaat ctcgataact caaaaaatac     780
gcccggtagt gatcttattt cattatggtg aaagttggac cctcttacgt gccgatcaac     840
gtctcatttt cgccaaaagt tggcccagat caacgtctca ttttcgccaa agttggccc     900 agccatgtgc ctggcaccta ggtatcgata atacgactca ctatagggga attgtgagcg     960
gataacaatt cccctctaga aataatttg tttaacttta agaaggagat atacaatggg     1020
caatacgagc agcgagcgcg ccgcgctgga gcggcaggct ggccataaga cgccgcggag    1080
ggacagctcg gggggcacca aggatgggga caggcccaag atcctgatgg acagccccga    1140
agacgccgac atcttccaca ccgaggaaat gaaggctcca gagaaggagg agttcctggc    1200
gtggcagcac gacctcgagg tgaatgaaa agcccccgcc caggctcggc caccgtatt     1260 tcgatggaca gggggtggaa aggaggtcta cttgtctgga tccttcaaca actggagcaa    1320 attgccctc actagaagcc aaaacaactt cgtagccatc ctggacctgc ggaaggaga     1380 gcatcagtac aagttctttg tggatggcca gtggaccca gatccttccg agccaatagt     1440
aaccagccag cttggcacag ttaacaacat cattcaagtg aagaaaactg actttgaagt    1500
atttgatgct ttaatggtgg attcccaaaa gtgctccgat gtatctgagc tgtccagttc    1560
ccccccagga ccctaccacc aggagcctta catctctaaa ccagaggagc ggttcaaggc    1620
cccgcccatc ctcccgcctc acctgctgca ggtcatcttg aacaaggaca cgggcatctc    1680
ttgtgatcca gcgctgcttc cggagcccaa ccacgtcatg ctgaaccacc tctatgcact    1740
ctctatcaag gatggagtga tggtgctcag tgcgacccat cggtacaaga aaaagtacgt    1800
caccaccctc ctctacatgg tgagcaaggg cgaggagctg ttcaccgggg tggtgcccat    1860
cctggtcgag ctggacggcg acgtaaacgg ccacaagttc agcgtgtccg gcgagggcga    1920
```

| | |
|---|---|
| gggcgatgcc acctacggca agctgaccct gaagttcatc tgcaccaccg gcaagctgcc | 1980 |
| cgtgccctgg cccacccttcg tgaccacctt cggctacggc ctgcagtgct tcgcccgcta | 2040 |
| ccccgaccac atgaagcagc acgacttctt caagtccgcc atgcccgaag gctacgtcca | 2100 |
| ggagcgcacc atcttcttca aggacgacgg caactacaag acccgcgccg aggtgaagtt | 2160 |
| cgagggcgac accctggtga accgcatcga gctgaagggc atcgacttca aggaggacgg | 2220 |
| caacatcctg gggcacaagc tggagtacaa ctacaacagc cacaacgtct atatcatggc | 2280 |
| cgacaagcag aagaacggca tcaaggtgaa cttcaagatc cgccacaaca tcgaggacgg | 2340 |
| cagcgtgcag ctcgccgacc actaccagca gaacacccc atcggcgacg gccccgtgct | 2400 |
| gctgcccgac aaccactacc tgagctacca gtccgccctg agcaaagacc ccaacgagaa | 2460 |
| gcgcgatcac atggtcctgc tggagttcgt gaccgccgcc gggatcactc tcggcatgga | 2520 |
| cgagctgtac aagtgataat atgaggcctc ggatcctgta aaacgacggc cagtgaattc | 2580 |
| cccgggaagc ttcgccaggg ttttcccagt cgagctcgat atcggtacca gcggataaca | 2640 |
| atttcacatc cggatcgcga acgcgtctcg agagatccgg ctgctaacaa agcccgaaag | 2700 |
| gaagctgagt tggctgctgc caccgctgag caataactag cataacccct tggggcctct | 2760 |
| aaacgggtct tgaggggttt tttggtttaa cccatgtgc ctggcagata acttcgtata | 2820 |
| atgtatgcta tacgaagtta tggtaccgcg gccgcgtaga ggatctgttg atcagcagtt | 2880 |
| caacctgttg atagtacgta ctaagctctc atgtttcacg tactaagctc tcatgtttaa | 2940 |
| cgtactaagc tctcatgttt aacgaactaa accctcatgg ctaacgtact aagctctcat | 3000 |
| ggctaacgta ctaagctctc atgtttcacg tactaagctc tcatgtttga acaataaaat | 3060 |
| taatataaat cagcaactta aatagcctct aaggttttaa gttttataag aaaaaaaaga | 3120 |
| atatataagg cttttaaagc ttttaaggtt taacggttgt ggacaacaag ccagggatgt | 3180 |
| aacgcactga gaagcccta gagcctctca aagcaatttt gagtgacaca ggaacactta | 3240 |
| acggctgaca gaattagctt cacgctgccg caagcactca gggcgcaagg gctgctaaag | 3300 |
| gaagcggaac acgtagaaag ccagtccgca gaaacggtgc tgaccccgga tgaatgtcag | 3360 |
| ctgggaggca gaataaatga tcatatcgtc aattattacc tccacgggga gagcctgagc | 3420 |
| aaactggcct caggcatttg agaagcacac ggtcacactg cttccggtag tcaataaacc | 3480 |
| ggtaaaccag caatagacat aagcggctat ttaacgaccc tgccctgaac cgacgaccgg | 3540 |
| gtcgaatttg ctttcgaatt tctgcc | 3566 |

<210> SEQ ID NO 97
<211> LENGTH: 506
<212> TYPE: PRT
<213> ORGANISM: Artificial sequence
<220> FEATURE:
<223> OTHER INFORMATION: Human beta1-YFP, KPI deletion

<400> SEQUENCE: 97

Met Gly Asn Thr Ser Ser Glu Arg Ala Ala Leu Glu Arg Gln Ala Gly
1               5                   10                  15

His Lys Thr Pro Arg Arg Asp Ser Ser Gly Gly Thr Lys Asp Gly Asp
            20                  25                  30

Arg Pro Lys Ile Leu Met Asp Ser Pro Glu Asp Ala Asp Ile Phe His
        35                  40                  45

Thr Glu Glu Met Lys Ala Pro Glu Lys Glu Glu Phe Leu Ala Trp Gln
    50                  55                  60

```
His Asp Leu Glu Val Asn Glu Lys Ala Pro Ala Gln Ala Arg Pro Thr
 65                  70                  75                  80

Val Phe Arg Trp Thr Gly Gly Lys Glu Val Tyr Leu Ser Gly Ser
                 85                  90                  95

Phe Asn Asn Trp Ser Lys Leu Pro Leu Thr Arg Ser Gln Asn Asn Phe
                100                 105                 110

Val Ala Ile Leu Asp Leu Pro Glu Gly Glu His Gln Tyr Lys Phe Phe
            115                 120                 125

Val Asp Gly Gln Trp Thr His Asp Pro Ser Glu Pro Ile Val Thr Ser
    130                 135                 140

Gln Leu Gly Thr Val Asn Asn Ile Ile Gln Val Lys Lys Thr Asp Phe
145                 150                 155                 160

Glu Val Phe Asp Ala Leu Met Val Asp Ser Gln Lys Cys Ser Asp Val
                165                 170                 175

Ser Glu Leu Ser Ser Ser Pro Pro Gly Pro Tyr His Gln Glu Pro Tyr
                180                 185                 190

Ile Ser Lys Pro Glu Arg Phe Lys Ala Pro Pro Ile Leu Pro Pro
        195                 200                 205

His Leu Leu Gln Val Ile Leu Asn Lys Asp Thr Gly Ile Ser Cys Asp
    210                 215                 220

Pro Ala Leu Leu Pro Glu Pro Asn His Val Met Leu Asn His Leu Tyr
225                 230                 235                 240

Ala Leu Ser Ile Lys Asp Gly Val Met Val Leu Ser Ala Thr His Arg
                245                 250                 255

Tyr Lys Lys Lys Tyr Val Thr Thr Leu Leu Tyr Met Val Ser Lys Gly
            260                 265                 270

Glu Glu Leu Phe Thr Gly Val Val Pro Ile Leu Val Glu Leu Asp Gly
        275                 280                 285

Asp Val Asn Gly His Lys Phe Ser Val Ser Gly Glu Gly Glu Gly Asp
    290                 295                 300

Ala Thr Tyr Gly Lys Leu Thr Leu Lys Phe Ile Cys Thr Thr Gly Lys
305                 310                 315                 320

Leu Pro Val Pro Trp Pro Thr Leu Val Thr Thr Phe Gly Tyr Gly Leu
                325                 330                 335

Gln Cys Phe Ala Arg Tyr Pro Asp His Met Lys Gln His Asp Phe Phe
                340                 345                 350

Lys Ser Ala Met Pro Glu Gly Tyr Val Gln Glu Arg Thr Ile Phe Phe
            355                 360                 365

Lys Asp Asp Gly Asn Tyr Lys Thr Arg Ala Glu Val Lys Phe Glu Gly
    370                 375                 380

Asp Thr Leu Val Asn Arg Ile Glu Leu Lys Gly Ile Asp Phe Lys Glu
385                 390                 395                 400

Asp Gly Asn Ile Leu Gly His Lys Leu Glu Tyr Asn Tyr Asn Ser His
                405                 410                 415

Asn Val Tyr Ile Met Ala Asp Lys Gln Lys Asn Gly Ile Lys Val Asn
            420                 425                 430

Phe Lys Ile Arg His Asn Ile Glu Asp Gly Ser Val Gln Leu Ala Asp
        435                 440                 445

His Tyr Gln Gln Asn Thr Pro Ile Gly Asp Gly Pro Val Leu Leu Pro
    450                 455                 460

Asp Asn His Tyr Leu Ser Tyr Gln Ser Ala Leu Ser Lys Asp Pro Asn
465                 470                 475                 480

Glu Lys Arg Asp His Met Val Leu Leu Glu Phe Val Thr Ala Ala Gly
```

```
                485              490              495
Ile Thr Leu Gly Met Asp Glu Leu Tyr Lys
            500              505

<210> SEQ ID NO 98
<211> LENGTH: 2858
<212> TYPE: DNA
<213> ORGANISM: Artificial sequence
<220> FEATURE:
<223> OTHER INFORMATION: Human beta1 subunit, pDC plasmid

<400> SEQUENCE: 98
ctcctgaaaa tctcgataac tcaaaaaata cgcccggtag tgatcttatt tcattatggt     60
gaaagttgga ccctcttacg tgccgatcaa cgtctcattt tcgccaaaag ttggcccaga    120
tcaacgtctc attttcgcca aaagttggcc cagccatgtg cctggcacct aggtatcgat    180
aatacgactc actatagggg aattgtgagc ggataacaat tcccctctag aaataatttt    240
gtttaacttt aagaaggaga tatacaatgg caatacgag cagcgagcgc gccgcgctgg    300
agcggcaggc tggccataag acgccgcgga gggacagctc gggggcacc aaggatgggg    360 acaggcccaa gatcctgatg gacagccccg aagacgccga catcttccac accgaggaaa    420
tgaaggctcc agagaaggag gagttcctgg cgtggcagca cgacctcgag gtgaatgaga    480
aagcccccgc ccaggctcgg cccaccgtat ttcgatggac aggggtgga aaggaggtct    540 acttgtctgg atccttcaac aactggagca aattgcccct cactagaagc caaaacaact    600
tcgtagccat cctggacctg ccggaaggag agcatcagta caagttcttt gtggatggcc    660
agtggaccca cgatccttcc gagccaatag taaccagcca gcttggcaca gttaacaaca    720
tcattcaagt gaagaaaact gactttgaag tatttgatgc tttaatggtg gattcccaaa    780
agtgctccga tgtatctgag ctgtccagtt ccccccagg accctaccac caggagcctt    840
acatctctaa accagaggag cggttcaagg ccccgcccat cctcccgcct cacctgctgc    900
aggtcatctt gaacaaggac acgggcatct cttgtgatcc agcgctgctt ccggagccca    960
accacgtcat gctgaaccac ctctatgcac tctctatcaa ggatggagtg atggtgctca   1020
gtgcgaccca tcggtacaag aaaaagtacg tcaccaccct cctctacaag cccatatgat   1080
aatatgaggc ctcggatcct gtaaaacgac ggccagtgaa ttccccggga gcttcgcca   1140 gggttttccc agtcgagctc gatatcggta ccagcggata caatttcac atccggatcg   1200 cgaacgcgtc tcgagagatc cggctgctaa caaagcccga aggaagctg agttggctgc   1260 tgccaccgct gagcaataac tagcataacc ccttggggcc tctaaacggg tcttgagggg   1320
ttttttggtt taaacccatg tgcctggcag ataacttcgt ataatgtatg ctatacgaag   1380
ttatggtacc gcgccgcgt agaggatctg ttgatcagca gttcaacctg ttgatagtac   1440
gtactaagct ctcatgtttc acgtactaag ctctcatgtt taacgtacta agctctcatg   1500
tttaacgaac taaccctca tggctaacgt actaagctct catggctaac gtactaagct   1560
ctcatgtttc acgtactaag ctctcatgtt tgaacaataa aattaatata atcagcaac   1620 ttaaatagcc tctaaggttt taagtttat aagaaaaaa agaatatata aggcttttaa   1680
agcttttaag gtttaacggt tgtggacaac aagccaggga tgtaacgcac tgagaagccc   1740
ttagagcctc tcaaagcaat tttgagtgac acaggaacac ttaacggctg acagaattag   1800
cttcacgctg ccgcaagcac tcagggcgca agggctgcta aggaagcgg aacacgtaga   1860 aagccagtcc gcagaaacgg tgctgacccc ggatgaatgt cagctgggag cagaataaa   1920
```

```
tgatcatatc gtcaattatt acctccacgg ggagagcctg agcaaactgg cctcaggcat    1980
ttgagaagca cacggtcaca ctgcttccgg tagtcaataa accggtaaac cagcaataga    2040
cataagcggc tatttaacga ccctgccctg aaccgacgac cgggtcgaat ttgctttcga    2100
atttctgcca ttcatccgct tattatcact tattcaggcg tagcaaccag gcgtttaagg    2160
gcaccaataa ctgccttaaa aaaattacgc cccgccctgc cactcatcgc agtactgttg    2220
taattcatta agcattctgc cgacatggaa gccatcacaa acggcatgat gaacctgaat    2280
cgccagcggc atcagcacct tgtcgccttg cgtataatat ttgcccatgg tgaaaacggg    2340
ggcgaagaag ttgtccatat tggccacgtt taaatcaaaa ctggtgaaac tcacccaggg    2400
attggctgag acgaaaaaca tattctcaat aaacccttta gggaaatagg ccaggttttc    2460
accgtaacac gccacatctt gcgaatatat gtgtagaaac tgccggaaat cgtcgtggta    2520
ttcactccag agcgatgaaa acgtttcagt ttgctcatgg aaaacggtgt aacaagggtg    2580
aacactatcc catatcacca gctcaccgtc tttcattgcc atacggaatt ccggatgagc    2640
attcatcagg cgggcaagaa tgtgaataaa ggccggataa aacttgtgct tatttttctt    2700
tacggtcttt aaaaaggccg taatatccag ctgaacggtc tggttatagg tacattgagc    2760
aactgactga aatgcctcaa aatgttcttt acgatgccat gggatatat caacggtggt    2820 atatccagtg atttttttct ccattttagc ttccttag                            2858
```

<210> SEQ ID NO 99
<211> LENGTH: 270
<212> TYPE: PRT
<213> ORGANISM: Artificial sequence
<220> FEATURE:
<223> OTHER INFORMATION: Human beta1 subunit

<400> SEQUENCE: 99

```
Met Gly Asn Thr Ser Ser Glu Arg Ala Ala Leu Glu Arg Gln Ala Gly
1               5                   10                  15

His Lys Thr Pro Arg Arg Asp Ser Ser Gly Gly Thr Lys Asp Gly Asp
            20                  25                  30

Arg Pro Lys Ile Leu Met Asp Ser Pro Glu Asp Ala Asp Ile Phe His
        35                  40                  45

Thr Glu Glu Met Lys Ala Pro Glu Lys Glu Glu Phe Leu Ala Trp Gln
    50                  55                  60

His Asp Leu Glu Val Asn Glu Lys Ala Pro Ala Gln Ala Arg Pro Thr
65                  70                  75                  80

Val Phe Arg Trp Thr Gly Gly Gly Lys Glu Val Tyr Leu Ser Gly Ser
                85                  90                  95

Phe Asn Asn Trp Ser Lys Leu Pro Leu Thr Arg Ser Gln Asn Asn Phe
            100                 105                 110

Val Ala Ile Leu Asp Leu Pro Glu Gly Glu His Gln Tyr Lys Phe Phe
        115                 120                 125

Val Asp Gly Gln Trp Thr His Asp Pro Ser Glu Pro Ile Val Thr Ser
    130                 135                 140

Gln Leu Gly Thr Val Asn Asn Ile Ile Gln Val Lys Lys Thr Asp Phe
145                 150                 155                 160

Glu Val Phe Asp Ala Leu Met Val Asp Ser Gln Lys Cys Ser Asp Val
                165                 170                 175

Ser Glu Leu Ser Ser Ser Pro Pro Gly Pro Tyr His Gln Glu Pro Tyr
            180                 185                 190

Ile Ser Lys Pro Glu Glu Arg Phe Lys Ala Pro Pro Ile Leu Pro Pro
```

-continued

```
            195                 200                 205
His Leu Leu Gln Val Ile Leu Asn Lys Asp Thr Gly Ile Ser Cys Asp
        210                 215                 220

Pro Ala Leu Leu Pro Glu Pro Asn His Val Met Leu Asn His Leu Tyr
225                 230                 235                 240

Ala Leu Ser Ile Lys Asp Gly Val Met Val Leu Ser Ala Thr His Arg
                245                 250                 255

Tyr Lys Lys Lys Tyr Val Thr Thr Leu Leu Tyr Lys Pro Ile
                260                 265                 270
```

FLUORESCENT AMP-KINASE BIOSENSORS

CROSS REFERENCE TO RELATED APPLICATIONS

The present application is the U.S. national phase under 35 U.S.C. 371 of international patent application number PCT/EP2015/063780 filed on Jun. 18, 2015, which designated the U.S.

SEQUENCE LISTING

The instant application contains a substitute Sequence Listing which has been submitted electronically in an ASCII text file named 7077-0003 SL 2019-07-30 on Jul. 31, 2019. The substitute Sequence Listing is hereby incorporated by reference in its entirety.

FIELD OF THE INVENTION

The invention relates to the field of optical biosensors.

BACKGROUND

Genetically encoded optical biosensors allow a real time readout of molecular or cellular events with potentially high spatial and temporal resolution. They are the tool of choice for high throughput screening and quantitative studies on distribution and concentration changes of ions and metabolites in living cells. Such sensors allow multi-scale analysis in space and time that is essential for modern systems biology approaches and advanced understanding of both healthy and diseased physiological states. Optical biosensors are also adequate tools for high throughput screening of compounds and treatments in vitro or in cells in vivo.

AMP-activated protein kinase (AMPK) is a central energy sensor and regulator that monitors and responds to variations in the cellular AMP:ATP and ADP:ATP ratio (Hardie et al., Annu Rev Biochem 67:821, 1998). Upon activation of AMPK, the kinase phosphorylates an ever increasing panel of substrates to decrease further ATP usage and to increase ATP generation by the cell. Structurally, AMPK forms a heterotrimeric complex consisting of a catalytic subunit ($\alpha$) and two regulatory subunits ($\beta$ and $\gamma$). This AMPK complex is evolutionarily conserved in eukaryotes from yeast to plants and mammals. Mammalian AMPK is an obligatory heterotrimer composed of different isoforms of subunits: $\alpha 1$, $\alpha 2$, $\beta 1$, $\beta 2$, $\gamma 1$, $\gamma 2$, and $\gamma 3$ (Hardie and Hawley, BioEssays 23:1112, 2001).

AMPK is activated by phosphorylation of the $\alpha$-subunit on Thr172 and small molecule activators like AMP or ADP. The latter follows three distinct, additive mechanisms; 1) direct allosteric activation (by AMP alone), 2) stimulation of Thr172 phosphorylation via upstream kinases, and 3) inhibition of Thr172 dephosphorylation via protein phosphatases (Hardie et al., Nat. Rev. Mol. Cell. Biol. 13:251, 2012).

The activation of AMPK results in many beneficial metabolic effects (Kahn et al., Cell Metab 10:15, 2005). First of all, AMPK acts as a master regulator of fat and glucose metabolism. When activated, it decreases fatty acid and cholesterol synthesis, but increases fatty acid oxidation (Carling et al., FEBS Letters 223:217, 1987). Activated AMPK also stimulates glucose transport into skeletal muscle and glycolysis, and regulates expression of key genes in fatty acid and glucose metabolism in liver (summarized in U.S. Pat. No. 7,119,205). Given these effects, pharmacological AMPK activators are intensely searched as drugs against the metabolic syndrome and type 2 diabetes (Hardie et al., Annu. Rev. Pharmacol. Toxicol. 47:185, 2007). AMPK is also involved in a number of pathways that are important for some other diseases like neurodegenerative disorders, fibrosis, osteoporosis, or heart failure (Srivastava et al., J. Lipid Res. 53:2490, 2012; Inoki et al., Annu. Rev. Pharmacol. Toxicol. 52:381, 2012).

Further, several tumour suppressors are part of the AMPK pathway, and activated AMPK negatively regulates mammalian target of rapamycin (mTOR), a key regulator of cell growth and proliferation. AMPK activators may therefore be also useful as anti-proliferative drugs (Motoshima et al., J. Physiol. 574:63, 2013). In support, the anti-diabetic drug metformin, a weak AMPK activator, has also anti-tumor effects as revealed in meta-studies (Evans et al., BMJ 330:1304, 2005).

All current anti-diabetic drugs (e.g. metformin, glitazones) are known as moderate AMPK activators, activating the kinase indirectly by inhibition of mitochondrial activity and a subsequent drop in ATP/AMP ratios, and having a number of other pleiotropic effects. Compounds that activate AMPK directly may have benefits for treating a variety of diseases mentioned above.

The activation mechanisms of AMPK are complex and not yet entirely understood. However, it is accepted now that during allosteric activation, binding of AMP or ADP to the $\gamma$ subunit involves a conformational change within the AMPK heterotrimer that activates the catalytic a subunit (Riek et al., J. Biol. Chem. 283:18331, 2008; Zhu et al., Structure 19:515, 2011; Chen et al., Nature Struct. Mol. Biol. 19: 716, 2012).

SUMMARY

The present invention deals with a heterotrimeric AMPK construct comprising a fluorophore pair, allowing detection and/or measurement of conformational changes of the kinase complex. In a more specific aspect, the heterotrimeric AMPK construct of the invention allows the detection and/or the measurement of the allosteric activation of the kinase.

The present invention describes the engineering and the use of heterotrimeric AMPK constructs. Such fluorescent biosensors are able to monitor the direct effect of adenine nucleotides (AMP, ADP, ATP) and also other allosteric activators on AMPK conformation and activation.

These biosensors consist in AMPK subunits tagged directly or via intervening spacer sequences to a fluorophore pair (FIG. 1). A particular aspect of the invention is the way of placing the fluorescent tags on the AMPK heterotrimer to translate conformational changes induced by allosteric AMPK activators into an exploitable change in fluorescence resonance energy transfer (or Foerster resonance energy transfer, FRET) or potentially in fluorescence quenching. As such, the present invention deals with the use a FRET signal to detect conformational changes of the AMPK complex.

The present invention deals in particular with a heterotrimeric AMP-activated protein kinase (AMPK) construct comprising or consisting in an $\alpha$-subunit, a $\beta$-subunit, a $\gamma$-subunit, mutants, or fragments thereof and a fluorescent dye pair tagging at least one of said $\alpha$-subunit, $\beta$-subunit or $\gamma$-subunit, said fluorescent dye pair being placed to allow detection of conformational changes within the AMPK construct.

By "AMP-activated", it is meant in the sense of the present invention that the AMPK responds to variations in the intracellular levels of adenosine monophosphate.

AMP activation of an AMPK can be measured for example with the AMPK constructs according to the present invention. In a cell in which the energy reserves are depleted, i.e. in which the concentration in AMP is high, the activation of AMPK by AMP or ADP will result in an increase in fluorescence resonance energy transfer. When the energy reserves of the cell increases, AMPK activation is decreased and the fluorescence resonance energy transfer signal declines proportionally to AMPK inactivation.

It is now well-established that yeast SNF-1 is not activated by AMP, but responds to variations in the glucose levels in the microorganism. The AMP-activated AMPK constructs according to the present invention are therefore not yeast SNF-1.

By "mutant", it is meant in the sense of the present invention that the wild-type AMPK is engineered by deletion, addition of amino-acids and/or mutation in the amino-acid sequence. Said α, β and/or γ subunits mutants are chosen in such a way that the AMPK retains its kinase activity and the regulatory domains, such as CBS1, CBS3 or the alpha/beta activation site, still allow allosteric activation of AMPK.

By "fragments", it is meant in the sense of the present invention that the α, β and/or γ subunits do not contain the entire amino-acid sequence of the wild type subunit. Some parts of a protein can be removed as they are not involved in regulation and/or activity. Said α, β and/or γ subunits fragments are chosen in such a way that the AMPK retains its kinase activity and the regulatory domains, such as CBS1 or CBS3, still allow allosteric activation of AMPK.

By "detection of conformational changes within the AMPK construct", it is meant in the sense of the present invention that the FRET signal resulting from the conformational changes induced by activation of the AMPK is measured using appropriate devices, well known to those skilled in the art.

By "said fluorescent dye pair being placed to allow detection of conformational changes within the AMPK construct", it is meant in the sense of the present invention that the fluorophores of the fluorescent dye pair are localized on one or more subunits in such a way that upon binding of AMP, ADP or any allosteric activator to the AMPK construct, a FRET signal is observed. Without wishing to being bound by this theory, it appears that the α-subunit C-terminus approaches the C-termini of the β- and γ-subunits upon allosteric activation. The fluorophores of the fluorescent dye pair may therefore be inserted in a position close to said C-termini or at said C-termini, either directly, or after engineering of said C-termini.

The AMP-activated AMPK according to the present invention is a metazoan AMPK, in particular a mammalian AMPK. In particular, said mammalian AMPK is selected from the group of murine, simian, equine, human, bovine and ovine AMPK.

The AMP-activated AMPK according to the present invention may also be a chimeric AMPK in which the α, β and γ subunits come from two or more different metazoans, advantageously selected from mammals, in particular from mice, rat, human, bovine and ovine.

In contrast to yeast SNF-1, AMP-activated AMPKs exist in the form of a stable trimer, whether in activated or inactivated form. The AMPK constructs according to the present invention are constitutively stable heterotrimers.

By "constitutively stable heterotrimer", it is meant in the sense of the present invention that the AMPK construct is constitutively composed of three subunits, under any physiological condition, and irrespective of analyzed in native tissue or as recombinantly expressed in different hosts. The metazoan, in particular mammalian AMPK protein is such a stable (or constitutive) heterotrimer, since it is purified from tissue or recombinantly expressing bacteria (or other hosts) always in form of heterotrimers which are stable during different purification steps and extended storage times. Metazoan AMPK differs from yeast SNF1 in that subunits of the SNF1 complex can exist as monomers, can be expressed individually and assembled into binary complexes in vitro. (e.g. Elbling et al 2006 JBC).

The heterotrimeric AMPK of the invention comprises one AMPK α subunit that is either α1 or α2 or a fragment thereof, one β subunit that is either β1 or β2 or a fragment thereof, and one γ subunit that is either γ1 or γ2, γ3, or a fragment thereof.

The α, β and γ subunits of the invention may originate from any organism such as mice, rat, human, bovine or ovine. Any combination of the subunits may be done as long as the subunits form a heterotrimeric functional AMPK.

An advantageous combination of subunits may be selected from the group consisting of rat α1, human β1 (SEQ ID NO: 99) and rat γ1 (SEQ ID NO: 15); rat α1, human β1 and rat γ2; rat α1, human β1 and rat γ3; rat α1, human β2 and rat γ1; rat α1, human β2 and rat γ2; rat α1, human β2 and rat γ3; rat α2, human β1 and rat γ1; rat α2, human β1 and rat γ2; rat α2, human β1 and rat γ3; rat α2, human β2 and rat γ1; rat α2, human β2 and rat γ2; and rat α2, human β2 and rat γ3, mutants or fragments of any of the foregoing subunits.

In one particular embodiment, the AMP-activated AMPK is a chimeric AMPK comprising or consisting in rodent, in particular rat, α and γ subunits and human β subunit. Preferably, said chimeric AMPK consists of rat α2 and γ1 subunits and human β2 subunit.

In another particular embodiment, the AMP-activated AMPK is a chimeric AMPK comprising or consisting in rodent, in particular rat, α and γ subunits and human β subunit. Preferably, said chimeric AMPK consists of rat α2 and γ1 subunits and human β1 subunit.

The fluorescent dye pair may be any fluorescent dye pair known to those skilled in the art, advantageously chosen among Förster (or fluorescence) resonance energy transfer (FRET) pairs.

Within the meaning of the invention, the fluorophore pair (or donor and acceptor pair) may be a small molecule dye or chosen among genetically encoded fluorescent proteins, such as those derived from green fluorescent protein (GFP), like CFP (SEQ ID NO: 53)/YFP (SEQ ID NO: 51), mseCFPΔ11 (SEQ ID NO: 67)/cpVenus (SEQ ID NO: 55) or derivatives thereof.

In a particular embodiment, the fluorescent dye pair consists in genetically encoded fluorescent proteins.

The genetically encoded fluorescent proteins may in particular be chosen from the group consisting in blue Fluorescent Proteins such as T-Sapphire, cyan Fluorescent Proteins such as eCFP, mCFP, CyPet, Cerulean, mTFP1 (Teal), green Fluorescent Proteins such as EGFP, AcGFP, TurboGFP, Emerald, Azami Green, yellow Fluorescent Proteins such as EYFP, Topaz, Venus, mCitrine, YPet, PhiYFP and Orange and Red Fluorescent Proteins, such as Kusabira Orange, mOrange, tdTomato, DsRed-Monomer, mTangerine, mStrawberry, mRFP1, mCherry, mRaspberry, mPlum, provided that the actual emission and absorption spectra of the fluorophores overlap.

Advantageously, said genetically encoded fluorescent proteins consist in GFP or a GFP derived protein, or constructs thereof, preferably chosen from among CFP/YFP and mseCFP$_{A11}$/cpVenus.

The fluorophore pair can be inserted in principle anywhere within the heterotrimeric AMPK. This includes fusion of fluorescent protein derivatives to the C- or N-termini of the AMPK subunit coding sequence (genetically encoded sensor), or chemical addition of a fluorescent dye pair to reactive residues within the subunits (e.g. cysteines).

In an advantageous embodiment, at least two of the α-subunit, β-subunit and γ-subunit of the AMPK construct are tagged with the fluorescent dye pair. More advantageously, two of the α-subunit, β-subunit and γ-subunit are tagged with the fluorescent dye pair.

By "two of the α-subunit, β-subunit and γ-subunit of the AMPK construct are tagged with the fluorescent dye pair", it is meant in the sense of the present invention that one fluorophore of the fluorescent dye pair is attached to one subunit and the other fluorophore of the fluorescent dye pair is attached to one of the remaining subunits.

In a particular embodiment, the α-subunit and either the β or the γ subunit are tagged with the fluorescent dye pair.

It is advantageous that the α-subunit is tagged with one fluorophore of the fluorescent dye pair at the C-terminus. It is also advantageous that the C-terminus of the β or the γ subunit is tagged by the fluorophore.

Preferably, the a subunit is tagged at the C-terminus and either the 3 or the γ subunit is tagged at the C-terminus.

More preferably, the a subunit is tagged at the C-terminus and either the 3 or the γ subunit is tagged at the C-terminus with genetically encoded fluorescent proteins, such as those cited above, in particular derived from green fluorescent protein (GFP), like CFP/YFP, mseCFP$_{A11}$/cpVenus or derivatives thereof. Even more preferably, said genetically encoded fluorescent protein consists in GFP or a GFP derived protein, or constructs thereof, preferably chosen from among CFP/YFP and mseCFP$_{A11}$/cpVenus. According to a specific aspect of the invention, the heterotrimeric AMPK comprises α, β and γ subunits, wherein the a subunit is tagged with CFP or mseGFPΔ11 at the C-terminus and the β or the γ subunit is tagged with YFP or cpVenus at the C-terminus.

The AMPK construct, i.e. one or more among the α, β and γ subunits, can be further engineered to improve the FRET response, for example by deletion, addition or substitution of sequences.

Further constructs wherein the linker sequence between AMPK subunit and dye is altered in length or its flexibility is reduced are therefore also parts of the invention.

Deletion includes the removal of amino-acids, in particular at the termini of one or more subunits.

In embodiments in which one fluorophore of the fluorescent dye pair is located on a terminus of a subunit, i.e. on the C-terminus or the N-terminus, the amino-acids are preferably deleted between said terminus and the fluorophore. Said deletion may be done on one or two of the tagged subunits.

Addition includes grafting additional amino-acids within one or more of the subunits. Advantageously, amino-acids are added at the terminus of one or more subunits, i.e. on the C-terminus or the N-terminus.

Amino-acids may be added for rigidifying the structure, in particular for amplifying the FRET signal observed.

In embodiments where a fluorophore of the fluorescent dye pair is located on a terminus of a subunit, i.e. on the C-terminus or the N-terminus, the amino-acids are preferably added between said terminus and the fluorophore.

In one particular embodiment, the amino-acids added between the terminus and the fluorophore fold into a rigid α-helix. The amino-acid sequence is in particular SEQ-ID NO: 1.

Examples of an a subunit in which a rigid α-helix added between said a subunit and the fluorophore are SEQ ID NO: 84 and SEQ ID NO: 85.

In a particular embodiment, the a subunit is engineered by deletion of the C-terminal amino-acids and addition of a rigid α-helix. Preferably, the β2 or γ1 tagged with the second fluorophore of the fluorescent dye pair is engineered by deletion of amino-acids at the terminus and said second fluorophore is attached to said β2 or γ1 subunit at the new terminus.

Substitution in the amino-acid sequence includes replacement of an amino-acid by another. Said modification may be introduced anywhere within one or more subunits, provided that the AMPK retains its activity and that the allosteric regulatory domains remain functional.

By "the allosteric regulatory domains remain functional", it is meant in the sense of the present invention that the domain(s) of the subunits to which the allosteric interactor, such as e.g. AMP or ADP, bind enables an activation of AMPK.

The inventors have for example discovered that the CBS3 domain of the γ1 subunit is mandatory for allosteric activation of AMPK. Indeed, replacing valine 275 and leucine 276 by glycine residues (SEQ ID NO: 33 and SEQ ID NO: 37), thereby altering AMP binding to the CBS3 regulatory domain, results in a lack of activation by AMP, as evidenced by the absence of a FRET signal.

Such an AMPK in which the CBS3 regulatory domain has been inactivated can however be used as a negative control, either in vitro or ex vivo, to validate the allosteric activation of AMPK via CBS3 binding.

Examples of such mutations are for example:
the replacement of Theonine 172 of the α2 subunit, in particular with alanine (such as SEQ ID NO: 25) or aspartic acid (such as SEQ ID NO: 27),
the replacement of amino-acids in the CBS domains, such as, for example, serine 315 of the γ1 subunit, in particular with proline (such as SEQ ID NO: 31 and SEQ ID NO 39), or
replacement of leucine 128 with aspartic acid and valine 129 with aspartic acid in the γ1 subunit (such as SEQ ID NO: 29 and SEQ ID NO 35).

In a particular embodiment, the AMPK construct consists in α2, β2 and γ1 subunits.

In the AMPK in which the subunits are α2, β2 and γ1:
the α2 subunit may be tagged at its N-terminus, for example with eCFP (such as SEQ ID NO: 7) or mseCFPΔ11 (such as SEQ ID NO: 69) or at its C-terminus, for example with eCFP (such as SEQ ID NO: 5) or mseCFPΔ11 (such as SEQ ID NO: 65),
the β2 subunit may be tagged at its N-terminus, for example with YFP (such as SEQ ID NO: 13) or cpVenus (such as SEQ ID NO: 59), or at its C-terminus, for example with cpVenus (such as SEQ ID NO: 63) or YFP (such as SEQ ID NO: 23),
the γ1 subunit may be tagged at its N-terminus, for example with cpVenus (such as SEQ ID NO: 63), YFP (such as SEQ ID NO: 47 and SEQ ID NO: 49), eCFP (such as SEQ ID NO: 19 and SEQ ID NO: 45) or mseCFPΔ11 (such as SEQ ID NO: 73) or at its C-terminus, for example with cpVenus (such as SEQ ID NO: 61), eCFP (such as SEQ ID NO: 17), YFP (such as SEQ ID NO: 47) or mseCFPΔ11 (such as SEQ ID NO: 71), provided that the actual emission and absorption spectra of the fluorophores overlap.

In the AMPK in which the subunits are α2, β2 and γ1, it is preferred that the α2 subunit is tagged at the C-terminus and either the β2 or the γ1 subunit is tagged at the C-terminus, in particular with genetically encoded fluorescent proteins, as defined above.

According to a specific aspect of the invention, the heterotrimeric AMPK comprises α2, β2 and γ1 subunits, wherein the α2 subunit is tagged with CFP (such as SEQ ID NO: 4) or mseGFPΔ11 (such as SEQ ID NO: 65) at the C-terminus and the β2 or the γ1 subunit is tagged with YFP (such as β2: SEQ ID NO: 11; γ1: SEQ ID NO: 21 and SEQ ID NO: 47) or cpVenus (such as β2: SEQ ID NO: 57; γ1: SEQ ID NO: 61) at the C-terminus.

In this specific aspect of the invention, the AMPK construct consists in α2, β2 and γ1 subunits, the α2 subunit is tagged with mseCFPΔ11 at the C-terminus and either the β2 or the γ1 subunit is tagged with cpVenus at the C-terminus or the α2 subunit is tagged with CFP at the C-terminus and either the β2 or the γ1 subunit is tagged with YFP at the C-terminus.

More specifically, said AMPK is selected from the following AMPK constructs:
  AMPK comprising or consisting in an α2 subunit tagged with CFP at the C-terminus, a β2 subunit tagged with YFP at the C-terminus and an untagged γ1 subunit,
  AMPK comprising or consisting in an α2 subunit tagged with CFP at the C-terminus, an untagged β2 subunit and a γ1 subunit tagged with YFP at the C-terminus,
  AMPK comprising or consisting in an α2 subunit tagged with mseCFPΔ11 at the C-terminus, an untagged β2 subunit and a γ1 subunit tagged with cpVenus at the C-terminus.

The AMPK construct may be further engineered by deletion, addition or substitution of sequences, as defined above.

In a particular embodiment, the AMPK construct consists in an α2 subunit tagged at the C-terminus, a β2 subunit tagged at the C-terminus and an untagged γ1 subunit, or a mutated γ1 subunit, as defined above wherein the C-terminus of the α2 subunit is connected to the fluorophore through a rigid α-helix, advantageously consisting of SEQ ID 1 (EEEEKKKK).

In another particular embodiment, the AMPK construct consists in an α2 subunit tagged at the C-terminus, a β2 subunit tagged at the C-terminus and an untagged γ1 subunit, or a mutated γ1 subunit, as defined above wherein the three C-terminal amino-acids of the β2 subunit are deleted and the fluorophore is connected to the engineered C-terminal amino-acid of the β2 subunit.

In a further particular embodiment, the AMPK construct consists in an α2 subunit tagged at the C-terminus, a β2 subunit tagged at the C-terminus and an untagged γ1 subunit, or a mutated γ1 subunit, as defined above wherein the C-terminus of the α2 subunit is connected to the fluorophore through a rigid α-helix, advantageously consisting of SEQ ID 1 (EEEEKKKK) and the three C-terminal amino-acids of the β2 subunit are deleted and the fluorophore is connected to the engineered C-terminal amino-acid of the β2 subunit.

In a more particular embodiment, the AMPK construct comprises at least the two following subunits:

SEQ ID NO: 75 and SEQ ID NO: 78,
SEQ ID NO: 82 and SEQ ID NO: 89,
SEQ ID NO: 75 and SEQ ID NO 80
SEQ ID NO: 82 and SEQ ID NO 93
SEQ ID NO: 85 and SEQ ID NO: 78
SEQ ID NO: 84 and SEQ ID NO: 89,
SEQ ID NO: 85 and SEQ ID NO: 80
SEQ ID NO: 84 and SEQ ID NO 93.

In specific embodiments, the AMPK construct is chosen from the group consisting of:
  SEQ ID NO: 75, SEQ ID NO: 78 and SEQ ID NO 15,
  SEQ ID NO: 82, SEQ ID NO: 89 and SEQ ID NO 15,
  SEQ ID NO: 75, SEQ ID NO: 9 and SEQ ID NO 80
  SEQ ID NO: 82, SEQ ID NO: 9 and SEQ ID NO 93
  SEQ ID NO: 85, SEQ ID NO: 78 and SEQ ID NO 15
  SEQ ID NO: 84, SEQ ID NO: 89 and SEQ ID NO 15
  SEQ ID NO: 85, SEQ ID NO: 9 and SEQ ID NO 80
  SEQ ID NO: 84, SEQ ID NO: 9 and SEQ ID NO 93

In another particular embodiment, the AMPK construct consists in α2, β1 and γ1 subunits.

In the AMPK in which the subunits are α2, β1 and γ1, it is preferred that the α2 subunit is tagged at the C-terminus and either the β1 or the γ1 subunit is tagged at the C-terminus, in particular with genetically encoded fluorescent proteins, as defined above.

According to a specific aspect of the invention, the heterotrimeric AMPK comprises α2, β1 and γ1 subunits, wherein the α2 subunit is tagged with CFP or mseGFPΔ11 at the C-terminus and the β1 or the γ1 subunit is tagged with YFP or cpVenus at the C-terminus.

In this specific aspect of the invention, the AMPK construct consists in α2, β1 and γ1 subunits, the α2 subunit is tagged with mseCFPΔ11 at the C-terminus and either the β1 or the γ1 subunit is tagged with cpVenus at the C-terminus or the α2 subunit is tagged with CFP at the C-terminus and either the β1 or the γ1 subunit is tagged with YFP at the C-terminus.

In this specific aspect of the invention, the AMPK construct consists in α2, β1 and γ1 subunits, the α2 subunit is tagged with mseCFPΔ11 at the C-terminus and either the β1 or the γ1 subunit is tagged with cpVenus at the C-terminus or the α2 subunit is tagged with CFP at the C-terminus and either the β1 or the γ1 subunit is tagged with YFP at the C-terminus.

More specifically, said AMPK is selected from the following AMPK constructs:
  AMPK comprising or consisting in an α2 subunit tagged with CFP at the C-terminus, a β1 subunit tagged with YFP at the C-terminus and an untagged γ1 subunit,
  AMPK comprising or consisting in an α2 subunit tagged with CFP at the C-terminus, an untagged β1 subunit and a γ1 subunit tagged with YFP at the C-terminus,
  AMPK comprising or consisting in an α2 subunit tagged with mseCFPΔ11 at the C-terminus, an untagged β1 subunit and a γ1 subunit tagged with cpVenus at the C-terminus.

The AMPK construct may be further engineered by deletion, addition or mutations, as defined above.

In a particular embodiment, the AMPK construct consists in an α2 subunit tagged at the C-terminus, a β1 subunit tagged at the C-terminus and an untagged γ1 subunit, or a mutated γ1 subunit, as defined above wherein the C-terminus of the α2 subunit is connected to the fluorophore through a rigid α-helix, advantageously consisting of SEQ ID 1 (EEEEKKKK).

In another particular embodiment, the AMPK construct consists in an α2 subunit tagged at the C-terminus, a β1 subunit tagged at the C-terminus and an untagged γ1 subunit, or a mutated γ1 subunit, as defined above wherein the five C-terminal amino-acids of the β1 subunit are deleted and the fluorophore is connected to the engineered C-terminal amino-acid of the β1 subunit.

In a further particular embodiment, the AMPK construct consists in an α2 subunit tagged at the C-terminus, a β1 subunit tagged at the C-terminus and an untagged γ1 subunit, or a mutated γ1 subunit, as defined above wherein the C-terminus of the α2 subunit is connected to the fluorophore through a rigid α-helix, advantageously consisting of SEQ ID 1 (EEEEKKKK) and the five C-terminal amino-acids of the β1 subunit are deleted and the fluorophore is connected to the engineered C-terminal amino-acid of the β1 subunit. In a more particular embodiment, the AMPK construct comprises at least the two following subunits:
SEQ ID NO: 75 and SEQ ID NO: 97,
SEQ ID NO: 85 and SEQ ID NO: 97.
In specific embodiments, the AMPK construct is chosen from the group consisting of:
SEQ ID NO: 75, SEQ ID NO: 97 and SEQ ID NO 15,
SEQ ID NO: 85, SEQ ID NO: 97 and SEQ ID NO 15.

According to another aspect of the invention, the CFP and YFP can be replaced by any one of said molecule variants.

The present invention also deals with the nucleic acid molecule encoding the trimeric AMPK and a fluorescent dye pair. The nucleic acid can be DNA.

The present invention deals particularly with the nucleic acid molecule encoding a heterotrimeric AMP-activated protein kinase (AMPK) construct comprising or consisting in an α-subunit, a β-subunit, a γ-subunit, mutants, or fragments thereof and a genetically encoded fluorescent dye pair tagging at least one of said α-subunit, β-subunit or γ-subunit, said fluorescent dye pair being placed to allow detection of conformational changes within the AMPK construct.

The nucleic acid defined above can be inserted in a vector. The vector of the invention may be an expression vector wherein the nucleic acid molecule is operatively linked to one or more control sequences allowing expression in prokaryotic and/or eukaryotic hosts. The hosts containing at least one vector or at least one nucleic acid molecule as described are further aspects of the invention.

Said host can be a bacteria, an insect, fungal, plant or animal cell and more preferably a human cell or human cell line.

In a particular embodiment, expression vectors comprising a nucleic acid sequence encoding for the α-subunit, the β-subunit or the γ-subunit is selected from the group consisting in:
α-subunit: SEQ ID NO: 2, SEQ ID NO: 4, SEQ ID NO: 6, SEQ ID NO: 24, SEQ ID NO: 26, SEQ ID NO: 64, SEQ ID NO: 68, SEQ ID NO: 74, SEQ ID NO: 81, SEQ ID NO: 76 and SEQ ID NO: 83,
β-subunit: SEQ ID NO: 12, SEQ ID NO: 56, SEQ ID NO: 58, SEQ ID NO: 77, SEQ ID NO: 86, SEQ ID NO: 88,
γ-subunit: SEQ ID NO: 14, SEQ ID NO: 16, SEQ ID NO: 18, SEQ ID NO: 20, SEQ ID NO: 22, SEQ ID NO: 28, SEQ ID NO: 30, SEQ ID NO: 34, SEQ ID NO: 38, SEQ ID NO: 40, SEQ ID NO: 42, SEQ ID NO: 44, SEQ ID NO: 46, SEQ ID NO: 48, SEQ ID NO: 60, SEQ ID NO: 62, SEQ ID NO: 70, SEQ ID NO: 72, SEQ ID NO: 79, SEQ ID NO: 90, SEQ ID NO: 92.

In an advantageous embodiment, the invention concerns expression vectors encoding for a pair of tagged subunits selected from the group consisting in:
SEQ ID NO: 74 and SEQ ID NO: 77,
SEQ. ID NO: 81 and SEQ ID NO: 88,
SEQ ID NO: 74 and SEQ ID NO 79
SEQ. ID NO: 81 and SEQ ID NO 92
SEQ ID NO: 76 and SEQ ID NO: 77
SEQ ID NO: 83 and SEQ ID NO: 88,
SEQ ID NO: 76 and SEQ ID NO: 79,
SEQ ID NO: 83 and SEQ ID NO 92,
SEQ ID NO: 74 and SEQ ID NO: 96, or
SEQ ID NO: 76 and SEQ ID NO: 96.

In a more advantageous embodiment, the invention concerns expression vectors encoding for an AMPK construct selected from the group consisting in:
SEQ ID NO: 74, SEQ ID NO: 77 and SEQ ID NO 14,
SEQ ID NO: 81, SEQ ID NO: 88 and SEQ ID NO 14,
SEQ ID NO: 74, SEQ ID NO: 8 and SEQ ID NO 79,
SEQ ID NO: 81, SEQ ID NO: 8 and SEQ ID NO 92,
SEQ ID NO: 76, SEQ ID NO: 77 and SEQ ID NO 14,
SEQ ID NO: 83, SEQ ID NO: 88 and SEQ ID NO 14,
SEQ ID NO: 76, SEQ ID NO: 8 and SEQ ID NO 79,
SEQ ID NO: 83, SEQ ID NO: 8 and SEQ ID NO 92,
SEQ ID NO: 74, SEQ ID NO: 96 and SEQ ID NO 14, or
SEQ ID NO: 76, SEQ ID NO: 96 and SEQ ID NO 14.

The fluorescent signal can be detected either with recombinant heterotrimeric protein in vitro or with transfected AMPK tagged subunits in cells ex vivo. The signals can be used to screen AMPK interactors (in vitro or in cells ex vivo), or for quantification of cellular AMP and ADP levels in the physiologically important low micromolar range (in cells ex vivo).

In another aspect, the present invention deals with a method for identifying an interactor of AMPK or its concentration in a sample.

The present invention also concerns a method for identifying an AMPK allosteric interactor and/or its concentration in a sample comprising the steps of:
a. contacting the sample with an heterotrimeric AMPK construct as defined above or a host cell as defined above,
b. detecting a modification of the FRET fluorescence by fluorescence techniques.

In an advantageous embodiment, the in vitro method for identifying an interactor of AMPK comprises the steps of:
a. contacting an AMPK with a candidate interactor,
b. detecting the fluorescence signal by fluorescence techniques,
c. comparing the fluorescence signal with the fluorescence signal under the same conditions in the absence of said candidate allosteric interactor.

Within the context of the invention, a "candidate interactor" is intended to mean any natural or synthetic small molecule.

By comparing the fluorescence signal in the presence of the test compound with the fluorescence signal in the absence of the candidate allosteric interactor, it is possible to determine if said candidate allosteric interactor interacts with the AMPK.

A FRET signal indicates that the candidate allosteric interactor activates AMPK. The absence of the FRET signal indicates that the candidate allosteric interactor does not activate AMPK.

The in vitro method described above may also be used for quantifying the concentration of an allosteric interactor in a sample. The intensity of the FRET signal measured by fluorescence techniques being proportional to the concentration of the allosteric interactor in the sample, comparing the intensity of the FRET signal with values of the fluorescence intensity determined under the same conditions with determined concentrations of the allosteric interactor, one can thereby determine the concentration of the allosteric interactor in the sample.

For example, the fluorescence intensity of the sample of unknown concentration in an allosteric interactor may be compared with a calibration curve established with samples of predetermined concentrations in said allosteric interactor.

A further aspect of the invention relates to an ex vivo method of screening an AMPK interactor, the method comprising:
  providing a cell culture comprising cells expressing the heterotrimeric AMPK of the invention;
  providing candidate interactor;
  contacting the cells with said candidate interactor and detecting a modification of the fluorescence by fluorescent techniques and more particularly detecting a FRET signal.

If an AMPK candidate interactor results in the detection of a FRET signal, either in vitro upon contact with the AMPK construct or ex vivo with a cell culture comprising cells expressing the heterotrimeric AMPK construct, then said AMPK candidate interactor can be considered an AMPK allosteric activator. Conversely, an allosteric interactor resulting in a decline of the FRET signal of the AMPK construct activated for example with AMP or ADP, can be considered an allosteric inhibitor of AMPK.

The present invention also deals with a kit for identifying the presence of an interactor of AMPK in a sample, the kit comprising a trimeric AMPK as defined above or a microarray of the invention, the reagents and instructions for use.

The present invention also deals with a kit for transfecting a cell or cell population, comprising the nucleic acid molecule encoding the trimeric AMPK and the fluorescent dye pair, the reagents and instructions for use.

Within the meaning of the invention, the allosteric interactor is a compound that interacts with the heterotrimeric AMPK leading to a conformational change that can be detected and/or measured. Said interactor can be either an inhibitor or an activator of the AMPK. Examples of already known direct activators are A-769662 or the AICAR (5'-Aminoimidazole-4-carboxamide ribonucleoside)-derivative ZMP.

In a specific embodiment of the invention, the FRET signal is used to identify an interactor of AMPK. Within a cell, the FRET signal corresponds to a physiological increase in AMP and ADP concentrations, and can thus be used as a direct readout of the cellular energy state.

The present invention further deals with the use of the AMPK construct defined above for the detection of conformational changes within AMPK.

Upon activation of the AMPK construct by an allosteric activator, such as AMP, the induced faint conformational changes are translated into a FRET signal.

The AMPK constructs according to the invention are particularly valuable, in that the FRET signal only reflects allosteric activation of the AMPK construct and not activation by other pathways, such as Thr172 phosphorylation.

In the sense of the present invention, allosteric activation is the regulation of enzymatic activity by binding of an effector molecule, such as adenine nucleotides or synthetic activators at a site different to the enzyme's active site. Known regulatory sites are located on the gamma subunit and at the alpha/beta interface.

In the sense of the present invention, the "conformational changes" are considered faint, as they lie at the detection limits of other techniques such as small angle X-ray scattering. Previous studies have shown that the difference in radius of gyration and the particle volume of the whole heterotrimer is of less than 5% between the inactive form (no nucleotide) and the active form (AMP-bound) with no change in maximal intramolecular distance, indicating minimal changes in the structure.

The liability of the AMPK construct to translate allosteric activation of AMPK into a FRET signal (or the deactivation of AMPK into fluorescence quenching) can hence be used for the identification of an allosteric interactor of AMPK.

The present invention also concerns a method for detecting conformational changes within AMPK, comprising measuring a FRET signal.

The present invention also concerns a method for identifying an allosteric interactor of AMPK comprising detecting conformational changes within AMPK by fluorescence technique, in particular FRET.

AMPK being involved in several pathologies, the present invention also concerns the use of an AMPK construct as described above for the identification of a drug useful for the treatment of metabolic syndrome, type 2 diabetes, neurodegenerative disorders, fibrosis, osteoporosis, heart failure and proliferative diseases such as cancer.

Most pathologies are associated with bioenergetic dysfunction, mostly concerning mitochondrial ATP production, whether this is part of the etiology of the disease or just one of its consequences. These pathologies include, but are not limited to cardiovascular diseases, metabolic syndrome, (neuro)muscular diseases, neurodegenerative diseases, and specific forms and stages of cancer development. Bioenergetic dysfunction is buffered to a certain degree, but beyond a threshold, it leads to decreased cellular energy state, i.e. decreased ATP and increased ADP and AMP concentrations. Exactly these early changes in AMP and ADP concentration that occur in the lower micromolar concentration range, are detected by AMPK via conformational changes, leading to kinase activation that triggers compensatory adaptations of metabolism. Thus, AMPfret can detect very early a potential onset of a pathological development.

The present invention therefore also concerns the use of an AMPK construct as defined above for detecting a pathological development, including, but not limited to, cardiovascular diseases, metabolic syndrome, (neuro)muscular diseases, neurodegenerative diseases, and specific forms and stages of cancer development.

Whether the AMPK construct is used for the detection of conformational changes within AMPK construct or the identification of the interactor of AMPK, change in fluorescence resonance energy transfer or in fluorescence quenching is measured.

By transfecting a cell with the AMPK constructs according to the invention, it is possible to obtain a real-time readout of the cellular energy state. In a cell in which the energy reserves are depleted, i.e. in which the concentration in AMP and ADP is high, this will result in an increase in fluorescence resonance energy transfer. Conversely, when the energy reserves of the cell increases, the fluorescence resonance energy transfer signal decreases (fluorescence decline).

The AMPK constructs according to the present invention may therefore be used to study the events occurring when a cell is subjected to an external stress, for example deprivation of oxygen or oxidative stress.

In a further embodiment, said AMPK constructs according to the present invention may be transfected in a pathological cell for assessing the effect of a candidate compound on the cell.

The present invention therefore also concerns the use of a pathological cell culture comprising cells expressing the heterotrimeric AMPK of the invention for screening a drug liable of treating said pathological cell.

The present invention also concerns an ex vivo method of screening a drug candidate against a pathology associated with AMPK, the method comprising:
- providing a pathological cell culture comprising cells expressing the heterotrimeric AMPK of the invention;
- providing candidate drug;
- contacting the cells with said candidate drug and
- detecting a modification of the fluorescence by fluorescent techniques and more particularly detecting a FRET signal.

The FRET signal observed with a pathological cell differs from the one of a healthy cell. By comparing the FRET signal of the pathological cell incubated with a candidate drug with the one of the healthy cell, one can determine if said candidate drug is liable to restore the normal functions of the cell and if said candidate drug is useful for treating and/or preventing said pathology.

The expression vectors, subunits and fluorophores according to the present invention are described thereafter:

| Nucleic acid | Protein | Description |
|---|---|---|
| | SEQ ID NO: 1 | EEEEKKKK, rigid α-helix |
| SEQ ID NO: 2 | SEQ ID NO: 3 | Rat α2 subunit |
| SEQ ID NO: 4 | SEQ ID NO: 5 | Rat α2 subunit tagged with eCFP at its C-terminus |
| SEQ ID NO: 6 | SEQ ID NO: 7 | Rat α2 subunit tagged with eCFP at its N-terminus |
| SEQ ID NO: 8 | SEQ ID NO: 9 | Human β2 subunit |
| SEQ ID NO: 10 | SEQ ID NO: 11 | Human β2 subunit tagged with YFP at its C-terminus |
| SEQ ID NO: 12 | SEQ ID NO: 13 | Human β2 subunit tagged with YFP at its N-terminus |
| SEQ ID NO: 14 | SEQ ID NO: 15 | Rat γ1 subunit |
| SEQ ID NO: 16 | SEQ ID NO: 17 | Rat γ1 subunit tagged with eCFP at its C-terminus |
| SEQ ID NO: 18 | SEQ ID NO: 19 | Rat γ1 subunit tagged with eCFP at its N-terminus |
| SEQ ID NO: 20 | SEQ ID NO: 21 | Rat γ1 subunit tagged with YFP at its C-terminus |
| SEQ ID NO: 22 | SEQ ID NO: 23 | Rat γ1 subunit tagged with YFP at its N-terminus |
| SEQ ID NO: 24 | SEQ ID NO: 25 | Rat α2 subunit tagged with eCFP at its C-terminus, threonine 172 replaced by alanine |
| SEQ ID NO: 26 | SEQ ID NO: 27 | Rat α2 subunit tagged with eCFP at its C-terminus, threonine 172 replaced by aspartic acid |
| SEQ ID NO: 28 | SEQ ID NO: 29 | Rat γ1 subunit, leucine 128 and valine 129 replaced by aspartic acid residues |
| SEQ ID NO: 30 | SEQ ID NO: 31 | Rat γ1 subunit, serine 315 replaced by proline |
| SEQ ID NO: 32 | SEQ ID NO: 33 | Rat γ1 subunit, valine 275 and leucine 276 replaced by glycine residues. Negative control |
| SEQ ID NO: 34 | SEQ ID NO: 35 | Rat γ1 subunit tagged with YFP at its C-terminus, leucine 128 and valine 129 replaced by aspartic acid residues |
| SEQ ID NO: 36 | SEQ ID NO: 37 | Rat γ1 subunit tagged with YFP at its C-terminus, valine 275 and leucine 276 replaced by glycine residues. Negative control |
| SEQ ID NO: 38 | SEQ ID NO: 39 | Rat γ1 subunit tagged with YFP at its C-terminus, serine 315 replaced by proline |
| SEQ ID NO: 40 | SEQ ID NO: 41 | Rat γ1 subunit, T7 vector |
| SEQ ID NO: 42 | SEQ ID NO: 43 | Rat γ1 subunit tagged with eCFP at its C-terminus, T7 vector |
| SEQ ID NO: 44 | SEQ ID NO: 45 | Rat γ1 subunit tagged with eCFP at its N-terminus, T7 vector |
| SEQ ID NO: 46 | SEQ ID NO: 47 | Rat γ1 subunit tagged with YFP at its C-terminus, T7 vector |
| SEQ ID NO: 48 | SEQ ID NO: 49 | Rat γ1 subunit tagged with YFP at its N-terminus, T7 vector |
| SEQ ID NO: 50 | SEQ ID NO: 51 | eYFP |
| SEQ ID NO: 52 | SEQ ID NO: 53 | eCFP |
| SEQ ID NO: 54 | SEQ ID NO: 55 | cpVenus |
| SEQ ID NO: 56 | SEQ ID NO: 57 | Human β2 subunit tagged with cpVenus at its C-terminus |
| SEQ ID NO: 58 | SEQ ID NO: 59 | Human β2 subunit tagged with cpVenus at its N-terminus |
| SEQ ID NO: 60 | SEQ ID NO: 61 | Rat γ1 subunit tagged with cpVenus at its C-terminus |
| SEQ ID NO: 62 | SEQ ID NO: 63 | Rat γ1 subunit tagged with cpVenus at its N-terminus |
| SEQ ID NO: 64 | SEQ ID NO: 65 | Rat α2 subunit tagged with mseCFPΔ11 at its C-terminus |
| SEQ ID NO: 66 | SEQ ID NO: 67 | mseCFPΔ11 |
| SEQ ID NO: 68 | SEQ ID NO: 69 | Rat α2 subunit tagged with mseCFPΔ11 at its N-terminus |
| SEQ ID NO: 70 | SEQ ID NO: 71 | Rat γ1 subunit tagged with mseCFPΔ11 at its C-terminus |
| SEQ ID NO: 72 | SEQ ID NO: 73 | Rat γ1 subunit tagged with mseCFPΔ11 at its N-terminus |
| SEQ ID NO: 74 | SEQ ID NO: 75 | Rat α2 subunit tagged with eCFP at its C-terminus, C-terminal AR residues deleted |
| SEQ ID NO: 77 | SEQ ID NO: 78 | Human β2 subunit tagged with YFP at its C-terminus, C-terminal KPI residues deleted |
| SEQ ID NO: 79 | SEQ ID NO: 80 | Rat γ1 subunit tagged with YFP at its C-terminus, C-terminal LTGGEKKP residues deleted |
| SEQ ID NO: 81 | SEQ ID NO: 82 | Rat α2 subunit tagged with mseCFPΔ11 at its C-terminus, C-terminal AR residues deleted |
| SEQ ID NO: 76 | SEQ ID NO: 85 | Rat α2 subunit-EEEEKKKK helix at its C-terminus, C-terminal AR residues deleted, tagged with eCFP with MVSK N-terminal residues deleted |
| SEQ ID NO: 83 | SEQ ID NO: 84 | Rat α2 subunit EEEEKKKK helix at its C-terminus, C-terminal AR residues deleted, tagged with mseCFPΔ11 with MVSK N-terminal residues deleted |
| SEQ ID NO: 86 | SEQ ID NO: 87 | Human β2 subunit, pMDK vector |
| SEQ ID NO: 88 | SEQ ID NO: 89 | Human β2 subunit tagged with cpVenus at its C-terminus, C-terminal KPI residues deleted |
| SEQ ID NO: 90 | SEQ ID NO: 91 | Rat γ1 subunit, pMDS vector |
| SEQ ID NO: 92 | SEQ ID NO: 93 | Rat γ1 subunit tagged with cpVenus at its C-terminus, C-terminal LTGGEKKP residues deleted |
| SEQ ID NO: 94 | SEQ ID NO: 95 | Rat γ1 subunit, valine 275 and leucine 276 replaced by glycine residues V275G + L276G. Negative control |
| SEQ ID NO: 96 | SEQ ID NO: 97 | Human β1 subunit tagged with YFP at its C-terminus, C-terminal KPI residues deleted |
| SEQ ID NO: 98 | SEQ ID NO: 99 | Human β1 subunit |

The present invention further concerns the following embodiments:

(a) A heterotrimeric AMP-activated protein Kinase (AMPK) comprising a fluorescent dye pair allowing detection and/or measurement of conformational changes within the AMPK complex.

(b) A heterotrimeric AMP-activated protein Kinase (AMPK) comprising a fluorescent dye pair allowing detection and/or measurement of conformational changes within the AMPK complex, allowing the detection and/or measurement of allosteric AMPK activation (c) The heterotrimeric AMPK as defined in embodiments (a) or (b), wherein the fluorescent dyes are chosen among Foerster transfer pairs, more particularly genetically encoded fluorescent proteins such as GFP and GFP derived proteins such as CFP/YFP, mseCFP$_{\Delta 11}$/cpVenus, or constructs thereof.

(d) A trimeric AMPK as defined in embodiments (a), (b) or (c) characterized in that it comprises an α-subunit, that is α1 or α2, a β-subunit that is either β1 or β2, and γ-subunit that is either γ1 or γ2 or γ3, or fragments thereof, two of the subunits being tagged with one of the fluorescent dyes.

(e) An AMPK as defined in embodiments (a), (b), (c) or (d) comprising α2, β2 and γ1 subunits, wherein the α2 subunit is tagged with CFP or mseCFP$_{A11}$ at the C-terminus and the β2 or the γ1 subunit is tagged with YFP or cpVenus at the C-terminus.

(f) A nucleic acid molecule encoding the trimeric AMPK as defined in embodiments (a) to (e).

(g) A vector comprising the nucleic acid molecule of embodiment (f).

(h) The vector of embodiment (h) which is an expression vector wherein the nucleic acid molecule of embodiment (h) is operatively linked to one or more control sequences allowing the expression in prokaryotic and/or eukaryotic hosts.

(i) A host containing at least one vector as defined in embodiments (g) or (h) or at least one nucleic acid molecule as defined in embodiment (f), the host being preferably a bacteria, an insect, fungal, plant or animal cell such as a mammalian cell and more preferably a human cell or human cell line.

(j) A method for identifying an AMPK allosteric interactor and/or its concentration in a sample comprising contacting the sample with AMPK as defined in anyone of embodiments (a) to (e) or a host cell as defined in embodiment (i) and detecting a modification of the fluorescence by fluorescent techniques such as FRET.

(k) An in vivo method of screening an AMPK allosteric interactor, the method comprising:
   providing a cell culture comprising cells expressing the trimeric AMPK as defined in anyone of embodiments (a) to (e);
   providing candidate allosteric interactors;
   contacting the cells with said candidate allosteric interactor; and
   detecting a modification of the fluorescence by fluorescent techniques such as FRET.

(l) Use of FRET signal to detect a conformational change of the AMPK as defined in anyone of embodiments (a) to (e).

(m) Use of FRET signal as defined in embodiment (l) to identify an allosteric interactor of the AMPK as defined in anyone of embodiments (a) to (e).

(n) Use of the AMPK as defined in anyone of embodiments (a) to (e) to quantify changes in cellular AMP and ADP levels.

(o) A kit for identifying the presence of an allosteric interactor of AMPK in a sample, the kit comprising a trimeric AMPK as defined in anyone of embodiments (a) to (e), the reagents and instructions for use.

AMPfret sensors are constructed from an AMPK heterotrimer (consisting of α-, β-, and γ-subunits) with two additional GFP-derived fluorescent proteins (CFP, YFP) fused to different N- and C-termini of AMPK subunits. Binding of AMP or ADP to two CBS domains in the AMPK γ-subunit induces a conformational change which reduces the distance between the fluorophore couple. This increases fluorescence (or Foerster) resonance energy transfer (FRET) between the two fluorophores. Experimentally, when CFP is excited at 439 nm, FRET reduces direct CFP fluorescence emission at 476 nm, while energy transferred to YFP increases YFP fluorescence emission at 527 nm.

Figure 1:
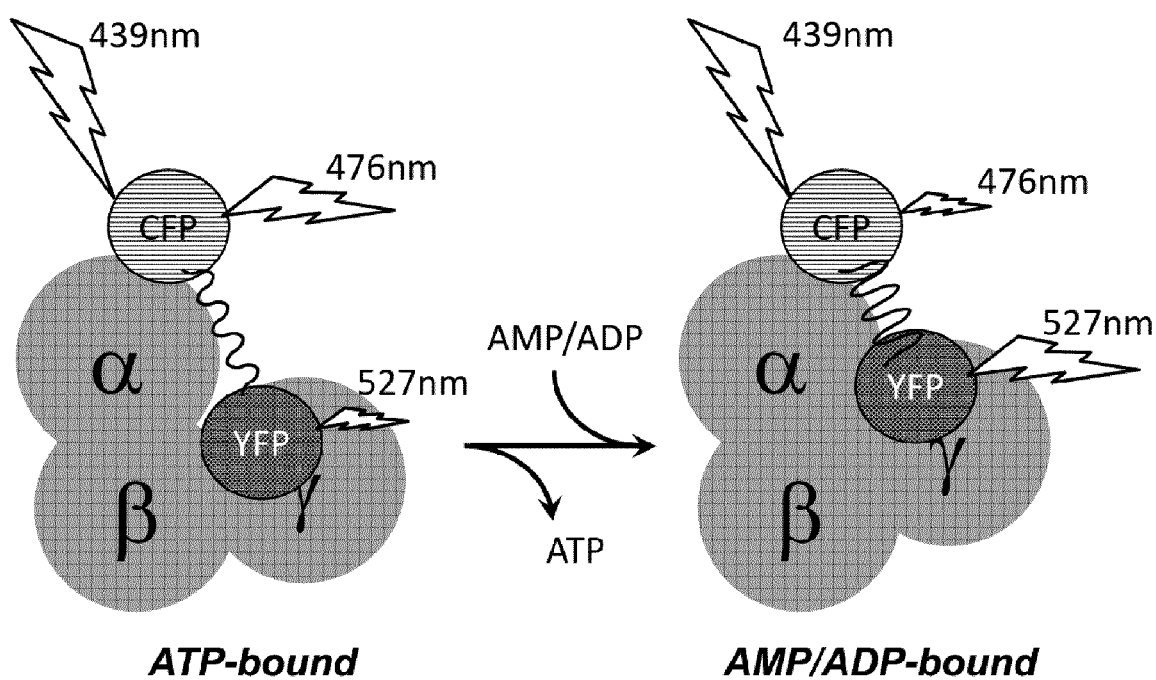
FIG. 1: Conformational change model showing operating mode of AMPfret sensors.
Figure 2:
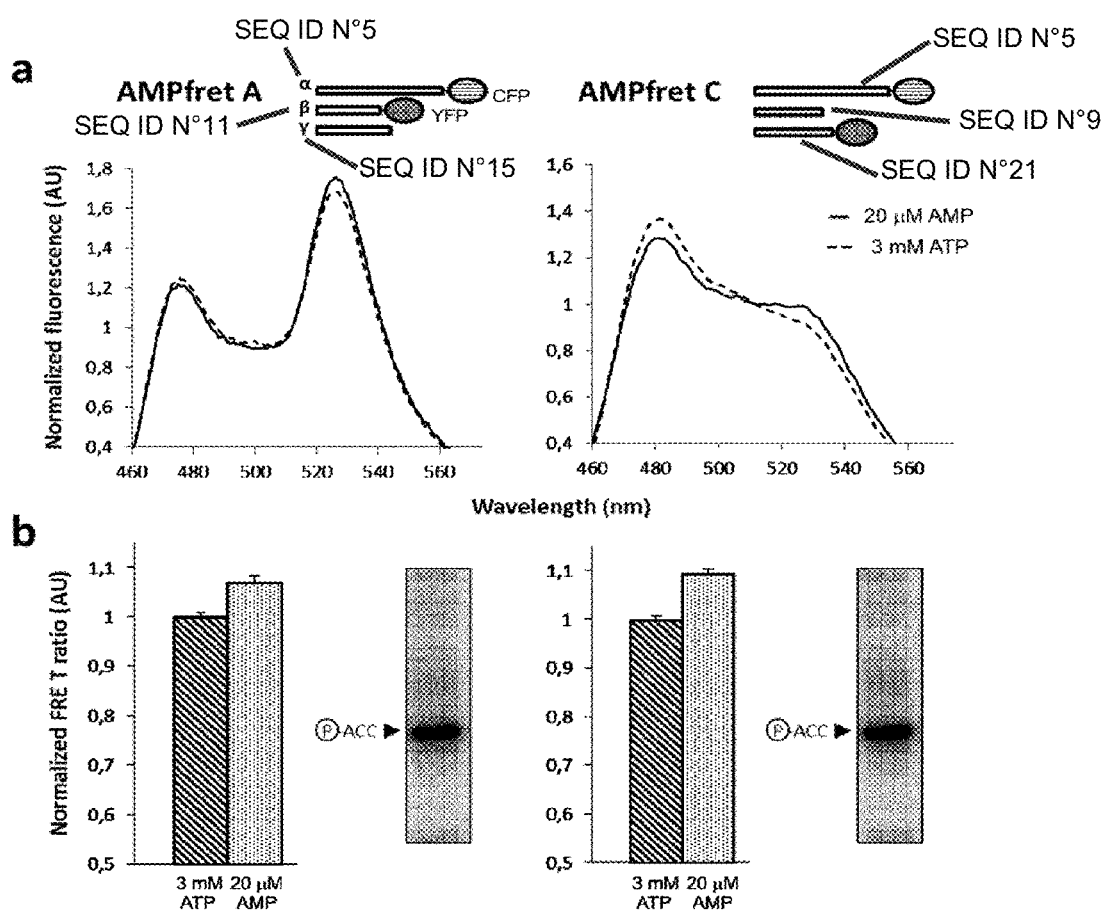

FIG. 2: Initial AMPfret constructs.

AMPfret A and C exhibit variation of FRET ratio upon AMP binding. Top: Schema showing structural organization of the sensors. CFP and YFP are respectively represented as hatched- and dotted-circles. (a) Fluorescence emission spectra of AMPfret constructs excited at 430 nm. Spectra show fluorescence peaks of CFP (476 nm) and YFP (527 nm), and their variation upon AMP binding (dotted line: 3 mM ATP, continuous line: 20 μM AMP). (b) FRET variation of AMPfret constructs calculated from data above (hatched column: 3 mM ATP, dotted column: 20 μM AMP) and autoradiograms of in vitro kinase activity assays with these constructs using acetyl-CoA carboxylase (ACC) as a substrate. Data correspond to mean±SEM (AMPfret A: n=7; AMPfret C: n=10). Note: AMPfret constructs exhibit similar activity as native AMPK.

Figure 3:
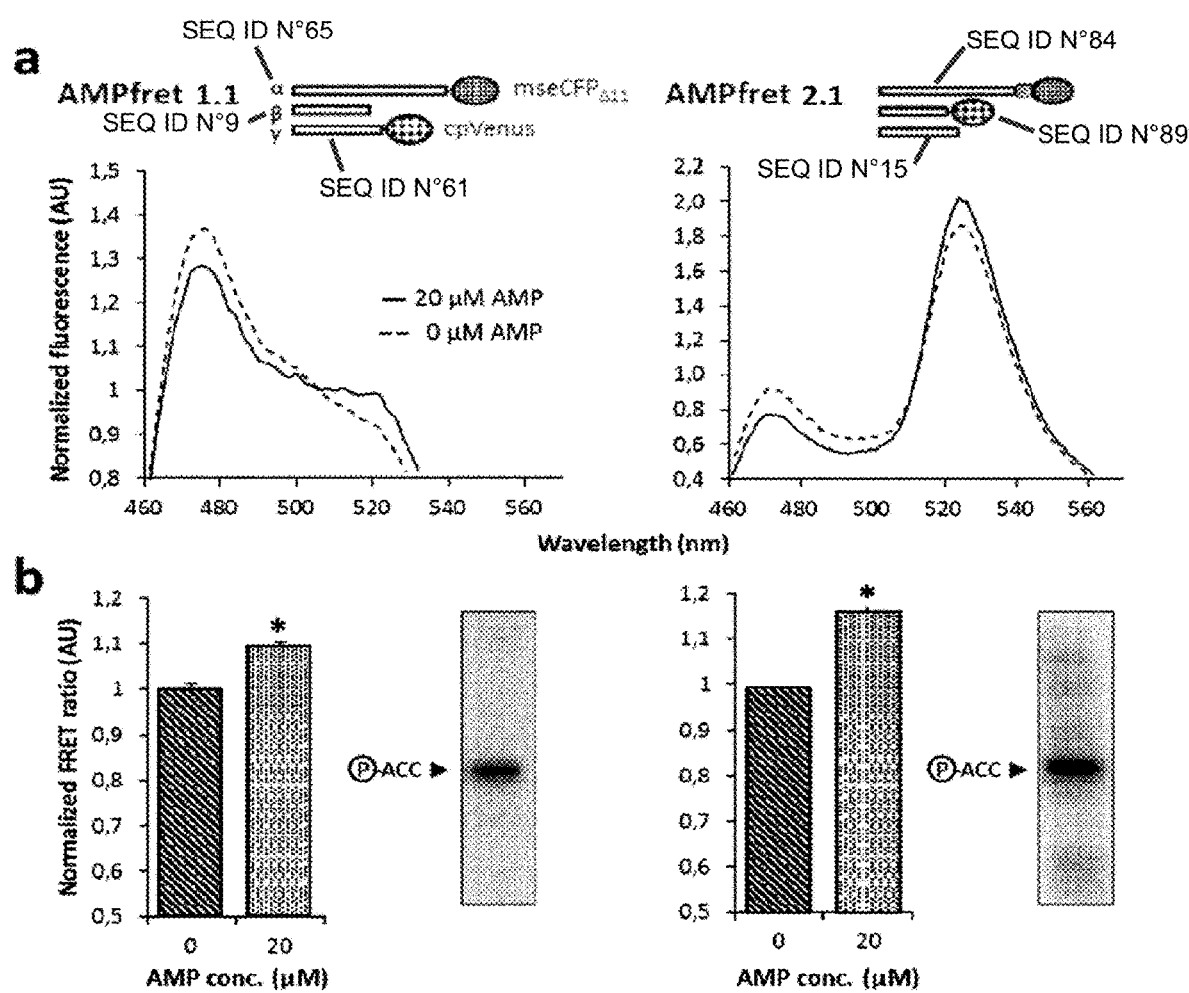

FIG. 3: Optimized AMPfret constructs.

Second generation of AMPfret constructs 1.1 and 2.1. based on constructs AMPfret C and A, respectively. Top: Schema showing structural organization of the sensors. Both optimized constructs contain mseCFP$_{A11}$/cpVenus as GFP-derived fluorescent couple instead of CFP/YFP. mseCFP$_{A11}$ and cpVenus are respectively represented as hatched- and checkered circles. AMPfret 2.1 α- and β-subunits also contain small deletions in their protein sequence to shorten C-terminal non-folded linker sequences ($A_{551}$ and $R_{552}$ in α and $K_{270}$, $P_{271}$ and $I_{272}$ in β). In addition, a putatively rigid helix (7 amino acids) was inserted between the α-subunit C-terminus and CFP (see small box with curled lines). (a) Fluorescence emission spectra of AMPfret constructs excited at 430 nm. Spectra show fluorescence peaks of mseCFP$_{A11}$ (476 nm) and cpVenus (527 nm), and their variation upon AMP binding (dotted line: no AMP, continuous line: 20 μM AMP). (b) FRET variation of AMPfret constructs calculated from data above (hatched column: no AMP, dotted column: 20 μM AMP) and autoradiograms of in vitro kinase activity assays with these constructs using acetyl-CoA carboxylase (ACC) as a substrate. Data correspond to mean±SEM (AMPfret 1.0: n=10; AMPfret 1.1: n=7); *=p<0.001 (significance assessed by a Student-Newman-Keuls test). Note: All AMPfret constructs exhibit similar activity as native AMPK. AMPfret 2.1 reveals improved FRET variation range as compared to AMPfret 1.1, providing proof of principle that optimization of FRET is possible.

Figure 4:
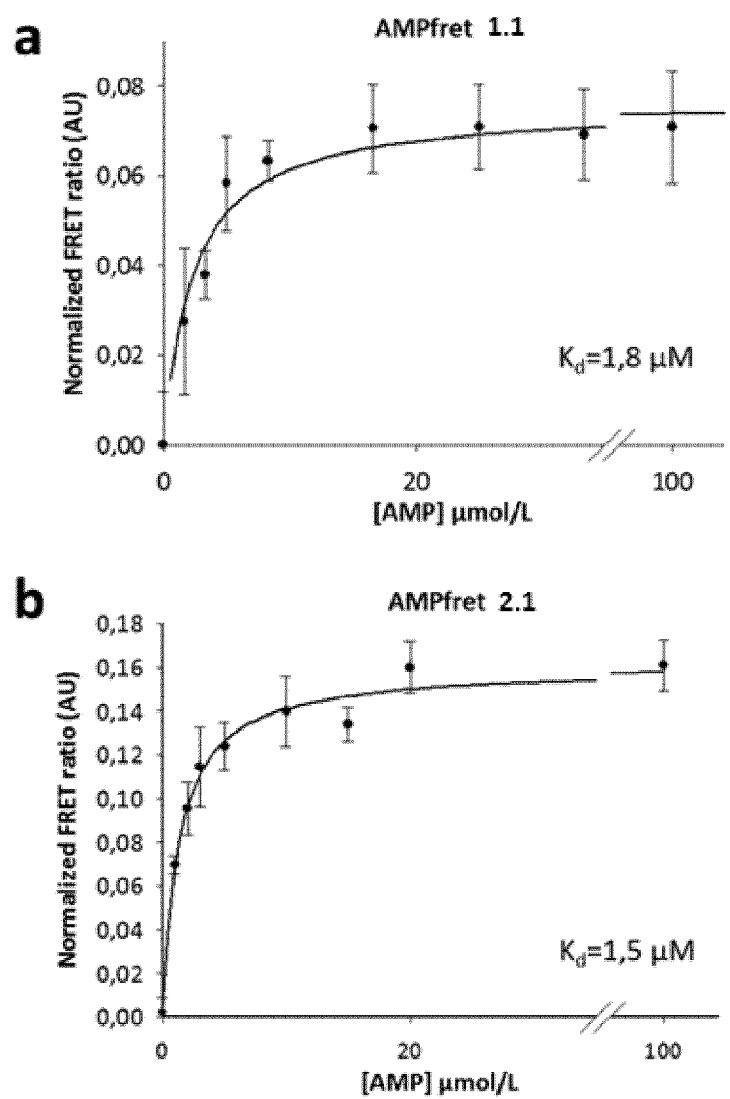

FIG. 4: FRET response of AMPfret sensors correlates with the concentration of AMPK activator AMP.

AMP concentration dependence of the normalized FRET ratio of AMPfret sensors (a) AMPfret 1.1 and (b) AMPfret 2.1. The FRET ratio was calculated from fluorescence emission spectra excited at 430 nm. Data points correspond to mean±SEM (n>3). Data were fitted with Sigma Plot 1.1 software to single site binding kinetics, yielding affinities of 1.8 μM (AMPfret 1.1) and 1.5 μM (AMPfret 2.1.). Note: AMPfret sensors are sensitive to AMP concentrations in a physiological range (0-20 μM)

Figure 5:
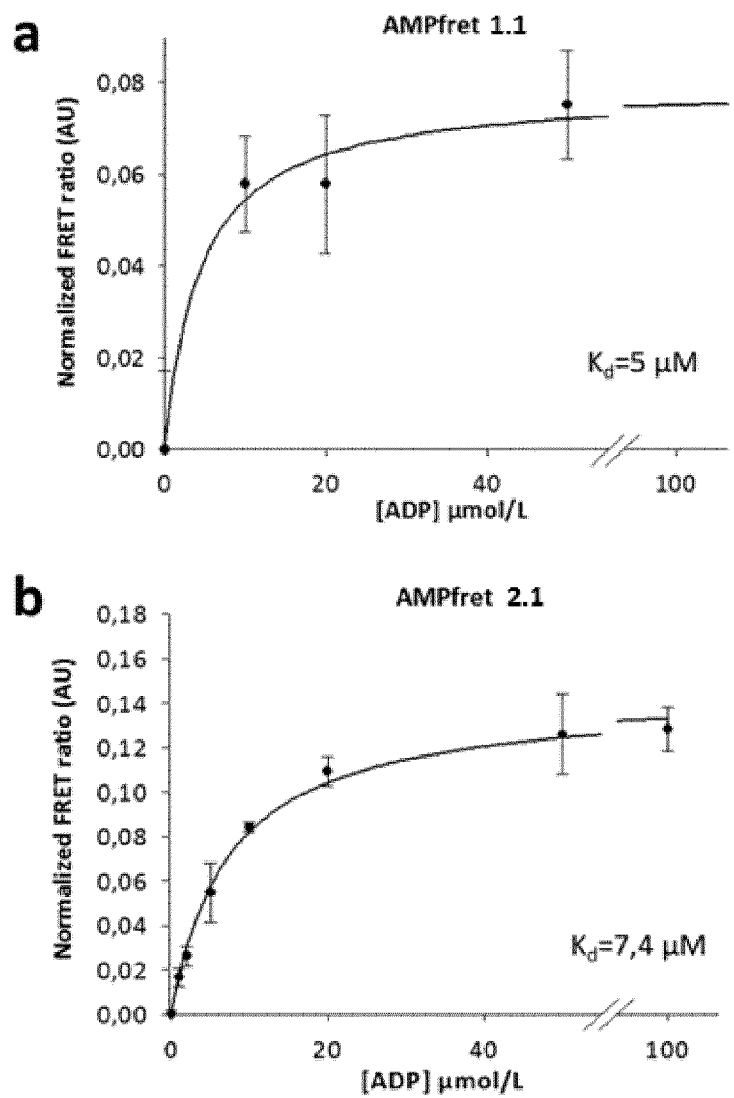

FIG. 5: FRET response of AMPfret sensors correlates with the concentration of AMPK activator ADP.

ADP concentration dependence of the normalized FRET ratio of AMPfret sensors (a) AMPfret 1.1 and (b) AMPfret 2.1. The FRET ratio was calculated from fluorescence emission spectra excited at 430 nm. Data points correspond to mean±SEM (n>3). Data were fitted with Sigma Plot 1.1 software to single site binding kinetics, yielding affinities of 5 μM (AMPfret 1.1) and 7.4 μM (AMPfret 2.1). Note:

AMPfret sensors are sensitive to ADP concentrations in a physiological range (0-50 µM for free ADP).

Figure 6:
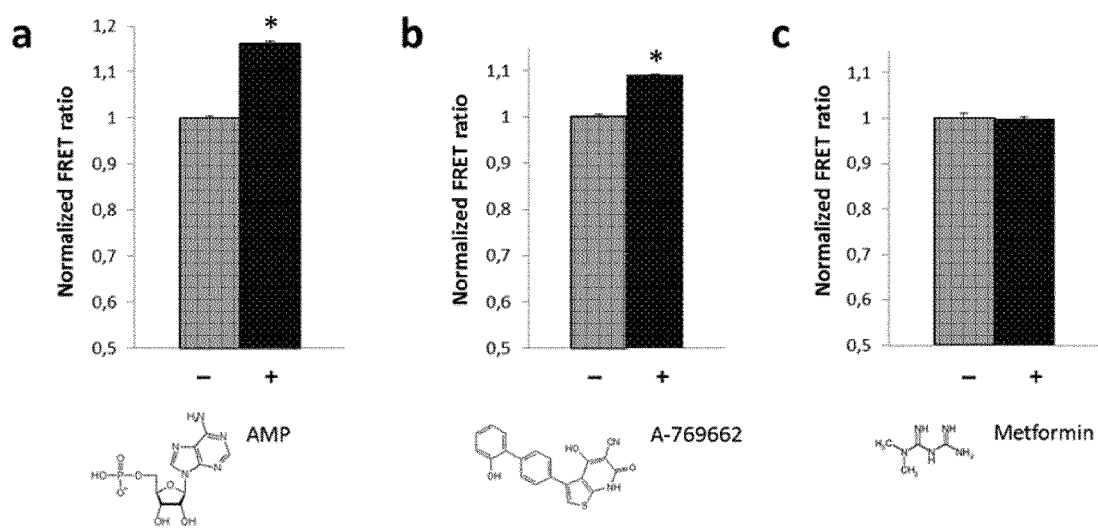

FIG. 6: AMPfret sensors as in vitro tools to identify AMPK allosteric activators.

AMPfret 2.1 is incubated in absence (grey mesh bars) or in presence (black bars) of (a) 20 µM AMP, (b) 50 µM A-769662 or (c) 500 µM Metformin. Structure and names of the molecules are given below the bars. Data correspond to mean±SEM (AMP: n=7; A-769662: n=4; Metformin: n=4); *=p<0.001 (significance assessed by paired T-test).

Figure 7:
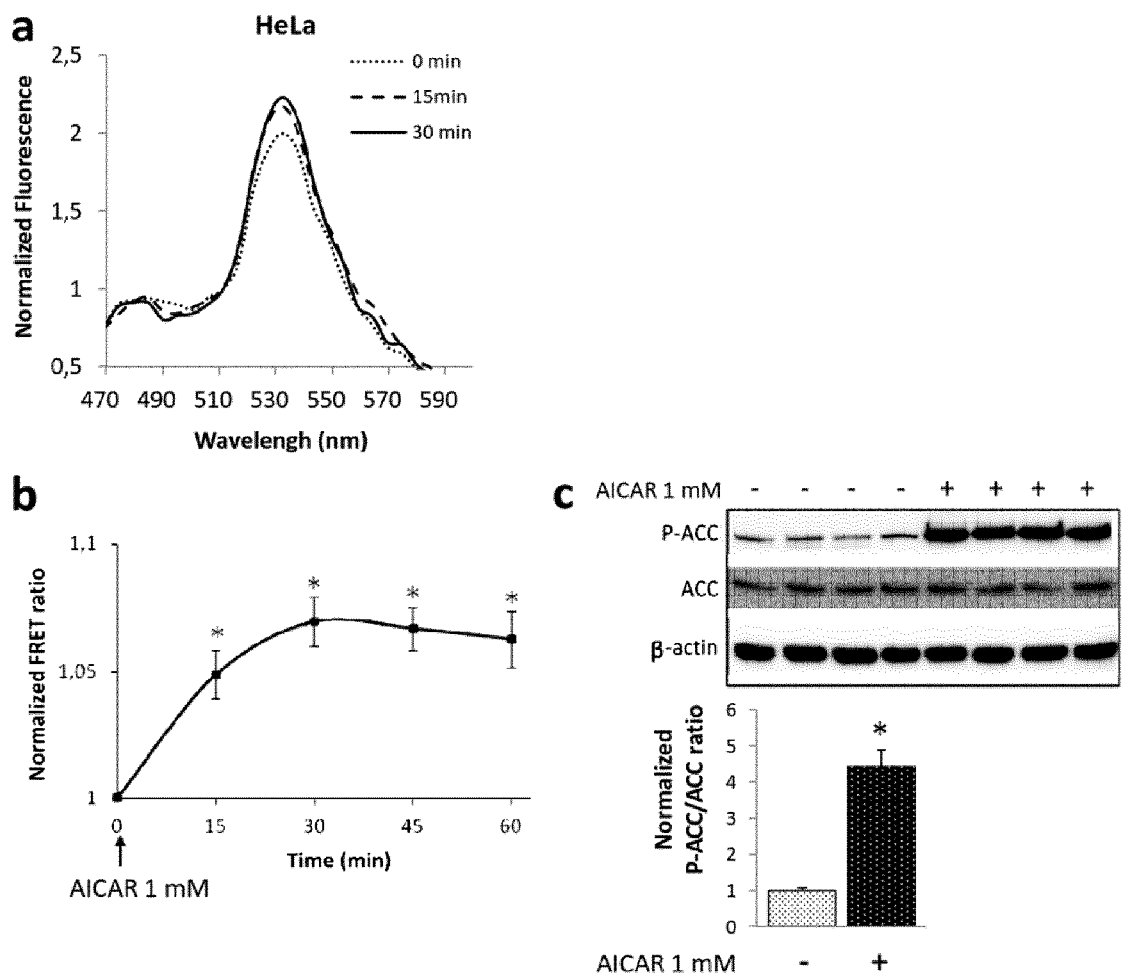

FIG. 7: AMPfret sensors as cellular in vivo tools to identify AMPK allosteric activators—HeLa cells HeLa cells transfected with AMPFret 2.1 were exposed for 60 min to 1 mM AICAR. (a) Fluorescence emission spectra showing the increase of cpVenus peak (527 nm) over time; dotted black line: 0 min; dashed black line: 15 min and solid black line: 30 min. (b) Time course of the FRET signal. Normalized FRET ratio determined each 15 minutes (mean±SEM; n=45; *=p<0.001 according to the performed Mann-Whitney Rank Sum Test). (c) AMPK activation at t=0 min and t=60 min. Phosphorylation of the AMPK substrate ACC as determined by immunoblotting (lower panel) and quantification of the resulting P-ACC/total ACC ratio (upper panel). P-ACC/total ACC ratios at t=0 and t=60 min are respectively represented as a white dotted bar and black dotted bar. Data correspond to mean±SEM (n=3).

Figure 8:
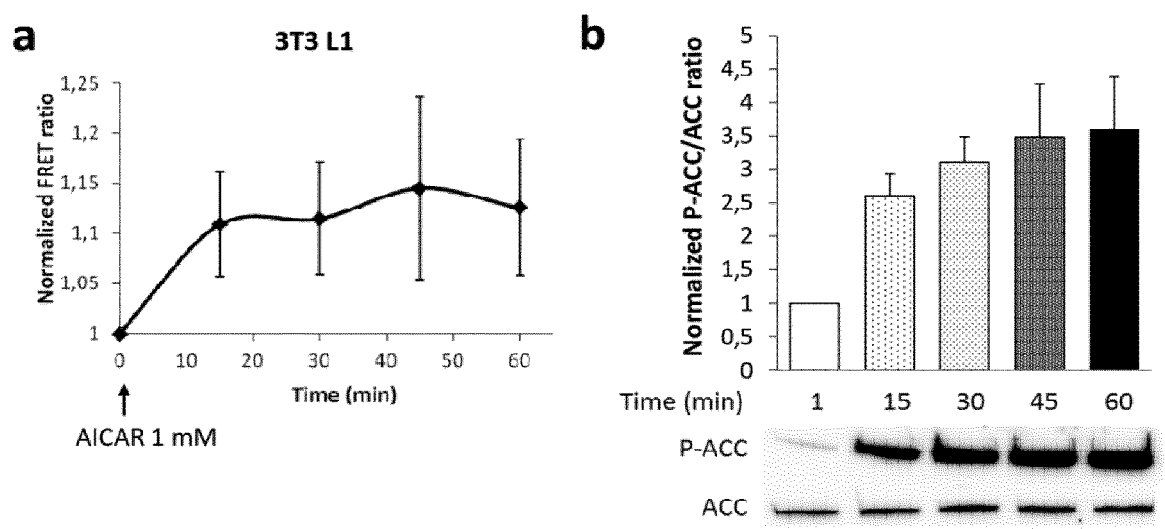

FIG. 8: AMPfret sensors as cellular in vivo tools to identify AMPK allosteric activators—3T3-L1 cells HeLa cells transfected with AMPfret 2.1 were exposed for 60 min to 1 mM AICAR. (a) Time course of the FRET signal. Normalized FRET ratio determined each 15 minutes (mean±SEM; n=9). (b) Time course of AMPK activation. Phosphorylation of the AMPK substrate ACC as determined by immunoblotting (lower panel) and quantification of the resulting P-ACC/total ACC ratio (upper panel). Data correspond to mean±SEM (n=3).

Figure 9:
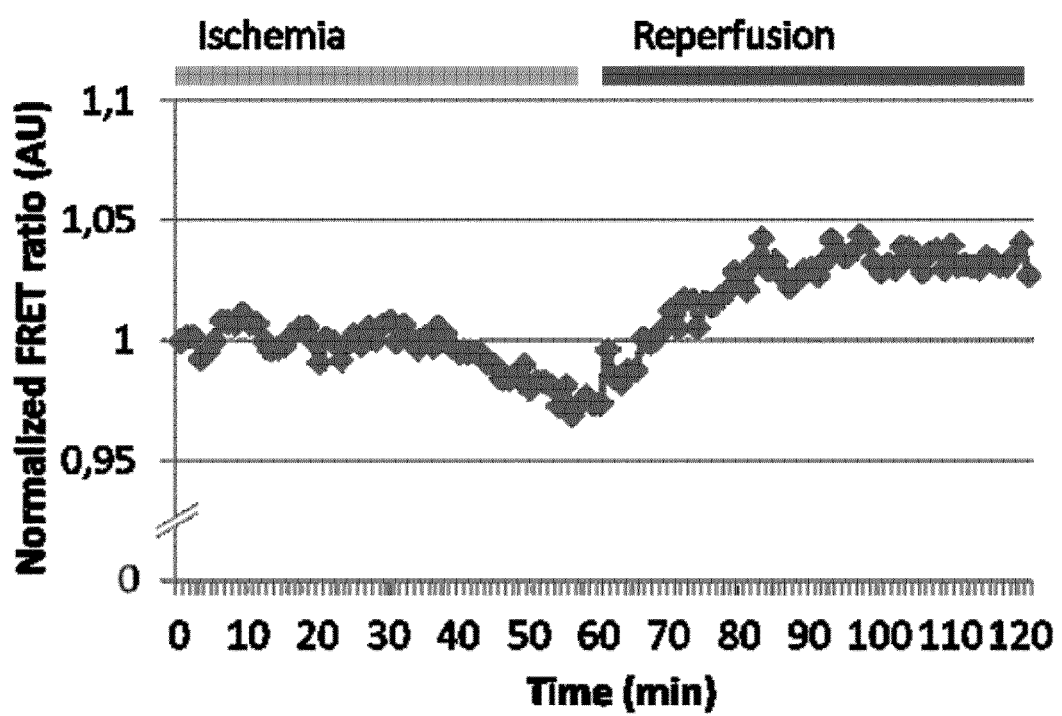

FIG. 9: Effect of 1 hour ischemia followed by 1 hour reperfusion on HepG2 cell followed by AMPfret.

AMPfret 2.1 normalized FRET ratio evolution during 1 h ischemia (light grey bar) and 1 h reperfusion (dark grey bar). Transfected HepG2 cells were cultured on a glass slide mountable onto the incubation flow-through chamber of our Leica TCS SP2 AOBS confocal microscope. At t=0, the cell was placed under ischemia-like conditions: hypoxic conditions (2% O2) and glucose-free medium at 37° C. Deprived medium was previously bubbled with N2 for at least 10 minutes before its addition onto the cells. After 1 hour of deprivation, started the 1 hour-reperfusion period with glucose-rich medium and 02 (21%). FRET values were record every minute from a single isolated cell using the Leica confocal software. The FRET ratio was followed by recording simultaneously mseCFPΔ11 (476 nm) and cpVenus (527 nm) fluorescence emitted within 4 nm windows using two independent channels, under excitation set at 458 nm. FRET ratio was normalized to 1 at t=0.

Figure 10:
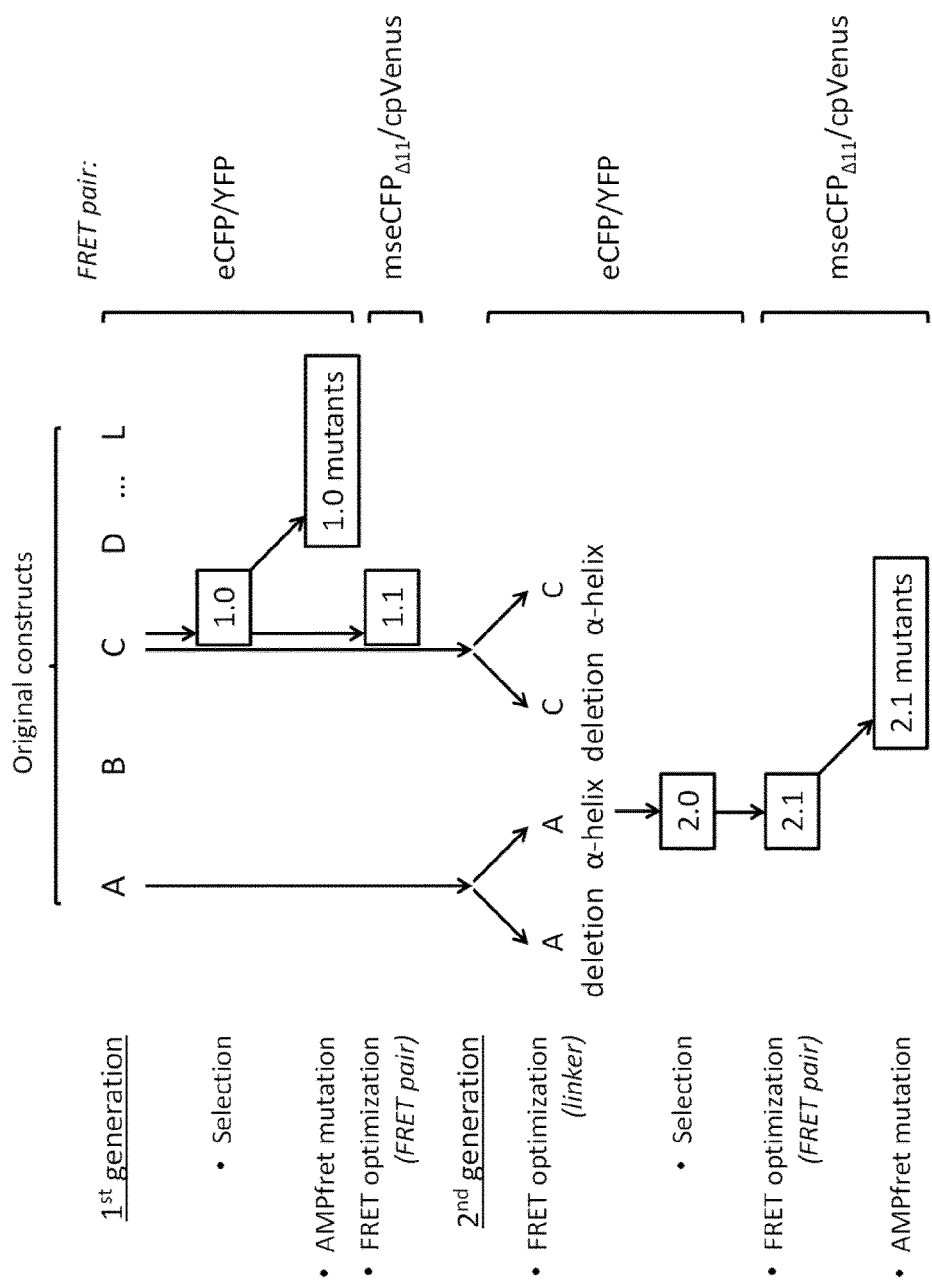

FIG. 10: Strategy for optimizing the AMPK sensors according to the present invention. Starting from the most promising original constructs, FRET signal was optimized by mutations, deletions and addition of sequences.

DETAILED DESCRIPTION

The compounds and processes of the present invention will be better understood in connection with the following examples, which are intended as an illustration only and not limiting of the scope of the invention Example 1: AMPK Constructs AMPK Constructs and Protein Preparation The $\alpha_2$, $\beta_2$ and $\gamma_1$ AMPK subunits tagged or not with fluorescent protein, were respectively cloned in the pACE, pDC and pDS vectors of the ACEMBL expression system (Bieniossek et al., Nat Meth 6:447, 2009) using SLIC (Li et al., Methods Mol Biol 852:51, 2012) and conventional cloning. Created vectors, containing a single subunit fluorescently tagged or not, were fused via their Lox-P site using the CRE-recombinase (EMBL Heidelberg): a single expression vector coding for a chimeric AMPK that contains two of its three subunits flanked with the mseCFP$_{A11}$/cpVenus fluorescent proteins pair (respectively variant of cyan fluorescent protein (CFP) and yellow fluorescent protein (YFP) at their termini was obtained. A decaHis-tap, cleavable by the TEV protease, was inserted at the N-terminus of the $\alpha_2$ subunit in order to purify easily the heterotrimer.

BL21 (DE3) Star cells were transformed by electroporation and protein expression was carried overnight at 18° C. in autoinducing medium. Cells were collected by centrifugation at 6000 rpm for 20 min using a Beckman Coulter centrifuge (rotor JLA-8.1000) and wash with PBS. Cells were then suspended in lysis buffer (0.5 M sucrose, 30% glycerol, 50 mM Tris pH8, 100 mM NaCl, 2 mM MgCl2, 2 mM β-mercaptoethanol, lysosyme 1 mg/mL, 20 mM imidazole, Complete EDTA free tablet (Roche), leupeptin, pepstatin). 200 U Benzonase were added to the suspension and it was gently stirred for 1 h in the cold room. Cells were then lysed by sonication using a MisonixSonicator 4000 (5 min total at 80%—20 s ON/1 min OFF).

Cell-free extract, obtained by centrifugation at 20'000 rpm for 80 min (rotor JS 25.50) was applied on Ni-NTA Superflow resin (Qiagen) pre-equilibrated with lysis buffer. Resin was washed using washing buffer (50 mM Tris pH 8, 100 mM NaCl, 20 mM imidazole, 2 mM MgCl2, 2 mM β-mercaptoethanol) and high salt buffer (wash buffer+1 M NaCl). Proteins were eluted by applying elution buffer (wash buffer+400 mM Imidazole). Imidazole was removed through a overnight dialysis in buffer A (50 mM Tris pH8, 100 mM NaCl, 2 mM MgCl2, 2 mM β-mercaptoethanol). Eluted proteins were passed over a 5 mL QXL column (GE Healthcare) in order to remove proteins bound to nucleic acids and non-stoichiometric AMPK complexes. Proteins were eluted using a gradient of buffer B (50 mM Tris pH8, 1 M NaCl, 2 mM MgCl2, 2 mM β-mercaptoethanol). Finally chimeric AMPK heterotrimers were applied to a Superose 6 gel filtration column (GE Healthcare) pre-equilibrated with SEC buffer (50 mM Tris pH8, 200 mM NaCl, 2 mM MgCl2, 2 mM β-mercaptoethanol, 5 mM spermidine). Spermidine diminished concentration dependent AMPK oligomer formation. After adding glycerol to a final concentration of 50%, the purified AMPK (untagged or AMPK 221WT) and AMPK heterotrimers of the invention (AMPK tagged hereafter AMPFret or AMPFret sensors) were stored at -20° C. for further experiments.

Finally, combinations of AMPK tagged with mseCFP$_{A11}$ and cpVenus on two of the termini of its 3 subunits were created in order to identify constructs that show FRET signal variation upon AMP binding (hereafter termed AMPFret).

TABLE 1

Overview of the AMPfret constructs containing two fluorescent permutated at the N- and C-termini of the three AMPK subunits. protein tags

| AM Pfret construct | Vector name and composition |
|---|---|
| AMPK 221 | pACEMBL $\alpha_2$-$\beta_2$-$\gamma_1$ |
| AMPfret A | pACEMBL $\alpha_2$-CFP-$\beta_2$-YFP-$\gamma_1$ |
| AMPfret C | pACEMBL $\alpha_2$-CFP-$\beta_2$-$\gamma_1$-YFP |

Abbreviations:
pACEMBL, plasmid resulting from the Cre-LoxP fusion of vectors pACE, pDC and pDS of the MutliColi expression system;
CFP, Cyan Fluorescent Protein;
YFP, Yellow Fluorescent Protein;
$\alpha 2$, $\beta 2$, $\gamma 1$, AMPK subunits.

AMPFret A is composed of rat alpha2-CFP (SEQ ID NO:5), human beta2-YFP (SEQ ID NO:11) and rat gamma1 (SEQ ID NO:15). AMPFret C is composed of rat alpha2-CFP (SEQ ID NO:5), human beta2 (SEQ ID NO:9) and rat gamma1-YFP (SEQ ID NO:21).

Characterization of AMPFret Sensors In Vitro

ATP containing buffers were always freshly prepared to limit AMP contamination. Aqueous solutions of nucleotides (adenine nucleotides, NAD) were analyzed by HPLC (stationary phase: Polaris C18/mobile phase: 60% $CH_3CN$ 40% $H_2O$) to evaluate spontaneous ATP and ADP hydrolysis and contaminations.

Enzymatic assay: AMPK 221WT and AMPfret constructs (3 pmol) were activated by incubation with purified CamKK$\beta$ (1 pmol) for 20 min at 30° C. in kinase buffer (200 µM ATP, 40 µM AMP, 5 mM $MgCl_2$, 1 mM DTT and 10 mM Hepes pH 7.4). Purified ACC fragment targeted by AMPK (200 pmol) was then incubated for 20 min at 37° C. in presence or absence of pre-activated AMPK 221WT or AMPFret sensor in kinase buffer containing [$\gamma$-$^{32}$P]ATP. Reaction mixtures were then load on SDS-PAGE gel, P-ACC signals were revealed using a Typhoon and activities were evaluated with ImageJ.

FRET assay: FRET signal variation in presence of different compounds (nucleotides, chemicals, ions) was measured using a fluorimeter (Photon Technology International). AMPfret constructs (20 pmol) were incubated in a quartz cuvette in a final volume of 150 µL (spectro buffer: 50 mM Tris pH8, 200 mM NaCl, 5 mM $MgCl_2$, 2 mM $\beta$-mercaptoethanol). Effects of nucleotides and others compounds (previously prepared in the spectro buffer) on the FRET ratio given by AMPfret sensor was determined by comparing FRET ratio (peak value at 527 nm/peak value at 476 nm) in presence or absence of the compounds. Excitation wavelength was set to 430 nm, and emission spectra were recorded from 450 to 600 nm with an integration time of 0.2 s. $Mg^{2+}$ effect on FRET was investigated in spectro buffer without $Mg^{2+}$.

The two constructs, AMPFret A ($\alpha_2$-CFP-$\beta_2$-YFP-$\gamma_1$; CFP tagged at the $\alpha 2$ C-terminus, and YFP at the $\beta 1$ C-terminus) and AMPFret C ($\alpha_2$-CFP-$\beta_2$-$\gamma_1$-YFP; CFP tagged at the $\alpha 2$ C-terminus, and YFP at the $\gamma 1$ C-terminus) showed both a significant difference in their FRET signal (~10%) depending on the presence of AMP or ADP (FIG. 2). It appears that, during allosteric activation, the $\alpha$-subunit C-terminus approaches the C-termini of the $\beta$- and $\gamma$-subunits.

Example 2: Optimized AMPK Constructs

Constructs were optimized to achieve a superior FRET signal amplitude. The construct AMPfret 1.1 is based on AMPfret C, containing full length AMPK subunits $\alpha 2$, $\beta 2$ and $\gamma 1$. The $\alpha$-subunit is tagged with mseCFP$\Delta 11$ at its C-terminus and the $\gamma$-subunit is tagged at its C-terminus with cpVenus; the $\beta$-subunit remains untagged. The construct AMPfret 2.1 is based on AMPfret A, where CFP/YFP were exchanged for the same different fluorophore pair as AMPfret 1.1. In addition, the sequence of the construct was modified. First, small truncations based on the crystal structure (PDB 2Y94) and secondary structure prediction (nps@consensus (ucbl)) were inserted via PCR and "self SLIC" between the N-terminus of fluorescent protein tags and the C-terminus of the tagged AMPK subunits. Such shortening of the sequence between AMPK core and tag may remove flexibility other than the conformational change induced by AMP. Second, a short insert supposed to fold into a rigid $\alpha$-helix (Sivaramakrishnan et al., PNAS 105:13356, 2008 and 108:20467, 2011) was inserted between the $\alpha 2$ C-terminus and the CFP N-terminus to rigidify the AMPK backbone of the invention and to stabilize the CFP tag in a given position relative to AMPK.

This engineering comprised the following mutations. The last 2 C-terminal amino acids (AR) of $\alpha 2$ and the first 3 N-terminal amino acids (MSK) of mseCFP$\Delta 11$ were removed and the new termini linked via 8 amino acids insert supposed to fold into an $\alpha$-helix (EEEEKKKK, SEQ ID No.1). Further, the last C-terminal (non-folded) 3 amino acids (KPI) of $\beta 2$ were also removed, and directly fused to the N-terminus of YFP. Since 2 amino acids resulting from the restriction site previously used were also removed by the SLIC technique, this yielded a construct lacking in total 5 amino acids between the $\beta 2$-subunit and YFP. The optimized AMPfret sensor showed an almost 100% increased FRET ratio (FIG. 3).

AMPFret 1.1 includes the alpha subunit of SEQ ID NO:65, the beta subunit of SEQ ID NO:9 and the gamma subunit of SEQ ID NO:61. AMPFret 2.1 includes the alpha subunit of SEQ ID NO:84, the beta subunit of SEQ ID NO:89 and the gamma subunit of SEQ ID NO:15.

The optimized AMPfret sensors allow titration of the allosteric AMPK-activators AMP and ADP, confirming that both induce conformational changes in the AMPK heterotrimer. The affinity (Kd) for AMP and ADP could be determined as 1.5 µM and 7.4 µM, respectively.

The AMPfret sensors thus represent a pioneering powerful and easy-to-use tool to decipher the activation mechanisms of AMPK. They contain full length AMPK heterotrimer that behaves the same way as native AMPK WT as judged by (i) its kinase activity after phosphorylation via CamKK$\beta$ and allosteric activation by AMP and (ii) its affinities for adenine nucleotides. The AMPfret FRET signal is directly dependent of the AMP concentration; in a physiological range (1-10 µM) it shows almost linear relationship (FIGS. 4 and 5).

Example 3: In Vitro Interaction of Optimized AMPfret with Allosteric Activators

The optimized AMPfret sensors not only translate the adenylate-dependent movements of the AMPK heterotrimer into a FRET signal, which are triggered by adenylate binding to specific sites at the $\gamma$-subunit. Their readout also reports conformational changes of other, pharmacological direct AMPK activators such as the compound A-769662 (FIG. 6). This molecule interacts with the $\beta$-subunit, but clearly induces a FRET signal comparable to AMP, even if the triggering conformational change may be of different nature according the different binding mode.

Metformin, a widely used anti-diabetes drug, which was postulated to directly interact with γ-subunit (Zhang et al., Mol Cell Biochem 368:69, 2012) did not induce any FRET variation emission of AMPfret (FIG. 6). This absence of conformational changes in vitro supports the generally accepted indirect mode of action, whereby this drug inhibits mitochondrial respiration and increases the AMP/ATP ratio, thus activating AMPK by the canonical AMP binding mechanism at the γ-subunit.

Taken together, AMPfret appears as a valuable and accurate tool for in vitro applications, notably screening for AMPK interactors.

Example 4: Ex Vivo Experiments with the Optimized AMPfret Constructs

For cellular ex vivo experiments, subunits of the optimized construct AMPfret 2.1 were cloned in the vectors (pACEMam2, pMDS and pMDK) of the MultiMam expression system. Created plasmids were fused via their Lox-P site to yield to a single mammalian expression vector coding for the sensor AMPFret 2.1 according to well-known techniques to the skilled man in the art.

3T3-L1 and HeLa cells were cultivated in glucose containing DMEM (4.5 g/L) supplemented with SVF, glutamine, penicillin and streptomycin. Once cells reached around 80% confluence, medium was replaced by OptiMEM (Lifetechnologies) and AMPfret 2.1 coding plasmid was transfected using Lipofectamine2000 (Lifetechnologies). After 5 h, OptiMEM was exchanged by complete DMEM and cells grew for >36 h until their observations under the confocal microscope.

3T3-L1 or HeLa cells, cultivated in 8 wells LabTek cover glass plates (Nunc), were observed with a Leica TCS SP2 AOBS confocal microscope. LabTek plates were placed in an incubation chamber in which the temperature and $O_2$ concentration were maintained at 37° C. and 21%, respectively. Without moving the Labtek, 200 µL medium was replaced by the same volume of complete medium containing 2 mM AICAR (1 mM final). Excitation wavelength was set to 458 nm and emission spectra showing FRET signal were monitored through λ scans from 463 nm to 600 nm every 15 min. ROI (region of interest) were drawn in order to cover entire cells. FRET ratio variations were calculated from those measured emission spectra.

Under the microscope, cells were treated with 1 mM AICAR (AMPK allosteric activator) to visualize the allosteric activation of AMPK through the FRET signal of AMPfret 2.1 and hence validate its use for ex vivo applications.

AMPfret 2.1 was excited using a 458 nm laser and emission spectra showing FRET signal were monitored through λ scans from 463 nm to 600 nm every 15 min. The AMPfret 2.1 FRET signal increased with time upon AICAR addition, suggesting that AMPfret 2.1 can monitor allosteric activation of AMPK in cells (FIGS. 7 and 8).

More than half-maximal response was already reached after 15 min of treatment, and the maximal effect reached after about 30 minutes.

The activation kinetics of AMPK upon AICAR addition was independently verified by Western blotting for the AMPK-specific phosphosite in acetyl-CoA carboxylase (ACC; widely used as reporter for AMPK activity) in 3T3-L1 cells.

All the results presented above show that the AMPfret sensor can be used as a suitable tool for cellular in vivo applications.

Example 5: AMPfret 2.1 During Ischemia-Reperfusion in a HepG2 Single Cell

Using an incubation flow-through chamber fitted to the confocal microscope which permits to control temperature as well as 02 concentration, HepG2 cells were placed under ischemia-like conditions, comprising hypoxic conditions (2% 02) and glucose free medium at 37° C. ATP pools may not be affected when hypoxia is applied in a high nutrient containing medium since cells can adapt to hypoxia by switching their energy metabolism through anaerobic pathways to compensate for aerobic ATP production. The deprivation period was followed by 1 hour of reperfusion with complete medium and $O_2$ (21%). During the 2 hours of the ischemia-reperfusion protocol, the FRET ratio was monitored every minute by recording simultaneously mseCFPΔ11 and cpVenus fluorescence emitted within 4 nm windows (corresponding to fluorescence emission) using two independent channels. Images were collected and processed using ImageJ in order to i) remove eventual background fluorescence and ii) isolate individual cells from acquired pictures. Then, the fluorescence intensities were extracted from single cell images using Volocity. Thus, the effect of ischemia-reperfusion on the AMPfret 2.1 signal in single cells was analyzed (FIG. 9).

During ischemia in HepG2 cells, the FRET signal did not vary. Changes in AMP/ATP ratio under such conditions were proposed to happen in the liver and AMPK becomes activated, but a recent study suggested that AMPK was activated during ischemia through adenylate-independent pathways. FIG. 9 shows results of a single cell.

During reperfusion of HepG2 cells, the FRET signal increases over the first 30 minutes indicating increased AMP and ADP concentrations. Subsequently, the FRET ratio remained at unchanged high values, suggesting that elevated AMP and ADP concentrations were maintained. In fact, AMPfret should revert the FRET ratio as soon as AMP and ADP levels drop again. These results suggest that in HepG2 cells, reperfusion represented a more drastic energy stress than ischemia regarding adenylate concentrations and AMPK allosteric activation.

Through these experiments, using AMPfret 2.1 in HepG2 cells, we did not detect any FRET signal changes during ischemia, suggesting that AMP and ADP concentrations remained unchanged. However, we showed an increase of AMPfret FRET signal during reperfusion, suggesting an elevation of intracellular AMP and ADP and allosteric activation of AMPK.

These experiments achieved in living cells using AMPfret 2.1 show that AMPfret 2.1 was properly transfected and its fluorescence monitored over time. These results show that AMPfret 2.1 provides a readout of AMP/ZMP concentrations and AMPK allosteric activation by reporting the related conformational changes. Experiments involving ischemia-reperfusion showed that AMPfret 2.1 can monitor endogenous changes of adenylates and AMPK allosteric activation over time.

Monitoring of transient events related to AMPK allosteric activation is promising to decipher or unravel new aspects of its regulation.

The invention claimed is:

1. A heterotrimeric mammalian AMP-activated protein kinase (AMPK) construct having AMPK activity and the capacity of being allosterically activated, the construct comprising a complex consisting of a first component, a second component, and a third component that together provide the construct's AMPK activity and capacity of being allosterically activated, wherein the first component comprises a mammalian AMPK α-subunit or a mutant or fragment thereof, the second component comprises a mammalian AMPK β-subunit or a mutant or fragment thereof, and the third component comprises a mammalian AMPK γ-subunit or a mutant or fragment thereof, wherein the first component is tagged with a first fluorophore, and either the second component or third component is tagged with a second fluorophore such that conformational changes within the AMPK construct changes the Förster Resonance Energy Transfer between the first fluorophore and the second fluorophore.

2. The AMPK construct of claim 1, wherein at least one of said first component, second component, and third component is tagged with the first fluorophore or the second fluorophore at its C-terminus.

3. The AMPK construct of claim 1, wherein the αsubunit is the α2 isoform, the β-subunit is the β2 isoform, and the γ-subunit is the γ1 isoform.

4. The AMPK construct of claim 3, wherein the α2 isoform is tagged with the first fluorophore at the C-terminus, and either the β2 or the γ1 isoform is tagged at the C-terminus with the second fluorophore.

5. The AMPK construct of claim 1, wherein first fluorophore and the second fluorophore are a Förster Resonance Energy Transfer (FRET) pair.

6. The AMPK construct of claim 1, wherein the first fluorophore and the second fluorophore are genetically encoded fluorescent proteins.

7. The AMPK construct of claim 5, wherein the first fluorophore and the second fluorophore are each independently selected from the group consisting of Green Fluorescent Proteins (GFP), Cyan Fluorescent Proteins CFP, Yellow Fluorescent Proteins (YFP), Orange Fluorescent Proteins and Red Fluorescent Proteins.

8. The AMPK construct of claim 7, wherein the first fluorophore and the second fluorophore are each independently selected from the group consisting of GFP, CFP and YFP.

9. The AMPK construct of claim 7, wherein the first fluorophore is CFP and the second fluorophore is YFP; or wherein the first fluorophore is mseCFP$_{A11}$ (SEQ ID NO: 67) and the second fluorophore is cpVenus (SEQ ID NO: 55).

10. The AMPK construct of claim 3, wherein the α2 isoform is tagged with mseCFP$_{A11}$ (SEQ ID NO: 67) at the C-terminus, and either the β2 or the γ1 isoform is tagged with cpVenus (SEQ ID NO: 55) at the C-terminus; or wherein the α2 isoform is tagged with CFP at the C-terminus, and either the β2 or the γ1 isoform is tagged with YFP at the C-terminus.

11. The AMPK construct of claim 1, wherein the α subunit is murine, rat, human, bovine or ovine; the β subunit is murine, rat, human, bovine or ovine; and the γ-subunit is murine, rat, human, bovine or ovine.

12. The AMPK construct of claim 1, wherein the AMPK construct is comprised within a host cell.

13. The AMPK construct of claim 1, which is comprised in a kit for identifying the presence of an allosteric interactor of AMPK in a sample, said kit further comprising instructions of use.

14. A method for identifying an AMPK allosteric interactor in a sample, the method comprising the steps of:
  (a) contacting the sample with a heterotrimeric mammalian
     AMP-activated protein kinase (AMPK) construct having AMPK activity and the capacity of being allosterically activated, the construct comprising a complex consisting of a first component, a second component, and a third component that together provide the construct's AMPK activity and capacity of being allosterically activated, wherein the first component comprises a mammalian AMPK α-subunit or a mutant or fragment thereof, the second component comprises a mammalian AMPK β-subunit or a mutant or fragment thereof, and the third component comprises a mammalian AMPK γ-subunit or a mutant or fragment thereof, wherein the first component is tagged with a first fluorophore, and either the second component or third component is tagged with a second fluorophore such that conformational changes within the AMPK construct changes the Förster Resonance Energy Transfer between the first fluorophore and the second fluorophore; and
  (b) detecting, in the sample, a modification of the FRET fluorescence by fluorescence techniques;
  wherein the detecting of the modification of the FRET fluorescence in the sample indicates the presence of an AMPK allosteric interactor in the sample.

15. An ex vivo method of screening for an AMPK allosteric interactor, the method comprising the steps of:
  (a) providing a cell culture comprising cells expressing a heterotrimeric mammalian
     AMP-activated protein kinase (AMPK) construct having AMPK activity and the capacity of being allosterically activated, the construct comprising a complex consisting of a first component, a second component, and a third component that together provide the construct's AMPK activity and capacity of being allosterically activated, wherein the first component comprises a mammalian AMPK α-subunit or a mutant or fragment thereof, the second component comprises a mammalian AMPK β-subunit or a mutant or fragment thereof, and the third component comprises a mammalian AMPK γ-subunit or a mutant or fragment thereof, wherein the first component is tagged with a first fluorophore, and either the second component or third component is tagged with a second fluorophore such that conformational changes within the AMPK construct changes the Förster Resonance Energy Transfer between the first fluorophore and the second fluorophore;
(b) providing candidate AMPK allosteric interactor;
(c) contacting the cells in the cell culture with said candidate AMPK allosteric interactor; and
(d) detecting a modification of the FRET fluorescence in the cells by fluorescent techniques;
  wherein detecting of the modification of the FRET fluorescence in the cells indicates that the candidate AMPK allosteric interactor is an AMPK allosteric interactor.

* * * * *